US005760029A

United States Patent [19]

Jadhav et al.

[11] Patent Number: 5,760,029

[45] Date of Patent: Jun. 2, 1998

[54] SPIROCYCLE INTEGRIN INHIBITORS

[75] Inventors: Prabhakar Kondaji Jadhav, Wilmington, Del.; Joanne Marie Smallheer, Landenberg, Pa.

[73] Assignee: The DuPont Merck Pharmaceutical Company, Wilmington, Del.

[21] Appl. No.: 816,580

[22] Filed: Mar. 13, 1997

Related U.S. Application Data

[60] Provisional application No. 60/013,539, Mar. 15, 1996.

[51] Int. Cl.$^6$ .......................... A61K 31/54; A61K 31/535; C07D 401/14; C07D 403/14

[52] U.S. Cl. .......................... 514/211; 514/212; 514/326; 514/364; 514/365; 514/385; 514/403; 514/396; 514/409; 514/406; 514/256; 514/255; 514/278; 540/543; 548/147; 548/300.7; 548/408; 548/216; 548/357.5; 548/131; 546/16; 546/256; 546/255; 546/268.7

[58] Field of Search .................................. 514/211, 212, 514/326, 364, 365, 385, 403, 396, 409, 406, 256, 255, 278; 540/543; 548/147, 408, 300.7, 216, 131, 357.5; 546/16, 256, 255, 268.7, 269.1, 269.7, 271.1, 271.4, 272.7, 275.4, 276.4, 279.1, 281.7; 544/6, 53, 59, 63, 70, 71, 96, 98, 119, 120, 139, 140, 122, 295, 333, 336

[56] References Cited

FOREIGN PATENT DOCUMENTS

| | | |
|---|---|---|
| 0529858 | 3/1993 | European Pat. Off. . |
| 9514682 | 6/1995 | WIPO . |
| 9514683 | 6/1995 | WIPO . |
| 9532710 | 12/1995 | WIPO . |
| 9637492 | 11/1996 | WIPO . |

*Primary Examiner*—Matthew V. Grumbling
*Attorney, Agent, or Firm*—Blair Q. Ferguson

[57] ABSTRACT

This invention relates to novel heterocycles, including (S)-2-phenylsulfonylamino-3-[[[8-(2-pyridinylaminomethyl)-]-1-oxa-2-azaspiro-[4.5]-dec-2-en-3-yl]carbonylamino] propionic acid, which are useful as antagonists of the $\alpha_v\beta_3$ integrin and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

7 Claims, No Drawings

SPIROCYCLE INTEGRIN INHIBITORS

FIELD OF THE INVENTION

This application claims priority under 35 U.S.C. § 119(e) from provisional application Ser. No. 60/013,539, filed Mar. 15, 1996.

This invention relates to novel heterocycles which are useful as antagonists of the $\alpha_v\beta_3$ integrin and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

BACKGROUND OF THE INVENTION

Angiogenesis or neovascularization is critical for normal physiological processes such as embryonic development and wound repair (Folkman and Shing, J. Biol. Chem. 1992, 27:10931–10934; D'Amore and Thompson, Ann. Rev. Physiol. 1987, 49:453–464). However, angiogenesis also occurs pathologically, for example, in ocular neovascularization (leading to diabetic. retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta., 1990, 1032:118–128).

Tumor dissemination, or metastasis, involves several distinct and complementary components, including the penetration and transversion of tumor cells through basement membranes and the establishment of self-sustaining tumor foci in diverse organ systems. To this end, the development and proliferation of new blood vessels, or angiogenesis, is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth (Herblin et al., Exp. Opin. Ther. Patents, 1994, 1–14). Many angiogenic inhibitors have been directed toward blocking initial cytokine-dependent induction of new vessel. growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$ is preferentially expressed on angiogenic blood vessels in chick and man (Brooks et al., Science, 1994, 264:569–571; Enenstein and Kramer, J. Invest. Dermatol., 1994, 103:381–386). Integrin $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$ the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell, smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis and are recognized as being useful as therapeutic agents for the treatment of human diseases such as cancer, restenosis, thromoembolic disorders, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing α- and β-subunits. Integrin subfamilies contain a common β-subunit combined with different α-subunits to form adhesion receptors with unique specificity. The genes for eight distinct β-subunits have been cloned and sequenced to date.

The $\alpha_v\beta_3$ heterodimer is a member of the $\beta_3$ integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombosponden in a manner mediated by the RGD sequence. A key event in bone resorption is the adhesion of osteoclasts to the matrix of bone. Studies with monoclonal antibodies have implicated the $\alpha_v\beta_3$ receptor in this process and suggest that a selective $\alpha_v\beta_3$ antagonist would have utility in blocking bone resorption (Horton et al., J. Bone Miner. Res., 1993, 8:239–247; Helfrich et al., J. Bone Miner. Res., 1992, 7:335–343).

PCT Patent Application Publication Number WO95/14683, published Jun. 1, 1995 discloses isoxazoline and isoxazole fibrinogen receptor antagonists of general formula shown below:

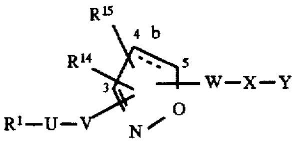

Copending, commonly assigned U.S. patent application Ser. No. 08/455,768 filed May 31, 1995, discloses integrin inhibitors of the general formula shown below:

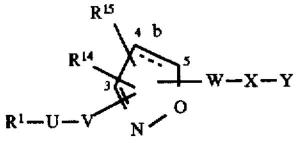

PCT Patent Application Publication No. WO95/32710, published Dec. 7, 1995 discloses compounds for inhibition of osteoclast-mediated bone resorption of general formula shown below:

X—Y—Z—Aryl—A—B wherein Aryl is a 6-membered aromatic ring system.

None of the above references discloses or suggests the spirocyclic compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis.

One aspect of this invention provides novel compounds of Formula I (described below) which are useful as antagonists of the $\alpha_v\beta_3$ integrin, which is also referred to as the vitronectin receptor. The compounds of the present invention inhibit the binding of vitronectin or other RGD-containing ligands to $\alpha_v\beta_3$ and inhibit cell adhesion. The present invention also includes pharmaceutical compositions containing such compounds of Formula I, and methods of using such compounds for the inhibition of angiogenesis, and/or for the treatment of disorders mediated by angiogenesis.

Another aspect of the present invention comprises agents that inhibit the binding of vitronectin to the $\alpha_v\beta_3$ receptor for the treatment (including prevention) of thrombosis which do not significantly alter hemostatic balance and do not significantly inhibit platelet aggregation and do not significantly inhibit coagulation. Also the compounds of the current invention can be used for the treatment or prevention of restenosis.

The present invention also provides novel compounds, pharmaceutical compositions and methods which may be used in the treatment or prevention of other diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, thrombosis, inflammatory bowel disease and other autoimmune diseases.

Also included in the present invention are pharmaceutical kits comprising one or more containers containing pharmaceutical dosage units comprising a compound of Formula I, for the therapeutic inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

DETAILED DESCRIPTION OF THE INVENTION

The present invention provides novel nonpeptide compounds of Formula I (described below) which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

One aspect of this invention provides novel compounds of Formula I which are useful as antagonists of the $\alpha_v\beta_3$ or vitronectin receptor. The compounds of the present invention inhibit the binding of vitronectin and other RGD-containing ligands to $\alpha_v\beta_3$ and inhibit cell adhesion. The present invention also includes pharmaceutical compositions containing such compounds of Formula I, and methods of using such compounds for the inhibition of angiogenesis, and/or for the treatment of angiogenic disorders.

[1] The present invention comprises spirocyclic compounds of Formula I:

$$R^1—Q—W—X—Y \quad (I)$$

including stereoisomeric forms thereof, or mixtures of stereoisomeric forms thereof, or pharmaceutically acceptable salt or prodrug forms thereof wherein:

Q is selected from

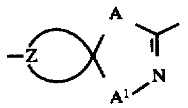 or 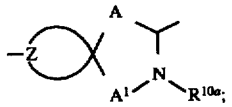

A is selected from $—N(R^{10})—$, $—(R^{11})—$ or $—O—$;

$A^1$ is selected from $—O—$ or $—N(R^{10})—$;

Z is a spiro-fused 4–7 membered ring system (including the sprio atom) containing 0–2 heteroatoms selected from O, S, or N, said ring system optionally being substituted on carbon with keto, or being substituted on carbon or nitrogen independently with 0–2 $R^9$ or $R^{10}$ or $R^{10a}$;

$R^1$ is selected from:

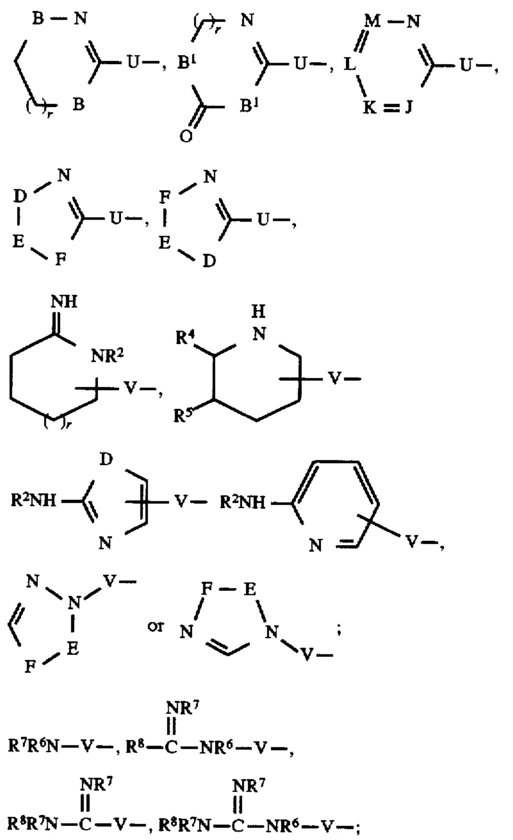

B is independently selected from $—CH_2—$, —O—, $—N(R^2)—$, or —C(=O)—;

$B^1$ is independently selected from $—CH_2—$ or $—N(R^3)—$;

D is $—N(R^2)—$, —O—, —S—, —C(=O)— or $—SO_2—$;

E—F is $—C(R^4)=C(R^5)—$, $—N=C(R^4)—$, $—C(R^4)=N—$, or $—C(R^4)_2C(R^5)_2—$;

J, K, L and M are independently selected from $—C(R^4)—$, $—C(R^5)—$ or —N—, provided that at least one of J, K, L and M is not —N—;

$R^2$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl $C_1$–$C_6$ alkyl, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, aryl($C_1$–$C_6$ alkoxy)carbonyl, wherein said aryl groups are substituted with 0–2 substituents independently selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl;

alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups independently selected from: $C_1$–$C_4$ alkyl, $C_1$–$C_4$ alkoxy, halo, cyano, amino, $CF_3$, or $NO_2$;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

U is selected from:

$—N(R^6)(CH_2)_n—$,
$—N(R^6)(CH_2)_mO—$,
$—N(R^6)(CH_2)_mN(R^7)—$
$—N(R^6)(CH_2)_nS(O)_p—$
$—N(R^6)C(=O)(CH_2)_n—$;
$—N(R^6)(CH_2)_mC(=O)—$;

V is selected from:

$—(CH_2)_n—$,
$—(CH_2)_mO—(CH_2)_n—$,
$—(CH_2)_mN(R^7)(CH_2)_n—$,
$—(CH_2)_nS(O)_p(CH_2)_n—$,
$—(CH_2)_mN(R^7)C(=O)(CH_2)_n—$,
$—(CH_2)_nC(=O)N(R^7)(CH_2)_n—$,
$—(CH_2)_nC(=O)(CH_2)_n—$;

$R^9$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

$R^{10}$ is selected from: H, $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–$R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is selected from:

$C_1$–$C_4$ alkylene,
$—(C(R^{12})_2)_qO(C(R^{12})_2)_q—$,
$—(C(R^{12})_2)_qC(=O)(C(R^{12})_2)_q—$,
$—(C(R^{12})_2)_qC(=O)N(R^{13})—$,
$—C(=O)—N(R^{13})—(C(R^{12})_2)_q—$;

X is $—(C(R^{12})_2)_qC(R^{12})(R^{14})—C(R^{12})(R^{15})—$;

alternatively, W and X can be taken together to be

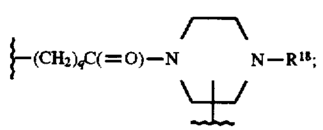

$R^{12}$ is selected from H, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from H, $C_1$–$C_6$ alkyl, $C_3$–$C_7$ cycloalkylmethyl, or aryl($C_1$–$C_6$ alkyl)-

$R^{14}$ is selected from:

H, $C_1$–$C_6$ alkylthio($C_1$–$C_6$ alkyl)-, aryl($C_1$–$C_{10}$ alkylthioalkyl)-, aryl ($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$alkenyl, $C_2$–$C_{10}$ alkynyl, $C_3$–$C_{10}$ cycloalkyl, $C_3$–$C_{10}$cycloalkylalkyl, aryl ($C_1$–$C_6$ alkyl)-, heteroaryl ($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may optionally be substituted independently with 0–1 $R^{16}$ or 0–2 $R^{11}$;

$R^{15}$ is selected from:

H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl , $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, $CO_2R^{17}$, $C(=O)R^{17}$, $CONR^{17}R^{20}$, $SO_2R^{17}$ or $SO_2NR^{17}R^{20}$, provided that any of the above alkyl, cycloalkyl, aryl or heteroaryl groups may optionally be substituted independently with 0–2 $R^{11}$;

Y is selected from:

$-COR^{19}$, $-SO_3H$, $-PO_3H$, tetrazolyl, $-CONHNHSO_2CF_3$, $-CONHSO_2R^{17}$, $-CONHSO_2NHR^{17}$, $-NHCOCF_3$, $-NHCONHSO_2R^{17}$, $-NHSO_2R^{17}$, $-OPO_3H_2$, $-OSO_3H$, $-PO_3H_2$, $-SO_3H$, $-SO_2NHCOR^{17}$, $-SO_2NHCO_2R^{17}$,

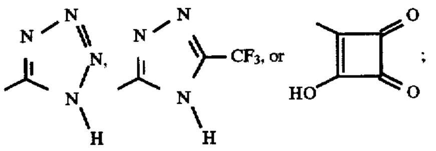

$R^{16}$ is selected from:

$-N(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$, or
$-N(R^{20})SO_2-NR^{20}R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, arylaryl($C_1$–$C_6$ alkyl)-, heteroarylaryl($C_1$–$C_6$ alkyl)-, arylheteroaryl($C_1$–$C_6$ alkyl)-, heteroarylheteroaryl ($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{18}$ is selected from:

H,
$-C(=O)-O-R^{17}$,
$-C(=O)-R^{17}$,
$-C(=O)-NH-R^{17}$,
$-SO_2-R^{17}$, or
$-SO_2-NR^{20}R^{17}$;

$R^{19}$ is selected from:

hydroxy,
$C_1$–$C_{10}$ alkyloxy,
$C_3$–$C_{11}$ cycloalkyloxy,
aryloxy,
aryl($C_1$–$C_6$ alkoxy)-,
$C_3$–$C_{10}$ alkylcarbonyloxyalkyloxy,
$C_3$–$C_{10}$ alkoxycarbonyloxyalkyloxy,
$C_2$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_7$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy,
$C_5$–$C_{10}$ (5-alkyl-1,3-dioxa-cyclopenten-2-one-yl) methyloxy,
$C_{10}$–$C_{14}$ (5-aryl-1,3-dioxa-cyclopenten-2-one-yl) methyloxy, or
$(R^{11})(R^{12})N-(C_1$–$C_{10}$ alkoxy)-;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl ($C_1$–$C_6$ alkyl)-;

m is 1–2;

n is 0–2;

p is 0–2;

q is 0–2; and r is 0–2;

provided that:

n, q, and r are chosen such that the number of in-chain atoms between $R^1$ and Y is in the range of 8–18.

[2] Preferred compounds of the invention as described above are spirocyclic compounds of Formula I:

$$R^1\text{—}Q\text{—}W\text{—}X\text{—}Y \quad (I)$$

including stereoisomeric forms thereof, or mixtures of stereoisomeric forms thereof, or pharmaceutically acceptable salt or prodrug forms thereof wherein:

Q is selected from

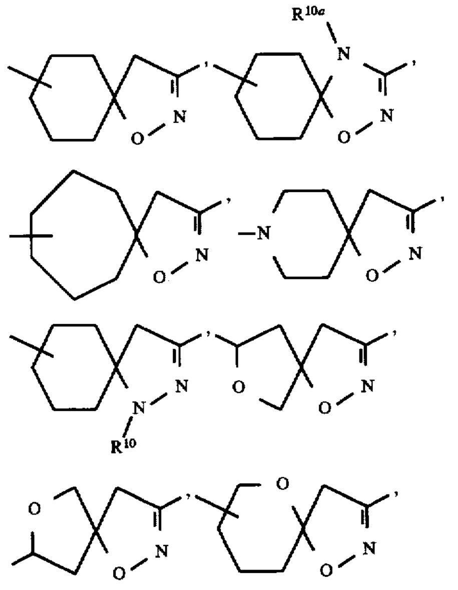

-continued

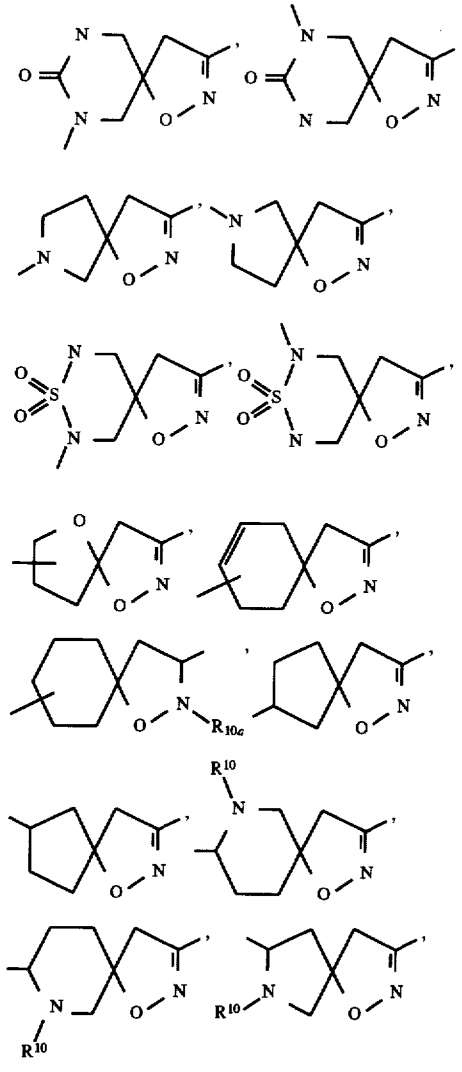

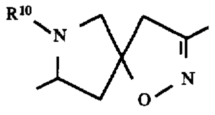

or

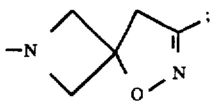

;

$R^1$ is selected from:

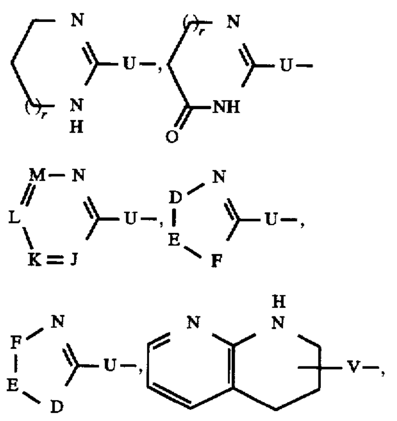

-continued

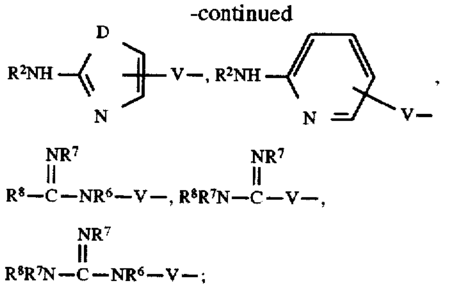

D is $-N(R^2)-$, $-O-$, $-S-$, $-C(=O)-$ or $-SO_2-$;

E—F is $-C(R^4)=C(R^5)-$, $-N=C(R^4)-$, $-C(R^4)=N-$, or $-C(R^4)_2C(R^5)_2-$;

J, K, L and M are independently selected from $-C(R^4)-$, $-C(R^5)-$ or $-N-$, provided that at least one of J, K, L and M is not $-N-$;

$R^2$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl ($C_1$–$C_6$ alkoxy)carbonyl, wherein said aryl groups are substituted with 0–2 substituents independently selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl ($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups independently selected from: $C_1$–$C_4$ alkyl, $C_1$–$C_4$ alkoxy, halo, cyano, amino, $CF_3$, or $NO_2$;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

U is selected from:

$-N(R^6)(CH_2)_n-$,
$-N(R^6)(CH_2)_mO-$,
$-N(R^6)(CH_2)_mN(R^7)-$
$-N(R^6)(CH_2)_nS(O)p-$
$-N(R^6)C(=O)(CH_2)_n-$;

V is selected from:

$-(CH_2)_n-$,
$-(CH_2)_mO-(CH_2)_n-$,
$-(CH_2)_mN(R^7)(CH_2)_n-$,
$-(CH_2)_nS(O)_p(CH_2)_n-$,
$-(CH_2)_mN(R^7)C(=O)(CH_2)_n-$,
$-(CH_2)_nC(=O)N(R^7)(CH_2)_n-$, $—(CH_2)_nC(=O)(CH_2)_n—$;

$R^9$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

$R^{10}$ is selected from: H, $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is selected from:

$C_1$–$C_4$ alkylene, $—(C(R^{12})_2)_qO(C(R^{12})_2)_q—$, $—(C(R^{12})_2)_qC(=O)(C(R^{12})_2)_q—$, $—(C(R^{12})_2)_qC(=O)N(R^{13})—$, $—C(=O)—N(R^{13})—(C(R^{12})_2)_q—$;

X is $—(C(R^{12})_2)_qC(R^{12})(R^{14})—C(R^{12})(R^{15})—$;

alternatively, W and X can be taken together to be

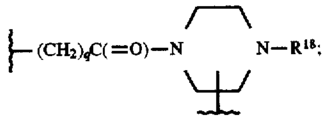;

$R^{12}$ is selected from H, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl($C_1$–$C_6$ alkyl)-;

$R^{13}$ is selected from H, $C_1$–$C_6$ alkyl, $C_3$–$C_7$ cycloalkylmethyl, or aryl ($C_1$–$C_6$ alkyl)-;

$R^{14}$ is selected from:

H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may optionally be substituted independently with 0–1 $R^{16}$ or 0–2 $R^{11}$;

$R^{15}$ is selected from:

H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$ or $SO_2NR^{17}R^{20}$, provided that any of the above alkyl, cycloalkyl, aryl or heteroaryl groups may optionally be substituted independently with 0–2 $R^{11}$;

Y is selected from:

$—COR^{19}$, $—SO_3H$, $—PO_3H$, tetrazolyl, $—CONHNHSO_2CF_3$, $—CONHSO_2R^{17}$, $—CONHSO_2NHR^{17}$, $—NHCOCF_3$, $—NHCONHSO_2R^{17}$, $—NHSO_2R^{17}$, $—OPO_3H_2$, $—OSO_3H$, $—PO_3H_2$, $—SO_3H$, $—SO_2NHCOR^{17}$, $—SO_2NHCO_2R^{17}$,

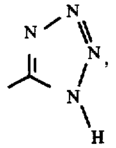,

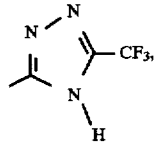 or

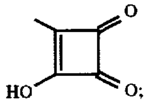;

$R^{16}$ is selected from:

$—N(R^{20})—C(=O)—O—R^{17}$, $—N(R^{20})—C(=O)—R^{17}$, $—N(R^{20})—C(=O)—NH—R^{17}$, $—N(R^{20})SO_2—R^{17}$, or $—N(R^{20})SO_2—NR^{20}R^{17}$;

$R^{17}$ is selected from:

$C_1$–$C_{10}$ alkyl, $C_3$–$C_{11}$cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, arylaryl($C_1$–$C_6$ alkyl)-, heteroarylaryl($C_1$–$C_6$ alkyl)-, arylheteroaryl($C_1$–$C_6$ alkyl)-, heteroarylheteroaryl($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{18}$ is selected from:

H, $—C(=O)—O—R^{17}$, $—C(=O)—R^{17}$, $—C(=O)—NH—R^{17}$, $—SO_2—R^{17}$, or $—SO_2—NR^{20}R^{17}$;

$R^{19}$ is selected from:

hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl) methyloxy, or $(R^{11})(R^{12})N$—($C_1$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

m is 1–2;

n is 0–2;

p is 0–2;

q is 0–2; and r is 0–2;

provided that:

n, q, and r are chosen such that the number of in-chain atoms between $R^1$ and Y is in the range of 8–18.

[3] Further preferred compounds of the invention as described above are compounds of the Formula I including stereoisomeric forms thereof, or mixtures of stereoisomeric forms thereof, or pharmaceutically acceptable salt or prodrug forms thereof wherein:

Q is selected from:

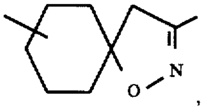
,

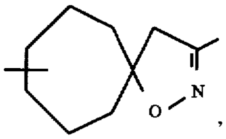
,

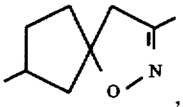
,

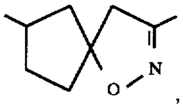
,

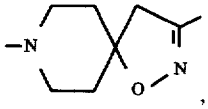
,

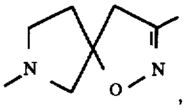
,

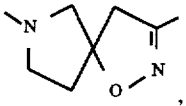
,

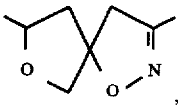
,

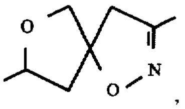
,

-continued

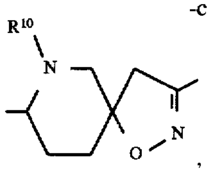
,

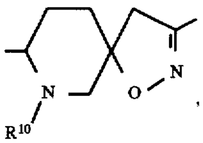
,

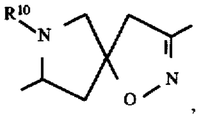
,

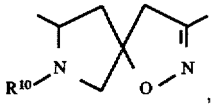
,

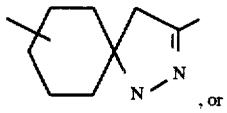
, or

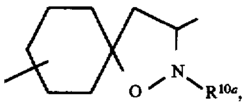

$R^1$ is selected from:

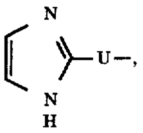
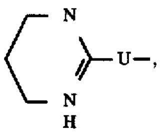
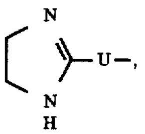

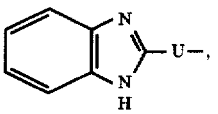
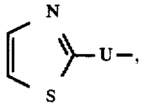

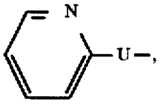
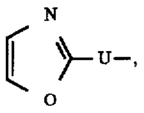
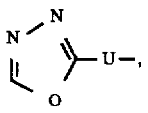

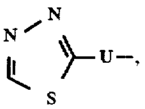
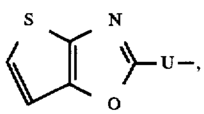

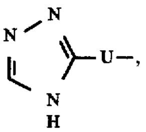
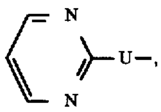

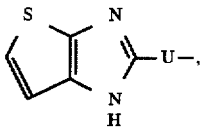
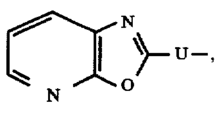

-continued

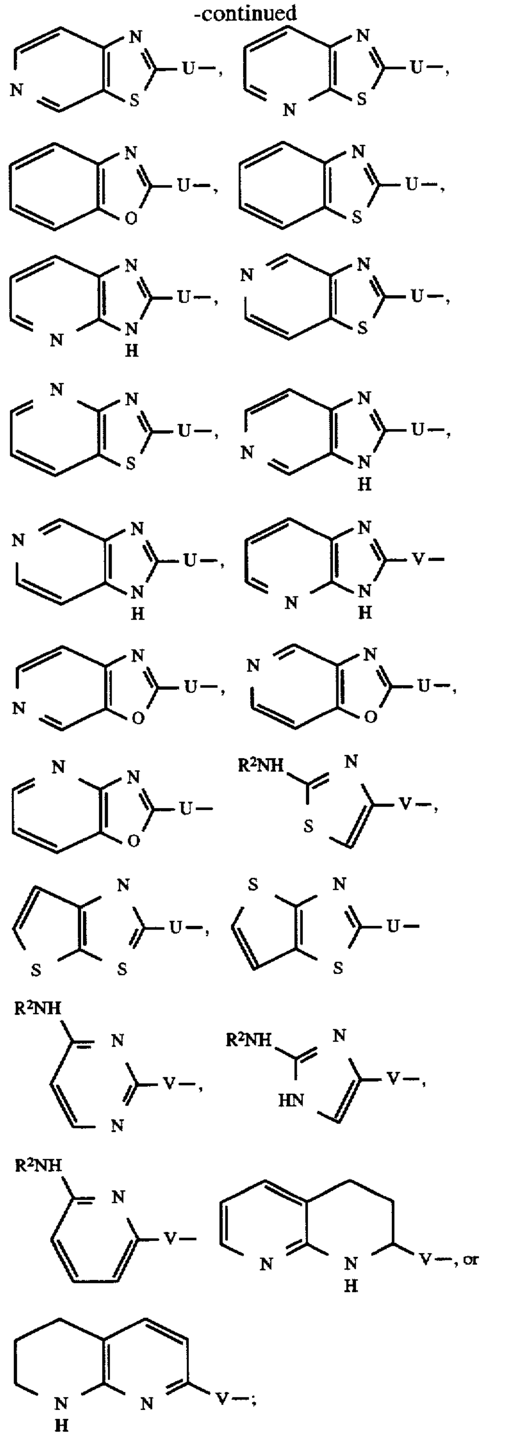

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

$R^2$ is selected from: H, $C_1$–$C_4$ alkyl or benzyl;

U is $—NH(CH_2)_n—$;

V is $—(CH_2)_n—$;

$R^{10}$ is selected from: H, $CO_2R^{17}$, $C(=O)R^{17}$, $CONR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $CONR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_{1-C4}$ alkylsulfonyl, or $C_1$–$C_4$ alkylaminosulfonyl;

W is $—C(=O)—N(R^{13})—$;

X is $—CH(R^{14})—CH(R^{15})—$;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $—C(=O)R^{19}$;

$R^{16}$ is selected from:

$—N(R^{20})—C(=O)—O—R^{17}$,
$—N(R^{20})—C(=O)—R^{17}$,
$—N(R^{20})—C(=O)—NH—R^{17}$,
$—N(R^{20})SO_2—R^{17}$, or
$—N(R^{20})SO_2—N(R^{20})R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl) heteroaryl, arylaryl($C_1$–$C_6$ alkyl)-, heteroarylaryl($C_1$–$C_6$ alkyl)-, arylheteroaryl($C_1$–$C_6$ alkyl)-, heteroarylheteroaryl($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is selected from:

hydroxy,
$C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
dimethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
or
1-(2-(2-methoxypropyl)carbonyloxy)ethoxy-;

$R^{20}$ is H or $CH_3$; and n is 0–1.

[4] Still further preferred compounds of the above invention as described above are compounds of the Formula I including stereoisomeric forms thereof, or mixtures of stereoisomeric forms thereof, or pharmaceutically acceptable salt or prodrug forms thereof wherein:

Q is selected from:

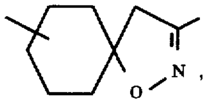, 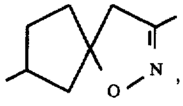,

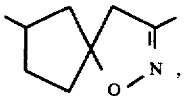, 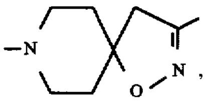,

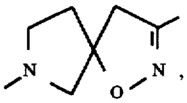, 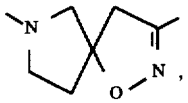,

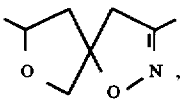, 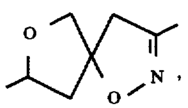,

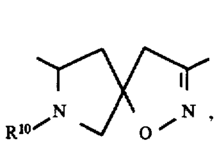, 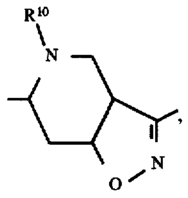,

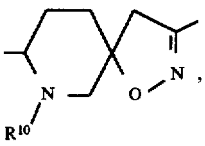, 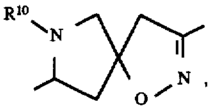,

;

$R^1$ is selected from:

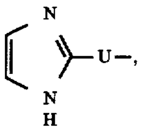, 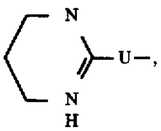, 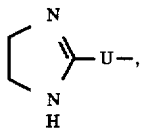,

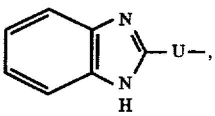, 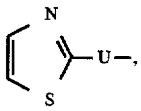,

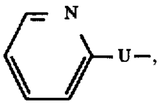, 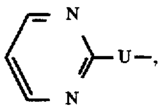,

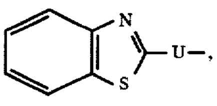, 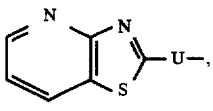,

-continued

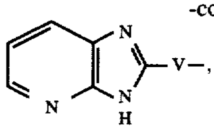, 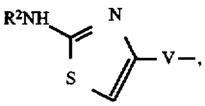,

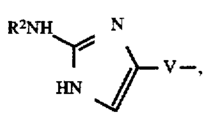, 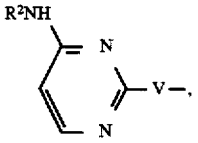,

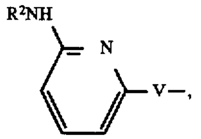, 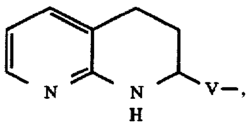, or

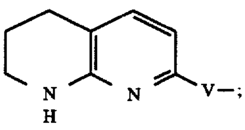;

$R^2$ is selected from: H, $C_1$–$C_4$ alkyl, or benzyl;

U is $—NH(CH_2)_n—$;

V is $—(CH_2)_n—$;

$R^{10}$ is selected from: H, $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from : $CO_2R^{17}$, $C(=O)R^{17}$, $CONR^{17}R^{20}$, $—SO_2R^{17}$, $—SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)-substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is $—C(=O)—N(R^{13})—$;

X is $—CH(R^{14})—CH(R^{15})—$;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $—C(=O)R^{19}$;

$R^{16}$ is selected from:

$—N(R^{20})—C(=O)—O—R^{17}{}_1$, $—N(R^{20})—C(=O)—R^{17}$, $—N(R^{20})SO_2—R^{17}$, $R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, arylaryl($C_1$–$C_6$ alkyl)-, heteroarylaryl ($C_1$–$C_6$ alkyl)-, arylheteroaryl ($C_1$–$C_6$ alkyl)-, heteroarylheteroaryl($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is selected from:
hydroxy,
$C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$; and n is 0–1.

[5] Specifically preferred compounds of the above invention are compounds including enantiomeric or diasteriomeric forms thereof, or mixtures of enantiomeric or diastereomeric forms thereof, or pharmaceutically acceptable salt or prodrug forms thereof, selected from the group consisting of:

(S)-2-phenylsulfonylamino-3-[[[8-(2-pyridinylaminomethyl)-]-1-oxa-2-azaspiro-[4.5]-dec-2-en-3-yl]carbonylamino]propionic acid, (S)-2-benzyloxycarbonylamino-3-[[[8-(2-pyridinylaminomethyl)-]-1-oxa-2-azaspiro-[4.5]-dec-2-en-3-yl]carbonylamino]propionic acid, (S)-2-[(2,4,6-trimethylphenyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(3,5-dimethylisoxazol4-yl)sulfonyl]amino-3-[[[8-(2-pyridinylaminomethyl)-]-1-oxa-2-azaspiro-[4.5]-dec-2-en-3-yl]carbonylamino]propionic acid, (S)-2-phenylsulfonylamino-3-[[[8-[(6-aminopyridin-2-yl) methyl]-]-1-oxa-2,8-diazaspiro-[4.5]-dec-2-en-3-yl] carbonylamino]propionic acid, (S)-2-phenylsulfonylamino-3-[[[8-[(6-aminopyridin-2-yl) methyl]]-1-oxa-2,8-diazaspiro-[4.4]-non-2-en-3-yl] carbonylamino]propionic acid, (S)-2-phenylsulfonylamino-3-[[[8-(2-pyridinylaminomethyl)-]-1-oxa-2-azaspiro-[4.4]-non-2-en-3-yl]carbonylamino]propionic acid, (S)-2-phenylsulfonylamino-3-[[[8-[2-(4,5-dihydroimidazol-2-yl)aminomethyl]-]-1-oxa-2-azaspiro-[4.5]-dec-2-en-3-yl]carbonylamino]propionic acid, (S)-2-[(2-methylphenyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(2-chloro-4-methylphenyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(4-biphenyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(2-bromophenyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(2-naphthyl)sulfonyl]amino-3-[[[8-(2-pyridinylaminomethyl)-]-1-oxa-2-azaspiro-[4.5]-dec-2-en-3-yl]carbonylamino]propionic acid, (S)-2-[(1-naphthyl)sulfonyl]amino-3-[[[8-(2-pyridinylaminomethyl)-]-1-oxa-2-azaspiro-[4.5]-dec-2-en-3-yl]carbonylamino]propionic acid, (S)-2-phenylsulfonylamino-3-[[[8-(2-imidazolylaminomethyl)-]-1-oxa-2-azaspiro-[4.5]-dec-2-en-3-yl]carbonylamino]propionic acid, (S)-2-benzyloxycarbonylamino-3-[[[8-(2-imidazolylaminomethyl)-]-1-oxa-2-azaspiro-[4.5]-dec-2-en-3-yl]carbonylamino]propionic acid, (S)-2-[(2,4,6-trimethylphenyl)sulfonyl]amino-3-[[[8-(2-imidazolylaminomethyl)-]-1-oxa-2-azaspiro-[4.5]-dec-2-en-3-yl]carbonylamino]propionic acid, (S)-2-[(2,6-dimethylphenyl)sulfonyl]amino-3-[[[8-(2-imidazolylaminomethyl)-]-1-oxa-2-azaspiro-[4.5]-dec-2-en-3-yl]carbonylamino]propionic acid, (S)-2-[(2,6-dichlorophenyl)sulfonyl]amino-3-[[[8-(2-imidazolylaminomethyl)-]-1-oxa-2-azaspiro-[4.5]-dec-2-en-3-yl]carbonylamino]propionic acid, (S)-2-[(2,6-dimethyl-4-phenyl)phenylsulfonyl]amino-3-[[[8-(2-imidazolylaminomethyl)-]-1-oxa-2-azaspiro-[4.5]-dec-2-en-3-yl]carbonylamino]propionic acid, (S)-2-[(2-naphthyl)sulfonyl]amino-3-[[[8-(2-imidazolylaminomethyl)-]-1-oxa-2-azaspiro-[4.5]-dec-2-en-3-yl]carbonylamino]propionic acid, (S)-2-[biphenylsulfonyl]amino-3-[[[8-(2-imidazolylaminomethyl)-]-1-oxa-2-azaspiro-[4.5]-dec-2-en-3-yl]carbonylamino]propionic acid, (S)-2-phenylsulfonylamino-3-[[7-benzyloxycarbonyl-8-(2-imidazolylaminomethyl)-1-oxa-2,7-diazaspiro-[4.4]-non-2-en-3-yl]carbonylamino]propionic acid, (S)-2-benzyloxycarbonylamino-3-[[7-benzyloxycarbonyl-8-(2-imidazolylaminomethyl)-1-oxa-2,7-diazaspiro-[4.4]-non-2-en-3-yl]carbonylamino]propionic acid, (S)-2-[(2,4,6-trimethylphenyl)sulfonyl]amino-3-[[7-benzyloxycarbonyl-8-(2-imidazolylaminomethyl)-1-oxa-2,7-diazaspiro-[4.4]-non-2-en-3-yl]carbonylamino] propionic acid, (S)-2-[(2,6-dimethylphenyl)sulfonyl]amino-3-[[7-benzyloxycarbonyl-8-(2-imidazolylaminomethyl)-1-oxa-2,7-diazaspiro-[4.4]-non-2-en-3-yl]carbonylamino] propionic acid, (S)-2-[(2,6-dichlorophenyl)sulfonyl]amino-3-[[7-benzyloxycarbonyl-8-(2-imidazolylaminomethyl)-1-oxa-2,7-diazaspiro-[4.4]-non-2-en-3-yl]carbonylamino] propionic acid, (S)-2-[(2,6-dimethyl-4-phenyl)phenylsulfonyl]amino-3-[[7-benzyloxycarbonyl-8-(2-imidazolylaminomethyl)-1-oxa-2,7-diazaspiro-[4.4]-non-2-en-3-yl]carbonylamino] propionic acid, (S)-2-[(2-naphthyl)sulfonyl]amino-3-[[7-benzyloxycarbonyl-8-(2-imidazolylaminomethyl)-1-oxa-2,7-diazaspiro-[4.4]-non-2-en-3-yl]carbonylamino] propionic acid, (S)-2-[biphenylsulfonyl]amino-3-[[7-benzyloxycarbonyl-8-(2-imidazolylaminomethyl)-1-oxa-2,7-diazaspiro-[4.4]-non-2-en-3-yl]carbonylamino]propionic acid, (S)-2-phenylsulfonylamino-3-[[8-(2-imidazolylaminomethyl)-1-oxa-2,7-diazaspiro-[4.4]-non-2-en-3-yl]carbonylamino]propionic acid, (S)-2-benzyloxycarbonylamino-3-[[8-(2-imidazolylaminomethyl)-1-oxa-2,7-diazaspiro-[4.4]-non-2-en-3-yl]carbonylamino]propionic acid, (S)-2-[(2,4,6-trimethylphenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dimethylphenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dichlorophenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[8-(2-imidazolylaminomethyl)-1-oxa-2,7-diazaspiro-[4,4]-non-2-en-3-yl]carbonylamino]propionic acid, (S)-2-[(2-naphthyl)sulfonyl]amino-3-[[8-(2-imidazolylaminomethyl)-1-oxa-2,7-diazaspiro-[4,4]-non-2-en-3-yl]carbonylamino]propionic acid, (S)-2-[biphenylsulfonyl]amino-3-[[8-(2-imidazolylaminomethyl)-1-oxa-2,7-diazaspiro-[4,4]-non-2-en-3-yl]carbonylamino]propionic acid, (S)-2-phenylsulfonylamino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-benzyloxycarbonylamino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,4,6-trimethylphenyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,6-dimethylphenyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,6-dichlorophenyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2-naphthyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[biphenylsulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-phenylsulfonylamino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-benzyloxycarbonylamino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,4,6-trimethylphenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethylphenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dichlorophenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2-naphthyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[biphenylsulfonyl]amino-3-[[7-benzyloxycarbonyl-8-8-(4,5-dihydroimidazol-2-yl)aminomethyl-1-oxa-2,7-diazaspiro-[4,4]-non-2-en-3-yl]carbonylamino]propionic acid, (S)-2-phenylsulfonylamino-3-[[8-(4,5-dihydroimidazol-2-yl)aminomethyl-1-oxa-2,7-diazaspiro-[4,4]-non-2-en-3-yl]carbonylamino]propionic acid, (S)-2-benzyloxycarbonylamino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,4,6-trimethylphenyl)sulfonyl]amino-3-[[8-(4,5-dihydroimidazol-2-yl)aminomethyl-1-oxa-2,7-diazaspiro-[4,4]non-2-en-3-yl]carbonylamino]propionic acid, (S)-2-[(2,6-dimethylphenyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,6-dichlorophenyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2-naphthyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[biphenylsulfonyl]amino-3-[[8-(4,5-dihydroimidazol-2-yl)aminomethyl-1-oxa-2,7-diazaspiro-[4,4]-non-2-en-3-yl]carbonylamino]propionic acid, and (S)-2-[(2,4,6-trimethylphenyl)sulfonyl]amino-3-[[8-(2-benzimidazolyl)aminomethyl-1-oxa-2,7-diazaspiro-[4,4]-non-2-en-3-yl]carbonylamino]propionic acid.

In the present invention it has been discovered that the compounds of Formula I above are useful as inhibitors of cell-matrix and cell-cell adhesion processes. The present invention includes novel compounds of Formula I and methods for using such compounds for the prevention or treatment of diseases resulting from abnormal cell adhesion to the extracellular matrix which comprises administering to a host in need of such treatment a therapeutically effective amount of such compound of Formula I. In the present invention it has also been discovered that the compounds of Formula I above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formula I and a pharmaceutically acceptable carrier.

The compounds of Formula I of the present invention are useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion, comprising administering to a mammal in need of such treatment a therapeutically effective amount of a compound of Formula I described above.

The compounds of Formula I of the present invention may be useful for the treatment or prevention of other diseases which involve cell adhesion processes, including, but not limited to, inflammation, bone degradation, thromboembolic disorders, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula I of the present invention may also be useful for wound healing.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of the present invention may be used for other ex vivo applications to prevent cellular adhesion in biological samples. The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as COUMADIN®) and heparin. The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs such as aspirin, ibuprofen, naproxen, sulindac, indomethacin, mefenamate, droxicam, diclofenac, sulfinpyrazone, and piroxicam, including pharmaceutically acceptable salts or prodrugs thereof. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof. The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication No. 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of vitronectin or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group $-N(R^{5a})_2$, each of the two $R^{5a}$ substituents on N is independently selected from the defined list of possible $R^{5a}$. Similarly, by way of example, for the group $-C(R^7)_2-$, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_0$–$C_{10}$" denotes alkyl having 0 to 10 carbon atoms; thus, $C_0$ denotes a direct bond between the groups linked by the $C_0$ group); "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or polycyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0] bicyclononane, [4.4.0]bicyclodecane (decalin), [2.2.2] bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocyclic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "prodrugs" refer to any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of Formula I wherein Q includes an isoxazoline ring as one ring of the spirocycle can be conveniently prepared by dipolar cycloaddition of nitrile oxides with appropriate dipolarophiles (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719). The requisite nitrile oxides are in turn prepared from commercially available precursors or appropriately substituted aldehydes via the intermediate oximes.

Scheme 1 illustrates one synthetic sequence which will provide compounds of Formula I of this invention.

Scheme 1

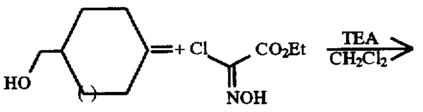

r = 0–2

-continued

Scheme 1

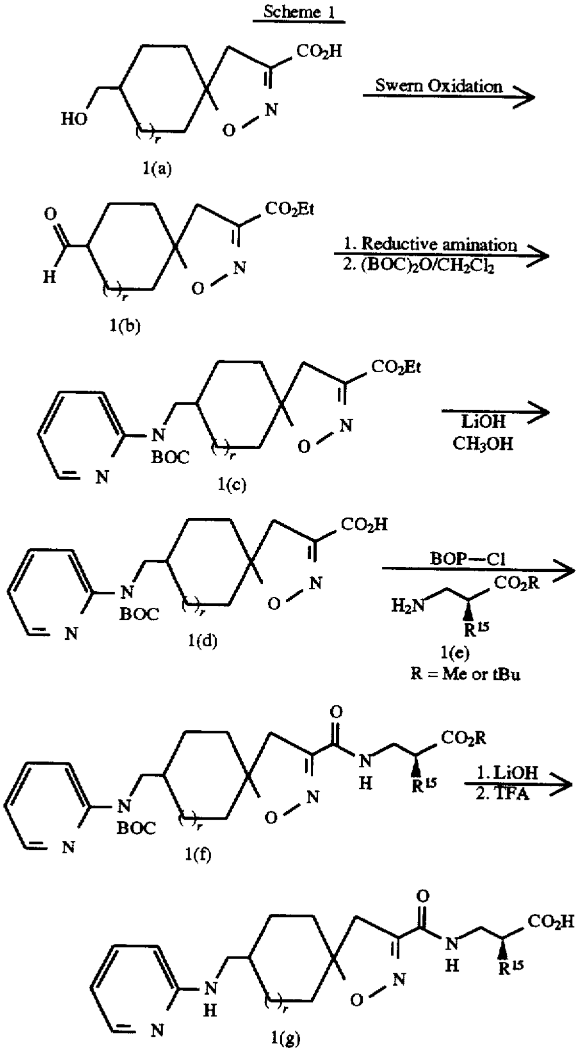

1(a)

1(b)

1(c)

1(d)

1(e)

1(f)

1(g)

Treatment of a methylenecycloalkylmethanol with ethyl chlorooximidoacetate in a suitable solvent, such as tetrahydrofuran or dichloromethane, in the presence of a mild base, such as sodium bicarbonate or triethylamine, provides a spirocycle intermediate, 1(a). Alternately, the cycloaddition can be carried out by thermal decomposition of diethyl nitromalonate in refluxing mesitylene by the method of Shimizu et al. (*Bull Chem. Soc. Jpn.*, 1985, 51, 2519–2522). The hydroxyl group in 1(a) can be subsequently oxidized to the corresponding aldehyde by any of a number of known methods for carrying out this transformation, i.e., (See Manacuso & Swern, *Synthesis*, 1981, 165; Tidwell, *Synthesis*, 1990, 857; D. B. Dess & J. C. Martin, *J. Org. Chem.*, 1983, 48, 4155; op cit. *J. Amer. Chem. Soc.*, 1991, 72, 77; R. E. Ireland & L. Liu, *J. Org. Chem*, 1993, 58, 2899). Reductive amination of the resulting aldehyde with an appropriate aminoheterocycle, such as 2-aminopyridine, can be achieved using sodium triacetoxyborohydride (Abdel-Magid, A. F.; Maryanoff, C. A. *Synlett*, 1990, 9, 537) to provide a secondary amine. Optional protection of the nitrogen as its BOC derivative yields 1(c). Subsequent hydrolysis of the ethyl ester using conventional methods known to one skilled in the art of organic synthesis gives the corresponding acid 1(d). Coupling of compound 1(d) to an appropriately substituted α- or β-amino ester, 1(e) affords compounds of formula 1(f).

The coupling is carried out using any of the many methods for the formation of amide bonds known to one skilled in the art of organic synthesis. These methods include but are not limited to conversion of the acid to the corresponding acid chloride or fluoride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, or coupling with phosphorus reagents such as BOP-Cl. Some of these methods (especially the carbodiimide) can be enhanced by the addition of 1-hydroxybenzotriazole. Deprotection of compound 1(f) is carried out using standard methods of removal of carboxy and amino protecting groups to provide target compounds of formula 1(g).

Additional compounds of formula I can be prepared as shown in Scheme 2. Cycloaddition product, 1(a) can be converted to the corresponding amino compound by conversion to azide 2(a) using diphenylphosphoryl azide under Mitsunobu conditions (Mitsunobu, O. *Synthesis* 1981, 1) and reduction of the resulting azide with triphenylphosphine (Staudinger, H.; Meyer, *J. Helv. Chim. Acta.* 1919, 2, 635) Protection of the resulting amino group as its BOC derivative provides intermediate 2(b). Alternately, the amine function can be introduced prior to cycloaddition by conversion of the starting methylenecycloalkylmethanol to the corresponding tosylate, displacement of the tosyl group with sodium azide, reduction to the amine and treatment with di-t-butyldicarbonate. Subsequent 1,3 dipolarcycloaddition provides 2(a). Ester hydrolysis and amide coupling as described above provides compounds of formula 2(d). Hydrolysis of the ester, removal of the BOC protecting group and treatment of the free amine with an appropriate heterocyclic isothiouronium salt, such as those listed in the scheme, provides compounds of Formula 2(f).

Scheme 2

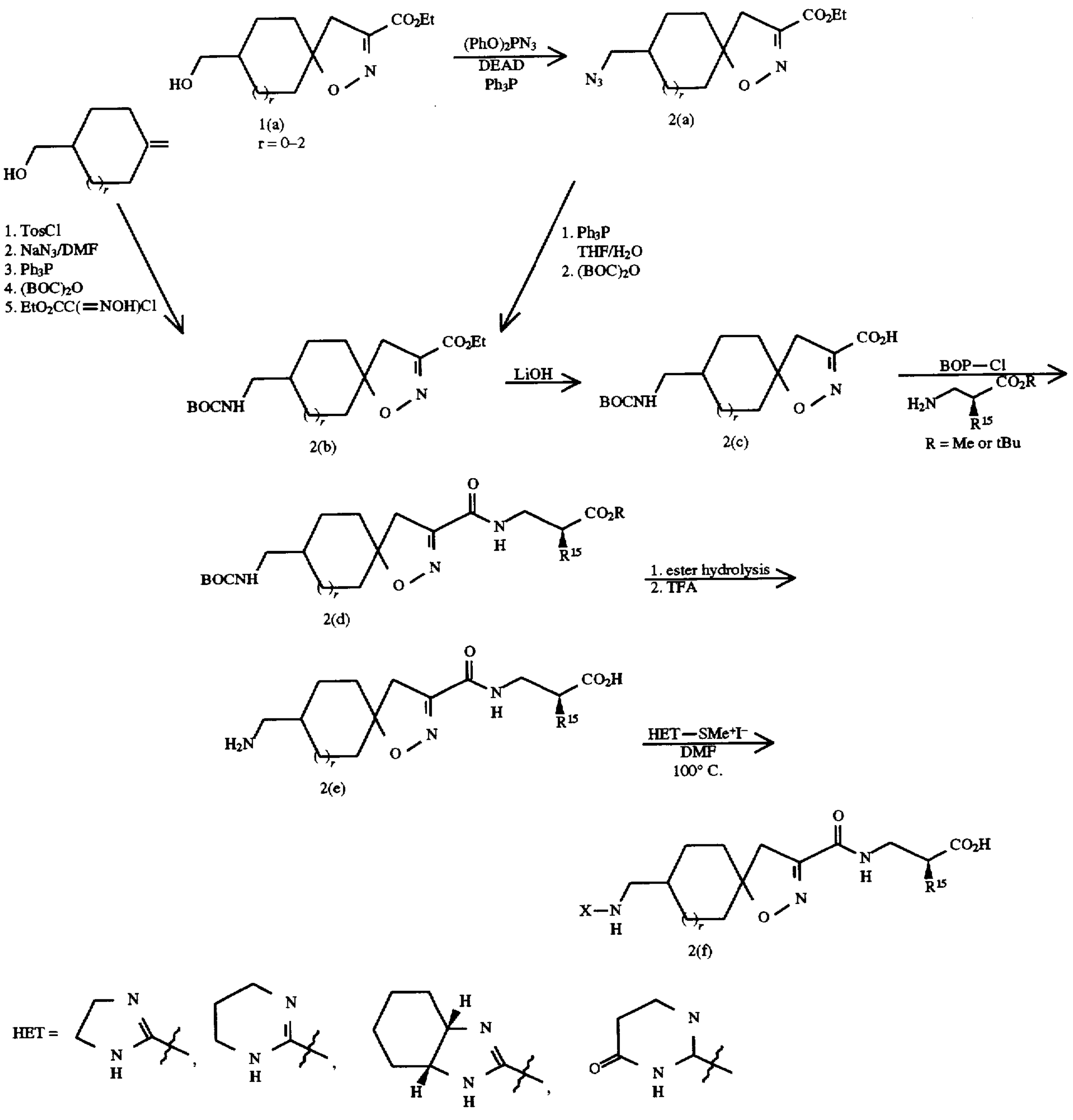

Compounds of Formula I, wherein $R^1$ is a 7-azabenzimidazol-2-yl, group can also be prepared from cycloaddition product 1(a) as depicted in Scheme 3. Jones oxidation of the primary hydroxyl group provides acid 3(a) which is condensed with 2,3-diaminopyridine to provide the 7-azabenzimidazole derivative, 3(b). This intermediate is converted to compounds of the invention by the steps of ester hydrolysis, coupling to compounds of formula 1(e) and deprotection described in detail above.

Scheme 3

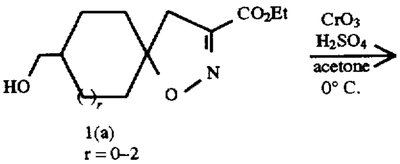

1(a)
r = 0–2

-continued

Scheme 3

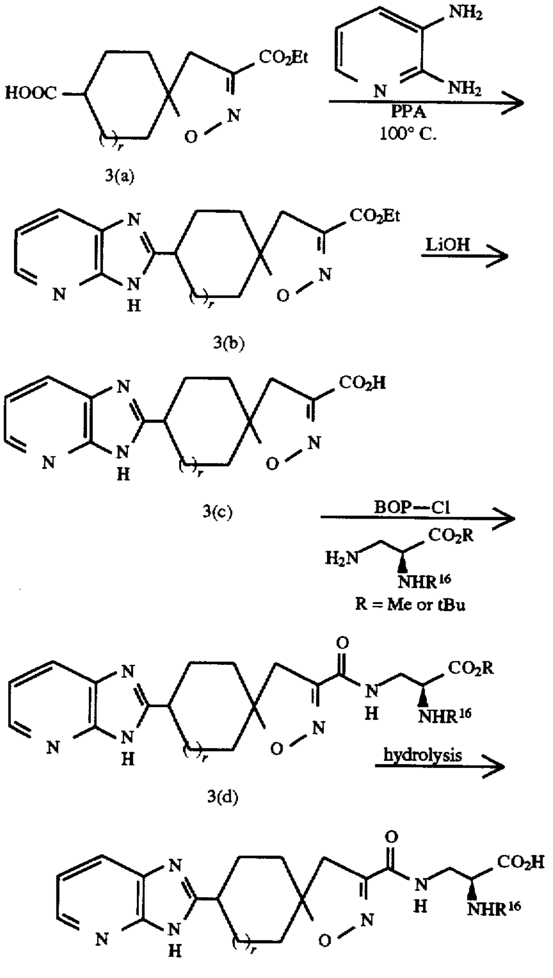

3(a) 3(b) 3(c) 3(d) 3(e)

Scheme 4

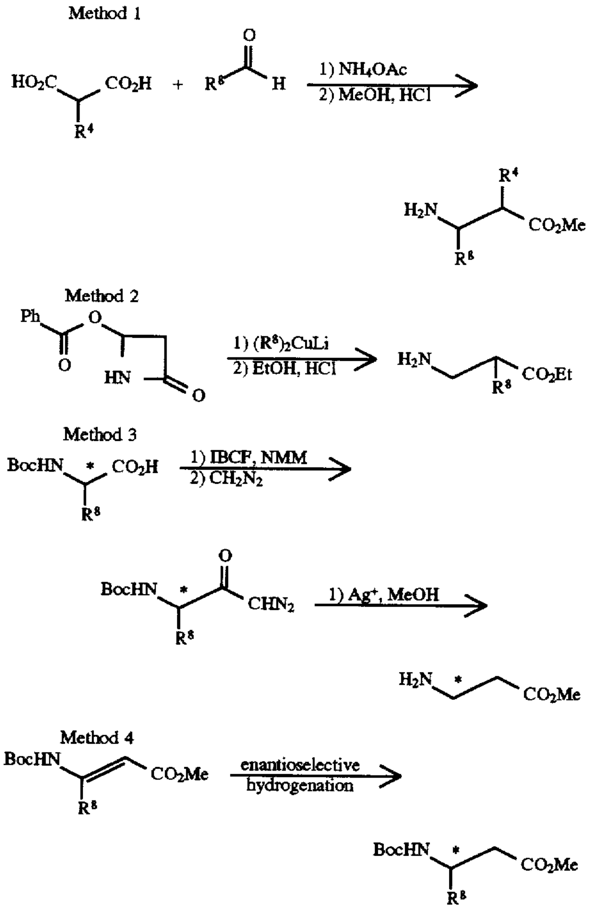

The appropriately substituted racemic β-amino acids may be purchased commercially or, as is shown in Scheme 4, Method 1, prepared from the appropriate aldehyde, malonic acid and ammonium acetate according to the procedure of Johnson and Livak (*J. Am. Chem. Soc.* 1936, 58, 299). Racemic β-substituted-β-amino esters may be prepared through the reaction of dialkylcuprates or alkyllithiums with 4-benzoyloxy-2-azetidinone followed by treatment with anhydrous ethanol (Scheme 4, Method 2) or by reductive amination of β-keto esters as is described in WO9316038. (Also see Rico et al., J. Org. Chem. 1993, 58, 7948–51.) Enantiomerically pure β-substituted-β-amino acids can be obtained through the optical resolution of the racemic mixture or can be prepared using numerous methods, including: Arndt-Eistert homologation of the corresponding α-amino acids as shown in Scheme 4, Method 3 (see Meier, and Zeller, *Angew. Chem. Int. Ed. Engl.* 1975, 14, 32; Rodriguez, et al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme 4, Method 4 (see Asymmetric Synthesis, Vol. 5, (Morrison, ed.) Academic Press, New York, 1985). A comprehensive treatise on the preparation of β-amino acid derivatives may be found in patent application WO 93/07867, the disclosure of which is hereby incorporated by reference.

The synthesis of $N^2$-substituted diaminopropionic acid derivatives can be carried out via Hoffman rearrangement of a wide variety of asparagine derivatives as described in Synthesis, 266–267, (1981) or by manipulation of the commercially available 3-amino-2-benzyloxycarbonylaminopropionic acid.

Additional dipolarophiles useful for the preparation of the compounds of this invention are either commercially available or may be prepared by numerous methods. Synthesis of representative examples and their conversion into compounds of Formula I are illustrated in the following schemes.

Heating a neat mixture of 8-aza-1,4-dioxaspiro(4.5) decane and 2,6-dibromopyridine provides bromopyridine intermediate 5(a) as shown in Scheme 5. Hydrolysis of the acetal protecting group gives the ketone, 5(b) which can then undergo olefination to compound 5(c). The olefination can be carried out by a number of methods known to one skilled in the art. (For suitable olefination methods, see S. H. Pine et al., *Synthesis* 1991, 165; *Bull. Chem Soc. Jpn.*, 1980, 53, 1698; or *J. Org. Chem.* 1968, 33, 780.) The alkene is then subjected to the 1,3-dipolar cycloaddition conditions described above to provide the spirocyclic system, 5(d). Amination with potassium amide in liquid ammonia followed by protection of the resulting amine as its BOC derivative gives compound 5(e). This intermediate is then carried on to compounds of Formula 5(g) using the steps previously described.

Scheme 5

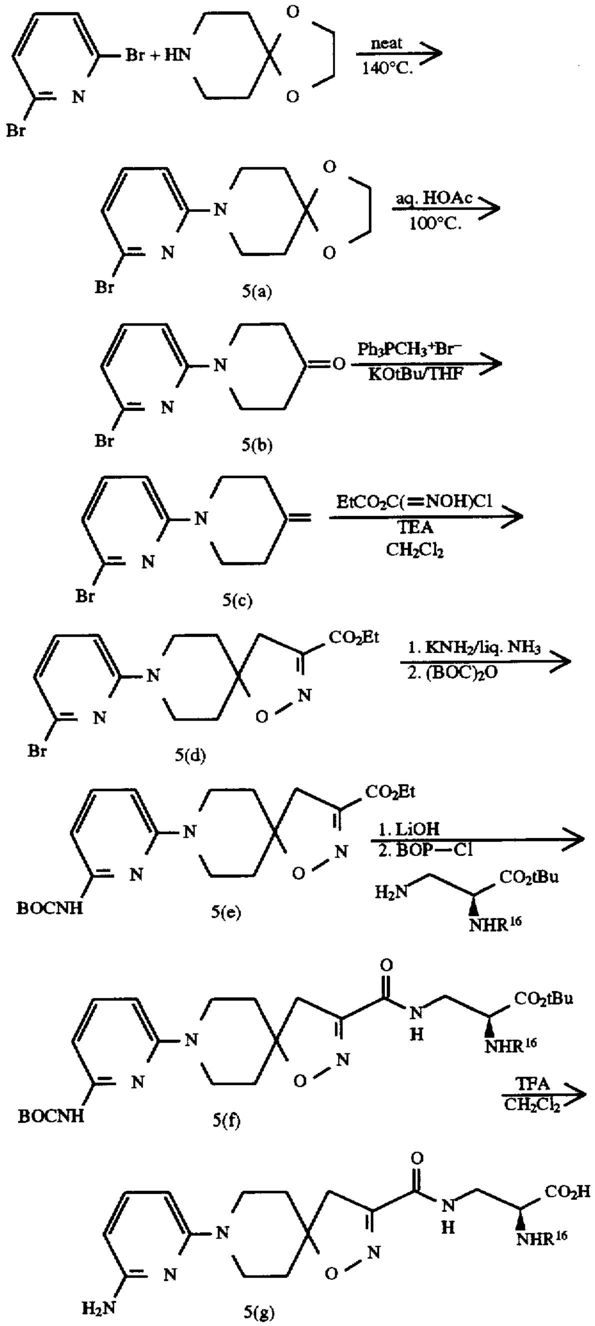

Preparation of the analogous (4,4) spiro system is outlined in Scheme 6. Hydrogenation of commercially available 1-benzyl-3-hydroxypyrolidine and selective reprotection of the amine as the t-butylcarbamate provides 6(a). Oxidation of the hydroxyl to the ketone 6(b) by Swern oxidation or other standard methods followed by olefination as described above provides alkene 6(c). This alkene is then subjected to 1,3-dipolar cycloaddition as previously described to provide the spirocycle 6(d). Ester hydrolysis and coupling to a suitable β-amino ester gives 6(e). Removal of the BOC protecting group and treatment with 2-bromo-6-t-butoxycarbonylaminopyridine (Aust. *J. Chem.* 1982, 35, 2025) gives intermediate 6(f). Finally, deprotection provides compounds of this invention of Formula 6(g).

Scheme 6

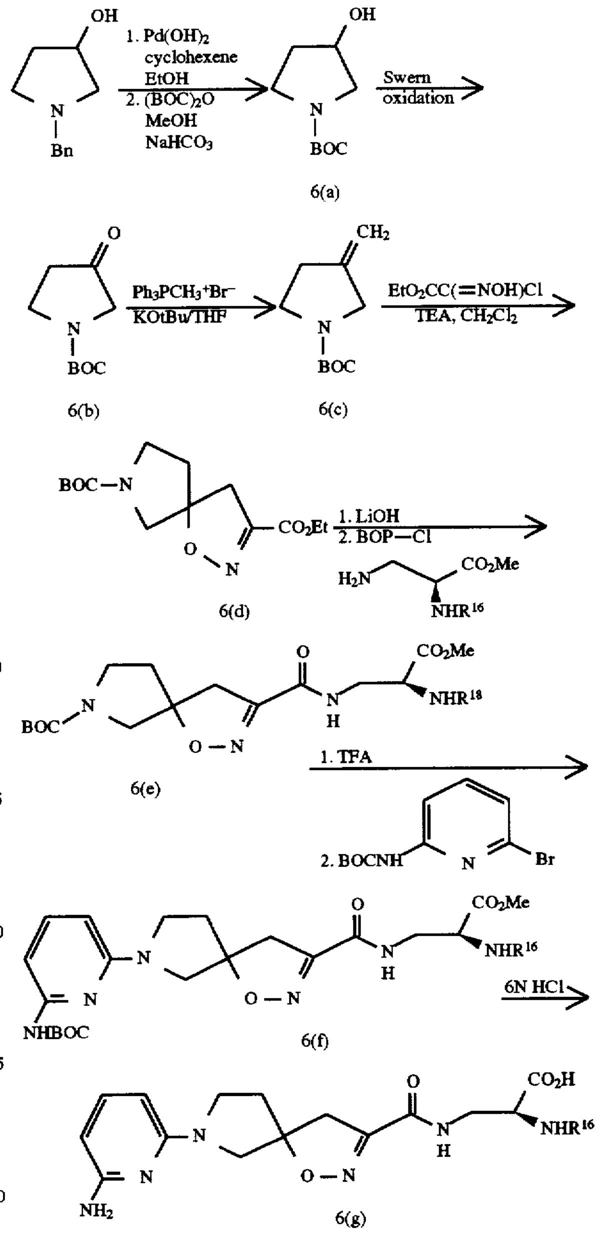

A further class of spirocycles useful in the present invention is prepared as outlined in Scheme 7. Reduction of N-Cbz 4-hydroxyproline with borane-dimethyl sulfide complex in tetrahydrofuran provides diol 7(a). The primary hydroxyl is then selectively protected as its t-butyldimethylsilyl ether, 7(b). Oxidation of the remaining secondary alcohol using methods described above provides ketone 7(c) which can be converted to alkene 7(d) by olefination. Compound 7(d) then undergoes 1,3-dipolarcycloaddition to provide spirocycle 7(e). Deprotection of the silyl ether by treatment with fluoride ion followed by Swern oxidation of the resulting alcohol provides aldehyde 7(f). Reductive amination with 2-aminopyridine followed by Boc protection of the resulting secondary amine yields 7(g). Ester hydrolysis, coupling to the desired 2,3- diaminopropionate derivative and deprotection gives 7(h). Alternately prior to deprotection the Cbz group can be selectively removed and alternate $R^{10}$ groups introduced using standard methods known to one skilled in the art to provide compounds 7(i).

Scheme 7

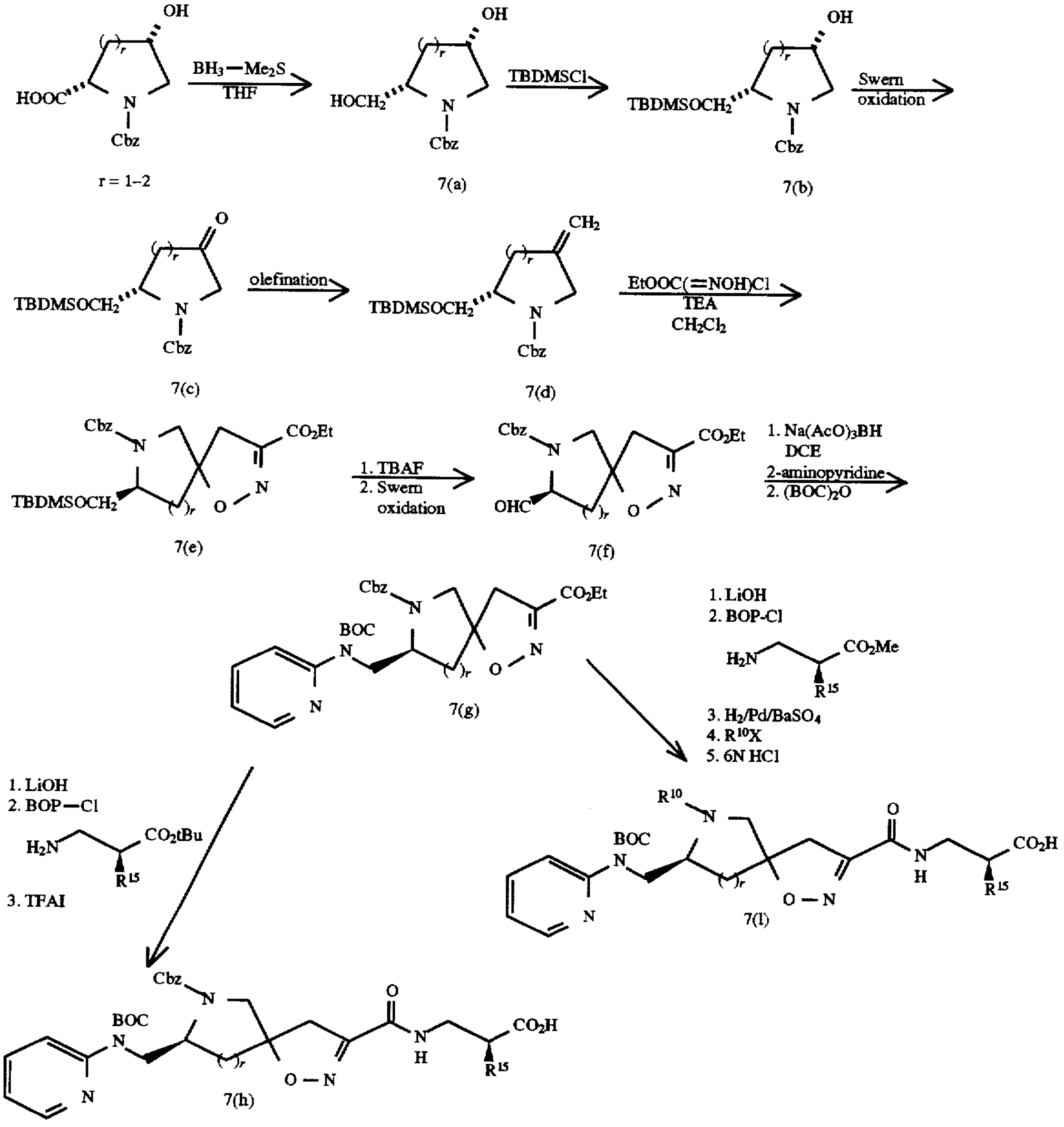

Compounds of Formula I wherein Q includes a 1,2,4-oxadiazoline as one ring of the spriocycle are prepared as shown in Scheme 8. Protection of 4-methylenecyclohexylmethanol as its t-butyldimethylsilyl ether followed by ozonolysis of the double bond provides ketone 8(a). Treatment of compound 8(a) with a suitable amine provides an imine 8(b) which can undergo 1,3-dipolarcycloaddition with a nitrile oxide to provide spirocycle 8(c). Further elaboration as described above would provide additional compounds of the present invention of Formula 8(h).

Scheme 8

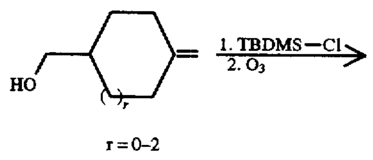

-continued

Scheme 8

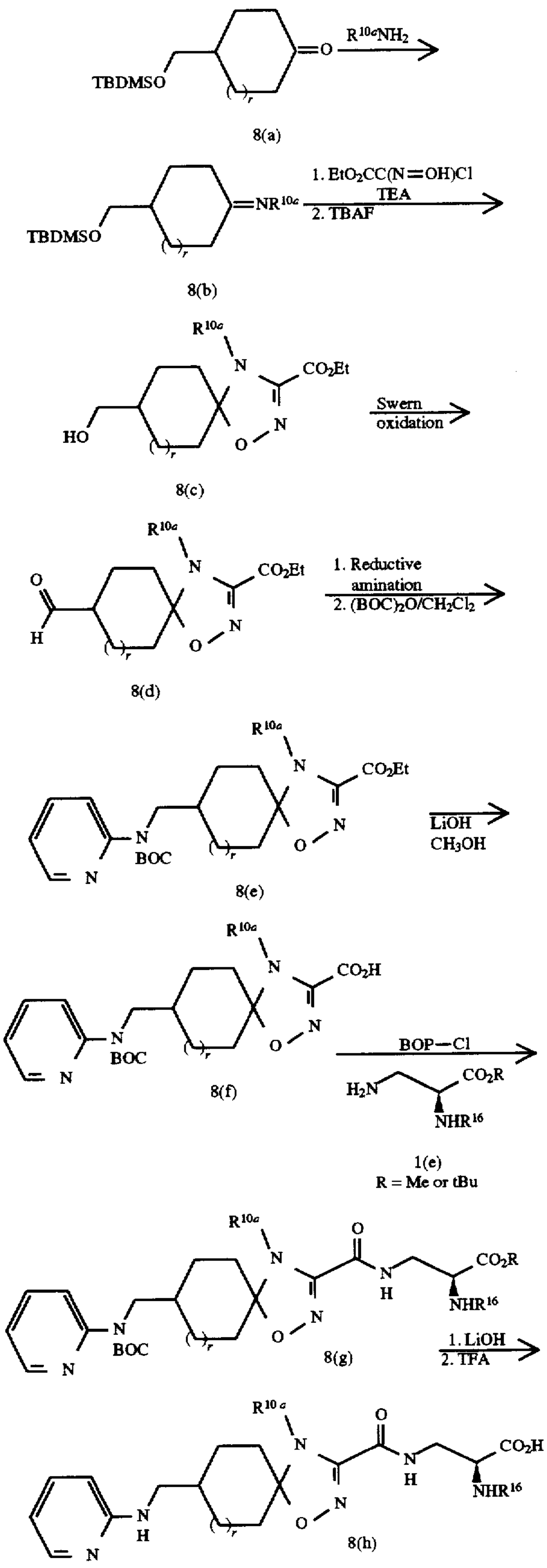

Additional spirocyclic compounds useful in the present invention can be prepared as outlined in Scheme 9 wherein 1,3-dipolarcycloaddition is carried using ethyl diazoacetate (E. Keller et al., *Tetrahedron,* 1993, 49, 8899) to provide spirocycle 9(b) ($R^{10}$=H). The nitrogen of the resulting pyrazole ring may be optionally functionalized using standard methodology prior to carrying out the remaining steps leading to compounds of formula 9(g).

Scheme 9

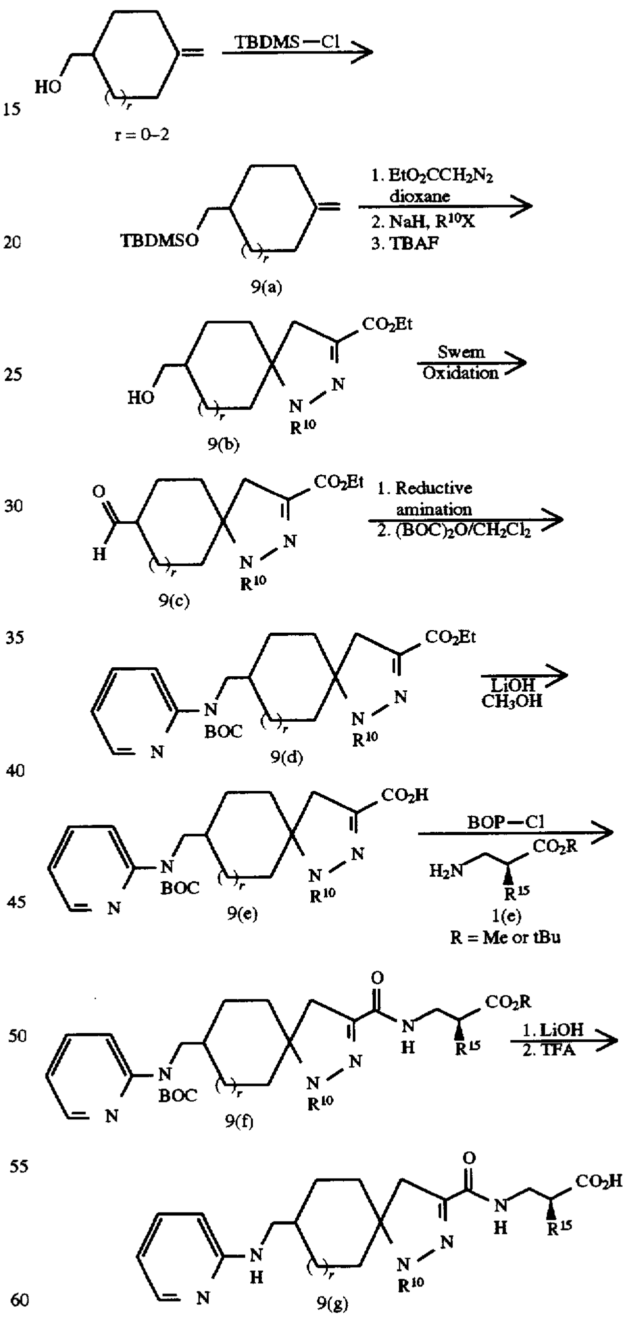

Fully saturated spirocycles are obtained by 1,3-dipolarcycloadditon of α-methoxycarbonylnitrones to an appropriately substituted alkene as illustrated in Scheme 10. (Y. Inouye et al., *Bull Chem. Soc. Jpn,* 1979, 52, 3763; J. Hara et al., ibid., 1981, 54, 3871).

Scheme 10

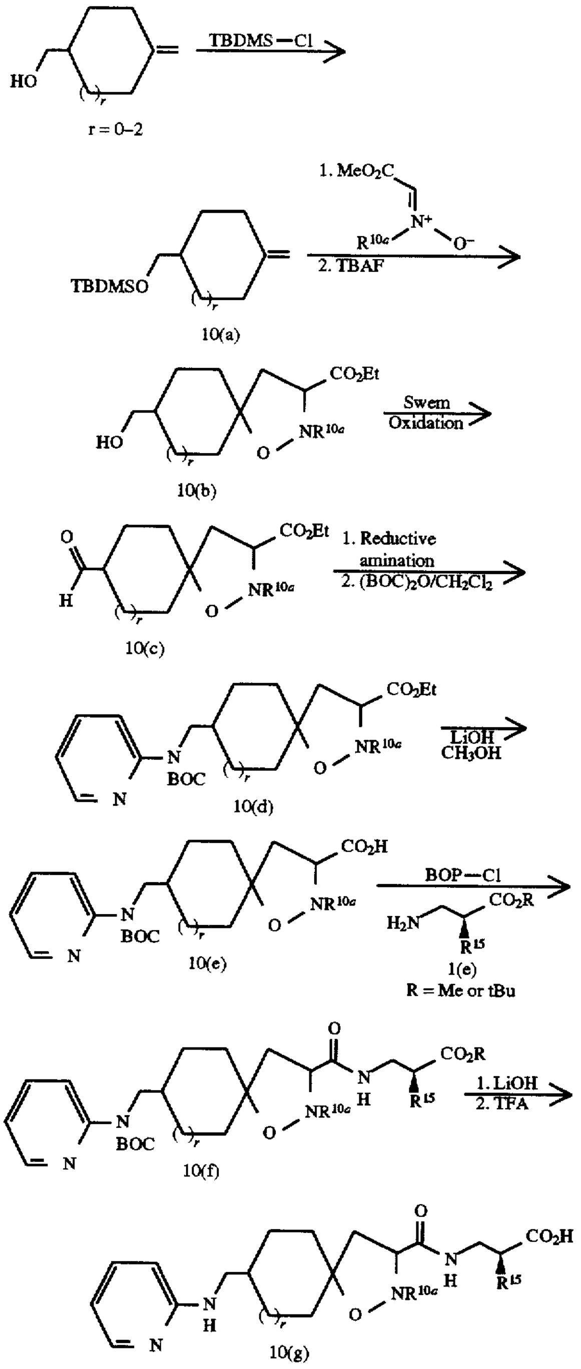

The detailed processes for preparing the compounds of Formula I are illustrated by the following Examples. It is, however, understood that this invention is not limited to the specific details of these examples. Melting points (mp) are uncorrected. Proton nuclear magnetic resonance spectra (NMR) were measured in chloroform-d ($CDCl_3$) unless otherwise specified and the peaks are reported in parts per million (ppm) downfield from tetramethylsilane (TMS). The coupling patterns are reported as follows: s, singlet; d, doublet; t, triplet; q, quartet; m, multiplet; bs, broad singlet; bm, broad multiplet. Infrared spectra are reported in reciprocal centimeters ($cm^{-1}$). All final compounds gave satisfactory nmr and HRMS data and were analyzed to be >98% pure by reverse phase analytical HPLC.

EXAMPLES

Example 1081

(S)-2-benzyloxycarbonylamino-3-[[8-(2-pyridinylamino)methyl-1-oxa-2-azaspiro-[4.5]-dec-2-en-3-yl]carbonylamino]propionic acid Ethyl [(8-hydroxymethyl)-1-oxa-2-azaspiro-[4.5]-dec-2-en-3-yl]carboxylate: 1(a)

Method A

4-Methylenecyclohexylmethanol (2.52 g, 20 mmol, Wiley Organics, 63% purity) and sodium bicarbonate (8.4 g, 100 mmol) in 45 ml of 2:1 THF:$H_2O$ was cooled in an ice bath. Ethyl chlorooximidoacetate (5.00 g, 33 mmol) in 30 ml 2:1 THF:$H_2O$ was then added, and the mixture stirred at room temperature for 18 hours. The mixture was then diluted with ethyl acetate and washed with water. The aqueous layer was extracted with one more portion of ethyl acetate. The organic layers were combined, dried ($MgSO_4$), filtered, concentrated and the residue purified by flash chromatography (silica gel column/1:1 EtOAc:Hexane) to afford 1(a) as a colorless oil (57.6% yield). HRMS calcd. for $C_{12}H_{19}NO_4$ ($[M+H]^+$): 242.139233; found: 242.140376.

Method B

A mixture of 4-Methylenecyclohexylmethanol (10 g, mol, Wiley Organics, 63% purity, 0.051 mol) and diethylnitromalonate (14 ml, 0.08 mol) in 100 ml mesitylene was refluxed for 4–5 hrs under a nitrogen atmosphere with stirring. The resulting yellow solution was evaporated on a rotary evaporator in vacuo and the residue purified by flash chromatography (silica gel/70:30 Hexane/ethyl acetate) to provide 6.4 g of 1(a) (52%) as 3/2 mixture of diastereomers by nmr.

Ethyl [(8-formyl)-1-oxa-2-azaspiro-[4.5]-dec-2-en-3-yl] carboxylate: 1(b)

Oxalyl chloride (0.70 ml, 8 mmol) in 5 ml $CH_2Cl_2$ was cooled to −78° C. in dry ice-acetone bath and treated with dimethylsulfoxide (0.74 ml, 10.4 mmol) in 10 ml $CH_2Cl_2$ and stirred at −78° C. for 15 minutes. Intermediate 1(a) (992 mg, 4 mmol) in 10 ml $CH_2Cl_2$ was then added, and the mixture stirred at −78° C. for 1 hour. Triethylamine (2.0 g, 20 mmol) in 5 ml $CH_2Cl_2$ was then added, and the mixture stirred at −78° C. for 15 minutes. The bath was removed and the mixture allowed to warm up over a 30 minute period, diluted with $CH_2Cl_2$ (50 ml) and washed with water followed by brine. The organic layer was separated, dried over anhydrous magnesium sulfate, filtered and concentrated to afford 0.68 g of 1(b) as a clear oil. HRMS calcd. for $C_{12}H_{17}NO_4$ ($[M+H]^+$): 240.123583; found: 240.123665.

Ethyl [8-[(N-t-butoxycarbonyl)-(N-2-pyridinyl) aminomethyl]-1-oxa-2-azaspiro-[4.5]-dec-2-en-3-yl] carboxylate 1(c):

The intermediate 1(b) (1.068 g, 4 mmol crude) and acetic acid (240 mg, 4 mmol) in 15 ml 1,2-dichloroethane were treated with sodium triacetoxyborohydride (1.19 g, 5.6 mmol), and the mixture stirred at room temperature for 18 hours. The mixture was diluted with ethyl acetate and washed with sat. sodium bicarbonate and then brine. The organic layer was separated, dried over anhydrous magnesium sulfate, filtered and concentrated to afford 1.32 g of amine as an oil. HRMS calcd. for $C_{17}H_{23}N_3O_3$ ($[M+H]^+$): 318.181767; found: 318.183254. The crude amine and triethylamine (1.0 g, 10 mmol) in 20 ml dichloromethane were treated with di-t-butyldicarbonate (2.18 g, 10 mmol), and stirred at room temperature for 18 hours. The mixture was diluted with dichloromethane and washed with water and brine. The organic layer was separated, dried over anhydrous magnesium sulfate, filtered, concentrated and the residue purified by flash chromatography (silica gel/1:3 EtOAc:Hexane) to afford 845 mg of 1(c) as a colorless oil (50.6% yield from 1(a)). HRMS calcd. for $C_{22}H_{31}N_3O_5$ ($[M+H]^+$): 418.234197; found: 418.233666.

[8-[(N-t-Butoxycarbonyl)-(N-2-pyridinyl)aminomethyl]-1-oxa-2-azaspiro-[4.5]-dec-2-en-3-yl]carboxylic acid 1(d)

The intermediate 1(c) (209 mg, 0.5 mmol) in 4.5 ml of 2:1 THF:$H_2O$ was treated with lithium hydroxide monohydrate (25 mg, 0.6 mmol) and the mixture stirred at room temperature for 18 hours. The mixture was quenched with 0.6 ml of 1N HCl and extracted with ethyl acetate (2×25 ml). The organic layer was separated, dried over anhydrous magnesium sulfate, filtered, concentrated to afford 199 mg of 1(d) as a colorless foam. HRMS calcd. for C20H27N3O5 ($[M+H]^+$): 390.202896; found: 390.202306.

Methyl (S)-2-benzyloxycarbonylamino-3-[[8-[N-(t-butoxycarbonyl)-N-(2-pyridinyl)amino]methyl-1-oxa-2-azaspiro-[4.5]-dec-2-en-3-yl]carbonylamino]propionate 1(f) ($R^{15}$=NHCbz, R=Me): The intermediate 1(d) (199 mg, 0.5 mmol crude), 1(e) ($R^{15}$=NHCbz, R=Me, 144 mg, 0.5 mmol) and BOP Reagent (265 mg, 0.6 mmol) in 3 ml DMF were treated with 4-N-methylmorpholine (152 mg, 1.5 mmol) in 2 ml DMF and the mixture stirred at room temperature for 18 hours. The mixture was diluted with ethyl acetate and washed with sat. sodium bicarbonate, water and then brine. The organic layer was separated, dried over anhydrous magnesium sulfate, filtered, concentrated and the residue purified by flash chromatography (silica gel column/1:1 EtOAc:Hexane followed by 10:1:10 EtOAc:EtOH:Hexane) to afford 213 mg of 1(f) ($R^{15}$=NHCbz, R=Me) as a white solid (68.3% yield from 1(c)). HRMS calcd. for $C_{32}H_{41}N_5O_8$ ($[M+H]^+$): 624.303339; found: 624.303031.

(S)-2-benzyloxycarbonylamino-3-[[8-(2-pyridinylamino) methyl-1-oxa-2-azaspiro-[4.5]-dec-2-en-3-yl] carbonylamino]propionic acid 1(g) ($R^{15}$↑NHCbz): The intermediate 1(f) (205 mg, 0.33 mmol crude) in 4 ml of 1:1 MeOH:$H_2O$ was treated with lithium hydroxide monohydrate (21 mg, 0.5 mmol) and the mixture stirred at room temperature for 18 hours. The mixture was neutralised with 0.5 ml of 1N HCl and extracted with EtOAc. The organic layer was separated, dried over anhydrous magnesium sulfate, filtered, concentrated to afford 205 mg of the free acid as a white solid. HRMS calcd. for $C_{31}H_{39}N_5O_8$ ($[M+H]^+$): 610.287689; found: 610.290115. Crude acid was treated with 3 ml of 4M HCl in dioxane and stirred at room temperature for 18 hours. The mixture was concentrated in vacuo and the residue purified by preparative HPLC (C18/80% $CH_3CN$:20% $H_2O$:0.05% TFA) to afford 132 mg of a white solid. The compound was lyophilyzed from 2 ml of 1:1 $CH_3CN$:$H_2O$ to afford 107 mg of 1(g) ($R^{15}$=NHCbz) as a white solid (52.0% yield from 1(f)). $^1$H NMR (DMSO-D6; Mixture of diastereoisomers) d 7.8 (m, 2H), 7.35 (bs, 5H), 6.8 (m, 2H), 5.11 (s, 2H), 4.44 (s, 1H), 3.4 (bm, 2H), 3.2 (m, 2H), 2.8 (s, 2H),2.0–1.2 (bm, 8H); HRMS calcd. for $C_{26}H_{31}N_5O_6$ ($[M+H]^+$): 510.235259; found: 510.236039.

Similarly prepared from 1(d) were the following:

Example 1111

(S)-2-phenylsulfonylamino-3-[[8-(2-pyridinylamino) methyl-1-oxa-2-azaspiro-[4.5]-dec-2-en-3-yl] carbonylamino]propionic acid $^1$H NMR (DMSO-D6) d 8.8 (bs,1H), 8.23 (t, 1H, J=6), 8.18 (d, 1H, J=9), 7.85–7.40 (m, 5H), 7.03 (d, 1H, J=9), 6.8 (t, 1H, J=7), 3.93 (dd, 1H, J=13, 7), 3.38 (m, 1H), 3.19 (bm, 3H), 2.8 (s, 2H), 1.85–1.2 (bm, 8H); MS calcd. for $C_{24}H_{29}N_5O_6S$ ($[M+H]^+$): 516.2; found: 516.1.

Example 1121

(S)-2-[(2,5-dimethylisoxazol-2-yl)sulfonyl]amino-3-[[8-(2-pyridinylamino)methyl-1-oxa-2-azaspiro-[4,5] -dec-2-en-3-yl]carbonylamino]propionic acid $^1$H NMR (DMSO-D6) d 8.8 (bs,1H), 8.54 (d, 1H, J=9), 8.27 (t, 1H, J=6), 7.86 (m, 1H), 7.03 (d, 1H, J=9), 3.94 (m, 1H), 3.44 (m, 1H), 3.19 (bm, 3H), 2.8 (s, 2H), 2.45 (s, 3H), 2.5 (s, 3H), 2.9–1.2 (bm, 8H); MS calcd. for $C_{23}H_{30}N_6O_7S$ ($[M+H]^+$): 535.2; found: 535.1.

Example 3055

(S)-2-[(2,4,6-trimethylphenyl)sulfonyl]amino-3-[[7-benzyloxycarbonyl-8-(2-imidazolylamino)methyl-1-oxa-2,7-diazaspiro-[4,4]-non-2-en-3-yl] carbonylamino]propionic acid Part A: N-Cbz-4-hydroxy-L-prolinol A solution of N-Cbz-4-hydroxy-L-proline (50 gm, 0.188 mol) in tetrahydrofuran (400 ml) was cooled to 0° C. in an ice bath under nitrogen and a solution of borane dimethylsulfide complex (2.0M in THF, 122 ml, 0.244 mol) was added dropwise over 1 h. The resulting mixture is then allowed to stir overnight at room temperature. the reaction mixture was recooled to 0° C. and a second portion of borane-dimethylsulfide complex was added as described above. Reaction was again stirred at room temperature overnight, then cooled to 0° C. and quenched by addition of approximately 200 ml of 1:1 methanol/water. Solvents were removed on rotary evaporator and residue diluted with water and extracted 4× with ethyl acetate. The combined extracts were washed with saturated aqueous sodium bicarbonate solution (2×) and brine (1×) then dried over anhydrous magnesium sulfate, filtered and evaporated to a clear oil (46.77 g, 99%) which was used without purification in part B below.

Part B. 1-benzyloxycarbonyl-2-(S)-t-butyldimethylsilyloxymethyl-4-hydroxypyrrolidine A mixture of the compound of Part A above (46.77 g, 0.186 mol), triethylamine (51.8 g, 0.372 mol), and t-butyldimethylsilylchloride (30.86 g, 0.205 mol) in methylene chloride (375 ml) was stirred under nitrogen overnight at room temperature. An additional aliquot of silyl chloride (5 g, 0.033 mol) was added and stirring continued for 4–5 h. Reaction mixture was transferred to a separatory funnel and washed with water (4×) and brine (1×) then dried over anhydrous sodium sulfate, filtered and solvent removed in vacuo. The residue was chromatographed on silica gel (hexane-hexane/ethyl acetate 8:2-hexane/ethyl acetate 7:3) to provide the silyl ether (47.11 g, 69%)

Part C. 1-benzyloxycarbonyl-2(S)-t-butyldimethylsilyloxymethyl-4-pyrrolidinone

To a solution of oxalyl chloride (12.4 ml, 0.142 mol) in methylene chloride (330 ml) precooled to −70° C. in an acetone/dry ice bath was added a solution of anhydrous dimethylsulfoxide (20.60 ml, 0.29 mol) in methylene chloride (66 ml) dropwise under nitrogen over 30 min at T<−65° C. The resulting mixture was stirred 15 min, followed by dropwise addition of a solution of the compound of part B above in methylene chloride (130 ml) over 45 min at T<−65° C. The reaction was stirred for 30 min followed by dropwise addition of triethylamine (119.2 ml, 0.855 mol) over 30 min again at T<−65° C. The cooling bath was removed and the reaction temperature was allowed to rise to 5°–10° C., and then quenched by addition of 645 ml of 10% aqueous potassium hydrogen sulfate solution. The mixture was then transferred to a separatory funnel and layers separated. The aqueous was extracted with methylene chloride and the combined organic layers are washed with 10% citric acid solution (3×) and brine (1×) then dried over anhydrous sodium sulfate, filtered and concentrated to a clear oil (46.8 g, 100%) which was used without purification in part D below.

Part D. 1-benzyloxycarbonyl-2(S)-t-butyldimethylsilyloxymethyl-4-methylenepyrrolidine Methyltriphenylphosphonium bromide (68.98 g, 0.193 mol) is added to a suspension of potassium t-butoxide (20.27 g, 0.181 mol) in anhydrous ether (700 ml) with stirring at 0° C. under nitrogen. The resulting bright yellow solution is stirred for an additional 15 min. To this is added a solution of the compound of part D above (46.8 g, 0.129 mol) in ether (100 ml). The mixture is allowed to assume room temperature and stirred overnight. The resulting mixture was cooled in an ice bath and quenched by addition 700 ml of a saturated solution of ammonium chloride. The phases were separated and aqueous reextracted 2× with ether. The combined organics were washed with brine and dried over anhydrous sodium sulfate, filtered and evaporated in vacuo. The crude product was purified by flash chromatography (silica gel, hexane-ether 9:1) to provide the olefin (42.6 g, 91%) as a pale yellow oil.

Part E: 7-benzyloxycarbonyl-8-t-butyldimethylsilyloxymethyl-3-ethoxycarbonyl-1-oxa-2,7-diazaspiro-[4,4]-non-2-ene The compound of part D above (13.04 g, 0.036 mol) was dissolved in methylene chloride (50 ml), treated with ethyl chlorooximidoacetate (8.18 g., 0.054 mol), and the mixture was cooled to 0° C. followed by dropwise addition of triethylamine (7.53 ml, 0.054 mol). The reaction was allowed to come to room temperature over several hours then stirred overnight. An additional 1.5 eq. of the chlorooxime was then added, and the mixture was cooled to 0° C. and treated with triethylamine (1.5 eq) as described above. Resulting mixture was stirred at room temperature for 48 h, then diluted with additional methylene chloride and washed with 10% aqueous citric acid (3×), and brine (1×) then dried over anhydrous sodium sulfate, filtered and evaporated in vacuo. The crude was charged to silica gel and eluted first with Hexane/ether(80:20) to provide unreacted starting material (6.64 g, 51%) and then with hexane/ethyl acetate (75:25) to provide the two diastereomers of the product (S,S isomer, 5.54 g, 32%; S,R isomer, 1.34 g, 8%). Anal. Calcd. for $C_{24}H_{36}N_2O_6Si$: C, 60.48; H, 7.61; N, 5.89. Found: C, 60.46; H, 7.33; N, 5.96.

Part F: 7-benzyloxycarbonyl-8-t-butyldimethylsilyloxymethyl-3-carboxy-1-oxa-2,7-diazaspiro-[4,4]-non-2-ene The compound of Part E above (18.7 g, 0.038 mol) was dissolved in methanol (200 ml) and treated at room temperature with a solution of lithium hydroxide monohydrate (2.4 g, 0.057 mol) in water (50 ml). The whole was stirred for 5 h and then solvent removed in vacuo. Water was added and the pH of the solution was adjusted to 4.4 with 10% aq. citric acid solution. The resulting mixture was extracted 3× with ethyl acetate with adjustment of pH back to 4.4 between extractions. The combined extracts were washed with brine and dried over anhydrous sodium sulfate, filtered and evaporated. The residue was dried under vacuum to provide the acid (16.2 g, 95%) as a foam which was used without purification in Part G below. MS(esi) m/z 449.4 $(M+H)^+$, 335.2 $(M+H\text{-}TBMDS)^+$ Part G: t-Butyl (S)-2-[(2,4,6-trimethylphenyl)sulfonyl]-amino-3-[[7-benzyloxycarbonyl-8-(t-butyldimethylsilyloxy)methyl-1-oxa-2,7-diazaspiro-[4,4]-non-2-en-3-yl] carbonylamino]propionic acid A mixture of the compound of Part F above (10 g, 0.022 mol), t-butyl 3-amino-2-(2,4,6-trimethylphenylsulfonylamino)propionate (7.6 g, 0.022 mol), N-methylmorpholine (5.4 ml, (0.049 mol) and Castro's reagent (14.8 g, 0.033 mol) in N,N-dimethylformamide (100 ml) was stirred under nitrogen at room temperature overnight. The DMF was removed in vacuo and the residue diluted with 500 ml water and extracted 3× with ethyl acetate. The combined extracts were washed with water (2×), 10% citric acid (1×), saturated sodium bicarbonate (1X) and brine (1X) then dried over anhydrous sodium sulfate, filtered and evaporated. The coupling product was purified by filtration through a pad of silica gel eluted with hexane/ethyl acetate (4:1) to provide the product as a white foam (15 gm, 88%). MS(esi) m/z 773.4 $(M+H)^+$ 795.4 $(M+Na)^+$.

Part H: t-Butyl (S)-2-[(2,4,6-trimethylphenyl)sulfonyl]-amino-3-[[7-benzyloxycarbonyl-8-hydroxymethyl-1-oxa-2,7-diazaspiro-[4,4]-non-2-en-3-yl]carbonylamino] propionic acid The compound of Part G above (2.8 g, 3.62 mmol) was dissolved in tetrahydrofuran (12 ml) and treated with tetra-n-butylammonium floride (5.8 ml of a 1.0M solution in THF, 5.8 mmol). The resulting solution was stirred overnight at room temperature. Reaction was quenched by addition of water and THF removed on rotary evaporator. The remaining aqueous was extracted 3× with ethyl acetate. The combined extracts were washed with water and brine, dried over anhydrous sodium sulfate, filtered and evaporated. Chromatography on silica gel (hexane/ethyl acetate 1:1 followed by methylene chloride/methanol 95:5) provided the alcohol (2.02 g., 85%) ms m/z 659.3 $(M+H)^+$.

Part I: t-Butyl (S)-2-[(2,4,6-trimethylphenyl)sulfonyl]-amino-3-[[7-benzyloxycarbonyl-8-formyl-1-oxa-2,7-diazaspiro-[4,4]-non-2-en-3-yl]carbonylamino]propionic acid A solution of the compound of Part H above (0.8 g, 1.21 mmol) in anhydrous methylene chloride (1 ml) was added dropwise to a a solution of Dess-Martin periodinane (0.59 g, 1.30 mmol) in approximately 4 ml of dry methylene chloride at room temperature under nitrogen. The resulting mixture was stirred for 1 hr, the diluted with ethyl acetate and poured into a solution of saturated sodium bicarbonate (20 ml) containing 5 g sodium thiosulfate. This was stirred for 10 min. The phases were separated, aqueous reextracted with ethyl acetate, and combined organics washed with saturated sodium bicarbonate, water and brine, then dried over anhydrous magnesium sulfate, filtered and evaporated to give the aldehyde as a clear oil (0.74 g, 93%).

Part J: t-Butyl (S)-2-[(2,4,6-trimethylphenyl)sulfonyl]-amino-3-[[7-benzyloxycarbonyl-8-(imidazol-2-ylamino) methyl-1-oxa-2,7-diazaspiro-[4,4]-non-2-en-3-yl] carbonylamino]propionic acid To a solution of the compound of Part I above (0.73 g, 1.11 mmol) in benzene was added anhydrous magnesium sulfate (0.588 g, 4.88 mmol) and 2-amino-1-tritylimidazole (0.398 g, 1.22 mmol) and the whole was refluxed for 4 hrs under nitrogen. The mixture was cooled to room temperature, filtered under nitrogen and benzene removed in vacuo. The residue was taken up in 1,2-dichloroethane, treated under nitrogen at room temperature with sodium triacetoxyborohydride (0.588 g, 2.78 mmol), and the whole was stirred overnight. The reaction was quenched by addition of water and then diluted with ethyl acetate. Aqueous was reextracted with ethyl acetate, and combined organic layers were washed with saturated sodium bicarbonate, water and brine, then dried over anhydrous magnesium sulfate, filtered and evaporated. Filtration through silica gel provided the desired product (0.682 g, 63%) as an off-white foam which was used without further purification in part K below.

Part K: (S)-2-[(2,4,6-trimethylphenyl)sulfonyl]-amino-3-[[7-benzyloxycarbonyl-8-(imidazol-2-ylamino)methyl-1-oxa-2,7-diazaspiro-[4,4]-non-2-en-3-yl]carbonylamino] propionic acid The compound of part J above (0.3 g, 0.31 mmol) was dissolved in 20% acetic acid in methanol (10 ml) and refluxed for 24 h under nitrogen. The reaction was cooled to room temperature, methanol removed by evaporation and residue diluted with ethyl acetate. This solution was washed with saturated sodium bicarbonate (2×), water and brine then dried over anhydrous magnesium sulfate, filtered and evaporated. Filtration through silica gel (eluted with (i)methylene chloride/methanol 95:5; (2) methylene chloride/methanol/conc. ammonium hydroxide 95:5:0/5; (3) 90/10/1) provided the intermediate detritylated t-butyl ester 0.139 mg, 62%). This was taken up in methylene chloride (8 ml) and trifluoroacetic acid (2 ml) was added. The solution was stirred for 72 h, then evaporated and triturated with ether. The resulting solid was purified by prep HPLC (C18, gradient from 100% A to 100% B: A=90/10/0.05 $H_2O/CH_3CN/TFA$; B=90/10/0.05 $CH_3CN/H_2O/TFA$) to provide the title compound (0.078 g, 50%). MS m/z 690.4 $(M+Na)^+$ 668.4 $(M+H)^+$.

Example 3063

(S)-2-[(2,4,6-trimethylphenyl)sulfonyl]-amino-3-[[8-(imidazol-2-ylamino)methyl-1-oxa-2,7-diazaspiro-[4,4]-non-2-en-3-yl]carbonylamino]-propionic acid The compound of Example 3055, Part J, (0.1 g, 0.1 mmol) was taken up in neat trifluoroacetic acid (3 ml) and the mixture refluxed for 1.5 h. Reaction was cooled to room temperature and TFA removed in vacuo. The residue was purified by prep HPLC using the system described under Ex. 3055, Part K above to provide the title compound (0.043 g, 80%). MS m/z 534.4 $(M+H)^+$.

Using the methods described above and modifications thereof known to one skilled in the art of organic synthesis, additional compounds of the present invention can be prepared, including, but not limited to the representative compounds listed in the Tables below.

Utility

The compounds of Formula I of the present invention possess activity as antagonists of integrins such as, for example, the $\alpha_v\beta_3$ or vitronectin receptor, $\alpha_v\beta_5$ or $\alpha_5\beta1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their lack of activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula I of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula I have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta)—Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 μM for the inhibition of $\alpha_v\beta_3$-Vitronectin Binding Assay, with compounds preferably having $K_i$ values of less than about 0.1 μM. Tested compounds of the present invention are active in the $\alpha_v\beta_3$-Vitronectin Binding Assay as well as in cell-based assays of integrin adhesion mediated by the $\alpha_v\beta_3$-receptor.

Purified $\alpha_v\beta_3$ (human placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\alpha_v\beta_3$ or $\alpha_v\beta_5$ in the ELISA.

A submaximal concentration of biotinylated vitronectin was selected based on conc. response curve with fixed receptor conc. and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM $CaCl_2$, 1.0 MM $MgCl_2.6H_2O$, 1.0 mM $MnCl_2.4H_2O$) and coated (100 µL/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM $CaCl_2$,1.0 mM $MgCl_2.6H_2O$.1.0 mM $MnCl_2.4H_2O$). Receptor is then blocked (200 µL/well) with 3.5% BSA in B/B buffer for 2 hours at room temperature. After washing once with 1.0% BSA in B/B buffer, biotinylated vitronectin (100 µL) and either inhibitor (11 µL) or B/B buffer w/1.0% BSA (11 µL)is added to each well. The plates are incubated 2 hours at room temperature. The plates are washed twice with B/B buffer and incubated 1 hour at room temperature with anti-biotin alkaline phosphatase (100 µL/well) in B/B buffer containing 1.0% BSA. The plates are washed twice with B/B buffer and alkaline phosphatase substrate (100 µL) is added. Color is developed at room temperature. Color development is stopped by addition of 2N NaOH (25 µL/well) and absorbance is read at 405 nm. The $IC_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 µL of PRP ($5\times10^8$ platelets/mL) were added to each micro test tube, and transmittance was set to 0%. 20 µL of ADP (10 µM) was added to each tube, and the aggregation profiles were plotted (% transmittance versus time). Test agent (20 µL) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95:713–724).

In Vivo Angiogenesis Model

A quantitative method for assessing angiogenesis and antiangiogenic agents is described in Passaniti et al., *Laboratory Investigation* (1992) 67:519–528

Pig Restenosis Model

A method for assessing restenosis and agents which inhibit restenosis is described in Schwartz et al., *J. Am. College of Cardiology* (1992) 19:267–274.

Mouse Retinopathy Model

A method for assessing retinopathy and agents which inhibit retinopathy is described in Smith et al., *Invest. Ophthal. & Visual Science* (1994) 35:101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Representative compounds of the present invention are listed in the Tables below.

TABLE 1

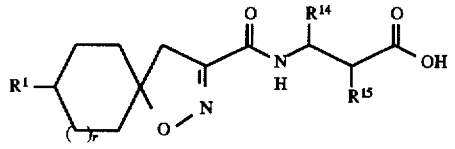

| Ex. No. | $R^1$ | r | $R^{14}$ | $R^{15}$ | MS |
|---|---|---|---|---|---|
| 1001 | imidazol-2-yl-aminomethyl | 1 | H | H | |
| 1002 | imidazol-2-yl-aminomethyl | 1 | H | $NHCO_2Bn$ | |
| 1003 | imidazol-2-yl-aminomethyl | 1 | H | $NHCO_2CH_2C_6H_4$-(2-$CH_3$) | |
| 1004 | imidazol-2-yl-aminomethyl | 1 | H | $NHCO_2CH_2C_6H_4$-(3-$CH_3$) | |
| 1005 | imidazol-2-yl-aminomethyl | 1 | H | $NHCO_2CH_2C_6H_4$-(4-$CH_3$) | |
| 1006 | imidazol-2-yl-aminomethyl | 1 | H | $NHCO_2CH_2$(2-pyridinyl) | |
| 1007 | imidazol-2-yl-aminomethyl | 1 | H | $NHCO_2CH_2$(3-pyridinyl) | |
| 1008 | imidazol-2-yl-aminomethyl | 1 | H | $NHCO_2CH_2$(4-pyridinyl) | |
| 1009 | imidazol-2-yl-aminomethyl | 1 | H | $NHCO_2CH_2$(2-thiazolyl) | |
| 1010 | imidazol-2-yl-aminomethyl | 1 | H | $NHCO_2CH_2$(4-thiazolyl) | |
| 1011 | imidazol-2-yl-aminomethyl | 1 | H | $NHCO_2CH_2$(5-thiazolyl) | |
| 1012 | imidazol-2-yl-aminomethyl | 1 | H | $NHCO_2CH_2$(4-isoxazolyl) | |
| 1013 | imidazol-2-yl-aminomethyl | 1 | H | $NHCO_2CH_2$(2-thienyl) | |
| 1014 | imidazol-2-yl-aminomethyl | 1 | H | $NHCO_2CH_2$(5-isoxazolyl) | |
| 1015 | imidazol-2-yl- | 1 | H | $NHCO_2$n-Bu | |

TABLE 1-continued

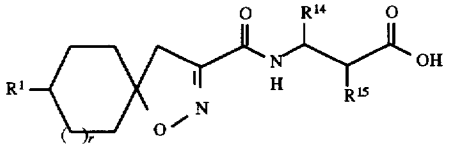

| Ex. No. | $R^1$ | r | $R^{14}$ | $R^{15}$ | MS |
|---|---|---|---|---|---|
| | aminomethyl | | | | |
| 1016 | imidazol-2-yl aminomethyl | 1 | H | $NHCO_2$i-Bu | |
| 1017 | imidazol-2-yl-aminomethyl | 1 | H | $NHCO_2$t-Bu | |
| 1018 | imidazol-2-yl aminomethyl | 1 | H | $NHCOCH_2Ph$ | |
| 1019 | imidazol-2-yl-aminomethyl | 1 | H | $NHCOCH_2C_6H_4$-(2-$CH_3$) | |
| 1020 | imidazol-2-yl-aminomethyl | 1 | H | $NHCOCH_2C_6H_4$-(3-$CH_3$) | |
| 1021 | imidazol-2-yl-aminomethyl | 1 | H | $NHCOCH_2C_6H_4$-(4-$CH_3$) | |
| 1022 | imidazol-2-yl-aminomethyl | 1 | H | $NHCOCH_2$(2-pyridinyl) | |
| 1023 | imidazol-2-yl-aminomethyl | 1 | H | $NHCOCH_2$(3-pyridinyl) | |
| 1024 | imidazol-2-yl-aminomethyl | 1 | H | $NHCOCH_2$(4-pyridinyl) | |
| 1025 | imidazol-2-yl-aminomethyl | 1 | H | $NHCOCH_2$(2-thiazolyl) | |
| 1026 | imidazol-2-yl-aminomethyl | 1 | H | $NHCOCH_2$(4-thiazolyl) | |
| 1027 | imidazol-2-yl-aminomethyl | 1 | H | $NHCOCH_2$(5-thiazolyl) | |
| 1028 | imidazol-2-yl aminomethyl | 1 | H | $NHCOCH_2$(4-isoxazol) | |
| 1029 | imidazol-2-yl-aminomethyl | 1 | H | $NHCOCH_2$(2-thienyl) | |
| 1030 | imidazol-2-yl-aminomethyl | 1 | H | NHCOn-Bu | |
| 1031 | imidazol-2-yl aminomethyl | 1 | H | NHCOt-Bu | |
| 1032 | imidazol-2-yl-aminomethyl | 1 | H | $NHSO_2Ph$ | 505.2 |
| 1033 | imidazol-2-yl-aminomethyl | 1 | H | $NHSO_2C_6H_4$-(2-$CH_3$) | |
| 1034 | imidazol-2-yl-aminomethyl | 1 | H | $NHSO_2C_6H_4$-(3-$CH_3$) | |
| 1035 | imidazol-2-yl-aminomethyl | 1 | H | $NHSO_2C_6H_4$-(4-$CH_3$) | |
| 1036 | imidazol-2-yl-aminomethyl | 1 | H | $NHSO_2$(2-pyridyl) | |
| 1037 | imidazol-2-yl-aminomethyl | 1 | H | $NHSO_2$(3-pyridyl) | |
| 1038 | imidazol-2-yl-aminomethyl | 1 | H | $NHSO_2$(4-pyridyl) | |
| 1039 | imidazol-2-yl-aminomethyl | 1 | H | $NHSO_2$(2-thiaz-olyl) | |
| 1040 | imidazol-2-yl-aminomethyl | 1 | H | $NHSO_2$(3-thiazolyl) | |
| 1041 | imidazol-2-yl-aminomethyl | 1 | H | $NHSO_2$(4-isoxazolyl) | |
| 1042 | imidazol-2-yl-aminomethyl | 1 | H | $NHSO_2$[4-(3,5-dimethyl)isoxaz olyl] | |
| 1043 | imidazol-2-yl-aminomethyl | 1 | H | $NHSO_2C_6H_4$-(2-Br) | |
| 1044 | imidazol-2-yl-aminomethyl | 1 | H | $NHSO_2C_6H_4$-(3-Br) | |
| 1045 | imidazol-2-yl-aminomethyl | 1 | H | $NHSO_2C_6H_4$-(4-Br) | |
| 1046 | imidazol-2-yl-aminomethyl | 1 | H | $NHSO_2C_6H_4$-(2-F) | |
| 1047 | imidazol-2-yl-aminomethyl | 1 | H | $NHSO_2C_6H_4$-(3-F) | |
| 1048 | imidazol-2-yl-aminomethyl | 1 | H | $NHSO_2C_6H_4$-(4-F) | |

TABLE 1-continued

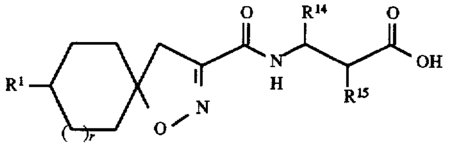

| Ex. No. | $R^1$ | r | $R^{14}$ | $R^{15}$ | MS |
|---|---|---|---|---|---|
| 1049 | imidazol-2-yl-aminomethyl | 1 | H | $NHSO_2$(2-naphthyl) | 555.2 |
| 1050 | imidazol-2-yl-aminomethyl | 1 | H | $NHSO_2$(1-naphthyl) | |
| 1051 | imidazol-2-yl aminomethyl | 1 | H | $NHSO_2CH{=}CHPh$ | |
| 1052 | imidazol-2-yl-aminomethyl | 1 | H | $NHSO_2CH_2Ph$ | |
| 1053 | imidazol-2-yl-aminomethyl | 1 | H | $NHSO_2CH_2CH{=}CH{-}Ph$ | |
| 1054 | imidazol-2-yl-aminomethyl | 1 | H | $NHSO_2$-n-Bu | |
| 1055 | imidazol-2-yl-aminomethyl | 1 | H | $NHSO_2$-i-Bu | |
| 1056 | imidazol-2-yl-aminomethyl | 1 | H | $NHSO_2$-t-Bu | |
| 1057 | imidazol-2-yl-aminomethyl | 1 | H | $NHSO_2NHPh$ | |
| 1058 | imidazol-2-yl-aminomethyl | 1 | H | $NHSO_2NHC_6H_4$-(2-$CH_3$) | |
| 1059 | imidazol-2-yl-aminomethyl | 1 | H | $NHSO_2NHC_6H_4$-(3-$CH_3$) | |
| 1060 | imidazol-2-yl-aminomethyl | 1 | H | $NHSO_2NHC_6H_4$-(4-$CH_3$) | |
| 1061 | imidazol-2-yl-aminomethyl | | H | $NHSO_2NH$(2-pyridyl) | |
| 1062 | imidazol-2-yl-aminomethyl | 1 | H | $NHSO_2NH$(3-pyridyl) | |
| 1063 | imidazol-2-yl-aminomethyl | 1 | H | $NHSO_2NH$(4-pyridyl) | |
| 1064 | imidazol-2-yl-aminomethyl | 1 | H | $NHSO_2NH$(2-thiazolyl) | |
| 1065 | imidazol-2-yl-aminomethyl | 1 | H | $NHSO_2NH$(4-thiazolyl) | |
| 1066 | imidazol-2-yl-aminomethyl | 1 | H | $NHSO_2NH$(4-isoxazolyl) | |
| 1067 | imidazol-2-yl-aminomethyl | 1 | H | $NHSO_2$[4-(3,5-dimethyl)isoxazolyl] | |
| 1068 | imidazol-2-yl-aminomethyl | 1 | H | $NHSO_2NHC_6H_4$-(2-Br) | |
| 1069 | imidazol-2-yl-aminomethyl | 1 | H | $NHSO_2NHC_6H_4$-(3-Br) | |
| 1070 | imidazol-2-yl-aminomethyl | 1 | H | $NHSO_2NHC_6H_4$-(4-Br) | |
| 1071 | imidazol-2-yl-aminomethyl | 1 | H | $NHSO_2NHC_6H_4$-(3-F) | |
| 1072 | imidazol-2-yl-aminomethyl | 1 | H | $NHSO_2NHC_6H_4$-(4-F) | |
| 1073 | imidazol-2-yl-aminomethyl | 1 | H | $NHSO_2NH$(2-naphthyl) | |
| 1074 | imidazol-2-yl-aminomethyl | 1 | H | $NHSO_2NH$(1-naphthyl) | |
| 1075 | imidazol-2-yl-aminomethyl | 1 | H | $NHSO_2NHCH{=}CH{-}Ph$ | |
| 1076 | imidazol-2-yl-aminomethyl | 1 | H | $NHSO_2NHCH_2Ph$ | |
| 1077 | imidazol-2-yl-aminomethyl | 1 | H | $NHSO_2NHCH_2CH{=}CH$-Ph | |
| 1078 | imidazol-2-yl-aminomethyl | 1 | H | $NHSO_2NH$-n-Bu | |
| 1079 | imidazol-2-yl-aminomethyl | 1 | H | $NHSO_2NH$-i-Bu | |
| 1080 | imidazol-2-yl-aminomethyl | 1 | H | $NHSO_2NH$-t-Bu | |
| 1081 | pyridin-2-yl-aminomethyl | 1 | H | $NHCO_2Bn$ | 510.2 |
| 1082 | pyridin-2-yl- | 1 | H | $NHCO_2CH_2C_6H_4$-(2- | |

TABLE 1-continued

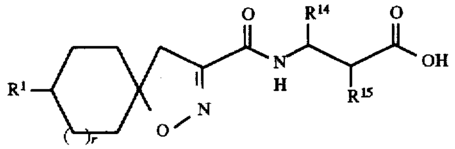

| Ex. No. | $R^1$ | r | $R^{14}$ | $R^{15}$ | MS |
|---|---|---|---|---|---|
| | aminomethyl | | | $CH_3$) | |
| 1083 | pyridin-2-yl-aminomethyl | 1 | H | $NHCO_2CH_2C_6H_4$-(3-$CH_3$) | |
| 1084 | pyridin-2-yl-aminomethyl | 1 | H | $NHCO_2CH_2C_6H_4$-(4-$CH_3$) | |
| 1085 | pyridin-2-yl-aminomethyl | 1 | H | $NHCO_2CH_2$(2-pyridinyl) | |
| 1086 | pyridin-2-yl-aminomethyl | 1 | H | $NHCO_2CH_2$(3-pyridinyl) | |
| 1087 | pyridin-2-yl-aminomethyl | 1 | H | $NHCO_2CH_2$(4-pyridinyl) | |
| 1088 | pyridin-2-yl-aminomethyl | 1 | H | $NHCO_2CH_2$(2-thiazolyl) | |
| 1089 | pyridin-2-yl-aminomethyl | 1 | H | $NHCO_2CH_2$(4-thiazolyl) | |
| 1090 | pyridin-2-yl-aminomethyl | 1 | H | $NHCO_2CH_2$(5-thiazolyl) | |
| 1091 | pyridin-2-yl-aminomethyl | 1 | H | $NHCO_2CH_2$(4-isoxazolyl) | |
| 1092 | pyridin-2-yl-aminomethyl | 1 | H | $NHCO_2CH_2$(2-thienyl) | |
| 1093 | pyridin-2-yl-aminomethyl | 1 | H | $NHCO_2$n-Bu | |
| 1094 | pyridin-2-yl-aminomethyl | 1 | H | $NHCO_2$i-Bu | |
| 1095 | pyridin-2-yl-aminomethyl | 1 | H | $NHCO_2$t-Bu | |
| 1096 | pyridin-2-yl-aminomethyl | 1 | H | $NHCOCH_2Ph$ | |
| 1097 | pyridin-2-yl-aminomethyl | 1 | H | $NHCOCH_2C_6H_4$-(2-$CH_3$) | |
| 1098 | pyridin-2-yl-aminomethyl | 1 | H | $NHCOCH_2-C_6H_4$-(3-$CH_3$) | |
| 1099 | pyridin-2-yl-aminomethyl | 1 | H | $NHCOCH_2C_6H_4$-(4-$CH_3$) | |
| 1100 | pyridin-2-yl-aminomethyl | 1 | H | $NHCOCH_2$(2-pyridinyl) | |
| 1101 | pyridin-2-yl-aminomethyl | 1 | H | $NHCOCH_2$(3-pyridinyl) | |
| 1102 | pyridin-2-yl-aminomethyl | 1 | H | $NHCOCH_2$(4-pyridinyl) | |
| 1103 | pyridin-2-yl-aminomethyl | 1 | H | $NHCOCH_2$(2-thiazolyl) | |
| 1104 | pyridin-2-yl-aminomethyl | 1 | H | $NHCOCH_2$-(4-thiazolyl) | |
| 1105 | pyridin-2-yl-aminomethyl | 1 | H | $NHCOCH_2$(5-thiazolyl) | |
| 1106 | | | | | |
| 1107 | pyridin-2-yl-aminomethyl | 1 | H | $NHCOCH_2$(4-isoxazolyl) | |
| 1108 | pyridin-2-yl-aminomethyl | 1 | H | $NHCOCH_2$(2-thienyl) | |
| 1109 | pyridin-2-yl-aminomethyl | 1 | H | NHCOn-Bu | |
| 1110 | pyridin-2-yl-aminomethyl | 1 | H | NHCOt-Bu | |
| 1111 | pyridin-2-yl-aminomethyl | 1 | H | $NHSO_2Ph$ | 516.1 |
| 1112 | pyridin-2-yl-aminomethyl | 1 | H | $NHSO_2C_6H_4$-(2-$CH_3$) | |
| 1113 | pyridin-2-yl-aminomethyl | 1 | H | $NHSO_2C_6H_4$-(3-$CH_3$) | |
| 1114 | pyridin-2-yl-aminomethyl | 1 | H | $NHSO_2C_6H_4$-(4-$CH_3$) | |
| 1115 | pyridin-2-yl-aminomethyl | I | H | $NHSO_2$(2-pyridyl) | |
| 1116 | pyridin-2-yl-aminomethyl | 1 | H | $NHSO_2$(3-pyridyl) | |

TABLE 1-continued

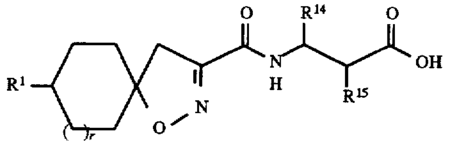

| Ex. No. | R1 | r | R14 | R15 | MS |
|---|---|---|---|---|---|
| 1117 | pyridin-2-yl-aminomethyl | 1 | H | $NHSO_2$(4-pyridyl) | |
| 1118 | pyridin-2-yl-aminomethyl | 1 | H | $NHSO_2$(2-thiazolyl) | |
| 1119 | pyridin-2-yl-aminomethyl | 1 | H | $NHSO_2$(4-thiazolyl) | |
| 1120 | pyridin-2-yl-aminomethyl | 1 | H | $NHSO_2$(4-isoxazolyl) | |
| 1121 | pyridin-2-yl-aminomethyl | 1 | H | $NHSO_2$-[4-(3,5-dimethyl)isoxazolyl] | 535.1 |
| 1122 | pyridin-2-yl-aminomethyl | 1 | H | $NHSO_2C_6H_4$-(2-Br) | |
| 1123 | pyridin-2-yl-aminomethyl | 1 | H | $NHSO_2C_6H_4$-(3-Br) | |
| 1124 | pyridin-2-yl-aminomethyl | 1 | H | $NHSO_2C_6H_4$-(4-Br) | |
| 1125 | pyridin-2-yl-aminomethyl | 1 | H | $NHSO_2C_6H_4$-(2-F) | |
| 1126 | pyridin-2-yl-aminomethyl | 1 | H | $NHSO_2C_6H_4$-(3-F) | |
| 1127 | pyridin-2-yl-aminomethyl | 1 | H | $NHSO_2C_6H_4$-(4-F) | |
| 1128 | pyridin-2-yl-aminomethyl | 1 | H | $NHSO_2$(2-naphthyl) | |
| 1129 | pyridin-2-yl-aminomethyl | 1 | H | $NHSO_2$(1-naphthyl) | |
| 1130 | pyridin-2-yl-aminomethyl | 1 | H | $NHSO_2CH{=}CH-Ph$ | |
| 1131 | pyridin-2-yl-aminomethyl | 1 | H | $NHSO_2CH_2Ph$ | |
| 1132 | pyridin-2-yl-aminomethyl | 1 | H | $NHSO_2$-$CH_2CH{=}CH-Ph$ | |
| 1133 | pyridin-2-yl-aminomethyl | 1 | H | $NHSO_2$-n-Bu | |
| 1134 | pyridin-2-yl-aminomethyl | 1 | H | $NHSO_2$-i-Bu | |
| 1135 | pyridin-2-yl-aminomethyl | 1 | H | $NHSO_2$-t-Bu | |
| 1136 | pyridin-2-yl-aminomethyl | 1 | H | $NHSO_2NHPh$ | |
| 1137 | pyridin-2-yl-aminomethyl | 1 | H | $NHSO_2NHC_6H_4$-(2-$CH_3$) | |
| 1138 | pyridin-2-yl-aminomethyl | 1 | H | $NHSO_2NHC_6H_4$-(3-$CH_3$) | |
| 1139 | pyridin-2-yl-aminomethyl | 1 | H | $NHSO_2NHC_6H_4$-(4-$CH_3$) | |
| 1140 | pyridin-2-yl-aminomethyl | 1 | H | $NHSO_2NH$(2-pyridyl) | |
| 1141 | pyridin-2-yl-aminomethyl | 1 | H | $NHSO_2NH$(3-pyridyl) | |
| 1142 | pyridin-2-yl-aminomethyl | 1 | H | $NHSO_2NH$(4-pyridyl) | |
| 1143 | pyridin-2-yl-aminomethyl | 1 | H | $NHSO_2NH$(2-thiazolyl) | |
| 1144 | pyridin-2-yl-aminomethyl | 1 | H | $NHSO_2NH$-(4-thiazolyl) | |
| 1145 | pyridin-2-yl-aminomethyl | 1 | H | $NHSO_2NH$(4-isoxazolyl) | |
| 1146 | pyridin-2-yl-aminomethyl | 1 | H | $NHSO_2$-[4-(3,5-dimethyl)isoxazolyl] | |
| 1147 | pyridin-2-yl-aminomethyl | 1 | H | $NHSO_2NHC_6H_4$-(2-Br) | |
| 1148 | pyridin-2-yl-aminomethyl | 1 | H | $NHSO_2NHC_6H_4$-(3-Br) | |
| 1149 | pyridin-2-yl-aminomethyl | 1 | H | $NHSO_2NHC_6H_4$-(4-Br) | |

TABLE 1-continued

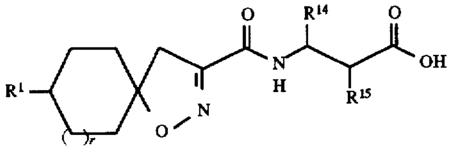

| Ex. No. | $R^1$ | r | $R^{14}$ | $R^{15}$ | MS |
|---|---|---|---|---|---|
| 1150 | pyridin-2-yl-aminomethyl | 1 | H | $NHSO_2NHC_6H_4$-(3-F) | |
| 1151 | pyridin-2-yl-aminomethyl | 1 | H | $NHSO_2NHC_6H_4$-(4-F) | |
| 1152 | pyridin-2-yl-aminomethyl | 1 | H | $NHSO_2NH$(2-naphthyl) | |
| 1153 | pyridin-2-yl-aminomethyl | 1 | H | $NHSO_2NH$)1-naphthyl) | |
| 1154 | pyridin-2-yl aminomethyl | 1 | H | $NHSO_2NHCH{=}CH-Ph$ | |
| 1155 | pyridin-2-yl-aminomethyl | 1 | H | $NHSO_2NHCH_2Ph$ | |
| 1156 | pyridin-2-yl aminomethyl | 1 | H | $NHSO_2NHCH_2CH{=}CH-Ph$ | |
| 1157 | pyridin-2-yl-aminomethyl | 1 | H | $NHSO_2NH$-n-Bu | |
| 1158 | pyridin-2-yl-aminomethyl | 1 | H | $NHSO_2NH$-i-Bu | |
| 1159 | pyridin-2-yl-aminomethyl | 1 | H | $NHSO_2NH$-t-Bu | |
| 1160 | tetrahydropyrimidin-2-ylaminomethyl | 1 | H | NHCOOBn | |
| 1161 | tetrahydropyrimidin-2-ylaminomethyl | 1 | H | $NHCO_2CH_2C_6H_4$-(2-$CH_3$) | |
| 1162 | tetrahydropyrimidin-2-ylaminomethyl | 1 | H | $NHCO_2CH_2C_6H_4$-(3-$CH_3$) | |
| 1163 | tetrahydropyrimidin-2-ylaminomethyl | 1 | H | $NHCO_2CH_2C_6H_4$-(4-$CH_3$) | |
| 1164 | tetrahydropyrimidin-2-ylaminomethyl | 1 | H | $NHCO_2CH_2$(2-pyridinyl) | |
| 1165 | tetrahydropyrimidin-2-ylaminomethyl | 1 | H | $NHCO_2CH_2$(3-pyridinyl) | |
| 1166 | tetrahydropyrimidin-2-ylaminomethyl | 1 | H | $NHCO_2CH_2$(4-pyridinyl) | |
| 1167 | tetrahydropyrimidin-2-ylaminomethyl | | H | $NHCO_2CH_2$(2-thiazolyl) | |
| 1168 | tetrahydropyrimidin-2-ylaminomethyl | 1 | H | $NHCO_2CH_2$(4-thiazolyl) | |
| 1169 | tetrahydropyrimidin-2-ylaminomethyl | 1 | H | $NHCO_2CH_2$(5-thiazolyl) | |
| 1170 | tetrahydropyrimidin-2-ylaminomethyl | 1 | H | $NHCO_2CH_2$(4-isoxazolyl) | |
| 1171 | tetrahydropyrimidin-2-ylaminomethyl | 1 | H | $NHCO_2CH_2$(2-thienyl) | |
| 1172 | tetrahydropyrimidin-2-ylaminomethyl | 1 | H | $NHCO_2$n-Bu | |
| 1173 | tetrahydropyrimidin-2-ylaminomethyl | 1 | H | $NHCO_2$i-Bu | |
| 1174 | tetrahydropyrimidin-2-ylaminomethyl | 1 | H | $NHCO_2$t-Bu | |
| 1175 | tetrahydropyrimidin-2-ylaminomethyl | 1 | H | $NHSO_2Ph$ | 521.3 |
| 1176 | tetrahydropyrimidin-2-ylaminomethyl | 1 | H | $NHSO_2C_6H_4$-(2-$CH_3$) | |
| 1177 | tetrahydropyrimidin-2-ylaminomethyl | 1 | H | $NHSO_2C_6H_4$-(3-$CH_3$) | |
| 1178 | tetrahydropyrimidin-2-ylaminomethyl | 1 | H | $NHSO_2C_6H_4$-(4-$CH_3$) | |
| 1179 | tetrahydropyrimidin-2-ylaminomethyl | 1 | H | $NHSO_2$(2-pyridyl) | |
| 1180 | tetrahydropyrimidin-2-ylaminomethyl | 1 | H | $NHSO_2$(3-pyridyl) | |
| 1181 | tetrahydropyrimidin-2-ylaminomethyl | 1 | H | $NHSO_2$(4-pyridyl) | |
| 1182 | tetrahydropyrimidin-2-ylaminomethyl | 1 | H | $NHSO_2$(2-thiazolyl) | |
| 1183 | tetrahydropyrimidin-2-ylaminomethyl | 1 | H | $NHSO_2$(4-thiazolyl) | |

TABLE 1-continued

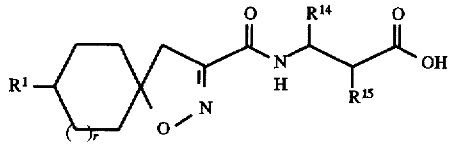

| Ex. No. | $R^1$ | r | $R^{14}$ | $R^{15}$ | MS |
|---|---|---|---|---|---|
| 1184 | tetrahydropyrimidin-2-ylaminomethyl | 1 | H | $NHSO_2$(4-isoxazolyl) | |
| 1185 | tetrahydropyrimidin-2-ylaminomethyl | 1 | H | $NHSO_2$-[4-(3,5-dimethyl)isoxazolyl] | |
| 1186 | tetrahydropyrimidin-2-ylaminomethyl | 1 | H | $NHSO_2C_6H_4$-(2-Br) | |
| 1187 | tetrahydropyrimidin-2-ylaminomethyl | 1 | H | $NHSO_2C_6H_4$-(3-Br) | |
| 1188 | tetrahydropyrimidin-2-ylaminomethyl | 1 | H | $NHSO_2C_6H_4$-(2-F) | |
| 1189 | tetrahydropyrimidin-2-ylaminomethyl | 1 | H | $NHSO_2C_6H_4$-(3-F) | |
| 1190 | tetrahydropyrimidin-2-ylaminomethyl | 1 | H | $NHSO_2C_6H_4$-(4-F) | |
| 1191 | tetrahydropyrimidin-2-ylaminomethyl | 1 | H | $NHSO_2$(2-naphthyl) | |
| 1192 | tetrahydropyrimidin-2-ylaminomethyl | 1 | H | $NHSO_2$(1-naphthyl) | |
| 1193 | tetrahydropyrimidin-2-ylaminomethyl | 1 | H | $NHSO_2CH{=}CHPh$ | |
| 1194 | tetrahydropyrimidin-2-ylaminomethyl | 1 | H | $NHSO_2CH_2Ph$ | |
| 1195 | tetrahydropyrimidin-2-ylaminomethyl | 1 | H | $NHSO_2CH_2CH{=}CHPh$ | |
| 1196 | tetrahydropyrimidin-2-ylaminomethyl | 1 | H | $NHSO_2$-n-Bu | |
| 1197 | tetrahydropyrimidin-2-ylaminomethyl | 1 | H | $NHSO_2$-i-Bu | |
| 1198 | imidazolin-2-yl-aminomethyl | 1 | H | NHCOOBn | |
| 1199 | imidazolin-2-yl-aminomethyl | 1 | H | $NHCO_2CH_2C_6H_4$-(2-$CH_3$) | |
| 1200 | imidazolin-2-yl-aminomethyl | 1 | H | $NHCO_2CH_2C_6H_4$-(3-$CH_3$) | |
| 1201 | imidazolin-2-yl-aminomethyl | 1 | H | $NHCO_2CH_2C_6H_4$-(4-$CH_3$) | |
| 1202 | imidazolin-2-yl-aminomethyl | 1 | H | $NHCO_2CH_2$(2-pyridinyl) | |
| 1203 | imidazolin-2-yl-aminomethyl | 1 | H | $NHCO_2CH_2$(3-pyridinyl) | |
| 1204 | imidazolin-2-yl-aminomethyl | 1 | H | $NHCO_2CH_2$(4-pyridinyl) | |
| 1205 | imidazolin-2-yl-aminomethyl | 1 | H | $NHCO_2CH_2$(2-thiazolyl) | |
| 1206 | imidazolin-2-yl-aminomethyl | 1 | H | $NHCO_2CH_2$(4-thiazolyl) | |
| 1207 | imidazolin-2-yl-aminomethyl | 1 | H | $NHCO_2CH_2$(5-thiazolyl) | |
| 1208 | imidazolin-2-yl-aminomethyl | 1 | H | $NHCO_2CH_2$(4-isoxazolyl) | |
| 1209 | imidazolin-2-yl-aminomethyl | 1 | H | $NHCO_2CH_2$(2-thienyl) | |
| 1210 | imidazolin-2-yl-aminomethyl | 1 | H | $NHCO_2$n-Bu | |
| 1211 | imidazolin-2-yl-aminomethyl | 1 | H | $NHCO_2$i-Bu | |
| 1212 | imidazolin-2-yl-aminomethyl | 1 | H | $NHCO_2$t-Bu | |
| 1213 | imidazolin-2-yl-aminomethyl | 1 | H | $NHSO_2Ph$ | 507.3 |
| 1214 | imidazolin-2-yl-aminomethyl | 1 | H | $NHSO_2C_6H_4$-(2-$CH_3$) | |
| 1215 | imidazolin-2-yl-aminomethyl | 1 | H | $NHSO_2C_6H_4$-(3-$CH_3$) | |
| 1216 | imidazolin-2-yl-aminomethyl | 1 | H | $NHSO_2C_6H_4$-(4-$CH_3$) | |
| 1217 | imidazolin-2-yl- | 1 | H | $NHSO_2$(2-pyridyl) | |

TABLE 1-continued

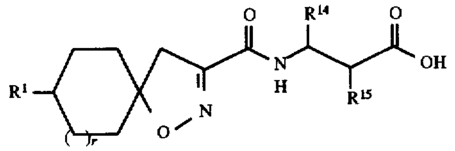

| Ex. No. | $R^1$ | r | $R^{14}$ | $R^{15}$ | MS |
|---|---|---|---|---|---|
| | aminomethyl | | | | |
| 1218 | imidazolin-2-yl-aminomethyl | 1 | H | $NHSO_2$(3-pyridyl) | |
| 1219 | imidazolin-2-yl-aminomethyl | 1 | H | $NHSO_2$(4-pyridyl) | |
| 1220 | imidazolin-2-yl-aminomethyl | 1 | H | $NHSO_2$(2-thiazolyl) | |
| 1221 | imidazolin-2-yl-aminomethyl | 1 | H | $NHSO_2$(4-isoxazolyl) | |
| 1222 | imidazolin-2-yl-aminomethyl | 1 | H | $NHSO_2$-[4-(3,5-dimethyl)isoxazolyl] | |
| 1223 | imidazolin-2-yl-aminomethyl | 1 | H | $NHSO_2C_6H_4$-(2-Br) | |
| 1224 | imidazolin-2-yl-aminomethyl | 1 | H | $NHSO_2C_6H_4$-(3-Br) | |
| 1225 | imidazolin-2-yl-aminomethyl | 1 | H | $NHSO_2C_6H_4$-(2-F) | |
| 1226 | imidazolin-2-yl-aminomethyl | 1 | H | $NHSO_2C_6H_4$-(3-F) | |
| 1227 | imidazolin-2-yl-aminomethyl | 1 | H | $NHSO_2C_6H_4$-(4-F) | |
| 1228 | imidazolin-2-yl-aminomethyl | 1 | H | $NHSO_2$(2-naphthyl) | |
| 1229 | imidazolin-2-yl-aminomethyl | 1 | H | $NHSO_2$(1-naphthyl) | |
| 1230 | imidazolin-2-yl-aminomethyl | 1 | H | $NHSO_2CH{=}CHPh$ | |
| 1231 | imidazolin-2-yl-aminomethyl | 1 | H | $NHSO_2CH_2Ph$ | |
| 1232 | imidazolin-2-yl-aminomethyl | 1 | H | $NHSO_2CH_2CH{=}CHPh$ | |
| 1233 | imidazolin-2-yl-aminomethyl | 1 | H | $NHSO_2$-n-Bu | |
| 1234 | imidazolin-2-yl-aminomethyl | 1 | H | $NHSO_2$-i-Bu | |
| 1235 | benzimidazol-2-yl-aminomethyl | 1 | H | $NHSO_2Ph$ | |
| 1236 | benzimidazol-2-yl-aminomethyl | 1 | H | $NHSO_2C_6H_4$-(2-$CH_3$) | |
| 1237 | benzimidazol-2-yl-aminomethyl | 1 | H | $NHSO_2C_6H_4$-(3-$CH_3$) | |
| 1238 | benzimidazol-2-yl-aminomethyl | 1 | H | $NHSO_2C_6H_4$-(4-$CH_3$) | |
| 1239 | benzimidazol-2-yl-aminomethyl | 1 | H | $NHSO_2$(2-pyridyl) | |
| 1240 | benzimidazol-2-yl-aminomethyl | 1 | H | $NHSO_2$(3-pyridyl) | |
| 1241 | benzimidazol-2-yl-aminomethyl | 1 | H | $NHSO_2$(4-pyridyl) | |
| 1242 | benzimidazol-2-yl-aminomethyl | 1 | H | $NHSO_2$(2-thiazolyl) | |
| 1243 | benzimidazol-2-yl-aminomethyl | 1 | H | $NHSO_2$(4-isoxazolyl) | |
| 1244 | benzimidazol-2-yl-aminomethyl | 1 | H | $NHSO_2$-[4-(3,5-dimethyl)isoxazolyl] | |
| 1245 | benzimidazol-2-yl-aminomethyl | 1 | H | $NHSO_2C_6H_4$-(2-Br) | |
| 1246 | benzimidazol-2-yl-aminomethyl | 1 | H | $NHSO_2C_6H_4$-(3-Br) | |
| 1247 | benzimidazol-2-yl-aminomethyl | 1 | H | $NHSO_2C_6H_4$-(2-F) | |
| 1248 | benzimidazol-2-yl-aminomethyl | 1 | H | $NHSO_2C_6H_4$-(3-F) | |
| 1249 | benzimidazol-2-yl-aminomethyl | 1 | H | $NHSO_2C_6H_4$-(4-F) | |
| 1250 | benzimidazol-2-yl- | 1 | H | $NHCO_2CH_2Ph$ | |

TABLE 1-continued

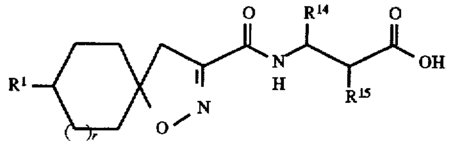

| Ex. No. | $R^1$ | r | $R^{14}$ | $R^{15}$ | MS |
|---|---|---|---|---|---|
| | aminomethyl | | | | |
| 1251 | benzimidazol-2-yl-aminomethyl | 1 | H | $NHCO_2$n-Bu | |
| 1252 | benzimidazol-2-yl-aminomethyl | 1 | H | $NHCO_2$i-Bu | |
| 1253 | 2-aminopyridin-6-ylmethyl | 1 | H | $NHSO_2Ph$ | |
| 1254 | 2-aminopyridin-6-ylmethyl | 1 | H | $NHSO_2C_6H_4$-(2-$CH_3$) | |
| 1255 | 2-aminopyridin-6-ylmethyl | 1 | H | $NHSO_2C_6H_4$-(3-$CH_3$) | |
| 1256 | 2-aminopyridin-6-ylmethyl | 1 | H | $NHSO_2C_6H_4$-(4-$CH_3$) | |
| 1257 | 2-aminopyridin-6-ylmethyl | 1 | H | $NHSO_2$(2-pyridyl) | |
| 1258 | 2-aminopyridin-6-ylmethyl | 1 | H | $NHSO_2$(3-pyridyl) | |
| 1259 | 2-aminopyridin-6-ylmethyl | 1 | H | $NHSO_2$(4-pyridyl) | |
| 1260 | 2-aminopyridin-6-ylmethyl | 1 | H | $NHSO_2$(2-thiazolyl) | |
| 1261 | 2-aminopyridin-6-ylmethyl | 1 | H | $NHSO_2$(4-isoxazolyl) | |
| 1262 | 2-aminopyridin-6-ylmethyl | 1 | H | $NHSO_2$-[4-(3,5-dimethyl)isoxazolyl] | 535.1 |
| 1263 | 2-aminopyridin-6-ylmethyl | 1 | H | $NHSO_2C_6H_4$-(2-Br) | |
| 1264 | 2-aminopyridin-6-ylmethyl | 1 | H | $NHSO_2C_6H_4$-(3-Br) | |
| 1265 | 2-aminopyridin-6-ylmethyl | 1 | H | $NHSO_2C_6H_4$-(2-F) | |
| 1266 | 2-aminopyridin-6-ylmethyl | 1 | H | $NHSO_2C_6H_4$-(3-F) | |
| 1267 | 2-aminopyridin-6-ylmethyl | 1 | H | $NHSO_2C_6H_4$-(4-F) | |
| 1268 | 2-aminopyridin-6-ylmethyl | 1 | H | $NHCO_2CH_2Ph$ | |
| 1269 | 2-aminopyridin-6-ylmethyl | 1 | H | $NHCO_2$n-Bu | |
| 1270 | 2-aminopyridin-6-ylmethyl | 1 | H | $NHCO_2$i-Bu | |
| 1271 | 7-azabenimidazol-2-yl | 1 | H | $NHSO_2Ph$ | |
| 1272 | 7-azabenimidazol-2-yl | 1 | H | $NHSO_2C_6H_4$-(2-$CH_3$) | |
| 1273 | 7-azabenimidazol-2-yl | 1 | H | $NHSO_2C_6H_4$-(3-$CH_3$) | |
| 1274 | 7-azabenimidazol-2-yl | 1 | H | $NHSO_2C_6H_4$-(4-$CH_3$) | |
| 1275 | 7-azabenimidazol-2-yl | 1 | H | $NHSO_2$(2-naphthyl) | |
| 1276 | 7-azabenimidazol-2-yl | 1 | H | $NHSO_2$(1-naphthyl) | |
| 1277 | 7-azabenimidazol-2-yl | 1 | H | $NHSO_2$(biphenyl) | |
| 1278 | 7-azabenimidazol-2 yl | 1 | H | $NHSO_2C_6H_4$-(2,4,6-$(CH_3)_3$) | 569.4 |
| 1279 | 7-azabenimidazol-2-yl | 1 | H | $NHSO_2$(2-thienyl) | |
| 1280 | 7-azabenimidazol-2-yl | 1 | H | $NHSO_2$-[4-(3,5-dimethyl)isoxazolyl] | |
| 1281 | 7-azabenimidazol-2-yl | 1 | H | $NHSO_2C_6H_4$-(2-Br) | |
| 1282 | 7-azabenimidazol-2-yl | 1 | H | $NHSO_2C_6H_4$-(3-Br) | |
| 1283 | 7-azabenimidazol-2- | 1 | H | $NHSO_2C_6H_4$-(2-F) | |

TABLE 1-continued

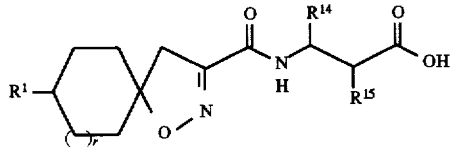

| Ex. No. | $R^1$ | r | $R^{14}$ | $R^{15}$ | MS |
|---|---|---|---|---|---|
| | yl | | | | |
| 1284 | 7-azabenimidazol-2-yl | 1 | H | $NHSO_2C_6H_4$-(3-F) | |
| 1285 | 7-azabenimidazol-2-yl | 1 | H | $NHSO_2C_6H_4$-(4-F) | |
| 1286 | 7-azabenimidazol-2-yl | 1 | H | $NHCO_2CH_2Ph$ | |
| 1287 | 7-azabenimidazol-2-yl | 1 | H | $NHCO_2$n-Bu | |
| 1288 | 7-azabenimidazol-2-yl | 1 | H | $NHCO_2$i-Bu | |
| 1289 | 4,5,6,7-tetrahydro-benzimidazol-2-yl-aminomethyl | 1 | H | $NHSO_2Ph$ | 561.4 |
| 1290 | 4,5,6,7-tetrahydro-benzimidazol-2-yl-aminomethyl | 1 | H | $NHSO_2C_6H_4$-(2-$CH_3$) | |
| 1291 | 4,5,6,7-tetrahydro-benzimidazol-2-yl-aminomethyl | 1 | H | $NHSO_2C_6H_4$-(3-$CH_3$) | |
| 1292 | 4,5,6,7-tetrahydro-benzimidazol-2-yl-aminomethyl | 1 | H | $NHSO_2C_6H_4$-(4-$CH_3$) | |
| 1293 | 4,5,6,7-tetrahydro-benzimidazol-2-yl-aminomethyl | 1 | H | $NHSO_2$(2-naphthyl) | |
| 1294 | 4,5,6,7-tetrahydro-benzimidazol-2-yl-aminomethyl | 1 | H | $NHSO_2$(1-naphthyl) | |
| 1295 | 4,5,6,7-tetrahydro-benzimidazol-2-yl-aminomethyl | 1 | H | $NHSO_2$(biphenyl) | |
| 1296 | 4,5,6,7-tetrahydro-benzimidazol-2-yl-aminomethyl | 1 | H | $NHSO_2C_6H_4$-(2,4,6-$(CH_3)_3$) | |
| 1297 | 4,5,6,7-tetrahydro-benzimidazol-2-yl-aminomethyl | 1 | H | $NHSO_2$(2-thienyl) | |
| 1298 | 4,5,6,7-tetrahydro-benzimidazol-2-yl-aminomethyl | 1 | H | $NHSO_2$-[4-(3,5-dimethyl)isoxazolyl] | |
| 1299 | 4,5,6,7-tetrahydro-benzimidazol-2-yl-aminomethyl | 1 | H | $NHSO_2C_6H_4$-(2-Br) | |
| 1300 | 4,5,6,7-tetrahydro-benzimidazol-2-yl-aminomethyl | 1 | H | $NHSO_2C_6H_4$-(3-Br) | |
| 1301 | 4,5,6,7-tetrahydro-benzimidazol-2-yl-aminomethyl | 1 | H | $NHSO_2C_6H_4$-(2-F) | |
| 1302 | 4,5,6,7-tetrahydro-benzimidazol-2-yl-aminomethyl | 1 | H | $NHSO_2C_6H_4$-(3-F) | |
| 1303 | 4,5,6,7-tetrahydro-benzimidazol-2-yl-aminomethyl | 1 | H | $NHSO_2C_6H_4$-(4-F) | |
| 1304 | 4,5,6,7-tetrahydro-benzimidazol-2-yl-aminomethyl | 1 | H | $NHCO_2CH_2Ph$ | |
| 1305 | 4,5,6,7-tetrahydro-benzimidazol-2-yl-aminomethyl | 1 | H | $NHCO_2$n-Bu | |
| 1306 | 4,5,6,7-tetrahydro-benzimidazol-2-yl-aminomethyl | 1 | H | $NHCO_2$i-Bu | |
| 1307 | 4-oxo-3,4,5,6-tetrahydro-pyrimidin-2-yl- | 1 | H | $NHSO_2Ph$ | 549.3 |

TABLE 1-continued

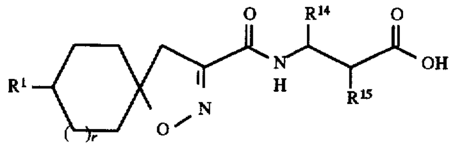

| Ex. No. | $R^1$ | r | $R^{14}$ | $R^{15}$ | MS |
|---|---|---|---|---|---|
| | aminomethyl | | | | |
| 1308 | 4-oxo-3,4,5,6-tetrahydro-pyrimidin-2-yl-aminomethyl | 1 | H | $NHSO_2C_6H_4$-(2-$CH_3$) | |
| 1309 | 4-oxo-3,4,5,6-tetrahydro-pyrimidin-2-yl-aminomethyl | 1 | H | $NHSO_2C_6H_4$-(3-$CH_3$) | |
| 1310 | 4-oxo-3,4,5,6-tetrahydro-pyrimidin-2-yl-aminomethyl | 1 | H | $NHSO_2C_6H_4$-(4-$CH_3$) | |
| 1311 | 4-oxo-3,4,5,6-tetrahydro-pyrimidin-2-yl-aminomethyl | 1 | H | $NHSO_2$(2-naphthyl) | |
| 1312 | 4-oxo-3,4,5,6-tetrahydro-pyrimidin-2-yl-aminomethyl | 1 | H | $NHSO_2$(1-naphthyl) | |
| 1313 | 4-oxo-3,4,5,6-tetrahydro-pyrimidin-2-yl-aminomethyl | 1 | H | $NHSO_2$(biphenyl) | |
| 1314 | 4-oxo-3,4,5,6-tetrahydro-pyrimidin-2-yl-aminomethyl | 1 | H | $NHSO_2C_6H_4$-(2,4,6-$(CH_3)_3$) | |
| 1315 | 4-oxo-3,4,5,6-tetrahydro-pyrimidin-2-yl-aminomethyl | 1 | H | $NHSO_2$(2-thienyl) | |
| 1316 | 4-oxo-3,4,5,6-tetrahydro-pyrimidin-2-yl-aminomethyl | 1 | H | $NHSO_2$-[4-(3,5-dimethyl)isoxazolyl] | |
| 1317 | 4-oxo-3,4,5,6-tetrahydro-pyrimidin-2-yl-aminomethyl | 1 | H | $NHSO_2C_6H_4$-(2-Br) | |
| 1318 | 4-oxo-3,4,5,6-tetrahydro-pyrimidin-2-yl-aminomethyl | 1 | H | $NHSO_2C_6H_4$-(3-Br) | |
| 1319 | 4-oxo-3,4,5,6-tetrahydro-pyrimidin-2-yl-aminomethyl | 1 | H | $NHSO_2C_6H_4$-(2-F) | |
| 1320 | 4-oxo-3,4,5,6-tetrahydro-pyrimidin-2-yl-aminomethyl | 1 | H | $NHSO_2C_6H_4$-(3-F) | |
| 1321 | 4-oxo-3,4,5,6-tetrahydro-pyrimidin-2-yl-aminomethyl | 1 | H | $NHSO_2C_6H_4$-(4-F) | |
| 1322 | 4-oxo-3,4,5,6-tetrahydro-pyrimidin-2-yl-aminomethyl | 1 | H | $NHCO_2CH_2Ph$ | |
| 1323 | 4-oxo-3,4,5,6-tetrahydro-pyrimidin-2-yl-aminomethyl | 1 | H | $NHCO_2$n-Bu | |
| 1324 | 4-oxo-3,4,5,6-tetrahydro-pyrimidin-2-yl- | 1 | H | $NHCO_2$i-Bu | |

TABLE 1-continued

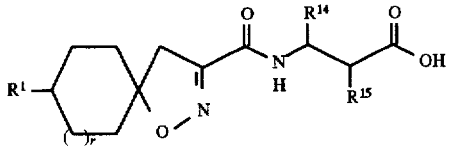

| Ex. No. | $R^1$ | r | $R^{14}$ | $R^{15}$ | MS |
|---|---|---|---|---|---|
| | aminomethyl | | | | |
| 1325 | 2-iminoazepin-7-ylmethyl | 1 | H | $NHSO_2Ph$ | |
| 1326 | 1,2-pyrazol-3-ylaminomethyl | | H | $NHSO_2Ph$ | |
| 1327 | 1,2,4-triazol-5-ylaminomethyl | 1 | H | $NHSO_2Ph$ | |
| 1328 | imidazol-4-ylaminomethyl | 1 | H | $NHSO_2Ph$ | |
| 1329 | 1,3,4-oxadiazol-2ylaminomethyl | 1 | H | $NHSO_2Ph$ | |
| 1330 | 1,2,4-thiadiazol-5-ylaminomethyl | 1 | H | $NHSO_2Ph$ | |
| 1331 | 1,2,5-oxadiazol-3-ylaminomethyl | 1 | H | $NHSO_2Ph$ | |
| 1332 | 1,2,4-oxadiazol-5-ylaminomethyl | 1 | H | $NHSO_2Ph$ | |
| 1333 | 2-iminoazepin-7-ylmethyl | 1 | H | $NHSO_2$(4-isoxazolyl) | |
| 1334 | 1,2-pyrazol-3-ylaminomethyl | 1 | H | $NHSO_2$(4-isoxazolyl) | |
| 1335 | 1,2,4-triazol-5-ylaminomethyl | 1 | H | $NHSO_2$(4-isoxazolyl) | |
| 1336 | imidazol-4-ylaminomethyl | 1 | H | $NHSO_2$(4-isoxazolyl) | |
| 1337 | 1,3,4-oxadiazol-2ylaminomethyl | 1 | H | $NHSO_2$(4-isoxazolyl) | |
| 1338 | 1,2,4-thiadiazol-5-ylaminomethyl | 1 | H | $NHSO_2$(4-isoxazolyl) | |
| 1339 | 1.2.5-oxadiazol-3-ylaminomethyl | 1 | H | $NHSO_2$(4-isoxazolyl) | |
| 1340 | 1.2.4-oxadiazol-5-ylaminomethyl | 1 | H | $NHSO_2$(4-isoxazolyl) | |
| 1341 | 2-iminoazepin-7-ylmethyl | 1 | H | $NHSO_2$-[4-(3,5-dimethyl)isoxazolyl] | |
| 1342 | 1,2-pyrazol-3-ylaminomethyl | 1 | H | $NHSO_2$-[4-(3,5-dimethyl)isoxazolyl] | |
| 1343 | 1,2,4-triazol-5-ylaminomethyl | 1 | H | $NHSO_2$-[4-(3,5-dimethyl)isoxazolyl] | |
| 1344 | imidazol-4-ylaminomethyl | 1 | H | $NHSO_2$-[4-(3,5-dimethyl)isoxazolyl] | |
| 1345 | 1,3,4-oxadiazol-2ylaminomethyl | 1 | H | $NHSO_2$-[4-(3,5-dimethyl)isoxazolyl] | |
| 1346 | 1,2,4-thiadiazol-5-ylaminomethyl | 1 | H | $NHSO_2$-[4-(3,5-dimethyl)isoxazolyl] | |
| 1347 | 1.2.5-oxadiazol-3-ylaminomethyl | 1 | H | $NHSO_2$-[4-(3,5-dimethyl)isoxazolyl] | |
| 1348 | 1.2.4-oxadiazol-5-ylaminomethyl | 1 | H | $NHSO_2$-[4-(3,5-dimethyl)isoxazolyl] | |
| 1349 | imidazol-2-yl-aminomethyl | 1 | 3-pyridinyl | H | |
| 1350 | pyridin-2-ylaminomethyl | 1 | 3-pyridinyl | H | |
| 1351 | imidazolin-2-yl-aminomethyl | 1 | 3-pyridinyl | H | |
| 1352 | tetrahydropyrimidin-2-ylaminomethyl | 1 | 3-pyridinyl | H | |
| 1353 | benzimidazol-2-yl-aminomethyl | 1 | 3-pyridinyl | H | |
| 1354 | 2-aminopyridin-6- | 1 | 3-pyridinyl | H | |

TABLE 1-continued

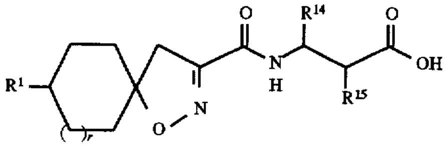

| Ex. No. | $R^1$ | r | $R^{14}$ | $R^{15}$ | MS |
|---|---|---|---|---|---|
| | ylmethyl | | | | |
| 1355 | 2-iminoazepin-7-ylmethyl | 1 | 3-pyridinyl | H | |
| 1356 | 1,2-pyrazol-3-ylaminomethyl | 1 | 3-pyridinyl | H | |
| 1357 | 1,2,4-triazol-5-ylaminomethyl | 1 | 3-pyridinyl | H | |
| 1358 | imidazol-4-ylaminomethyl | 1 | 3-pyridinyl | H | |
| 1359 | 1,3,4-oxadiazol-2ylaminomethyl | 1 | 3-pyridinyl | H | |
| 1360 | 1,2,4-thiadiazol-5-ylaminomethyl | 1 | 3-pyridinyl | H | |
| 1361 | 1,2,5-oxadiazol-3-ylaminomethyl | 1 | 3-pyridinyl | H | |
| 1362 | 1.2.4-oxadiazol-5-ylaminomethyl | 1 | 3-pyridinyl | H | |
| 1363 | imidazol-2-yl-aminomethyl | 1 | (3,4-methylene-dioxy)phenyl | H | |
| 1364 | pyridin-2-ylaminomethyl | 1 | (3,4-methylene-dioxy)phenyl | H | |
| 1365 | imidazolin-2-yl-aminomethyl | 1 | (3,4-methylene-dioxy)phenyl | H | |
| 1366 | tetrahydropyrimidin-2-ylaminomethyl | 1 | (3,4-methylene-dioxy)phenyl | H | |
| 1367 | benzimidazol-2-yl-aminomethyl | 1 | (3,4-methylene-dioxy)phenyl | H | |
| 1368 | 2-aminopyridin-6-ylmethyl | 1 | (3,4-methylene-dioxy)phenyl | H | |
| 1369 | 2-iminoazepin-7-ylmethyl | 1 | (3,4-methylene-dioxy)phenyl | H | |
| 1370 | 1,2-pyrazol-3-ylaminomethyl | 1 | (3,4-methylene-dioxy)phenyl | H | |
| 1371 | 1,2,4-triazol-5-ylaminomethyl | 1 | (3,4-methylene-dioxy)phenyl | H | |
| 1372 | imidazol-4-ylaminomethyl | 1 | (3,4-methylene-dioxy)phenyl | H | |
| 1373 | 1,3,4-oxadiazol-2ylaminomethyl | 1 | (3,4-methylene-dioxy)phenyl | H | |
| 1374 | 1,2,4-thiadiazol-5-ylaminomethyl | 1 | (3,4-methylene-dioxy)phenyl | H | |
| 1375 | 1,2,5-oxadiazol-3-ylaminomethyl | 1 | (3,4-methylene-dioxy)phenyl | H | |
| 1376 | 1.2.4-oxadiazol-5-ylaminomethyl | 1 | (3,4-methylene-dioxy)phenyl | H | |
| 1377 | imidazol-2-yl-aminomethyl | 1 | 3-pyridinyl | $NHSO_2Ph$ | |
| 1378 | pyridin-2-ylaminomethyl | 1 | 3-pyridinyl | $NHSO_2Ph$ | |
| 1379 | imidazol-2-yl-aminomethyl | 1 | (3,4-methylene-dioxy)phenyl | $NHSO_2Ph$ | |
| 1380 | pyridin-2-ylamino | 1 | (3,4-methylene- | $NHSO_2Ph$ | |

TABLE 1-continued

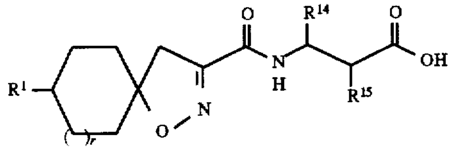

| Ex. No. | $R^1$ | r | $R^{14}$ | $R^{15}$ | MS |
|---|---|---|---|---|---|
| | | | dioxy)phenyl | | |
| 1381 | imidazol-2-yl-amino | 1 | H | $NHSO_2Ph$ | |
| 1382 | pyridin-2-ylamino | 1 | H | $NHSO_2Ph$ | |
| 1383 | imidazolin-2-yl-amino | 1 | H | $NHSO_2Ph$ | |
| 1384 | tetrahydropyrimidin-2-ylamino | 1 | H | $NHSO_2Ph$ | |
| 1385 | benzimidazol-2-yl-amino | 1 | H | $NHSO_2Ph$ | |
| 1386 | 2-aminopyridin-6-ylmethyl | 1 | H | $NHSO_2Ph$ | |
| 1387 | 2-iminoazepin-7-yl | 1 | H | $NHSO_2Ph$ | |
| 1388 | 1,2-pyrazol-3-ylamino | 1 | H | $NHSO_2Ph$ | |
| 1389 | 1,2,4-triazol-5-ylamino | 1 | H | $NHSO_2Ph$ | |
| 1390 | imidazol-4-ylamino | 1 | H | $NHSO_2Ph$ | |
| 1391 | 1,3,4-oxadiazol-2ylaminomethyl | 1 | H | $NHSO_2Ph$ | |
| 1392 | 1,2,4-thiadiazol-5-ylaminomethyl | 1 | H | $NHSO_2Ph$ | |
| 1393 | 1,2,5-oxadiazol-3-ylaminomethyl | 1 | H | $NHSO_2Ph$ | |
| 1394 | 1.2.4-oxadiazol-5-ylaminomethyl | 1 | H | $NHSO_2Ph$ | |
| 1395 | imidazol-2-yl-aminoethyl | 1 | H | $NHSO_2Ph$ | |
| 1396 | pyridin-2-ylaminoethyl | 1 | H | $NHSO_2Ph$ | |
| 1397 | imidazolin-2-yl-aminoethyl | 1 | H | $NHSO_2Ph$ | |
| 1398 | tetrahydropyrimidin-2-ylaminoethyl | 1 | H | $NHSO_2Ph$ | |
| 1399 | benzimidazol-2-yl-aminoethyl | 1 | H | $NHSO_2Ph$ | |
| 1400 | 2-aminopyridin-6-ylethyl | 1 | H | $NHSO_2Ph$ | |
| 1401 | 2-iminoazepin-7-ylethyl | 1 | H | $NHSO_2Ph$ | |
| 1402 | 1,2-pyrazol-3-ylaminoethyl | 1 | H | $NHSO_2Ph$ | |
| 1403 | 1,2,4-triazol-5-ylaminoethyl | 1 | H | $NHSO_2Ph$ | |
| 1404 | imidazol-4-ylaminoethyl | 1 | H | $NHSO_2Ph$ | |
| 1405 | 1,3,4-oxadiazol-2ylaminoethyl | 1 | H | $NHSO_2Ph$ | |
| 1406 | 1,2,4-thiadiazol-5-ylaminoethyl | 1 | H | $NHSO_2Ph$ | |
| 1407 | 1,2,5-oxadiazol-3-ylaminoethyl | 1 | H | $NHSO_2Ph$ | |
| 1408 | 1,2,4-oxadiazol-5-ylaminoethyl | 1 | H | $NHSO_2Ph$ | |
| 1409 | imidazol-2-yl-aminomethyl | 2 | H | $NHSO_2Ph$ | |
| 1410 | pyridin-2-ylaminomethyl | 2 | H | $NHSO_2Ph$ | |
| 1411 | imidazolin-2-yl-aminomethyl | 2 | H | $NHSO_2Ph$ | |
| 1412 | tetrahydropyrimidin-2-ylaminomethyl | 2 | H | $NHSO_2Ph$ | |
| 1413 | benzimidazol-2-yl-aminomethyl | 2 | H | $NHSO_2Ph$ | |
| 1414 | 7-azabenimidazol-2-yl | 2 | H | $NHSO_2Ph$ | |
| 1415 | 4,5,6,7-tetrahydro-benzimidazol-2-yl-aminomethyl | 2 | H | $NHSO_2Ph$ | |

TABLE 1-continued

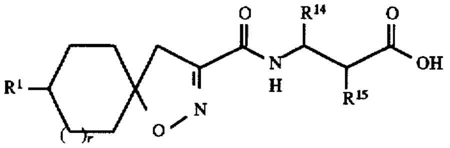

| Ex. No. | $R^1$ | r | $R^{14}$ | $R^{15}$ | MS |
|---|---|---|---|---|---|
| 1416 | 4-oxotetrahydro-pyrimidin-2-yl-aminomethyl | 2 | H | $NHSO_2Ph$ | |
| 1417 | 2-aminopyridin-6-ylmethyl | 2 | H | $NHSO_2Ph$ | |
| 1418 | 2-iminoazepin-7-ylmethyl | 2 | H | $NHSO_2Ph$ | |
| 1419 | 1,2-pyrazol-3-ylaminomethyl | 2 | H | $NHSO_2Ph$ | |
| 1420 | 1,2,4-triazol-5-ylaminomethyl | 2 | H | $NHSO_2Ph$ | |
| 1421 | imidazol-4-ylaminomethyl | 2 | H | $NHSO_2Ph$ | |
| 1422 | 1,3,4-oxadiazol-2ylaminomethyl | 2 | H | $NHSO_2Ph$ | |
| 1423 | 1,2,4-thiadiazol-5-ylaminomethyl | 2 | H | $NHSO_2Ph$ | |
| 1424 | 1.2.5-oxadiazol-3-ylaminomethyl | 2 | H | $NHSO_2Ph$ | |
| 1425 | 1.2.4-oxadiazol-5-ylaminomethyl | 2 | H | $NHSO_2Ph$ | |
| 1426 | imidazol-2-yl-aminomethyl | 0 | H | $NHSO_2Ph$ | |
| 1427 | pyridin-2-ylaminomethyl | 0 | H | $NHSO_2Ph$ | |
| 1428 | imidazolin-2-yl-aminomethyl | 0 | H | $NHSO_2Ph$ | |
| 1429 | tetrahydropyrimidin-2-ylaminomethyl | 0 | H | $NHSO_2Ph$ | |
| 1430 | benzimidazol-2-yl-aminomethyl | 0 | H | $NHSO_2Ph$ | |
| 1431 | 7-azabenimidazol-2-yl | 0 | H | $NHSO_2Ph$ | |
| 1432 | 4,5,6,7-tetrahydro-benzimidazol-2-yl-aminomethyl | 0 | H | $NHSO_2Ph$ | |
| 1433 | 4-oxotetrahydro-pyrimidin-2-yl-aminomethyl | 0 | H | $NHSO_2Ph$ | |
| 1434 | 2-aminopyridin-6-ylmethyl | 0 | H | $NHSO_2Ph$ | |
| 1435 | 2-iminoazepin-7-ylmethyl | 0 | H | $NHSO_2Ph$ | |
| 1436 | 1,2-pyrazol-3-ylaminomethyl | 0 | H | $NHSO_2Ph$ | |
| 1437 | 1,2,4-triazol-5-ylaminomethyl | 0 | H | $NHSO_2Ph$ | |
| 1438 | imidazol-4-ylaminomethyl | 0 | H | $NHSO_2Ph$ | |
| 1439 | 1,3,4-oxadiazol-2ylaminomethyl | 0 | H | $NHSO_2Ph$ | |
| 1440 | 1,2,4-thiadiazol-5-ylaminomethyl | 0 | H | $NHSO_2Ph$ | |
| 1441 | 1,2,5-oxadiazol-3-ylaminomethyl | 0 | H | $NHSO_2Ph$ | |
| 1442 | 1.2.4-oxadiazol-5-ylaminomethyl | 0 | H | $NHSO_2Ph$ | |
| 1443 | benzimidazol-2-ylaminomethyl | 1 | H | $NHSO_2$(2,4,6-trimethyl phenyl) | 597.4 |
| 1444 | 2-quinolinylaminomethyl | 1 | H | $NHSO_2$(2,4,6-trimethyl phenyl) | 608.5 |
| 1445 | benzimidazol-2-ylaminocarbonyl | 1 | H | $NHSO_2$(2,4,6-trimethyl phenyl) | 611.3 |
| 1446 | benzimidazol-2-yl | 1 | H | $NHSO_2$(2,4,6-trimethyl | 568.5 |

TABLE 1-continued

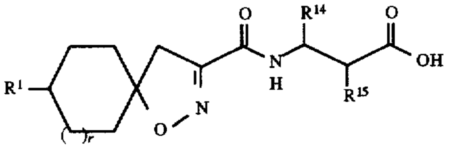

| Ex. No. | $R^1$ | r | $R^{14}$ | $R^{15}$ | MS |
|---|---|---|---|---|---|
| | | | | phenyl) | |
| 1447 | imidazol-2-ylaminocarbonyl | 1 | H | $NHSO_2$(2,4,6-trimethyl phenyl) | 561.4 |
| 1448 | imidazol-2-ylaminocarbonyl | 1 | H | $NHSO_2$(2-naphthyl) | 569.2 |
| 1449 | imidazol-2-ylaminocarbonyl | 1 | H | $NHSO_2$(2,6-dichlorophenyl) | 587.3/ 589.4 |
| 1450 | pyridin-2-ylaminomethyl | 1 | H | $NHSO_2$(2,4,6-trimethyl phenyl) | 547.3 |
| 1451 | imidazol-2-ylaminomethyl | 1 | H | $NHSO_2$(2,4,6-trimethyl phenyl) | 547.2 |
| 1452 | imidazol-2-ylaminomethyl | 1 | H | $NHSO_2$biphenyl | 581.2 |
| 1453 | imidazol-2-ylaminomethyl | 1 | H | $NHSO_2$[(2,6-dichloro-4-phenyl)phenyl] | 649.1 |
| 1454 | imidazol-2-ylaminomethyl | 1 | H | $NHSO_2$[(2,6-dimethyl-4-phenyl)phenyl] | 609.2 |
| 1455 | imidazol-2-ylaminomethyl | 1 | H | $NHSO_2$(2,6-dimethylphenyl) | 533.2 |
| 1456 | imidazol-2-ylaminomethyl | 1 | H | $NHSO_2$(2-chloro-6-methylphenyl) | 553.2 |
| 1457 | imidazol-2-ylaminomethyl | 1 | H | $NHSO_2$(2,6-dichlorophenyl) | 573.1 |

TABLE 2

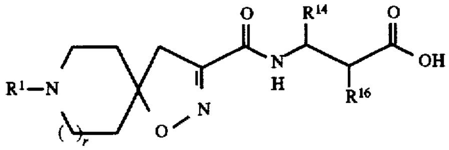

| Ex. No. | $R^{1*}$ | r | $R^{14}$ | $R^{15}$ | MS |
|---|---|---|---|---|---|
| 2001 | 2-aminopyridin-6-yl | 0 | H | H | |
| 2002 | 2-aminopyridin-6-yl | 0 | H | $NHCO_2Bn$ | |
| 2003 | 2-aminopyridin-6-yl | 0 | H | $NHCO_2CH_2C_6H_4$-(2-$CH_3$) | |
| 2004 | 2-aminopyridin-6-yl | 0 | H | $NHCO_2CH_2C_6H_4$-(3-$CH_3$) | |
| 2005 | 2-aminopyridin-6-yl | 0 | H | $NHCO_2CH_2C_6H_4$-(4-$CH_3$) | |
| 2006 | 2-aminopyridin-6-yl | 0 | H | $NHCO_2CH_2$ (2-pyridinyl) | |
| 2007 | 2-aminopyridin-6-yl | 0 | H | $NHCO_2CH_2$ (3-pyridinyl) | |
| 2008 | 2-aminopyridin-6-yl | 0 | H | $NHCO_2CH_2$ (4-pyridinyl) | |
| 2009 | 2-aminopyridin-6-yl | 0 | H | $NHCO_2CH_2$ (2-thiazolyl) | |
| 2010 | 2-aminopyridin-6-yl | 0 | H | $NHCO_2CH_2$ (4-thiazolyl) | |
| 2011 | 2-aminopyridin-6-yl | 0 | H | $NHCO_2CH_2$ (5-thiazolyl) | |
| 2012 | 2-aminopyridin-6-yl | 0 | H | $NHCO_2CH_2$ (4-isoxazolyl) | |
| 2013 | 2-aminopyridin-6-yl | 0 | H | $NHCO_2CH_2$ (2-thienyl) | |
| 2014 | 2-aminopyridin-6-yl | 0 | H | $NHCO_2CH_2$ (5-isoxazolyl) | |
| 2015 | 2-aminopyridin-6-yl | 0 | H | $NHCO_2$n-Bu | |
| 2016 | 2-aminopyridin-6-yl | 0 | H | $NHCO_2$i-Bu | |

TABLE 2-continued

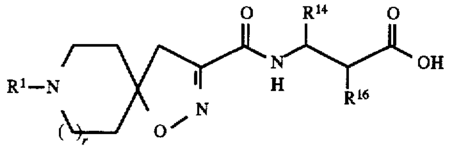

| Ex. No. | $R^{1a}$ | r | $R^{14}$ | $R^{15}$ | MS |
|---|---|---|---|---|---|
| 2017 | 2-aminopyridin-6-yl | 0 | H | $NHCO_2$t-Bu | |
| 2018 | 2-aminopyridin-6-yl | 0 | H | $NHCOCH_2Ph$ | |
| 2019 | 2-aminopyridin-6-yl | 0 | H | $NHCOCH_2C_6H_4$-(2-$CH_3$) | |
| 2020 | 2-aminopyridin-6-yl | 0 | H | $NHCOCH_2C_6H_4$-(3-$CH_3$) | |
| 2021 | 2-aminopyridin-6-yl | 0 | H | $NHCOCH_2C_6H_4$-(4-$CH_3$) | |
| 2022 | 2-aminopyridin-6-yl | 0 | H | $NHCO(CH_2)_2Ph$ | |
| 2023 | 2-aminopyridin-6-yl | 0 | H | NHCOn-Bu | |
| 2024 | 2-aminopyridin-6-yl | 0 | H | NHCOt-Bu | |
| 2025 | 2-aminopyridin-6-yl | 0 | H | $NHSO_2Ph$ | |
| 2026 | 2-aminopyridin-6-yl | 0 | H | $NHSO_2C_6H_4$-(2-$CH_3$) | |
| 2027 | 2-aminopyridin-6-yl | 0 | H | $NHSO_2C_6H_4$-(3-$CH_3$) | |
| 2028 | 2-aminopyridin-6-yl | 0 | H | $NHSO_2C_6H_4$-(4-$CH_3$) | |
| 2029 | 2-aminopyridin-6-yl | 0 | H | $NHSO_2$ (2-pyridyl) | |
| 2030 | 2-aminopyridin-6-yl | 0 | H | $NHSO_2$ (3-pyridyl) | |
| 2031 | 2-aminopyridin-6-yl | 0 | H | $NHSO_2$ (4-pyridyl) | |
| 2032 | 2-aminopyridin-6-yl | 0 | H | $NHSO_2$ (2-thiaz-olyl) | |
| 2033 | 2-aminopyridin-6-yl | 0 | H | $NHSO_2$ (3-thiazolyl) | |
| 2034 | 2-aminopyridin-6-yl | 0 | H | $NHSO_2$ (4-isoxazolyl) | |
| 2035 | 2-aminopyridin-6-yl | 0 | H | $NHSO_2$[4-(3,5-dimethyl) isoxazolyl] | |
| 2036 | 2-aminopyridin-6-yl | 0 | H | $NHSO_2C_6H_4$-(2-Br) | |
| 2037 | 2-aminopyridin-6-yl | 0 | H | $NHSO_2C_6H_4$-(3-Br) | |
| 2038 | 2-aminopyridin-6-yl | 0 | H | $NHSO_2C_6H_4$-(4-Br) | |
| 2039 | 2-aminopyridin-6-yl | 0 | H | $NHSO_2C_6H_4$-(2-F) | |
| 2040 | 2-aminopyridin-6-yl | 0 | H | $NHSO_2C_6H_4$-(3-F) | |
| 2041 | 2-aminopyridin-6-yl | 0 | H | $NHSO_2C_6H_4$-(4-F) | |
| 2042 | 2-aminopyridin-6-yl | 0 | H | $NHSO_2$ (2-naphthyl) | |
| 2043 | 2-aminopyridin-6-yl | 0 | H | $NHSO_2$ (1-naphthyl) | |
| 2044 | 2-aminopyridin-6-yl | 0 | H | $NHSO_2CH{=}CHPh$ | |
| 2045 | 2-aminopyridin-6-yl | 0 | H | $NHSO_2CH_2Ph$ | |
| 2046 | 2-aminopyridin-6-yl | 0 | H | $NHSO_2CH_2CH{=}CH{-}Ph$ | |
| 2047 | 2-aminopyridin-6-yl | 0 | H | $NHSO_2$-n-Bu | |
| 2048 | 2-aminopyridin-6-yl | 0 | H | $NHSO_2$-i-Bu | |
| 2049 | 2-aminopyridin-6-yl | 0 | H | $NHSO_2$-t-Bu | |
| 2050 | 2-aminopyridin-6-yl | 0 | H | $NHSO_2NHPh$ | |
| 2051 | 2-aminopyridin-6-yl | 0 | H | $NHSO_2NHC_6H_4$-(2-$CH_3$) | |
| 2052 | 2-aminopyridin-6-yl | 0 | H | $NHSO_2NHC_6H_4$-(3-$CH_3$) | |
| 2053 | 2-aminopyridin-6-yl | 0 | H | $NHSO_2NHC_6H_4$-(4-$CH_3$) | |
| 2054 | 2-aminopyridin-6-yl | 0 | H | $NHSO_2NH$ (2-pyridyl) | |
| 2055 | 2-aminopyridin-6-yl | 0 | H | $NHSO_2NH$ (3-pyridyl) | |
| 2056 | 2-aminopyridin-6-yl | 0 | H | $NHSO_2NH$ (4-pyridyl) | |
| 2057 | 2-aminopyridin-6-yl | 0 | H | $NHSO_2NH$ (2-thiazolyl) | |
| 2058 | 2-aminopyridin-6-yl | 0 | H | $NHSO_2NH$ (4-thiazolyl) | |
| 2059 | 2-aminopyridin-6-yl | 0 | H | $NHSO_2NH$ (4-isoxazolyl) | |
| 2060 | 2-aminopyridin-6-yl | 0 | H | $NHSO_2$[4-(3,5-dimethyl) isoxazolyl] | |
| 2061 | 2-aminopyridin-6-yl | 0 | H | $NHSO_2NHC_6H_4$-(2-Br) | |
| 2062 | 2-aminopyridin-6-yl | 0 | H | $NHSO_2NHC_6H_4$-(3-Br) | |
| 2063 | 2-aminopyridin-6-yl | 0 | H | $NHSO_2NHC_6H_4$-(4-Br) | |
| 2064 | 2-aminopyridin-6-yl | 0 | H | $NHSO_2NHC_6H_4$-(3-F) | |
| 2065 | 2-aminopyridin-6-yl | 0 | H | $NHSO_2NHC_6H_4$-(4-F) | |
| 2066 | 2-aminopyridin-6-yl | 0 | H | $NHSO_2NH$ (2-naphthyl) | |
| 2067 | 2-aminopyridin-6-yl | 0 | H | $NHSO_2NH$ (1-naphthyl) | |
| 2068 | 2-aminopyridin-6-yl | 0 | H | $NHSO_2NHCH{=}CH{-}Ph$ | |
| 2069 | 2-aminopyridin-6-yl | 0 | H | $NHSO_2NHCH_2Ph$ | |
| 2070 | 2-aminopyridin-6-yl | 0 | H | $NHSO_2NHCH_2CH{=}CH{-}Ph$ | |
| 2071 | 2-aminopyridin-6-yl | 0 | H | $NHSO_2NH$-n-Bu | |
| 2072 | 2-aminopyridin-6-yl | 0 | H | $NHSO_2NH$-i-Bu | |
| 2073 | 2-aminopyridin-6-yl | 0 | H | $NHSO_2NH$-t-Bu | |
| 2074 | 2-aminopyridin-6-yl | 1 | H | $NHCO_2Bn$ | 497.2 |
| 2075 | 2-aminopyridin-6-yl | 1 | H | $NHCO_2CH_2C_6H_4$-(2-$CH_3$) | |
| 2076 | 2-aminopyridin-6-yl | 1 | H | $NHCO_2CH_2C_6H_4$-(3-$CH_3$) | |
| 2077 | 2-aminopyridin-6-yl | 1 | H | $NHCO_2CH_2C_6H_4$-(4-$CH_3$) | |
| 2078 | 2-aminopyridin-6-yl | 1 | H | $NHCO_2CH_2$ (2-pyridinyl) | |
| 2079 | 2-aminopyridin-6-yl | 1 | H | $NHCO_2CH_2$ (3-pyridinyl) | |

TABLE 2-continued

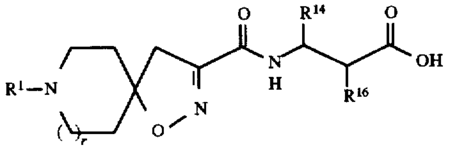

| Ex. No. | $R^{1a}$ | r | $R^{14}$ | $R^{15}$ | MS |
|---|---|---|---|---|---|
| 2080 | 2-aminopyridin-6-yl | 1 | H | $NHCO_2CH_2$ (4-pyridinyl) | |
| 2081 | 2-aminopyridin-6-yl | 1 | H | $NHCO_2CH_2$ (2-thiazolyl) | |
| 2082 | 2-aminopyridin-6-yl | 1 | H | $NHCO_2CH_2$ (4-thiazolyl) | |
| 2083 | 2-aminopyridin-6-yl | 1 | H | $NHCO_2CH_2$ (5-thiazolyl) | |
| 2084 | 2-aminopyridin-6-yl | 1 | H | $NHCO_2CH_2$(4-isoxazolyl) | |
| 2085 | 2-aminopyridin-6-yl | 1 | H | $NHCO_2CH_2$ (2-thienyl) | |
| 2086 | 2-aminopyridin-6-yl | 1 | H | $NHCO_2$n-Bu | |
| 2087 | 2-aminopyridin-6-yl | 1 | H | $NHCO_2$i-Bu | |
| 2088 | 2-aminopyridin-6-yl | 1 | H | $NHCO_2$t-Bu | |
| 2089 | 2-aminopyridin-6-yl | 1 | H | $NHCOCH_2Ph$ | |
| 2090 | 2-aminopyridin-6-yl | 1 | H | $NHCOCH_2C_6H_4$-(2-$CH_3$) | |
| 2091 | 2-aminopyridin-6-yl | 1 | H | $NHCOCH_2C_6H_4$-(3-$CH_3$) | |
| 2092 | 2-aminopyridin-6-yl | 1 | H | $NHCOCH_2C_6H_4$-(4-$CH_3$) | |
| 2093 | 2-aminopyridin-6-yl | 1 | H | $NHCOCH_2$ (2-pyridinyl) | |
| 2094 | 2-aminopyridin-6-yl | 1 | H | $NHCOCH_2$ (3-pyridinyl) | |
| 2095 | 2-aminopyridin-6-yl | 1 | H | $NHCOCH_2$ (4-pyridinyl) | |
| 2096 | 2-aminopyridin-6-yl | 1 | H | $NHCOCH_2$ (2-thiazolyl) | |
| 2097 | 2-aminopyridin-6-yl | 1 | H | $NHCOCH_2$ (4-thiazolyl) | |
| 2098 | 2-aminopyridin-6-yl | 1 | H | $NHCOCH_2$ (5-thiazolyl) | |
| 2099 | 2-aminopyridin-6-yl | 1 | H | $NHCOCH_2$ (4-isoxazolyl) | |
| 2100 | 2-aminopyridin-6-yl | 1 | H | $NHCOCH_2$ (2-thienyl) | |
| 2101 | 2-aminopyridin-6-yl | 1 | H | NHCOn-Bu | |
| 2102 | 2-aminopyridin-6-yl | 1 | H | NHCOt-Bu | |
| 2103 | 2-aminopyridin-6-yl | 1 | H | $NHSO_2Ph$ | |
| 2104 | 2-aminopyridin-6-yl | 1 | H | $NHSO_2C_6H_4$-(2-$CH_3$) | |
| 2105 | 2-aminopyridin-6-yl | 1 | H | $NHSO_2C_6H_4$-(3-$CH_3$) | |
| 2106 | 2-aminopyridin-6-yl | 1 | | $NHSO_2C_6H_4$-(4-$CH_3$) | |
| 2107 | 2-aminopyridin-6-yl | 1 | H | $NHSO_2$ (2-pyridyl) | |
| 2108 | 2-aminopyridin-6-yl | 1 | H | $NHSO_2$ (3-pyridyl) | |
| 2109 | 2-aminopyridin-6-yl | 1 | H | $NHSO_2$ (4-pyridyl) | |
| 2110 | 2-aminopyridin-6-yl | 1 | H | $NHSO_2$ (2-thiazolyl) | |
| 2111 | 2-aminopyridin-6-yl | 1 | H | $NHSO_2$ (4-thiazolyl) | |
| 2112 | 2-aminopyridin-6-yl | 1 | H | $NHSO_2$ (4-isoxazolyl) | |
| 2113 | 2-aminopyridin-6-yl | 1 | H | $NHSO_2$-[4-(3,5-dimethyl) isoxazolyl] | |
| 2114 | 2-aminopyridin-6-yl | 1 | H | $NHSO_2C_6H_4$-(2-Br) | |
| 2115 | 2-aminopyridin-6-yl | 1 | H | $NHSO_2C_6H_4$-(3-Br) | |
| 2116 | 2-aminopyridin-6-yl | 1 | H | $NHSO_2C_6H_4$-(4-Br) | |
| 2117 | 2-aminopyridin-6-yl | 1 | H | $NHSO_2C_6H_4$-(2-F) | |
| 2118 | 2-aminopyridin-6-yl | 1 | H | $NHSO_2C_6H_4$-(3-F) | |
| 2119 | 2-aminopyridin-6-yl | 1 | H | $NHSO_2C_6H_4$-(4-F) | |
| 2120 | 2-aminopyridin-6-yl | 1 | H | $NHSO_2$ (2-naphthyl) | |
| 2121 | 2-aminopyridin-6-yl | 1 | H | $NHSO_2$ (1-naphthyl) | |
| 2122 | 2-aminopyridin-6-yl | 1 | H | $NHSO_2CH{=}CH{-}Ph$ | |
| 2123 | 2-aminopyridin-6-yl | 1 | H | $NHSO_2CH_2Ph$ | |
| 2124 | 2-aminopyridin-6-yl | 1 | H | $NHSO_2{-}CH_2CH{=}CH{-}Ph$ | |
| 2125 | 2-aminopyridin-6-yl | 1 | H | $NHSO_2$-n-Bu | |
| 2126 | 2-aminopyridin-6-yl | 1 | H | $NHSO_2$-i-Bu | |
| 2127 | 2-aminopyridin-6-yl | 1 | H | $NHSO_2$-t-Bu | |
| 2128 | 2-aminopyridin-6-yl | 1 | H | $NHSO_2NHPh$ | |
| 2129 | 2-aminopyridin-6-yl | 1 | H | $NHSO_2NHC_6H_4$-(2-$CH_3$) | |
| 2130 | 2-aminopyridin-6-yl | 1 | H | $NHSO_2NHC_6H_4$-(3-$CH_3$) | |
| 2131 | 2-aminopyridin-6-yl | 1 | H | $NHSO_2NHC_6H_4$-(4-$CH_3$) | |
| 2132 | 2-aminopyridin-6-yl | 1 | H | $NHSO_2NH$ (2-pyridyl) | |
| 2133 | 2-aminopyridin-6-yl | 1 | H | $NHSO_2NH$ (3-pyridyl) | |
| 2134 | 2-aminopyridin-6-yl | 1 | H | $NHSO_2NH$ (4-pyridyl) | |
| 2135 | 2-aminopyridin-6-yl | 1 | H | $NHSO_2NH$ (2-thiazolyl) | |
| 2136 | 2-aminopyridin-6-yl | 1 | H | $NHSO_2NH$-(4-thiazolyl) | |
| 2137 | 2-aminopyridin-6-yl | 1 | H | $NHSO_2NH$ (4-isoxazolyl) | |
| 2138 | 2-aminopyridin-6-yl | 1 | H | $NHSO_2$-[4-(3,5- | |

TABLE 2-continued

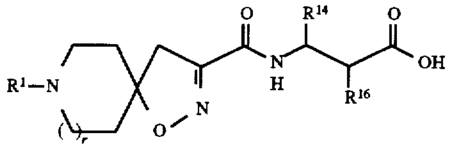

| Ex. No. | $R^{1a}$ | r | $R^{14}$ | $R^{15}$ | MS |
|---|---|---|---|---|---|
| | | | | dimethyl) isoxazolyl] | |
| 2139 | 2-aminopyridin-6-yl | 1 | H | $NHSO_2NHC_6H_4$-(2-Br) | |
| 2140 | 2-aminopyridin-6-yl | 1 | H | $NHSO_2NHC_6H_4$-(3-Br) | |
| 2141 | 2-aminopyridin-6-yl | 1 | H | $NHSO_2NHC_6H_4$-(4-Br) | |
| 2142 | 2-aminopyridin-6-yl | 1 | H | $NHSO_2NHC_6H_4$-(3-F) | |
| 2143 | 2-aminopyridin-6-yl | 1 | H | $NHSO_2NHC_6H_4$-(4-F) | |
| 2144 | 2-aminopyridin-6-yl | 1 | H | $NHSO_2NH$ (2-naphthyl) | |
| 2145 | 2-aminopyridin-6-yl | 1 | H | $NHSO_2NH$) 1-naphthyl) | |
| 2146 | 2-aminopyridin-6-yl | 1 | H | $NHSO_2NHCH{=}CH{-}Ph$ | |
| 2147 | 2-aminopyridin-6-yl | 1 | H | $NHSO_2NHCH_2Ph$ | |
| 2148 | 2-aminopyridin-6-yl | 1 | H | $NHSO_2NHCH_2CH{=}CH{-}Ph$ | |
| 2149 | 2-aminopyridin-6-yl | 1 | H | $NHSO_2NH$-n-Bu | |
| 2150 | 2-aminopyridin-6-yl | 1 | H | $NHSO_2NH$-i-Bu | |
| 2151 | 2-aminopyridin-6-yl | 1 | H | $NHSO_2NH$-t-Bu | |
| 2152 | 2-aminoimidazol-5-yl | 0 | H | NHCOOBn | |
| 2153 | 2-aminoimidazol-5-yl | 0 | H | $NHCO_2CH_2C_6H_4$-(2-$CH_3$) | |
| 2154 | 2-aminoimidazol-5-yl | 0 | H | $NHCO_2CH_2C_6H_4$-(3-$CH_3$) | |
| 2155 | 2-aminoimidazol-5-yl | 0 | H | $NHCO_2CH_2C_6H_4$-(4-$CH_3$) | |
| 2156 | 2-aminoimidazol-5-yl | 0 | H | $NHCO_2CH_2$ (2-pyridinyl) | |
| 2157 | 2-aminoimidazol-5-yl | 0 | H | $NHCO_2CH_2$ (3-pyridinyl) | |
| 2158 | 2-aminoimidazol-5-yl | 0 | H | $NHCO_2CH_2$ (4-pyridinyl) | |
| 2159 | 2-aminoimidazol-5-yl | 0 | H | $NHCO_2CH_2$ (2-thiazolyl) | |
| 2160 | 2-aminoimidazol-5-yl | 0 | H | $NHCO_2CH_2$ (4-thiazolyl) | |
| 2161 | 2-aminoimidazol-5-yl | 0 | H | $NHCO_2CH_2$ (5-thiazolyl) | |
| 2162 | 2-aminoimidazol-5-yl | 0 | H | $NHCO_2CH_2$ (4-isoxazolyl) | |
| 2163 | 2-aminoimidazol-5-yl | 0 | H | $NHCO_2CH_2$ (2-thienyl) | |
| 2164 | 2-aminoimidazol-5-yl | 0 | H | $NHCO_2$n-Bu | |
| 2165 | 2-aminoimidazol-5-yl | 0 | H | $NHCO_2$i-Bu | |
| 2166 | 2-aminoimidazol-5-yl | 0 | H | $NHCO_2$t-Bu | |
| 2167 | 2-aminoimidazol-5-yl | | H | $NHSO_2Ph$ | |
| 2168 | 2-aminoimidazol-5-yl | 0 | H | $NHSO_2C_6H_4$-(2-$CH_3$) | |
| 2169 | 2-aminoimidazol-5-yl | 0 | H | $NHSO_2C_6H_4$-(3-$CH_3$) | |
| 2170 | 2-aminoimidazol-5-yl | 0 | H | $NHSO_2C_6H_4$-(4-$CH_3$) | |
| 2171 | 2-aminoimidazol-5-yl | 0 | H | $NHSO_2$ (2-pyridyl) | |
| 2172 | 2-aminoimidazol-5-yl | 0 | H | $NHSO_2$ (3-pyridyl) | |
| 2173 | 2-aminoimidazol-5-yl | 0 | H | $NHSO_2$ (4-pyridyl) | |
| 2174 | 2-aminoimidazol-5-yl | 0 | H | $NHSO_2$ (2-thiazolyl) | |
| 2175 | 2-aminoimidazol-5-yl | 0 | H | $NHSO_2$ (4-thiazolyl) | |
| 2176 | 2-aminoimidazol-5-yl | 0 | H | $NHSO_2$ (4-isoxazolyl) | |
| 2177 | 2-aminoimidazol-5-yl | 0 | H | $NHSO_2$-[4-(3,5-dimethyl) isoxazolyl] | |
| 2178 | 2-aminoimidazol-5-yl | 0 | H | $NHSO_2C_6H_4$-(2-Br) | |
| 2179 | 2-aminoimidazol-5-yl | 0 | H | $NHSO_2C_6H_4$-(3-Br) | |
| 2180 | 2-aminoimidazol-5-yl | 0 | H | $NHSO_2C_6H_4$-(2-F) | |
| 2181 | 2-aminoimidazol-5-yl | 0 | H | $NHSO_2C_6H_4$-(3-F) | |
| 2182 | 2-aminoimidazol-5-yl | 0 | H | $NHSO_2C_6H_4$-(4-F) | |
| 2183 | 2-aminoimidazol-5-yl | 0 | H | $NHSO_2$ (2-naphthyl) | |
| 2184 | 2-aminoimidazol-5-yl | 0 | H | $NHSO_2$ (1-naphthyl) | |
| 2185 | 2-aminoimidazol-5-yl | 0 | H | $NHSO_2CH{=}CHPh$ | |
| 2186 | 2-aminoimidazol-5-yl | 0 | H | $NHSO_2CH_2Ph$ | |
| 2187 | 2-aminoimidazol-5-yl | 0 | H | $NHSO_2CH_2CH{=}CHPh$ | |
| 2188 | 2-aminoimidazol-5-yl | 0 | H | $NHSO_2$-n-Bu | |
| 2189 | 2-aminoimidazol-5-yl | 0 | H | $NHSO_2$-i-Bu | |
| 2190 | 2-aminoimidazol-5-yl | 1 | H | NHCOOBn | |
| 2191 | 2-aminoimidazol-5-yl | 1 | H | $NHCO_2CH_2C_6H_4$-(2-$CH_3$) | |
| 2192 | 2-aminoimidazol-5-yl | 1 | H | $NHCO_2CH_2C_6H_4$-(3-$CH_3$) | |
| 2193 | 2-aminoimidazol-5-yl | 1 | H | $NHCO_2CH_2C_6H_4$-(4-$CH_3$) | |
| 2194 | 2-aminoimidazol-5-yl | 1 | H | $NHCO_2CH_2$ (2-pyridinyl) | |
| 2195 | 2-aminoimidazol-5-yl | 1 | H | $NHCO_2CH_2$ (3-pyridinyl) | |

TABLE 2-continued

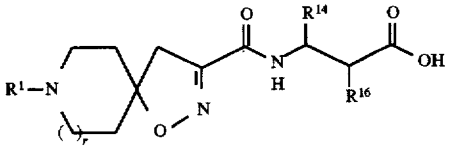

| Ex. No. | $R^{1a}$ | r | $R^{14}$ | $R^{15}$ | MS |
|---|---|---|---|---|---|
| 2196 | 2-aminoimidazol-5-yl | 1 | H | $NHCO_2CH_2$ (4-pyridinyl) | |
| 2197 | 2-aminoimidazol-5-yl | 1 | H | $NHCO_2CH_2$ (2-thiazolyl) | |
| 2198 | 2-aminoimidazol-5-yl | 1 | H | $NHCO_2CH_2$ (4-thiazolyl) | |
| 2199 | 2-aminoimidazol-5-yl | 1 | H | $NHCO_2CH_2$ (5-thiazolyl) | |
| 2200 | 2-aminoimidazol-5-yl | 1 | H | $NHCO_2CH_2$ (4-isoxazolyl) | |
| 2201 | 2-aminoimidazol-5-yl | 1 | H | $NHCO_2CH_2$ (2-thienyl) | |
| 2202 | 2-aminoimidazol-5-yl | 1 | H | $NHCO_2$n-Bu | |
| 2203 | 2-aminoimidazol-5-yl | 1 | H | $NHCO_2$i-Bu | |
| 2204 | 2-aminoimidazol-5-yl | 1 | H | $NHCO_2$t-Bu | |
| 2205 | 2-aminoimidazol-5-yl | 1 | H | $NHSO_2Ph$ | |
| 2206 | 2-aminoimidazol-5-yl | 1 | H | $NHSO_2C_6H_4$-(2-$CH_3$) | |
| 2207 | 2-aminoimidazol-5-yl | 1 | H | $NHSO_2C_6H_4$-(3-$CH_3$) | |
| 2208 | 2-aminoimidazol-5-yl | 1 | H | $NHSO_2C_6H_4$-(4-$CH_3$) | |
| 2209 | 2-aminoimidazol-5-yl | 1 | H | $NHSO_2$ (2-pyridyl) | |
| 2210 | 2-aminoimidazol-5-yl | 1 | H | $NHSO_2$ (3-pyridyl) | |
| 2211 | 2-aminoimidazol-5-yl | 1 | H | $NHSO_2$ (4-pyridyl) | |
| 2212 | 2-aminoimidazol-5-yl | 1 | H | $NHSO_2$ (2-thiaz-olyl) | |
| 2213 | 2-aminoimidazol-5-yl | 1 | H | $NHSO_2$ (4-isoxazolyl) | |
| 2214 | 2-aminoimidazol-5-yl | 1 | H | $NHSO_2$-[4-(3,5-dimethyl) isoxazolyl] | |
| 2215 | 2-aminoimidazol-5-yl | 1 | H | $NHSO_2C_6H_4$-(2-Br) | |
| 2216 | 2-aminoimidazol-5-yl | 1 | H | $NHSO_2C_6H_4$-(3-Br) | |
| 2217 | 2-aminoimidazol-5-yl | 1 | H | $NHSO_2C_6H_4$-(2-F) | |
| 2218 | 2-aminoimidazol-5-yl | 1 | H | $NHSO_2C_6H_4$-(3-F) | |
| 2219 | 2-aminoimidazol-5-yl | 1 | H | $NHSO_2C_6H_4$-(4-F) | |
| 2220 | 2-aminoimidazol-5-yl | 1 | H | $NHSO_2$ (2-naphthyl) | |
| 2221 | 2-aminoimidazol-5-yl | 1 | H | $NHSO_2$ (1-naphthyl) | |
| 2222 | 2-aminoimidazol-5-yl | 1 | H | $NHSO_2CH{=}CHPh$ | |
| 2223 | 2-aminoimidazol-5-yl | 1 | H | $NHSO_2CH_2Ph$ | |
| 2224 | 2-aminoimidazol-5-yl | 1 | H | $NHSO_2CH_2CH{=}CHPh$ | |
| 2225 | 2-aminoimidazol-5-yl | 1 | H | $NHSO_2$-n-Bu | |
| 2226 | 2-aminoimidazol-5-yl | 1 | H | $NHSO_2$-i-Bu | |
| 2227 | 2-aminoimidazol-5-yl | 1 | H | $NHSO_2Ph$ | |
| 2228 | 2-aminoimidazol-5-yl | 1 | H | $NHSO_2C_6H_4$-(2-$CH_3$) | |
| 2229 | 2-aminoimidazol-5-yl | 1 | H | $NHSO_2C_6H_4$-(3-$CH_3$) | |
| 2230 | 2-aminoimidazol-5-yl | 1 | H | $NHSO_2C_6H_4$-(4-$CH_3$) | |
| 2231 | 2-aminoimidazol-5-yl | 1 | H | $NHSO_2$ (2-pyridyl) | |
| 2232 | 2-aminoimidazol-5-yl | 1 | H | $NHSO_2$ (3-pyridyl) | |
| 2233 | 2-aminoimidazol-5-yl | 1 | H | $NHSO_2$ (4-pyridyl) | |
| 2234 | 2-aminoimidazol-5-yl | 1 | H | $NHSO_2$ (2-thiazolyl) | |
| 2235 | 2-aminoimidazol-5-yl | 1 | H | $NHSO_2$ (4-isoxazolyl) | |
| 2236 | 2-aminoimidazol-5-yl | 1 | H | $NHSO_2$-[4-(3,5-dimethyl) isoxazolyl] | |
| 2237 | 2-aminoimidazol-5-yl | 1 | H | $NHSO_2C_6H_4$-(2-Br) | |
| 2238 | 2-aminoimidazol-5-yl | 1 | H | $NHSO_2C_6H_4$-(3-Br) | |
| 2239 | 2-aminoimidazol-5-yl | 1 | H | $NHSO_2C_6H_4$-(2-F) | |
| 2240 | 2-aminoimidazol-5-yl | 1 | H | $NHSO_2C_6H_4$-(3-F) | |
| 2241 | 2-aminoimidazol-5-yl | 1 | H | $NHSO_2C_6H_4$-(4-F) | |
| 2242 | 2-aminoimidazol-5-yl | 1 | H | $NHCO_2CH_2Ph$ | |
| 2243 | 2-aminoimidazol-5-yl | 1 | H | $NHCO_2$n-Bu | |
| 2244 | 2-aminoimidazol-5-yl | 1 | H | $NHCO_2$i-Bu | |
| 2245 | 2-aminothiazol-4-yl | 0 | H | $NHSO_2Ph$ | |
| 2246 | 2-aminothiazol-4-yl | 0 | H | $NHSO_2C_6H_4$-(2-$CH_3$) | |
| 2247 | 2-aminothiazol-4-yl | 0 | H | $NHSO_2C_6H_4$-(3-$CH_3$) | |
| 2248 | 2-aminothiazol-4-yl | 0 | H | $NHSO_2C_6H_4$-(4-$CH_3$) | |
| 2249 | 2-aminothiazol-4-yl | 0 | H | $NHSO_2$ (2-pyridyl) | |
| 2250 | 2-aminothiazol-4-yl | 0 | H | $NHSO_2$ (3-pyridyl) | |
| 2251 | 2-aminothiazol-4-yl | 0 | H | $NHSO_2$ (4-pyridyl) | |
| 2252 | 2-aminothiazol-4-yl | 0 | H | $NHSO_2$ (2-thiazolyl) | |
| 2253 | 2-aminothiazol-4-yl | 0 | H | $NHSO_2$ (4-isoxazolyl) | |
| 2254 | 2-aminothiazol-4-yl | 0 | H | $NHSO_2$-[4-(3,5-dimethyl) isoxazolyl] | |
| 2255 | 2-aminothiazol-4-yl | 0 | H | $NHSO_2C_6H_4$-(2-Br) | |

TABLE 2-continued

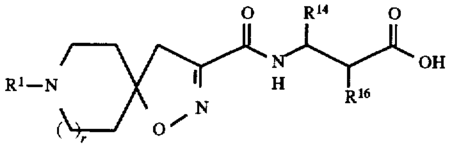

| Ex. No. | $R^{1a}$ | r | $R^{14}$ | $R^{15}$ | MS |
|---|---|---|---|---|---|
| 2256 | 2-aminothiazol-4-yl | 0 | H | $NHSO_2C_6H_4$-(3-Br) | |
| 2257 | 2-aminothiazol-4-yl | 0 | H | $NHSO_2C_6H_4$-(2-F) | |
| 2258 | 2-aminothiazol-4-yl | 0 | H | $NHSO_2C_6H_4$-(3-F) | |
| 2259 | 2-aminothiazol-4-yl | 0 | H | $NHSO_2C_6H_4$-(4-F) | |
| 2260 | 2-aminothiazol-4-yl | 0 | H | $NHCO_2CH_2Ph$ | |
| 2261 | 2-aminothiazol-4-yl | 0 | H | $NHCO_2$n-Bu | |
| 2262 | 2-aminothiazol-4-yl | 0 | H | $NHCO_2$i-Bu | |
| 2263 | 2-aminothiazol-4-yl | 1 | H | $NHSO_2Ph$ | |
| 2264 | 2-aminothiazol-4-yl | 1 | H | $NHSO_2C_6H_4$-(2-$CH_3$) | |
| 2265 | 2-aminothiazol-4-yl | 1 | H | $NHSO_2C_6H_4$-(3-$CH_3$) | |
| 2266 | 2-aminothiazol-4-yl | 1 | H | $NHSO_2C_6H_4$-(4-$CH_3$) | |
| 2267 | 2-aminothiazol-4-yl | 1 | H | $NHSO_2$ (2-pyridyl) | |
| 2268 | 2-aminothiazol-4-yl | 1 | H | $NHSO_2$ (3-pyridyl) | |
| 2269 | 2-aminothiazol-4-yl | 1 | H | $NHSO_2$ (4-pyridyl) | |
| 2270 | 2-aminothiazol-4-yl | 1 | H | $NHSO_2$ (2-thiazolyl) | |
| 2271 | 2-aminothiazol-4-yl | 1 | H | $NHSO_2$ (4-isoxazolyl) | |
| 2272 | 2-aminothiazol-4-yl | 1 | H | $NHSO_2$-[4-(3,5-dimethyl) isoxazolyl] | |
| 2273 | 2-aminothiazol-4-yl | 1 | H | $NHSO_2C_6H_4$-(2-Br) | |
| 2274 | 2-aminothiazol-4-yl | 1 | H | $NHSO_2C_6H_4$-(3-Br) | |
| 2275 | 2-aminothiazol-4-yl | 1 | H | $NHSO_2C_6H_4$-(2-F) | |
| 2276 | 2-aminothiazol-4-yl | 1 | H | $NHSO_2C_6H_4$-(3-F) | |
| 2277 | 2-aminothiazol-4-yl | 1 | H | $NHSO_2C_6H_4$-(4-F) | |
| 2278 | 2-aminothiazol-4-yl | 1 | H | $NHCO_2CH_2Ph$ | |
| 2279 | 2-aminothiazol-4-yl | 1 | H | $NHCO_2$n-Bu | |
| 2280 | 2-aminothiazol-4-yl | 1 | H | $NHCO_2$i-Bu | |
| 2281 | 2-aminopyridin-6-ylmethyl | 0 | H | $NHSO_2Ph$ | |
| 2282 | 2-aminopyridin-6-ylmethyl | 0 | H | $NHSO_2C_6H_4$-(2-$CH_3$) | |
| 2283 | 2-aminopyridin-6-ylmethyl | 0 | H | $NHSO_2C_6H_4$-(3-$CH_3$) | |
| 2284 | 2-aminopyridin-6-ylmethyl | 0 | H | $NHSO_2C_6H_4$-(4-$CH_3$) | |
| 2285 | 2-aminopyridin-6-ylmethyl | 0 | H | $NHSO_2$ (2-naphthyl) | |
| 2286 | 2-aminopyridin-6-ylmethyl | 0 | H | $NHSO_2$ (1-naphthyl | |
| 2287 | 2-aminopyridin-6-ylmethyl | 0 | H | $NHSO_2$ (biphenyl) | |
| 2288 | 2-aminopyridin-6-ylmethyl | 0 | H | $NHSO_2$ (2,4,6-trimethylphenyl) | |
| 2289 | 2-aminopyridin-6-ylmethyl | 0 | H | $NHSO_2$ (2-thienyl) | |
| 2290 | 2-aminopyridin-6-ylmethyl | 0 | H | $NHSO_2$-[4-(3,5-dimethyl) isoxazolyl] | |
| 2291 | 2-aminopyridin-6-ylmethyl | 0 | H | $NHSO_2C_6H_4$-(2-Br) | |
| 2292 | 2-aminopyridin-6-ylmethyl | 0 | H | $NHSO_2C_6H_4$-(3-Br) | |
| 2293 | 2-aminopyridin-6-ylmethyl | 0 | H | $NHSO_2C_6H_4$-(2-F) | |
| 2294 | 2-aminopyridin-6 ylmethyl | 0 | H | $NHSO_2C_6H_4$-(3-F) | |
| 2295 | 2-aminopyridin-6-ylmethyl | 0 | H | $NHSO_2C_6H_4$-(4-F) | |
| 2296 | 2-aminopyridin-6-ylmethyl | 0 | H | $NHCO_2CH_2Ph$ | |
| 2297 | 2-aminopyridin-6-ylmethyl | 0 | H | $NHCO_2$n-Bu | |
| 2298 | 2-aminopyridin-6-ylmethyl | 0 | H | $NHCO_2$i-Bu | |
| 2299 | 2-aminopyridin-6-ylmethyl | 1 | H | $NHSO_2Ph$ | |
| 2300 | 2-aminopyridin-6-ylmethyl | 1 | H | $NHSO_2C_6H_4$-(2-$CH_3$) | |
| 2301 | 2-aminopyridin-6-ylmethyl | 1 | H | $NHSO_2C_6H_4$-(3-$CH_3$) | |

TABLE 2-continued

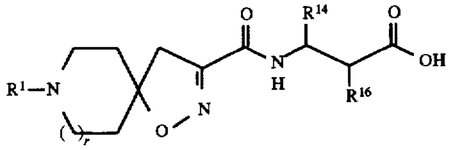

| Ex. No. | $R^{1a}$ | r | $R^{14}$ | $R^{15}$ | MS |
|---|---|---|---|---|---|
| 2302 | 2-aminopyridin-6-ylmethyl | 1 | H | $NHSO_2C_6H_4$-(4-$CH_3$) | |
| 2303 | 2-aminopyridin-6-ylmethyl | 1 | H | $NHSO_2$ (2-naphthyl) | |
| 2304 | 2-aminopyridin-6-ylmethyl | 1 | H | $NHSO_2$ (1-naphthyl) | |
| 2305 | 2-aminopyridin-6-ylmethyl | 1 | H | $NHSO_2$ (biphenyl) | |
| 2306 | 2-aminopyridin-6-ylmethyl | 1 | H | $NHSO_2$ (2,4,6-trimethylphenyl) | |
| 2307 | 2-aminopyridin-6-ylmethyl | 1 | H | $NHSO_2$ (2-thienyl) | |
| 2308 | 2-aminopyridin-6-ylmethyl | 1 | H | $NHSO_2$-[4-(3,5-dimethyl) isoxazolyl] | |
| 2309 | 2-aminopyridin-6-ylmethyl | 1 | H | $NHSO_2C_6H_4$-(2-Br) | |
| 2310 | 2-aminopyridin-6-ylmethyl | 1 | H | $NHSO_2C_6H_4$-(3-Br) | |
| 2311 | 2-aminopyridin-6-ylmethyl | 1 | H | $NHSO_2C_6H_4$-(2-F) | |
| 2312 | 2-aminopyridin-6-ylmethyl | 1 | H | $NHSO_2C_6H_4$-(3-F) | |
| 2313 | 2-aminopyridin-6-ylmethyl | 1 | H | $NHSO_2C_6H_4$-(4-F) | |
| 2314 | 2-aminopyridin-6-ylmethyl | 1 | H | $NHCO_2CH_2Ph$ | |
| 2315 | 2-aminopyridin-6-ylmethyl | 1 | H | $NHCO_2$n-Bu | |
| 2316 | 2-aminopyridin-6-ylcarbonyl | 0 | H | $NHSO_2Ph$ | |
| 2317 | 2-aminopyridin-6-ylcarbonyl | 0 | H | $NHSO_2C_6H_4$-(2-$CH_3$) | |
| 2318 | 2-aminopyridin-6-ylcarbonyl | 0 | H | $NHSO_2C_6H_4$-(3-$CH_3$) | |
| 2319 | 2-aminopyridin-6-ylcarbonyl | 0 | H | $NHSO_2C_6H_4$-(4-$CH_3$) | |
| 2320 | 2-aminopyridin-6-ylcarbonyl | 0 | H | $NHSO_2$ (2-naphthyl) | |
| 2321 | 2-aminopyridin-6-ylcarbonyl | 0 | H | $NHSO_2$ (1-naphthyl) | |
| 2322 | 2-aminopyridin-6-ylcarbonyl | 0 | H | $NHSO_2$ (biphenyl) | |
| 2323 | 2-aminopyridin-6-ylcarbonyl | 0 | H | $NHSO_2$ (2,4,6-trimethylphenyl) | |
| 2324 | 2-aminopyridin-6-ylcarbonyl | 0 | H | $NHSO_2$ (2-thienyl) | |
| 2325 | 2-aminopyridin-6-ylcarbonyl | 0 | H | $NHSO_2$-[4-(3,5-dimethyl) isoxazolyl] | |
| 2326 | 2-aminopyridin-6-ylcarbonyl | 0 | H | $NHSO_2C_6H_4$-(2-Br) | |
| 2327 | 2-aminopyridin-6-ylcarbonyl | 0 | H | $NHSO_2C_6H_4$-(3-Br) | |
| 2328 | 2-aminopyridin-6-ylcarbonyl | 0 | H | $NHSO_2C_6H_4$-(2-F) | |
| 2329 | 2-aminopyridin-6-ylcarbonyl | 0 | | $NHSO_2C_6H_4$-(3-F) | - |
| 2330 | 2-aminopyridin-6-ylcarbonyl | 0 | H | $NHSO_2C_6H_4$-(4-F) | |
| 2331 | 2-aminopyridin-6-ylcarbonyl | 0 | H | $NHCO_2CH_2Ph$ | |
| 2332 | 2-aminopyridin-6-ylcarbonyl | 0 | H | $NHCO_2$n-Bu | |
| 2333 | 2-aminopyridin-6-ylcarbonyl | 0 | H | $NHCO_2$i-Bu | |
| 2334 | 2-aminopyridin-6-ylcarbonyl | 1 | H | $NHSO_2Ph$ | |
| 2335 | 2-aminopyridin-6-ylcarbonyl | 1 | H | $NHSO_2C_6H_4$-(2-$CH_3$) | |

TABLE 2-continued

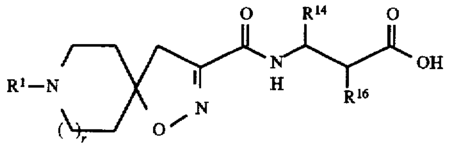

| Ex. No. | R[1a] | r | $R^{14}$ | $R^{15}$ | MS |
|---|---|---|---|---|---|
| 2336 | 2-aminopyridin-6-ylcarbonyl | 1 | H | $NHSO_2C_6H_4$-(3-$CH_3$) | |
| 2337 | 2-aminopyridin-6-ylcarbonyl | 1 | H | $NHSO_2C_6H_4$-(4-$CH_3$) | |
| 2338 | 2-aminopyridin-6-ylcarbonyl | 1 | H | $NHSO_2$ (2-naphthyl) | |
| 2339 | 2-aminopyridin-6-ylcarbonyl | 1 | H | $NHSO_2$ (1-naphthyl) | |
| 2340 | 2-aminopyridin-6-ylcarbonyl | 1 | H | $NHSO_2$ (biphenyl) | |
| 2341 | 2-aminopyridin-6-ylcarbonyl | 1 | H | $NHSO_2$ (2,4,6-trimethylphenyl) | |
| 2342 | 2-aminopyridin-6 ylcarbonyl | 1 | H | $NHSO_2$ (2-thienyl) | |
| 2343 | 2-aminopyridin-6-ylcarbonyl | 1 | H | $NHSO_2$-[4-(3,5-dimethyl) isoxazolyl] | |
| 2344 | 2-aminopyridin-6-ylcarbonyl | 1 | H | $NHSO_2C_6H_4$-(2-Br) | |
| 2345 | 2-aminopyridin-6-ylcarbonyl | 1 | H | $NHSO_2C_6H_4$-(3-Br) | |
| 2346 | 2-aminopyridin-6-ylcarbonyl | 1 | H | $NHSO_2C_6H_4$-(2-F) | |
| 2347 | 2-aminopyridin-6-ylcarbonyl | 1 | H | $NHSO_2C_6H_4$-(3-F) | |
| 2348 | 2-aminopyridin-6-ylcarbonyl | 1 | H | $NHSO_2C_6H_4$-(4-F) | |
| 2349 | 2-aminopyridin-6-ylcarbonyl | 1 | H | $NHCO_2CH_2Ph$ | |
| 2350 | 2-aminopyridin-6-ylcarbonyl | 1 | H | $NHCO_2$n-Bu | |
| 2351 | 2-aminoimidazol-5-ylmethyl | 1 | H | $NHSO_2Ph$ | |
| 2352 | 2-aminoimidazol-5 ylmethyl | 1 | H | $NHSO_2C_6H_4$-(2-$CH_3$) | |
| 2353 | 2-aminoimidazol-5-ylmethyl | 1 | H | $NHSO_2C_6H_4$-(3-$CH_3$) | |
| 2354 | 2-aminoimidazol-5-ylmethyl | 1 | H | $NHSO_2C_6H_4$-(4-$CH_3$) | |
| 2355 | 2-aminoimidazol-5-ylmethyl | 1 | H | $NHSO_2$ (2-naphthyl) | |
| 2356 | 2-aminoimidazol-5-ylmethyl | 1 | H | $NHSO_2$ (1-naphthyl) | |
| 2357 | 2-aminoimidazol-5 ylmethyl | 1 | H | $NHSO_2$ (biphenyl) | |
| 2358 | 2-aminoimidazol-5-ylmethyl | 1 | H | $NHSO_2$ (2,4,6-trimethylphenyl) | |
| 2359 | 2-aminoimidazol-5-ylmethyl | 1 | H | $NHSO_2$ (2-thienyl) | |
| 2360 | 2-aminoimidazol-5 ylmethyl | 1 | H | $NHSO_2$-[4-(3,5-dimethyl) isoxazolyl] | |
| 2361 | 2-aminoimidazol-5-ylmethyl | 1 | H | $NHSO_2C_6H_4$-(2-Br) | |
| 2362 | 2-aminoimidazol-5-ylmethyl | 1 | H | $NHSO_2C_6H_4$-(3-Br) | |
| 2363 | 2-aminoimidazol-5-ylmethyl | 1 | H | $NHSO_2C_6H_4$-(2-F) | |
| 2364 | 2-aminoimidazol-5-ylmethyl | 1 | H | $NHSO_2C_6H_4$-(3-F) | |
| 2365 | 2-aminoimidazol-5-ylmethyl | 1 | H | $NHSO_2C_6H_4$-(4-F) | |
| 2366 | 2-aminoimidazol-5-ylmethyl | 1 | H | $NHCO_2CH_2Ph$ | |
| 2367 | 2-aminoimidazol-5-ylmethyl | 1 | H | $NHCO_2$n-Bu | |
| 2368 | 2-amino-1,3,4-triazol-5-yl-carbonyl | 0 | H | $NHSO_2Ph$ | |

TABLE 2-continued

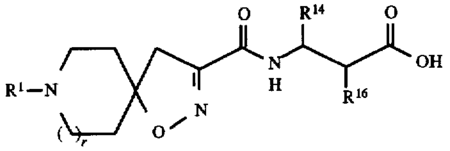

| Ex. No. | $R^{1a}$ | r | $R^{14}$ | $R^{15}$ | MS |
|---|---|---|---|---|---|
| 2369 | 4-imidazolyl-carbonyl | 0 | H | $NHSO_2Ph$ | |
| 2370 | 2-aminoimidazol-5-ylmethyl | 0 | H | $NHSO_2Ph$ | |

TABLE 3

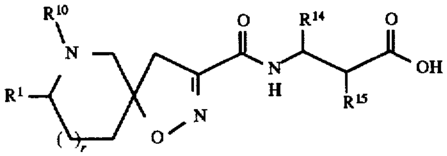

| Ex. No. | $R^1$ | r | $R^{10}$ | $R^{14}$ | $R^{15}$ | MS $(M + H)^+$ |
|---|---|---|---|---|---|---|
| 3001 | 2-pyridinylaminomethyl | 0 | Cbz | H | $NHSO_2Ph$ | |
| 3002 | 2-pyridinylaminomethyl | 0 | $SO_2Ph$ | H | $NHSO_2Ph$ | |
| 3003 | 2-pyridinylaminomethyl | 0 | $CO(CH_2)_2Ph$ | H | $NHSO_2Ph$ | |
| 3004 | 2-pyridinylaminomethyl | 0 | Bn | H | $NHSO_2Ph$ | |
| 3005 | 2-pyridinylaminomethyl | 0 | n-Bu | H | $NHSO_2Ph$ | |
| 3006 | 2-pyridinylaminomethyl | 0 | $COCH_2$(3-indolyl) | H | $NHSO_2Ph$ | |
| 3007 | 2-pyridinylaminomethyl | 0 | SO2-(biphenyl) | H | $NHSO_2Ph$ | |
| 3008 | 2-pyridinylaminomethyl | 0 | $CO_2$-n-Bu | H | $NHSO_2Ph$ | |
| 3009 | 2-pyridinylaminomethyl | 0 | $CO_2$-i-Bu | H | $NHSO_2Ph$ | |
| 3010 | 2-pyridinylaminomethyl | 0 | $CO_2$-t-Bu | H | $NHSO_2Ph$ | |
| 3011 | 2-pyridinylaminomethyl | 0 | H | H | $NHSO_2Ph$ | |
| 3012 | 2-pyridinylaminomethyl | 0 | $-(CH_2)_4NH_2$ | H | $NHSO_2Ph$ | |
| 3013 | 2-pyridinylaminomethyl | 0 | COPh | H | $NHSO_2Ph$ | |
| 3014 | 2-pyridinylaminomethyl | 0 | cyclopropylmethyl | H | $NHSO_2Ph$ | |
| 3015 | 2-pyridinylaminomethyl | 0 | $SO_2$-n-Bu | H | $NHSO_2Ph$ | |
| 3016 | 2-pyridinylaminomethyl | 0 | Cbz | H | $NHSO_2$-(2,4,6-trimethylphenyl) | 679.4 |
| 3017 | 2-pyridinylaminomethyl | 0 | $SO_2Ph$ | H | $NHSO_2$-(2,4,6-trimethylphenyl) | |
| 3018 | 2-pyridinylaminomethyl | 0 | $CO(CH_2)_2Ph$ | H | $NHSO_2$-(2,4,6-trimethylphenyl) | |
| 3019 | 2-pyridinylaminomethyl | 0 | Bn | H | $NHSO_2$-(2,4,6-trimethylphenyl) | |
| 3020 | 2-pyridinylaminomethyl | 0 | n-Bu | H | $NHSO_2$-(2,4,6-trimethylphenyl) | |
| 3021 | 2-pyridinylaminomethyl | 0 | $CO_2$-n-Bu | H | $NRSO_2$-(2,4,6-trimethylphenyl) | |
| 3022 | 2-pyridinylaminomethyl | 0 | $CO_2$-i-Bu | H | $NHSO_2$-(2,4,6-trimethylphenyl) | |
| 3023 | 2-pyridinylaminomethyl | 0 | $CO_2$-t-Bu | H | $NHSO_2$-(2,4,6-trimethylphenyl) | |
| 3024 | 2-pyridinylaminomethyl | 0 | H | H | $NHSO_2$-(2,4,6-trimethylphenyl) | 545.5 |
| 3025 | 2-pyridinylaminomethyl | 0 | $-(CH_2)_4NH_2$ | H | $NHSO_2$-(2,4,6-trimethylphenyl) | |
| 3026 | 2-pyridinylaminomethyl | 0 | COPh | H | $NHSO_2$-(2,4,6-trimethylphenyl) | |
| 3027 | 2-pyridinylaminomethyl | 0 | $SO_2$-n-Bu | H | $NHSO_2$-(2,4,6-trimethylphenyl) | |
| 3028 | 2-pyridinylaminomethyl | 0 | Cbz | H | NHCbz | |
| 3029 | 2-pyridinylaminomethyl | 0 | $SO_2Ph$ | H | NHCbz | |
| 3030 | 2-pyridinylaminomethyl | 0 | $CO(CH_2)_2Ph$ | H | NHCbz | |
| 3031 | 2-pyridinylaminomethyl | 0 | Bn | H | NHCbz | |
| 3032 | 2-pyridinylaminomethyl | 0 | n-Bu | H | NHCbz | |
| 3033 | 2-pyridinylaminomethyl | 0 | $CO_2$-n-Bu | H | NHCbz | |
| 3034 | 2-pyridinylaminomethyl | 0 | $CO_2$-i-Bu | H | NHCbz | |
| 3035 | 2-pyridinylaminomethyl | 0 | $CO_2$-t-Bu | H | NHCbz | |
| 3036 | 2-pyridinylaminomethyl | 0 | H | H | NHCbz | |
| 3037 | 2-pyridinylaminomethyl | 0 | $-(CH_2)_4NH_2$ | H | NHCbz | |
| 3038 | 2-pyridinylaminomethyl | 0 | COPh | H | NHCbz | |
| 3039 | 2-pyridinylaminomethyl | 0 | $SO_2$-n-Bu | H | NHCbz | |
| 3040 | 2-imidazolylaminomethyl | 0 | Cbz | H | $NHSO_2Ph$ | |
| 3041 | 2-imidazolylaminomethyl | 0 | $SO_2Ph$ | H | $NHSO_2Ph$ | |
| 3042 | 2-imidazolylaminomethyl | 0 | $CO(CH_2)_2Ph$ | H | $NHSO_2Ph$ | |
| 3043 | 2-imidazolylaminomethyl | 0 | Bn | H | $NHSO_2Ph$ | |
| 3044 | 2-imidazolylaminomethyl | 0 | n-Bu | H | $NHSO_2Ph$ | |
| 3045 | 2-imidazolylaminomethyl | 0 | $COCH_2$(3-indolyl) | H | $NHSO_2Ph$ | |
| 3046 | 2-imidazolylaminomethyl | 0 | $SO_2$-(biphenyl) | H | $NHSO_2Ph$ | |
| 3047 | 2-imidazolylaminomethyl | 0 | $CO_2$-n-Bu | H | $NHSO_2Ph$ | |
| 3048 | 2-imidazolylaminomethyl | 0 | $CO_2$-i-Bu | H | $NHSO_2Ph$ | |

TABLE 3-continued

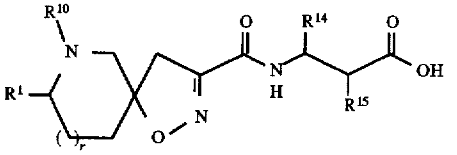

| Ex. No. | $R^1$ | r | $R^{10}$ | $R^{14}$ | $R^{15}$ | MS $(M + H)^+$ |
|---|---|---|---|---|---|---|
| 3049 | 2-imidazolylaminomethyl | 0 | $CO_2$-t-Bu | H | $NHSO_2Ph$ | |
| 3050 | 2-imidazolylaminomethyl | 0 | H | H | $NHSO_2Ph$ | 492.3 |
| 3051 | 2-imidazolylaminomethyl | 0 | $-(CH_2)_4NH_2$ | H | $NHSO_2Ph$ | |
| 3052 | 2-imidazolylaminomethyl | 0 | COPh | H | $NHSO_2Ph$ | |
| 3053 | 2-imidazolylaminomethyl | 0 | cyclopropylmethyl | H | $NHSO_2Ph$ | |
| 3054 | 2-imidazolylaminomethyl | 0 | $SO_2$-n-Bu | H | $NHSO_2Ph$ | |
| 3055 | 2-imidazolylaminomethyl | 0 | Cbz | H | $NHSO_2$-(2,4,6-trimethylphenyl) | 668.4 |
| 3056 | 2-imidazolylaminomethyl | 0 | $SO_2Ph$ | H | $NHSO_2$-(2,4,6-trimethylphenyl) | |
| 3057 | 2-imidazolylaminomethyl | 0 | $CO(CH_2)_2Ph$ | H | $NHSO_2$-(2,4,6-trimethylphenyl) | |
| 3058 | 2-imidazolylaminomethyl | 0 | Bn | H | $NHSO_2$-(2,4,6-trimethylphenyl) | |
| 3059 | 2-imidazolylaminomethyl | 0 | n-Bu | H | $NHSO_2$-(2,4,6-trimethylphenyl) | |
| 3060 | 2-imidazolylaminomethyl | 0 | $CO_2$-n-Bu | H | $NHSO_2$-(2,4,6-trimethylphenyl) | |
| 3061 | 2-imidazolylaminomethyl | 0 | $CO_2$-i-Bu | H | $NHSO_2$-(2,4,6-trimethylphenyl) | |
| 3062 | 2-imidazolylaminomethyl | 0 | $CO_2$-t-Bu | H | $NHSO_2$-(2,4,6-trimethylphenyl) | |
| 3063 | 2-imidazolylaminomethyl | 0 | H | H | $NHSO_2$-(2,4,6-trimethylphenyl) | 534.4 |
| 3064 | 2-imidazolylaminomethyl | 0 | $-(CH_2)_4NH_2$ | H | $NHSO_2$-(2,4,6-trimethylphenyl) | |
| 3065 | 2-imidazolylaminomethyl | 0 | COPh | H | $NHSO_2$-(2,4,6-trimethylphenyl) | |
| 3066 | 2-imidazolylaminomethyl | 0 | $SO_2$-n-Bu | H | $NHSO_2$-(2,4,6-trimethylphenyl) | |
| 3067 | 2-imidazolylaminomethyl | 0 | Cbz | H | NHCbz | |
| 3068 | 2-imidazolylaminomethyl | 0 | $SO_2Ph$ | H | NHCbz | |
| 3069 | 2-imidazolylaminomethyl | 0 | $CO(CH_2)_2Ph$ | H | NHCbz | |
| 3070 | 2-imidazolylaminomethyl | 0 | Bn | H | NHCbz | |
| 3071 | 2-imidazolylaminomethyl | 0 | n-Bu | H | NHCbz | |
| 3072 | 2-imidazolylaminomethyl | 0 | $CO_2$-n-Bu | H | NHCbz | |
| 3073 | 2-imidazolylaminomethyl | 0 | $CO_2$-i-Bu | H | NHCbz | |
| 3074 | 2-imidazolylaminomethyl | 0 | $CO_2$-t-Bu | H | NHCbz | |
| 3075 | 2-imidazolylaminomethyl | 0 | H | H | NHCbz | |
| 3076 | 2-imidazolylaminomethyl | 0 | $-(CH_2)_4NH_2$ | H | NHCbz | |
| 3077 | 2-imidazolylaminomethyl | 0 | COPh | H | NHCbz | |
| 3078 | 2-imidazolylaminomethyl | 0 | $SO_2$-n-Bu | H | NHCbz | |
| 3079 | 2-imidazolinylaminomethyl | 0 | Cbz | H | $NHSO_2Ph$ | |
| 3080 | 2-imidazolinylaminomethyl | 0 | $SO_2Ph$ | H | $NHSO_2Ph$ | |
| 3081 | 2-imidazolinylaminomethyl | 0 | $CO(CH_2)_2Ph$ | H | $NHSO_2Ph$ | |
| 3082 | 2-imidazolinylaminomethyl | 0 | Bn | H | $NHSO_2Ph$ | |
| 3083 | 2-imidazolinylaminomethyl | 0 | n-Bu | H | $NHSO_2Ph$ | |
| 3084 | 2-imidazolinylaminomethyl | 0 | $COCH_2$(3-indolyl) | H | $NHSO_2Ph$ | |
| 3085 | 2-imidazolinylaminomethyl | 0 | $SO_2$-(biphenyl) | H | $NHSO_2Ph$ | |
| 3086 | 2-imidazolinylaminomethyl | 0 | $CO_2$-n-Bu | H | $NHSO_2Ph$ | |
| 3087 | 2-imidazolinylaminomethyl | 0 | $CO_2$-i-Bu | H | $NHSO_2Ph$ | |
| 3088 | 2-imidazolinylaminomethyl | 0 | $CO_2$-t-Bu | H | $NHSO_2Ph$ | |
| 3089 | 2-imidazolinylaminomethyl | 0 | H | H | $NHSO_2Ph$ | |
| 3090 | 2-imidazolinylaminomethyl | 0 | $-(CH_2)_4NH_2$ | H | $NHSO_2Ph$ | |
| 3091 | 2-imidazolinylaminomethyl | 0 | COPh | H | $NHSO_2Ph$ | |
| 3092 | 2-imidazolinylaminomethyl | 0 | cyclopropylmethyl | H | $NHSO_2Ph$ | |
| 3093 | 2-imidazolinylaminomethyl | 0 | $SO_2$-n-Bu | H | $NHSO_2Ph$ | |
| 3094 | 2-imidazolinylaminomethyl | 0 | Cbz | H | $NHSO_2$-(2,4,6-trimethylphenyl) | |
| 3095 | 2-imidazolinylaminomethyl | 0 | $SO_2Ph$ | H | $NHSO_2$-(2,4,6-trimethylphenyl) | |
| 3096 | 2-imidazolinylaminomethyl | 0 | $CO(CH_2)_2Ph$ | H | $NHSO_2$-(2,4,6-trimethylphenyl) | |
| 3097 | 2-imidazolinylaminomethyl | 0 | Bn | H | $NHSO_2$-(2,4,6-trimethylphenyl) | |
| 3098 | 2-imidazolinylaminomethyl | 0 | n-Bu | H | $NHSO_2$-(2,4,6-trimethylphenyl) | |
| 3099 | 2-imidazolinylaminomethyl | 0 | $CO_2$-n-Bu | H | $NHSO_2$-(2,4,6-trimethylphenyl) | |
| 3100 | 2-imidazolinylaminomethyl | 0 | $CO_2$-i-Bu | H | $NHSO_2$-(2,4,6-trimethylphenyl) | |
| 3101 | 2-imidazolinylaminomethyl | 0 | $CO_2$-t-Bu | H | $NHSO_2$-(2,4,6-trimethylphenyl) | |
| 3102 | 2-imidazolinylaminomethyl | 0 | H | H | $NHSO_2$-(2,4,6-trimethylphenyl) | 536.3 |
| 3103 | 2-imidazolinylaminomethyl | 0 | $-(CH_2)_4NH_2$ | H | $NHSO_2$-(2,4,6-trimethylphenyl) | |
| 3104 | 2-imidazolinylaminomethyl | 0 | COPh | H | $NHSO_2$-(2,4,6-trimethylphenyl) | |
| 3105 | 2-imidazolinylaminomethyl | 0 | $SO_2$-n-Bu | H | $NHSO_2$-(2,4,6-trimethylphenyl) | |
| 3106 | 2-imidazolinylaminomethyl | 0 | Cbz | H | NHCbz | |
| 3107 | 2-imidazolinylaminomethyl | 0 | $SO_2Ph$ | H | NHCbz | |
| 3108 | 2-imidazolinylaminomethyl | 0 | $CO(CH_2)_2Ph$ | H | NHCbz | |
| 3109 | 2-imidazolinylaminomethyl | 0 | Bn | H | NHCbz | |
| 3110 | 2-imidazolinylaminomethyl | 0 | n-Bu | H | NHCbz | |
| 3111 | 2-imidazolinylaminomethyl | 0 | $CO_2$-n-Bu | H | NHCbz | |
| 3112 | 2-imidazolinylaminomethyl | 0 | $CO_2$-i-Bu | H | NHCbz | |
| 3113 | 2-imidazolinylaminomethyl | 0 | $CO_2$-t-Bu | H | NHCbz | |
| 3114 | 2-imidazolinylaminomethyl | 0 | H | H | NHCbz | |
| 3115 | 2-imidazolinylaminomethyl | 0 | $-(CH_2)_4NH_2$ | H | NHCbz | |
| 3116 | 2-imidazolinylaminomethyl | 0 | COPh | H | NHCbz | |

TABLE 3-continued

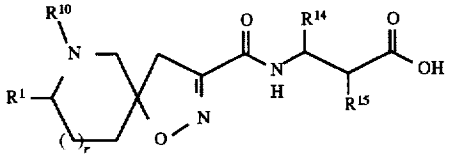

| Ex. No. | $R^1$ | r | $R^{10}$ | $R^{14}$ | $R^{15}$ | MS $(M + H)^+$ |
|---|---|---|---|---|---|---|
| 3117 | 2-imidazolinylaminomethyl | 0 | $SO_2$-n-Bu | H | NHCbz | |
| 3118 | 2-benzimidazolylaminomethyl | 0 | Cbz | H | $NHSO_2Ph$ | |
| 3119 | 2-benzimidazolylaminomethyl | 0 | $SO_2Ph$ | H | $NHSO_2Ph$ | |
| 3120 | 2-benzimidazolylaminomethyl | 0 | $CO(CH_2)_2Ph$ | H | $NHSO_2Ph$ | |
| 3121 | 2-benzimidazolylaminomethyl | 0 | Bn | H | $NHSO_2Ph$ | |
| 3122 | 2-benzimidazolylaminomethyl | 0 | n-Bu | H | $NHSO_2Ph$ | |
| 3123 | 2-benzimidazolylaminomethyl | 0 | $COCH_2$(3-indolyl) | H | $NHSO_2Ph$ | |
| 3124 | 2-benzimidazolylaminomethyl | 0 | SO2-(biphenyl) | H | $NHSO_2Ph$ | |
| 3125 | 2-benzimidazolylaminomethyl | 0 | $CO_2$-n-Bu | H | $NHSO_2Ph$ | |
| 3126 | 2-benzimidazolylaminomethyl | 0 | $CO_2$-i-Bu | H | $NHSO_2Ph$ | |
| 3127 | 2-benzimidazolylaminomethyl | 0 | $CO_2$-t-Bu | H | $NHSO_2Ph$ | |
| 3128 | 2-benzimidazolylaminomethyl | 0 | H | H | $NHSO_2Ph$ | |
| 3129 | 2-benzimidazolylaminomethyl | 0 | $-(CH_2)_4NH_2$ | H | $NHSO_2Ph$ | |
| 3130 | 2-benzimidazolylaminomethyl | 0 | COPh | H | $NHSO_2Ph$ | |
| 3131 | 2-benzimidazolylaminomethyl | 0 | cyclopropylmethyl | H | $NHSO_2Ph$ | |
| 3132 | 2-benzimidazolylaminomethyl | 0 | $SO_2$-n-Bu | H | $NHSO_2Ph$ | |
| 3133 | 2-benzimidazolylaminomethyl | 0 | Cbz | H | $NHSO_2$-(2,4,6-trimethylphenyl) | 718.4 |
| 3134 | 2-benzimidazolylaminomethyl | 0 | $SO_2Ph$ | H | $NHSO_2$-(2,4,6-trimethylphenyl) | |
| 3135 | 2-benzimidazolylaminomethyl | 0 | $CO(CH_2)_2Ph$ | H | $NHSO_2$-(2,4,6-trimethylphenyl) | |
| 3136 | 2-benzimidazolylaminomethyl | 0 | Bn | H | $NHSO_2$-(2,4,6-trimethylphenyl) | |
| 3137 | 2-benzimidazolylaminomethyl | 0 | n-Bu | H | $NHSO_2$-(2,4,6-trimethylphenyl) | |
| 3138 | 2-benzimidazolylaminomethyl | 0 | $CO_2$-n-Bu | H | $NHSO_2$-(2,4,6-trimethylphenyl) | |
| 3139 | 2-benzimidazolylaminomethyl | 0 | $CO_2$-i-Bu | H | $NHSO_2$-(2,4,6-trimethylphenyl) | |
| 3140 | 2-benzimidazolylaminomethyl | 0 | $CO_2$-t-Bu | H | $NHSO_2$-(2,4,6-trimethylphenyl) | |
| 3141 | 2-benzimidazolylaminomethyl | 0 | H | H | $NHSO_2$-(2,4,6-trimethylphenyl) | 584.2 |
| 3142 | 2-benzimidazolylaminomethyl | 0 | $-(CH_2)_4NH_2$ | H | $NHSO_2$-(2,4,6-trimethylphenyl) | |
| 3143 | 2-benzimidazolylaminomethyl | 0 | COPh | H | $NHSO_2$-(2,4,6-trimethylphenyl) | |
| 3144 | 2-benzimidazolylaminomethyl | 0 | $SO_2$-n-Bu | H | $NHSO_2$-(2,4,6-trimethylphenyl) | |
| 3145 | 2-benzimidazolylaminomethyl | 0 | Cbz | H | NHCbz | |
| 3146 | 2-benzimidazolylaminomethyl | 0 | $SO_2Ph$ | H | NHCbz | |
| 3147 | 2-benzimidazolylaminomethyl | 0 | $CO(CH_2)_2Ph$ | H | NHCbz | |
| 3148 | 2-benzimidazolylaminomethyl | 0 | Bn | H | NHCbz | |
| 3149 | 2-benzimidazolylaminomethyl | 0 | n-Bu | H | NHCbz | |
| 3150 | 2-benzimidazolylaminomethyl | 0 | $CO_2$-n-Bu | H | NHCbz | |
| 3151 | 2-benzimidazolylaminomethyl | 0 | $CO_2$-i-Bu | H | NHCbz | |
| 3152 | 2-benzimidazolylaminomethyl | 0 | $CO_2$-t-Bu | H | NHCbz | |
| 3153 | 2-benzimidazolylaminomethyl | 0 | H | H | NHCbz | |
| 3154 | 2-benzimidazolylaminomethyl | 0 | $-(CH_2)_4NH_2$ | H | NHCbz | |
| 3155 | 2-benzimidazolylaminomethyl | 0 | COPh | H | NHCbz | |
| 3156 | 2-benzimidazolylaminomethyl | 0 | $SO_2$-n-Bu | H | NHCbz | |
| 3157 | 7-aza-2-benzimidazolyl | 0 | Cbz | H | $NHSO_2Ph$ | |
| 3158 | 7-aza-2-benzimidazolyl | 0 | $SO_2Ph$ | H | $NHSO_2Ph$ | |
| 3159 | 7-aza-2-benzimidazolyl | 0 | $CO(CH_2)_2Ph$ | H | $NHSO_2Ph$ | |
| 3160 | 7-aza-2-benzimidazolyl | 0 | Bn | H | $NHSO_2Ph$ | |
| 3161 | 7-aza-2-benzimidazolyl | 0 | n-Bu | H | $NHSO_2Ph$ | |
| 3162 | 7-aza-2-benzimidazolyl | 0 | $COCH_2$(3-indolyl) | H | $NHSO_2Ph$ | |
| 3163 | 7-aza-2-benzimidazolyl | 0 | $SO_2$-(biphenyl) | H | $NHSO_2Ph$ | |
| 3164 | 7-aza-2-benzimidazolyl | 0 | $CO_2$-n-Bu | H | $NHSO_2Ph$ | |
| 3165 | 7-aza-2-benzimidazolyl | 0 | $CO_2$-i-Bu | H | $NHSO_2Ph$ | |
| 3166 | 7-aza-2-benzimidazolyl | 0 | $CO_2$-t-Bu | H | $NHSO_2Ph$ | |
| 3167 | 7-aza-2-benzimidazolyl | 0 | H | H | $NHSO_2Ph$ | |
| 3168 | 7-aza-2-benzimidazolyl | 0 | $-(CH_2)_4NH_2$ | H | $NHSO_2Ph$ | |
| 3169 | 7-aza-2-benzimidazolyl | 0 | COPh | H | $NHSO_2Ph$ | |
| 3170 | 7-aza-2-benzimidazolyl | 0 | cyclopropylmethyl | H | $NHSO_2Ph$ | |
| 3171 | 7-aza-2-benzimidazolyl | 0 | $SO_2$-n-Bu | H | $NHSO_2Ph$ | |
| 3172 | 7-aza-2-benzimidazolyl | 0 | Cbz | H | $NHSO_2$-(2,4,6-trimethylphenyl) | |
| 3173 | 7-aza-2-benzimidazolyl | 0 | $SO_2Ph$ | H | $NHSO_2$-(2,4,6-trimethylphenyl) | |
| 3174 | 7-aza-2-benzimidazolyl | 0 | $CO(CH_2)_2Ph$ | H | $NHSO_2$-(2,4,6-trimethylphenyl) | |
| 3175 | 7-aza-2-benzimidazolyl | 0 | Bn | H | $NHSO_2$-(2,4,6-trimethylphenyl) | |
| 3176 | 7-aza-2-benzimidazolyl | 0 | n-Bu | H | $NHSO_2$-(2,4,6-trimethylphenyl) | |
| 3177 | 7-aza-2-benzimidazolyl | 0 | $CO_2$-n-Bu | H | $NHSO_2$-(2,4,6-trimethylphenyl) | |
| 3178 | 7-aza-2-benzimidazolyl | 0 | $CO_2$-i-Bu | H | $NHSO_2$-(2,4,6-trimethylphenyl) | |
| 3179 | 7-aza-2-benzimidazolyl | 0 | $CO_2$-t-Bu | H | $NHSO_2$-(2,4,6-trimethylphenyl) | |
| 3180 | 7-aza-2-benzimidazolyl | 0 | H | H | $NHSO_2$-(2,4,6-trimethylphenyl) | |
| 3181 | 7-aza-2-benzimidazolyl | 0 | $-(CH_2)_4NH_2$ | H | $NHSO_2$-(2,4,6-trimethylphenyl) | |
| 3182 | 7-aza-2-benzimidazolyl | 0 | COPh | H | $NHSO_2$-(2,4,6-trimethylphenyl) | |
| 3183 | 7-aza-2-benzimidazolyl | 0 | $SO_2$-n-Bu | H | $NHSO_2$-(2,4,6-trimethylphenyl) | |
| 3184 | 7-aza-2-benzimidazolyl | 0 | Cbz | H | NHCbz | |

TABLE 3-continued

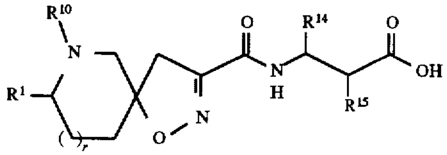

| Ex. No. | $R^1$ | r | $R^{10}$ | $R^{14}$ | $R^{15}$ | MS $(M + H)^+$ |
|---|---|---|---|---|---|---|
| 3185 | 7-aza-2-benzimidazolyl | 0 | $SO_2Ph$ | H | NHCbz | |
| 3186 | 7-aza-2-benzimidazolyl | 0 | $CO(CH_2)_2Ph$ | H | NHCbz | |
| 3187 | 7-aza-2-benzimidazolyl | 0 | Bn | H | NHCbz | |
| 3188 | 7-aza-2-benzimidazolyl | 0 | n-Bu | H | NHCbz | |
| 3189 | 7-aza-2-benzimidazolyl | 0 | $CO_2$-n-Bu | H | NHCbz | |
| 3190 | 7-aza-2-benzimidazolyl | 0 | $CO_2$-i-Bu | H | NHCbz | |
| 3191 | 7-aza-2-benzimidazolyl | 0 | $CO_2$-t-Bu | H | NHCbz | |
| 3192 | 7-aza-2-benzimidazolyl | 0 | H | H | NHCbz | |
| 3193 | 7-aza-2-benzimidazolyl | 0 | $-(CH_2)_4NH_2$ | H | NHCbz | |
| 3194 | 7-aza-2-benzimidazolyl | 0 | COPh | H | NHCbz | |
| 3195 | 7-aza-2-benzimidazolyl | 0 | $SO_2$-n-Bu | H | NHCbz | |
| 3196 | tetrahydropyrimidin-2-ylaminomethyl | 0 | Cbz | H | $NHSO_2Ph$ | |
| 3197 | tetrahydropyrimidin-2-ylaminomethyl | 0 | $SO_2Ph$ | H | $NHSO_2Ph$ | |
| 3198 | tetrahydropyrimidin-2-ylaminomethyl | 0 | $CO(CH_2)_2Ph$ | H | $NHSO_2Ph$ | |
| 3199 | tetrahydropyrimidin-2-ylaminomethyl | 0 | Bn | H | $NHSO_2Ph$ | |
| 3200 | tetrahydropyrimidin-2-ylaminomethyl | 0 | n-Bu | H | $NHSO_2Ph$ | |
| 3201 | tetrahydropyrimidin-2-ylaminomethyl | 0 | $COCH_2$(3-indolyl) | H | $NHSO_2Ph$ | |
| 3202 | tetrahydropyrimidin-2-ylaminomethyl | 0 | SO2-(biphenyl) | H | $NHSO_2Ph$ | |
| 3203 | tetrahydropyrimidin-2-ylaminomethyl | 0 | $CO_2$-n-Bu | H | $NHSO_2Ph$ | |
| 3204 | tetrahydropyrimidin-2-ylaminomethyl | 0 | $CO_2$-i-Bu | H | $NHSO_2Ph$ | |
| 3205 | tetrahydropyrimidin-2-ylaminomethyl | 0 | $CO_2$-t-Bu | H | $NHSO_2Ph$ | |
| 3206 | tetrahydropyrimidin-2-ylaminomethyl | 0 | H | H | $NHSO_2Ph$ | |
| 3207 | tetrahydropyrimidin-2-ylaminomethyl | 0 | $-(CH_2)_4NH_2$ | H | $NHSO_2Ph$ | |
| 3208 | tetrahydropyrimidin-2-ylaminomethyl | 0 | COPh | H | $NHSO_2Ph$ | |
| 3209 | tetrahydropyrimidin-2-ylaminomethyl | 0 | cyclopropylmethyl | H | $NHSO_2Ph$ | |
| 3210 | tetrahydropyrimidin-2-ylaminomethyl | 0 | $SO_2$-n-Bu | H | $NHSO_2Ph$ | |
| 3211 | tetrahydropyrimidin-2-ylaminomethyl | 0 | Cbz | H | $NHSO_2$-(2,4,6-trimethylphenyl) | |
| 3212 | tetrahydropyrimidin-2-ylaminomethyl | 0 | $SO_2Ph$ | H | $NHSO_2$-(2,4,6-trimethylphenyl) | |
| 3213 | tetrahydropyrimidin-2-ylaminomethyl | 0 | $CO(CH_2)_2Ph$ | H | $NHSO_2$-(2,4,6-trimethylphenyl) | |
| 3214 | tetrahydropyrimidin-2-ylaminomethyl | 0 | Bn | H | $NHSO_2$-(2,4,6-trimethylphenyl) | |
| 3215 | tetrahydropyrimidin-2-ylaminomethyl | 0 | n-Bu | H | $NHSO_2$-(2,4,6-trimethylphenyl) | |
| 3216 | tetrahydropyrimidin-2-ylaminomethyl | 0 | $CO_2$-n-Bu | H | $NHSO_2$-(2,4,6-trimethylphenyl) | |
| 3217 | tetrahydropyrimidin-2-ylaminomethyl | 0 | $CO_2$-i-Bu | H | $NHSO_2$-(2,4,6-trimethylphenyl) | |
| 3218 | tetrahydropyrimidin-2-ylaminomethyl | 0 | $CO_2$-t-Bu | H | $NHSO_2$-(2,4,6-trimethylphenyl) | |
| 3219 | tetrahydropyrimidin-2-ylaminomethyl | 0 | H | H | $NHSO_2$-(2,4,6-trimethylphenyl) | |
| 3220 | tetrahydropyrimidin-2-ylaminomethyl | 0 | $-(CH_2)_4NH_2$ | H | $NHSO_2$-(2,4,6-trimethylphenyl) | |
| 3221 | tetrahydropyrimidin-2-ylaminomethyl | 0 | COPh | H | $NHSO_2$-(2,4,6-trimethylphenyl) | |
| 3222 | tetrahydropyrimidin-2-ylaminomethyl | 0 | $SO_2$-n-Bu | H | $NHSO_2$-(2,4,6-trimethylphenyl) | |
| 3223 | tetrahydropyrimidin-2-ylaminomethyl | 0 | Cbz | H | NHCbz | |
| 3224 | tetrahydropyrimidin-2-ylaminomethyl | 0 | $SO_2Ph$ | H | NHCbz | |
| 3225 | tetrahydropyrimidin-2-ylaminomethyl | 0 | $CO(CH_2)_2Ph$ | H | NHCbz | |
| 3226 | tetrahydropyrimidin-2-ylaminomethyl | 0 | Bn | H | NHCbz | |
| 3227 | tetrahydropyrimidin-2-ylaminomethyl | 0 | n-Bu | H | NHCbz | |
| 3228 | tetrahydropyrimidin-2-ylaminomethyl | 0 | $CO_2$-n-Bu | H | NHCbz | |
| 3229 | tetrahydropyrimidin-2-ylaminomethyl | 0 | $CO_2$-i-Bu | H | NHCbz | |
| 3230 | tetrahydropyrimidin-2-ylaminomethyl | 0 | $CO_2$-t-Bu | H | NHCbz | |
| 3231 | tetrahydropyrimidin-2-ylaminomethyl | 0 | H | H | NHCbz | |
| 3232 | tetrahydropyrimidin-2-ylaminomethyl | 0 | $-(CH_2)_4NH_2$ | H | NHCbz | |
| 3233 | tetrahydropyrimidin-2-ylaminomethyl | 0 | COPh | H | NHCbz | |
| 3234 | tetrahydropyrimidin-2-ylaminomethyl | 0 | $SO_2$-n-Bu | H | NHCbz | |
| 3235 | 2-pyridinylaminomethyl | 1 | Cbz | H | $NHSO_2Ph$ | |
| 3236 | 2-pyridinylaminomethyl | 1 | $SO_2Ph$ | H | $NHSO_2Ph$ | |
| 3237 | 2-pyridinylaminomethyl | 1 | $CO(CH_2)_2Ph$ | H | $NHSO_2Ph$ | |
| 3238 | 2-pyridinylaminomethyl | 1 | Bn | H | $NHSO_2Ph$ | |
| 3239 | 2-pyridinylaminomethyl | 1 | n-Bu | H | $NHSO_2Ph$ | |
| 3240 | 2-pyridinylaminomethyl | 1 | $COCH_2$(3-indolyl) | H | $NHSO_2Ph$ | |
| 3241 | 2-pyridinylaminomethyl | 1 | SO2-(biphenyl) | H | $NHSO_2Ph$ | |
| 3242 | 2-pyridinylaminomethyl | 1 | $CO_2$-n-Bu | H | $NHSO_2Ph$ | |
| 3243 | 2-pyridinylaminomethyl | 1 | $CO_2$-i-Bu | H | $NHSO_2Ph$ | |
| 3244 | 2-pyridinylaminomethyl | 1 | $CO_2$-t-Bu | H | $NHSO_2Ph$ | |
| 3245 | 2-pyridinylaminomethyl | 1 | H | H | $NHSO_2Ph$ | |
| 3246 | 2-pyridinylaminomethyl | 1 | $-(CH_2)_4NH_2$ | H | $NHSO_2Ph$ | |
| 3247 | 2-pyridinylaminomethyl | 1 | COPh | H | $NHSO_2Ph$ | |
| 3248 | 2-pyridinylaminomethyl | 1 | cyclopropylmethyl | H | $NHSO_2Ph$ | |
| 3249 | 2-pyridinylaminomethyl | 1 | $SO_2$-n-Bu | H | $NHSO_2Ph$ | |
| 3250 | 2-pyridinylaminomethyl | 1 | Cbz | H | $NHSO_2$-(2,4,6-trimethylphenyl) | |
| 3251 | 2-pyridinylaminomethyl | 1 | $SO_2Ph$ | H | $NHSO_2$-(2,4,6-trimethylphenyl) | |
| 3252 | 2-pyridinylaminomethyl | 1 | $CO(CH_2)_2Ph$ | H | $NHSO_2$-(2,4,6-trimethylphenyl) | |

TABLE 3-continued

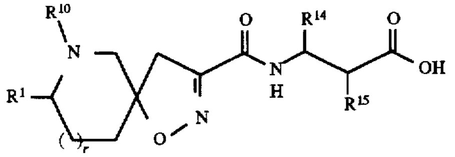

| Ex. No. | $R^1$ | r | $R^{10}$ | $R^{14}$ | $R^{15}$ | MS $(M + H)^+$ |
|---|---|---|---|---|---|---|
| 3253 | 2-pyridinylaminomethyl | 1 | Bn | H | $NHSO_2$-(2,4,6-trimethylphenyl) | |
| 3254 | 2-pyridinylaminomethyl | 1 | n-Bu | H | $NHSO_2$-(2,4,6-trimethylphenyl) | |
| 3255 | 2-pyridinylaminomethyl | 1 | $CO_2$-n-Bu | H | $NHSO_2$-(2,4,6-trimethylphenyl) | |
| 3256 | 2-pyridinylaminomethyl | 1 | $CO_2$-i-Bu | H | $NHSO_2$-(2,4,6-trimethylphenyl) | |
| 3257 | 2-pyridinylaminomethyl | 1 | $CO_2$-t-Bu | H | $NHSO_2$-(2,4,6-trimethylphenyl) | |
| 3258 | 2-pyridinylaminomethyl | 1 | H | H | $NHSO_2$-(2,4,6-trimethylphenyl) | |
| 3259 | 2-pyridinylaminomethyl | 1 | $-(CH_2)_4NH_2$ | H | $NHSO_2$-(2,4,6-trimethylphenyl) | |
| 3260 | 2-pyridinylaminomethyl | 1 | COPh | H | $NHSO_2$-(2,4,6-trimethylphenyl) | |
| 3261 | 2-pyridinylaminomethyl | 1 | $SO_2$-n-Bu | H | $NHSO_2$-(2,4,6-trimethylphenyl) | |
| 3262 | 2-pyridinylaminomethyl | 1 | Cbz | H | NHCbz | |
| 3263 | 2-pyridinylaminomethyl | 1 | $SO_2Ph$ | H | NHCbz | |
| 3264 | 2-pyridinylaminomethyl | 1 | $CO(CH_2)_2Ph$ | H | NHCbz | |
| 3265 | 2-pyridinylaminomethyl | 1 | Bn | H | NHCbz | |
| 3266 | 2-pyridinylaminomethyl | 1 | n-Bu | H | NHCbz | |
| 3267 | 2-pyridinylaminomethyl | 1 | $CO_2$-n-Bu | H | NHCbz | |
| 3268 | 2-pyridinylaminomethyl | 1 | $CO_2$-i-Bu | H | NHCbz | |
| 3269 | 2-pyridinylaminomethyl | 1 | $CO_2$-t-Bu | H | NHCbz | |
| 3270 | 2-pyridinylaminomethyl | 1 | H | H | NHCbz | |
| 3271 | 2-pyridinylaminomethyl | 1 | $-(CH_2)_4NH_2$ | H | NHCbz | |
| 3272 | 2-pyridinylaminomethyl | 1 | COPh | H | NHCbz | |
| 3273 | 2-pyridinylaminomethyl | 1 | $SO_2$-n-Bu | H | NHCbz | |
| 3274 | 2-imidazolylaminomethyl | 1 | Cbz | H | $NHSO_2Ph$ | |
| 3275 | 2-imidazolylaminomethyl | 1 | $SO_2Ph$ | H | $NHSO_2Ph$ | |
| 3276 | 2-imidazolylaminomethyl | 1 | $CO(CH_2)_2Ph$ | H | $NHSO_2Ph$ | |
| 3277 | 2-imidazolylaminomethyl | 1 | Bn | H | $NHSO_2Ph$ | |
| 3278 | 2-imidazolylaminomethyl | 1 | n-Bu | H | $NHSO_2Ph$ | |
| 3279 | 2-imidazolylaminomethyl | 1 | $COCH_2$(3-indolyl) | H | $NHSO_2Ph$ | |
| 3280 | 2-imidazolylaminomethyl | 1 | $SO_2$-(biphenyl) | H | $NHSO_2Ph$ | |
| 3281 | 2-imidazolylaminomethyl | 1 | $CO_2$-n-Bu | H | $NHSO_2Ph$ | |
| 3282 | 2-imidazolylaminomethyl | 1 | $CO_2$-i-Bu | H | $NHSO_2Ph$ | |
| 3283 | 2-imidazolylaminomethyl | 1 | $CO_2$-t-Bu | H | $NHSO_2Ph$ | |
| 3284 | 2-imidazolylaminomethyl | 1 | H | H | $NHSO_2Ph$ | |
| 3285 | 2-imidazolylaminomethyl | 1 | $-(CH_2)_4NH_2$ | H | $NHSO_2Ph$ | |
| 3286 | 2-imidazolylaminomethyl | 1 | COPh | H | $NHSO_2Ph$ | |
| 3287 | 2-imidazolylaminomethyl | 1 | cyclopropylmethyl | H | $NHSO_2Ph$ | |
| 3288 | 2-imidazolylaminomethyl | 1 | $SO_2$-n-Bu | H | $NHSO_2Ph$ | |
| 3289 | 2-imidazolylaminomethyl | 1 | Cbz | H | $NHSO_2$-(2,4,6-trimethylphenyl) | |
| 3290 | 2-imidazolylaminomethyl | 1 | $SO_2Ph$ | H | $NHSO_2$-(2,4,6-trimethylphenyl) | |
| 3291 | 2-imidazolylaminomethyl | 1 | $CO(CH_2)_2Ph$ | H | $NHSO_2$-(2,4,6-trimethylphenyl) | |
| 3292 | 2-imidazolylaminomethyl | 1 | Bn | H | $NHSO_2$-(2g4,6-trimethylphenyl) | |
| 3293 | 2-imidazolylaminomethyl | 1 | n-Bu | H | $NHSO_2$-(2,4,6-trimethylphenyl) | |
| 3294 | 2-imidazolylaminomethyl | 1 | $CO_2$-n-Bu | H | $NHSO_2$-(2,4,6-trimethylphenyl) | |
| 3295 | 2-imidazolylaminomethyl | 1 | $CO_2$-i-Bu | H | $NHSO_2$-(2,4,6-trimethylphenyl) | |
| 3296 | 2-imidazolylaminomethyl | 1 | $CO_2$-t-Bu | H | $NHSO_2$-(2,4,6-trimethylphenyl) | |
| 3297 | 2-imidazolylaminomethyl | 1 | H | H | $NHSO_2$-(2,4,6-trimethylphenyl) | |
| 3298 | 2-imidazolylaminomethyl | 1 | $-(CH_2)_4NH_2$ | H | $NHSO_2$-(2,4,6-trimethylphenyl) | |
| 3299 | 2-imidazolylaminomethyl | 1 | COPh | H | $NHSO_2$-(2,4,6-trimethylphenyl) | |
| 3300 | 2-imidazolylaminomethyl | 1 | $SO_2$-n-Bu | H | $NHSO_2$-(2,4,6-trimethylphenyl) | |
| 3301 | 2-imidazolylaminomethyl | 1 | Cbz | H | NHCbz | |
| 3302 | 2-imidazolylaminomethyl | 1 | $SO_2Ph$ | H | NHCbz | |
| 3303 | 2-imidazolylaminomethyl | 1 | $CO(CH_2)_2Ph$ | H | NHCbz | |
| 3304 | 2-imidazolylaminomethyl | 1 | Bn | H | NHCbz | |
| 3305 | 2-imidazolylaminomethyl | 1 | n-Bu | H | NHCbz | |
| 3306 | 2-imidazolylaminomethyl | 1 | $CO_2$-n-Bu | H | NHCbz | |
| 3307 | 2-imidazolylaminomethyl | 1 | $CO_2$-i-Bu | H | NHCbz | |
| 3308 | 2-imidazolylaminomethyl | 1 | $CO_2$-t-Bu | H | NHCbz | |
| 3309 | 2-imidazolylaminomethyl | 1 | H | H | NHCbz | |
| 3310 | 2-imidazolylaminomethyl | 1 | $-(CH_2)_4NH_2$ | H | NHCbz | |
| 3311 | 2-imidazolylaminomethyl | 1 | COPh | H | NHCbz | |
| 3312 | 2-imidazolylaminomethyl | 1 | $SO_2$-n-Bu | H | NHCbz | |
| 3313 | 2-imidazolinylaminomethyl | 1 | Cbz | H | $NHSO_2Ph$ | |
| 3314 | 2-imidazolinylaminomethyl | 1 | $SO_2Ph$ | H | $NHSO_2Ph$ | |
| 3315 | 2-imidazolinylaminomethyl | 1 | $CO(CH_2)_2Ph$ | H | $NHSO_2Ph$ | |
| 3316 | 2-imidazolinylaminomethyl | 1 | Bn | H | $NHSO_2Ph$ | |
| 3317 | 2-imidazolinylaminomethyl | 1 | n-Bu | H | $NHSO_2Ph$ | |
| 3318 | 2-imidazolinylaminomethyl | 1 | $COCH_2$(3-indolyl) | H | $NHSO_2Ph$ | |
| 3319 | 2-imidazolinylaminomethyl | 1 | $SO_2$-(biphenyl) | H | $NHSO_2Ph$ | |
| 3320 | 2-imidazolinylaminomethyl | 1 | $CO_2$-n-Bu | H | $NHSO_2Ph$ | |

TABLE 3-continued

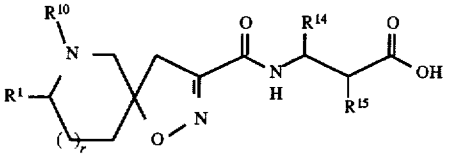

| Ex. No. | $R^1$ | r | $R^{10}$ | $R^{14}$ | $R^{15}$ | MS $(M + H)^+$ |
|---|---|---|---|---|---|---|
| 3321 | 2-imidazolinylaminomethyl | 1 | $CO_2$-i-Bu | H | $NHSO_2Ph$ | |
| 3322 | 2-imidazolinylaminomethyl | 1 | $CO_2$-t-Bu | H | $NHSO_2Ph$ | |
| 3323 | 2-imidazolinylaminomethyl | 1 | H | H | $NHSO_2Ph$ | |
| 3324 | 2-imidazolinylaminomethyl | 1 | $-(CH_2)_4NH_2$ | H | $NHSO_2Ph$ | |
| 3325 | 2-imidazolinylaminomethyl | 1 | COPh | H | $NHSO_2Ph$ | |
| 3326 | 2-imidazolinylaminomethyl | 1 | cyclopropylmethyl | H | $NHSO_2Ph$ | |
| 3327 | 2-imidazolinylaminomethyl | 1 | $SO_2$-n-Bu | H | NHSd2Ph | |
| 3328 | 2-imidazolinylaminomethyl | 1 | Cbz | H | $NHSO_2$-(2,4,6-trimethylphenyl) | |
| 3329 | 2-imidazolinylaminomethyl | 1 | $SO_2Ph$ | H | $NHSO_2$-(2,4,6-trimethylphenyl) | |
| 3330 | 2-imidazolinylaminomethyl | 1 | $CO(CH_2)_2Ph$ | H | $NHSO_2$-(2,4,6-trimethylphenyl) | |
| 3331 | 2-imidazolinylaminomethyl | 1 | Bn | H | $NHSO_2$-(2,4,6-trimethylphenyl) | |
| 3332 | 2-imidazolinylaminomethyl | 1 | n-Bu | H | $NHSO_2$-(2,4,6-trimethylphenyl) | |
| 3333 | 2-imidazolinylaminomethyl | 1 | $CO_2$-n-Bu | H | $NHSO_2$-(2,4,6-trimethylphenyl) | |
| 3334 | 2-imidazolinylaminomethyl | 1 | $CO_2$-i-Bu | H | $NHSO_2$-(2,4,6-trimethylphenyl) | |
| 3335 | 2-imidazolinylaminomethyl | 1 | $CO_2$-t-Bu | H | $NHSO_2$-(2,4,6-trimethylphenyl) | |
| 3336 | 2-imidazolinylaminomethyl | 1 | H | H | $NHSO_2$-(2,4,6-trimethylphenyl) | |
| 3337 | 2-imidazolinylaminomethyl | 1 | $-(CH_2)_4NH_2$ | H | $NHSO_2$-(2,4,6-trimethylphenyl) | |
| 3338 | 2-imidazolinylaminomethyl | 1 | COPh | H | $NHSO_2$-(2,4,6-trimethylphenyl) | |
| 3339 | 2-imidazolinylaminomethyl | 1 | $SO_2$-n-Bu | H | $NHSO_2$-(2,4,6-trimethylphenyl) | |
| 3340 | 2-imidazolinylaminomethyl | 1 | Cbz | H | NHCbz | |
| 3341 | 2-imidazolinylaminomethyl | 1 | $SO_2Ph$ | H | NHCbz | |
| 3342 | 2-imidazolinylaminomethyl | 1 | $CO(CH_2)_2Ph$ | H | NHCbz | |
| 3343 | 2-imidazolinylaminomethyl | 1 | Bn | H | NHCbz | |
| 3344 | 2-imidazolinylaminomethyl | 1 | n-Bu | H | NHCbz | |
| 3345 | 2-imidazolinylaminomethyl | 1 | $CO_2$-n-Bu | H | NHCbz | |
| 3346 | 2-imidazolinylaminomethyl | 1 | $CO_2$-i-Bu | H | NHCbz | |
| 3347 | 2-imidazolinylaminomethyl | 1 | $CO_2$-t-Bu | H | NHCbz | |
| 3348 | 2-imidazolinylaminomethyl | 1 | H | H | NHCbz | |
| 3349 | 2-imidazolinylaminomethyl | 1 | $-(CH_2)_4NH_2$ | H | NHCbz | |
| 3350 | 2-imidazolinylaminomethyl | 1 | COPh | H | NHCbz | |
| 3351 | 2-imidazolinylaminomethyl | 1 | $SO_2$-n-Bu | H | NHCbz | |
| 3352 | 2-benzimidazolylaminomethyl | 1 | Cbz | H | $NHSO_2Ph$ | |
| 3353 | 2-benzimidazolylaminomethyl | 1 | $SO_2Ph$ | H | $NHSO_2Ph$ | |
| 3354 | 2-benzimidazolylaminomethyl | 1 | $CO(CH_2)_2Ph$ | H | $NHSO_2Ph$ | |
| 3355 | 2-benzimidazolylaminomethyl | 1 | Bn | H | $NHSO_2Ph$ | |
| 3356 | 2-benzimidazolylaminomethyl | 1 | n-Bu | H | $NHSO_2Ph$ | |
| 3357 | 2-benzimidazolylaminomethyl | 1 | $COCH_2$(3-indolyl) | H | $NHSO_2Ph$ | |
| 3358 | 2-benzimidazolylaminomethyl | 1 | $SO_2$-(biphenyl) | H | $NHSO_2Ph$ | |
| 3359 | 2-benzimidazolylaminomethyl | 1 | $CO_2$-n-Bu | H | $NHSO_2Ph$ | |
| 3360 | 2-benzimidazolylaminomethyl | 1 | $CO_2$-i-Bu | H | $NHSO_2Ph$ | |
| 3361 | 2-benzimidazolylaminomethyl | 1 | $CO_2$-t-Bu | H | $NHSO_2Ph$ | |
| 3362 | 2-benzimidazolylaminomethyl | 1 | H | H | $NHSO_2Ph$ | |
| 3363 | 2-benzimidazolylaminomethyl | 1 | $-(CH_2)_4NH_2$ | H | $NHSO_2Ph$ | |
| 3364 | 2-benzimidazolylaminomethyl | 1 | COPh | H | $NHSO_2Ph$ | |
| 3365 | 2-benzimidazolylaminomethyl | 1 | cyclopropylmethyl | H | $NHSO_2Ph$ | |
| 3366 | 2-benzimidazolylaminomethyl | 1 | $SO_2$-n-Bu | H | $NHSO_2Ph$ | |
| 3367 | 2-benzimidazolylaminomethyl | 1 | Cbz | H | $NHSO_2$-(2,4,6-trimethylphenyl) | |
| 3368 | 2-benzimidazolylaminomethyl | 1 | $SO_2Ph$ | H | $NHSO_2$-(2,4,6-trimethylphenyl) | |
| 3369 | 2-benzimidazolylaminomethyl | 1 | $CO(CH_2)_2Ph$ | H | $NHSO_2$-(2,4,6-trimethylphenyl) | |
| 3370 | 2-benzimidazolylaminomethyl | 1 | Bn | H | $NHSO_2$-(2,4,6-trimethylphenyl) | |
| 3371 | 2-benzimidazolylaminomethyl | 1 | n-Bu | H | $NHSO_2$-(2,4,6-trimethylphenyl) | |
| 3372 | 2-benzimidazolylaminomethyl | 1 | $CO_2$-n-Bu | H | $NHSO_2$-(2,4,6-trimethylphenyl) | |
| 3373 | 2-benzimidazolylaminomethyl | 1 | $CO_2$-i-Bu | H | $NHSO_2$-(2,4,6-trimethylphenyl) | |
| 3374 | 2-benzimidazolylaminomethyl | 1 | $CO_2$-t-Bu | H | $NHSO_2$-(2,4,6-trimethylphenyl) | |
| 3375 | 2-benzimidazolylaminomethyl | 1 | H | H | $NHSO_2$-(2,4,6-trimethylphenyl) | |
| 3376 | 2-benzimidazolylaminomethyl | 1 | $-(CH_2)_4NH_2$ | H | $NHSO_2$-(2,4,6-trimethylphenyl) | |
| 3377 | 2-benzimidazolylaminomethyl | 1 | COPh | H | $NHSO_2$-(2,4,6-trimethylphenyl) | |
| 3378 | 2-benzimidazolylaminomethyl | 1 | $SO_2$-n-BU | H | $NHSO_2$-(2,4,6-trimethylphenyl) | |
| 3379 | 2-benzimidazolylaminomethyl | 1 | Cbz | H | NHCbz | |
| 3380 | 2-benzimidazolylaminomethyl | 1 | $SO_2Ph$ | H | NHCbz | |
| 3381 | 2-benzimidazolylaminomethyl | 1 | $CO(CH_2)_2Ph$ | H | NHCbz | |
| 3382 | 2-benzimidazolylaminomethyl | 1 | Bn | H | NHCbz | |
| 3383 | 2-benzimidazolylaminomethyl | 1 | n-Bu | H | NHCbz | |
| 3384 | 2-benzimidazolylaminomethyl | 1 | $CO_2$-n-Bu | H | NHCbz | |
| 3385 | 2-benzimidazolylaminomethyl | 1 | $CO_2$-i-Bu | H | NHCbz | |
| 3386 | 2-benzimidazolylaminomethyl | 1 | $CO_2$-t-Bu | H | NHCbz | |
| 3387 | 2-benzimidazolylaminomethyl | 1 | H | H | NHCbz | |
| 3388 | 2-benzimidazolylaminomethyl | 1 | $-(CH_2)_4NH_2$ | H | NHCbz | |

TABLE 3-continued

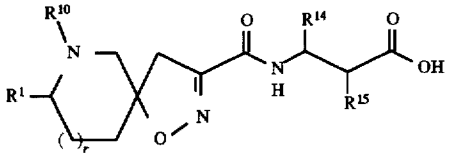

| Ex. No. | $R^1$ | r | $R^{10}$ | $R^{14}$ | $R^{15}$ | MS $(M + H)^+$ |
|---|---|---|---|---|---|---|
| 3389 | 2-benzimidazolylaminomethyl | 1 | COPh | H | NHCbz | |
| 3390 | 2-benzimidazolylaminomethyl | 1 | $SO_2$-n-Bu | H | NHCbz | |
| 3391 | 7-aza-2-benzimidazolyl | 1 | Cbz | H | $NHSO_2Ph$ | |
| 3392 | 7-aza-2-benzimidazolyl | 1 | $SO_2Ph$ | H | $NHSO_2Ph$ | |
| 3393 | 7-aza-2-benzimidazolyl | 1 | $CO(CH_2)_2Ph$ | H | $NHSO_2Ph$ | |
| 3394 | 7-aza-2-benzimidazolyl | 1 | Bn | H | $NHSO_2Ph$ | |
| 3395 | 7-aza-2-benzimidazolyl | 1 | n-Bu | H | $NHSO_2Ph$ | |
| 3396 | 7-aza-2-benzimidazolyl | 1 | $COCH_2$(3-indolyl) | H | $NHSO_2Ph$ | |
| 3397 | 7-aza-2-benzimidazolyl | 1 | $SO_2$-(biphenyl) | H | $NHSO_2Ph$ | |
| 3398 | 7-aza-2-benzimidazolyl | 1 | $CO_2$-n-Bu | H | $NHSO_2Ph$ | |
| 3399 | 7-aza-2-benzimidazolyl | 1 | $CO_2$-i-Bu | H | $NHSO_2Ph$ | |
| 3400 | 7-aza-2-benzimidazolyl | 1 | $CO_2$-t-Bu | H | $NHSO_2Ph$ | |
| 3401 | 7-aza-2-benzimidazolyl | 1 | H | H | $NHSO_2Ph$ | |
| 3402 | 7-aza-2-benzimidazolyl | 1 | $-(CH_2)_4NH_2$ | H | $NHSO_2Ph$ | |
| 3403 | 7-aza-2-benzimidazolyl | 1 | COPh | H | $NHSO_2Ph$ | |
| 3404 | 7-aza-2-benzimidazolyl | 1 | cyclopropylmethyl | H | $NHSO_2Ph$ | |
| 3405 | 7-aza-2-benzimidazolyl | 1 | $SO_2$-n-Bu | H | $NHSO_2Ph$ | |
| 3406 | 7-aza-2-benzimidazolyl | 1 | Cbz | H | $NHSO_2$-(2,4,6-trimethylphenyl) | |
| 3407 | 7-aza-2-benzimidazolyl | 1 | $SO_2Ph$ | H | $NHSO_2$-(2,4,6-trimethylphenyl) | |
| 3408 | 7-aza-2-benzimidazolyl | 1 | $CO(CH_2)_2Ph$ | H | $NHSO_2$-(2,4,6-trimethylphenyl) | |
| 3409 | 7-aza-2-benzimidazolyl | 1 | Bn | H | $NHSO_2$-(2,4,6-trimethylphenyl) | |
| 3410 | 7-aza-2-benzimidazolyl | 1 | n-Bu | H | $NHSO_2$-(2,4,6-trimethylphenyl) | |
| 3411 | 7-aza-2-benzimidazolyl | 1 | $CO_2$-n-Bu | H | $NHSO_2$-(2,4,6-trimethylphenyl) | |
| 3412 | 7-aza-2-benzimidazolyl | 1 | $CO_2$-i-Bu | H | $NHSO_2$-(2,4,6-trimethylphenyl) | |
| 3413 | 7-aza-2-benzimidazolyl | 1 | $CO_2$-t-Bu | H | $NHSO_2$-(2,4,6-trimethylphenyl) | |
| 3414 | 7-aza-2-benzimidazolyl | 1 | H | H | $NHSO_2$-(2,4,6-trimethylphenyl) | |
| 3415 | 7-aza-2-benzimidazolyl | 1 | $-(CH_2)_4NH_2$ | H | $NHSO_2$-(2,4,6-trimethylphenyl) | |
| 3416 | 7-aza-2-benzimidazolyl | 1 | COPh | H | $NHSO_2$-(2,4,6-trimethylphenyl) | |
| 3417 | 7-aza-2-benzimidazolyl | 1 | $SO_2$-n-Bu | H | $NHSO_2$-(2,4,6-trimethylphenyl) | |
| 3418 | 7-aza-2-benzimidazolyl | 1 | Cbz | H | NHCbz | |
| 3419 | 7-aza-2-benzimidazolyl | 1 | $SO_2Ph$ | H | NHCbz | |
| 3420 | 7-aza-2-benzimidazolyl | 1 | $CO(CH_2)_2Ph$ | H | NHCbz | |
| 3421 | 7-aza-2-benzimidazolyl | 1 | Bn | H | NHCbz | |
| 3422 | 7-aza-2-benzimidazolyl | 1 | n-Bu | H | NHCbz | |
| 3423 | 7-aza-2-benzimidazolyl | 1 | $CO_2$-n-Bu | H | NHCbz | |
| 3424 | 7-aza-2-benzimidazolyl | 1 | $CO_2$-i-Bu | H | NHCbz | |
| 3425 | 7-aza-2-benzimidazolyl | 1 | $CO_2$-t-Bu | H | NHCbz | |
| 3426 | 7-aza-2-benzimidazolyl | 1 | H | H | NHCbz | |
| 3427 | 7-aza-2-benzimidazolyl | 1 | $-(CH_2)_4NH_2$ | H | NHCbz | |
| 3428 | 7-aza-2-benzimidazolyl | 1 | COPh | H | NHCbz | |
| 3429 | 7-aza-2-benzimidazolyl | 1 | $SO_2$-n-Bu | H | NHCbz | |
| 3430 | tetrahydropyrimidin-2-ylaminomethyl | 1 | Cbz | H | $NHSO_2Ph$ | |
| 3431 | tetrahydropyrimidin-2-ylaminomethyl | 1 | $SO_2Ph$ | H | $NHSO_2Ph$ | |
| 3432 | tetrahydropyrimidin-2-ylaminomethyl | 1 | $CO(CH_2)_2Ph$ | H | $NHSO_2Ph$ | |
| 3433 | tetrahydropyrimidin-2-ylaminomethyl | 1 | Bn | H | $NHSO_2Ph$ | |
| 3434 | tetrahydropyrimidin-2-ylaminomethyl | 1 | n-Bu | H | $NHSO_2Ph$ | |
| 3435 | tetrahydropyrimidin-2-ylaminomethyl | 1 | $COCH_2$(3-indolyl) | H | $NHSO_2Ph$ | |
| 3436 | tetrahydropyrimidin-2-ylaminomethyl | 1 | SO2-(biphenyl) | H | $NHSO_2Ph$ | |
| 3437 | tetrahydropyrimidin-2-ylaminomethyl | 1 | $CO_2$-n-Bu | H | $NHSO_2Ph$ | |
| 3438 | tetrahydropyrimidin-2-ylaminomethyl | 1 | $CO_2$-i-Bu | H | $NHSO_2Ph$ | |
| 3439 | tetrahydropyrimidin-2-ylaminomethyl | 1 | $CO_2$-t-Bu | H | $NHSO_2Ph$ | |
| 3440 | tetrahydropyrimidin-2-ylaminomethyl | 1 | H | H | $NHSO_2Ph$ | |
| 3441 | tetrahydropyrimidin-2-ylaminomethyl | 1 | $-(CH_2)_4NH_2$ | H | $NHSO_2Ph$ | |
| 3442 | tetrahydropyrimidin-2-ylaminomethyl | 1 | COPh | H | $NHSO_2Ph$ | |
| 3443 | tetrahydropyrimidin-2-ylaminomethyl | 1 | cyclopropylmethyl | H | $NHSO_2Ph$ | |
| 3444 | tetrahydropyrimidin-2-ylaminomethyl | 1 | $SO_2$-n-Bu | H | $NHSO_2Ph$ | |
| 3445 | tetrahydropyrimidin-2-ylaminomethyl | 1 | Cbz | H | $NHSO_2$-(2,4,6-trimethylphenyl) | |
| 3446 | tetrahydropyrimidin-2-ylaminomethyl | 1 | $SO_2Ph$ | H | $NHSO_2$-(2,4,6-trimethylphenyl) | |
| 3447 | tetrahydropyrimidin-2-ylaminomethyl | 1 | $CO(CH_2)_2Ph$ | H | $NHSO_2$-(2,4,6-trimethylphenyl) | |
| 3448 | tetrahydropyrimidin-2-ylaminomethyl | 1 | Bn | H | $NHSO_2$-(2,4,6-trimethylphenyl) | |
| 3449 | tetrahydropyrimidin-2-ylaminomethyl | 1 | n-Bu | H | $NHSO_2$-(2,4,6-trimethylphenyl) | |
| 3450 | tetrahydropyrimidin-2-ylaminomethyl | 1 | $CO_2$-n-Bu | H | $NHSO_2$-(2,4,6-trimethylphenyl) | |
| 3451 | tetrahydropyrimidin-2-ylaminomethyl | 1 | $CO_2$-i-Bu | H | $NHSO_2$-(2,4,6-trimethylphenyl) | |
| 3452 | tetrahydropyrimidin-2-ylaminomethyl | 1 | $CO_2$-t-Bu | H | $NHSO_2$-(2,4,6-trimethylphenyl) | |
| 3453 | tetrahydropyrimidin-2-ylaminomethyl | 1 | H | H | $NHSO_2$-(2,4,6-trimethylphenyl) | |
| 3454 | tetrahydropyrimidin-2-ylaminomethyl | 1 | $-(CH_2)_4NH_2$ | H | $NHSO_2$-(2,4,6-trimethylphenyl) | |
| 3455 | tetrahydropyrimidin-2-ylaminomethyl | 1 | COPh | H | $NHSO_2$-(2,4,6-trimethylphenyl) | |
| 3456 | tetrahydropyrimidin-2-ylaminomethyl | 1 | $SO_2$-n-Bu | H | $NHSO_2$-(2,4,6-trimethylphenyl) | |

TABLE 3-continued

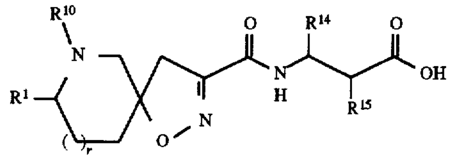

| Ex. No. | $R^1$ | r | $R^{10}$ | $R^{14}$ | $R^{15}$ | MS $(M + H)^+$ |
|---|---|---|---|---|---|---|
| 3457 | tetrahydropyrimidin-2-ylaminomethyl | 1 | Cbz | H | NHCbz | |
| 3458 | tetrahydropyrimidin-2-ylaminomethyl | 1 | $SO_2Ph$ | H | NHCbz | |
| 3459 | tetrahydropyrimidin-2-ylaminomethyl | 1 | $CO(CH_2)_2Ph$ | H | NHCbz | |
| 3460 | tetrahydropyrimidin-2-ylaminomethyl | 1 | Bn | H | NHCbz | |
| 3461 | tetrahydropyrimidin-2-ylaminomethyl | 1 | n-Bu | H | NHCbz | |
| 3462 | tetrahydropyrimidin-2-ylaminomethyl | 1 | $CO_2$-n-Bu | H | NHCbz | |
| 3463 | tetrahydropyrimidin-2-ylaminomethyl | 1 | $CO_2$-i-Bu | H | NHCbz | |
| 3464 | tetrahydropyrimidin-2-ylaminomethyl | 1 | $CO_2$-t-Bu | H | NHCbz | |
| 3465 | tetrahydropyrimidin-2-ylaminomethyl | 1 | H | H | NHCbz | |
| 3466 | tetrahydropyrimidin-2-ylaminomethyl | 1 | $-(CH_2)_4NH_2$ | H | NHCbz | |
| 3467 | tetrahydropyrimidin-2-ylaminomethyl | 1 | COPh | H | NHCbz | |
| 3468 | imidazol-2-ylaminomethyl | 0 | $CO_2Me$ | H | $NHSO_2$-(2,4,6-trimethylphenyl) | 592.4 |
| 3469 | benzamidazol-2-ylaminomethyl | 0 | Bn | H | $NHSO_2$-(2,4,6-trimethylphenyl) | 674.3 |
| 3470 | benzamidazol-2-ylaminomethyl | 0 | $CO_2Me$ | H | $NHSO_2$-(2,4,6-trimethylphenyl) | 642.3 |
| 3471 | benzamidazol-2-ylaminomethyl | 0 | $CO_2Bu$ | H | $NHSO_2$-(2,4,6-trimethylphenyl) | 684.4 |
| 3472 | imidazol-2-ylaminomethyl | 0 | $CO_2CH_2$(3-pyr) | H | $NHSO_2$-(2,4,6-trimethylphenyl) | 669.4 |
| 3473 | imidazol-2-ylaminomethyl | 0 | H | H | $NHSO_2$-(2,6-trimethylphenyl) | 520.3 |
| 3474 | imidazol-2-ylaminomethyl | 0 | H | H | $NHSO_2$biphenyl | 568.3 |
| 3475 | imidazolin-2-ylaminomethyl | 0 | Cbz | H | $NHSO_2$(2-naphthyl | 678.1 |
| 3476 | imidazolin-2-ylaminomethyl | 0 | H | H | $NHSO_2$biphenyl | 570.2 |

TABLE 4

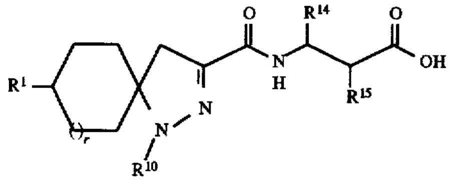

| Ex. No. | $R^1$ | r | $R^{10}$ | $R^{14}$ | $R^{15}$ |
|---|---|---|---|---|---|
| 4001 | 2-pyridinylaminomethyl | 0 | Cbz | H | $NHSO_2Ph$ |
| 4002 | 2-pyridinylaminomethyl | 0 | $SO_2Ph$ | H | $NHSO_2Ph$ |
| 4003 | 2-pyridinylaminomethyl | 0 | $CO(CH_2)_2Ph$ | H | $NHSO_2Ph$ |
| 4004 | 2-pyridinylaminomethyl | 0 | Bn | H | $NHSO_2Ph$ |
| 4005 | 2-pyridinylaminomethyl | 0 | n-Bu | H | $NHSO_2Ph$ |
| 4006 | 2-pyridinylaminomethyl | 0 | $COCH_2$ (3-indolyl) | H | $NHSO_2Ph$ |
| 4007 | 2-pyridinylaminomethyl | 0 | SO2-(biphenyl) | H | $NHSO_2Ph$ |
| 4008 | 2-pyridinylaminomethyl | 0 | $CO_2$-n-Bu | H | $NHSO_2Ph$ |
| 4009 | 2-pyridinylaminomethyl | 0 | $CO_2$-i-Bu | H | $NHSO_2Ph$ |
| 4010 | 2-pyridinylaminomethyl | 0 | $CO_2$-t-Bu | H | $NHSO_2Ph$ |
| 4011 | 2-pyridinylaminomethyl | 0 | H | H | $NHSO_2Ph$ |
| 4012 | 2-pyridinylaminomethyl | 0 | $-(CH_2)_4NH_2$ | H | $NHSO_2Ph$ |
| 4013 | 2-pyridinylaminomethyl | 0 | COPh | H | $NHSO_2Ph$ |
| 4014 | 2-pyridinylaminomethyl | 0 | cyclopropylmethyl | H | $NHSO_2Ph$ |
| 4015 | 2-pyridinylaminomethyl | 0 | $SO_2$-n-Bu | H | $NHSO_2Ph$ |
| 4016 | 2-pyridinylaminomethyl | 0 | Cbz | H | $NHSO_2$-(2,4,6-trimethylphenyl) |
| 4017 | 2-pyridinylaminomethyl | 0 | $SO_2Ph$ | H | $NHSO_2$-(2,4,6-trimethylphenyl) |
| 4018 | 2-pyridinylaminomethyl | 0 | $CO(CH_2)_2Ph$ | H | $NHSO_2$-(2,4,6-trimethylphenyl) |
| 4019 | 2-pyridinylaminomethyl | 0 | Bn | H | $NHSO_2$-(2,4,6-trimethylphenyl) |
| 4020 | 2-pyridinylaminomethyl | 0 | n-Bu | H | $NHSO_2$-(2,4,6-trimethylphenyl) |
| 4021 | 2-pyridinylaminomethyl | 0 | $CO_2$-n-Bu | H | $NHSO_2$-(2,4,6-trimethylphenyl) |
| 4022 | 2-pyridinylaminomethyl | 0 | $CO_2$-i-Bu | H | $NHSO_2$-(2,4,6-trimethylphenyl) |
| 4023 | 2-pyridinylaminomethyl | 0 | $CO_2$-t-Bu | H | $NHSO_2$-(2,4,6-trimethylphenyl) |

TABLE 4-continued

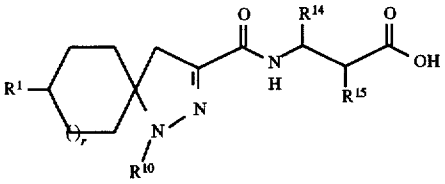

| Ex. No. | $R^1$ | r | $R^{10}$ | $R^{14}$ | $R^{15}$ |
|---|---|---|---|---|---|
| 4024 | 2-pyridinylaminomethyl | 0 | H | H | $NHSO_2$-(2,4,6-trimethylphenyl) |
| 4025 | 2-pyridinylaminomethyl | 0 | $-(CH_2)_4NH_2$ | H | $NHSO_2$-(2,4,6-trimethylphenyl) |
| 4026 | 2-pyridinylaminomethyl | 0 | COPh | H | $NHSO_2$-(2,4,6-trimethylphenyl) |
| 4027 | 2-pyridinylaminomethyl | 0 | $SO_2$-n-Bu | H | $NHSO_2$-(2,4,6-trimethylphenyl) |
| 4028 | 2-pyridinylaminomethyl | 0 | Cbz | H | NHCbz |
| 4029 | 2-pyridinylaminomethyl | 0 | $SO_2Ph$ | H | NHCbz |
| 4030 | 2-pyridinylaminomethyl | 0 | $CO(CH_2)_2Ph$ | H | NHCbz |
| 4031 | 2-pyridinylaminomethyl | 0 | Bn | H | NHCbz |
| 4032 | 2-pyridinylaminomethyl | 0 | n-Bu | H | NHCbz |
| 4033 | 2-pyridinylaminomethyl | 0 | $CO_2$-n-Bu | H | NHCbz |
| 4034 | 2-pyridinylaminomethyl | 0 | $CO_2$-i-Bu | H | NHCbz |
| 4035 | 2-pyridinylaminomethyl | 0 | $CO_2$-t-Bu | H | NHCbz |
| 4036 | 2-pyridinylaminomethyl | 0 | H | H | NHCbz |
| 4037 | 2-pyridinylaminomethyl | 0 | $-(CH_2)_4NH_2$ | H | NHCbz |
| 4038 | 2-pyridinylaminomethyl | 0 | COPh | H | NHCbz |
| 4039 | 2-pyridinylaminomethyl | 0 | $SO_2$-n-Bu | H | NHCbz |
| 4040 | 2-imidazolylaminomethyl | 0 | Cbz | H | $NHSO_2Ph$ |
| 4041 | 2-imidazolylaminomethyl | 0 | $SO_2Ph$ | H | $NHSO_2Ph$ |
| 4042 | 2-imidazolylaminomethyl | 0 | $CO(CH_2)_2Ph$ | H | $NHSO_2Ph$ |
| 4043 | 2-imidazolylaminomethyl | 0 | Bn | H | $NHSO_2Ph$ |
| 4044 | 2-imidazolylaminomethyl | 0 | n-Bu | H | $NHSO_2Ph$ |
| 4045 | 2-imidazolylaminomethyl | 0 | $COCH_2$ (3-indolyl) | H | $NHSO_2Ph$ |
| 4046 | 2-imidazolylaminomethyl | 0 | SO2-(biphenyl) | H | $NHSO_2Ph$ |
| 4047 | 2-imidazolylaminomethyl | 0 | $CO_2$-n-Bu | H | $NHSO_2Ph$ |
| 4048 | 2-imidazolylaminomethyl | 0 | $CO_2$-i-Bu | H | $NHSO_2Ph$ |
| 4049 | 2-imidazolylaminomethyl | 0 | $CO_2$-t-Bu | H | $NHSO_2Ph$ |
| 4050 | 2-imidazolylaminomethyl | 0 | H | H | $NHSO_2Ph$ |
| 4051 | 2-imidazolylaminomethyl | 0 | $-(CH_2)_4NH_2$ | H | $NHSO_2Ph$ |
| 4052 | 2-imidazolylaminomethyl | 0 | COPh | H | $NHSO_2Ph$ |
| 4053 | 2-imidazolylaminomethyl | 0 | cyclopropylmethyl | H | $NHSO_2Ph$ |
| 4054 | 2-imidazolylaminomethyl | 0 | $SO_2$-n-Bu | H | $NHSO_2Ph$ |
| 4055 | 2-imidazolylaminomethyl | 0 | Cbz | H | $NHSO_2$-(2,4,6-trimethylphenyl) |
| 4056 | 2-imidazolylaminomethyl | 0 | $SO_2Ph$ | H | $NHSO_2$-(2,4,6-trimethylphenyl) |
| 4057 | 2-imidazolylaminomethyl | 0 | $CO(CH_2)_2Ph$ | H | $NHSO_2$-(2,4,6-trimethylphenyl) |
| 4058 | 2-imidazolylaminomethyl | 0 | Bn | H | $NHSO_2$-(2,4,6-trimethylphenyl) |
| 4059 | 2-imidazolylaminomethyl | 0 | n-Bu | H | $NHSO_2$-(2,4,6-trimethylphenyl) |
| 4060 | 2-imidazolylaminomethyl | 0 | $CO_2$-n-Bu | H | $NHSO_2$-(2,4,6-trimethylphenyl) |
| 4061 | 2-imidazolylaminomethyl | 0 | $CO_2$-i-Bu | H | $NHSO_2$-(2,4,6-trimethylphenyl) |
| 4062 | 2-imidazolylaminomethyl | 0 | $CO_2$-t-Bu | H | $NHSO_2$-(2,4,6-trimethylphenyl) |
| 4063 | 2-imidazolylaminomethyl | 0 | H | H | $NHSO_2$-(2,4,6-trimethylphenyl) |
| 4064 | 2-imidazolylaminomethyl | 0 | $-(CH_2)_4NH_2$ | H | $NHSO_2$-(2,4,6-trimethylphenyl) |
| 4065 | 2-imidazolylaminomethyl | 0 | COPh | H | $NHSO_2$-(2,4,6-trimethylphenyl) |
| 4066 | 2-imidazolylaminomethyl | 0 | $SO_2$-n-Bu | H | $NHSO_2$-(2,4,6-trimethylphenyl) |
| 4067 | 2-imidazolylaminomethyl | 0 | Cbz | H | NHCbz |
| 4068 | 2-imidazolylaminomethyl | 0 | $SO_2Ph$ | H | NHCbz |
| 4069 | 2-imidazolylaminomethyl | 0 | $CO(CH_2)_2Ph$ | H | NHCbz |
| 4070 | 2-imidazolylaminomethyl | 0 | Bn | H | NHCbz |
| 4071 | 2-imidazolylaminomethyl | 0 | n-Bu | H | NHCbz |
| 4072 | 2-imidazolylaminomethyl | 0 | $CO_2$-n-Bu | H | NHCbz |
| 4073 | 2-imidazolylaminomethyl | 0 | $CO_2$-i-Bu | H | NHCbz |
| 4074 | 2-imidazolylaminomethyl | 0 | $CO_2$-t-Bu | H | NHCbz |

TABLE 4-continued

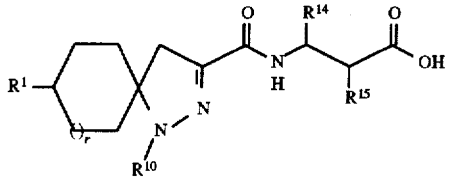

| Ex. No. | $R^1$ | r | $R^{10}$ | $R^{14}$ | $R^{15}$ |
|---|---|---|---|---|---|
| 4075 | 2-imidazolylaminomethyl | 0 | H | H | NHCbz |
| 4076 | 2-imidazolylaminomethyl | 0 | $-(CH_2)_4NH_2$ | H | NHCbz |
| 4077 | 2-imidazolylaminomethyl | 0 | COPh | H | NHCbz |
| 4078 | 2-imidazolylaminomethyl | 0 | $SO_2$-n-Bu | H | NHCbz |
| 4079 | 2-imidazolinylaminomethyl | 0 | Cbz | H | $NHSO_2Ph$ |
| 4080 | 2-imidazolinylaminomethyl | 0 | $SO_2Ph$ | H | $NHSO_2Ph$ |
| 4081 | 2-imidazolinylaminomethyl | 0 | $CO(CH_2)_2Ph$ | H | $NHSO_2Ph$ |
| 4082 | 2-imidazolinylaminomethyl | 0 | Bn | H | $NHSO_2Ph$ |
| 4083 | 2-imidazolinylaminomethyl | 0 | n-Bu | H | $NHSO_2Ph$ |
| 4084 | 2-imidazolinylaminomethyl | 0 | $COCH_2$ (3-indolyl) | H | $NHSO_2Ph$ |
| 4085 | 2-imidazolinylaminomethyl | 0 | SO2-(biphenyl) | H | $NHSO_2Ph$ |
| 4086 | 2-imidazolinylaminomethyl | 0 | $CO_2$-n-Bu | H | $NHSO_2Ph$ |
| 4087 | 2-imidazolinylaminomethyl | 0 | $CO_2$-i-Bu | H | $NHSO_2Ph$ |
| 4088 | 2-imidazolinylaminomethyl | 0 | $CO_2$-t-Bu | H | $NHSO_2Ph$ |
| 4089 | 2-imidazolinylaminomethyl | 0 | H | H | $NHSO_2Ph$ |
| 4090 | 2-imidazolinylaminomethyl | 0 | $-(CH_2)_4NH_2$ | H | $NHSO_2Ph$ |
| 4091 | 2-imidazolinylaminomethyl | 0 | COPh | H | $NHSO_2Ph$ |
| 4092 | 2-imidazolinylaminomethyl | 0 | cyclopropylmethyl | H | $NHSO_2Ph$ |
| 4093 | 2-imidazolinylaminomethyl | 0 | $SO_2$-n-Bu | H | $NHSO_2Ph$ |
| 4094 | 2-imidazolinylaminomethyl | 0 | Cbz | H | $NHSO_2$-(2,4,6-trimethylphenyl) |
| 4095 | 2-imidazolinylaminomethyl | 0 | $SO_2Ph$ | H | $NHSO_2$-(2,4,6-trimethylphenyl) |
| 4096 | 2-imidazolinylaminomethyl | 0 | $CO(CH_2)_2Ph$ | H | $NHSO_2$-(2,4,6-trimethylphenyl) |
| 4097 | 2-imidazolinylaminomethyl | 0 | Bn | H | $NHSO_2$-(2,4,6-trimethylphenyl) |
| 4098 | 2-imidazolinylaminomethyl | 0 | n-Bu | H | $NHSO_2$-(2,4,6-trimethylphenyl) |
| 4099 | 2-imidazolinylaminomethyl | 0 | $CO_2$-n-Bu | H | $NHSO_2$-(2,4,6-trimethylphenyl) |
| 4100 | 2-imidazolinylaminomethyl | 0 | $CO_2$-i-Bu | H | $NHSO_2$-(2,4,6-trimethylphenyl) |
| 4101 | 2-imidazolinylaminomethyl | 0 | $CO_2$-t-Bu | H | $NHSO_2$-(2,4,6-trimethylphenyl) |
| 4102 | 2-imidazolinylaminomethyl | 0 | H | H | $NHSO_2$-(2,4,6-trimethylphenyl) |
| 4103 | 2-imidazolinylaminomethyl | 0 | $-(CH_2)_4NH_2$ | H | $NHSO_2$-(2,4,6-trimethylphenyl) |
| 4104 | 2-imidazolinylaminomethyl | 0 | COPh | H | $NHSO_2$-(2,4,6-trimethylphenyl) |
| 4105 | 2-imidazolinylaminomethyl | 0 | $SO_2$-n-Bu | H | $NHSO_2$-(2,4,6-trimethylphenyl) |
| 4106 | 2-imidazolinylaminomethyl | 0 | Cbz | H | NHCbz |
| 4107 | 2-imidazolinylaminomethyl | 0 | $SO_2Ph$ | H | NHCbz |
| 4108 | 2-imidazolinylaminomethyl | 0 | $CO(CH_2)_2Ph$ | H | NHCbz |
| 4109 | 2-imidazolinylaminomethyl | 0 | Bn | H | NHCbz |
| 4110 | 2-imidazolinylaminomethyl | 0 | n-Bu | H | NHCbz |
| 4111 | 2-imidazolinylaminomethyl | 0 | $CO_2$-n-Bu | H | NHCbz |
| 4112 | 2-imidazolinylaminomethyl | 0 | $CO_2$-i-Bu | H | NHCbz |
| 4113 | 2-imidazolinylaminomethyl | 0 | $CO_2$-t-Bu | H | NHCbz |
| 4114 | 2-imidazolinylaminomethyl | 0 | H | H | NHCbz |
| 4115 | 2-imidazolinylaminomethyl | 0 | $-(CH_2)_4NH_2$ | H | NHCbz |
| 4116 | 2-imidazolinylaminomethyl | 0 | COPh | H | NHCbz |
| 4117 | 2-imidazolinylaminomethyl | 0 | $SO_2$-n-Bu | H | NHCbz |
| 4118 | 2-benzimidazolylaminomethyl | 0 | Cbz | H | $NHSO_2Ph$ |
| 4119 | 2-benzimidazolylaminomethyl | 0 | $SO_2Ph$ | H | $NHSO_2Ph$ |
| 4120 | 2-benzimidazolylaminomethyl | 0 | $CO(CH_2)_2Ph$ | H | $NHSO_2Ph$ |
| 4121 | 2-benzimidazolylaminomethyl | 0 | Bn | H | $NHSO_2Ph$ |
| 4122 | 2-benzimidazolylaminomethyl | 0 | n-Bu | H | $NHSO_2Ph$ |
| 4123 | 2-benzimidazolylaminomethyl | 0 | $COCH_2$ (3-indolyl) | H | $NHSO_2Ph$ |
| 4124 | 2-benzimidazolylaminomethyl | 0 | SO2-(biphenyl) | H | $NHSO_2Ph$ |
| 4125 | 2-benzimidazolylaminomethyl | 0 | $CO_2$-n-Bu | H | $NHSO_2Ph$ |
| 4126 | 2-benzimidazolylaminomethyl | 0 | $CO_2$-i-Bu | H | $NHSO_2Ph$ |
| 4127 | 2-benzimidazolylaminomethyl | 0 | $CO_2$-t-Bu | H | $NHSO_2Ph$ |
| 4128 | 2-benzimidazolylaminomethyl | 0 | H | H | $NHSO_2Ph$ |
| 4129 | 2-benzimidazolylaminomethyl | 0 | $-(CH_2)_4NH_2$ | H | $NHSO_2Ph$ |

TABLE 4-continued

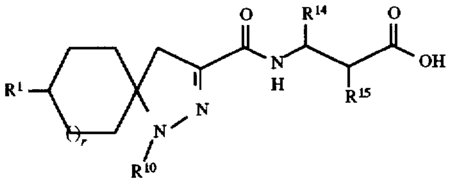

| Ex. No. | $R^1$ | r | $R^{10}$ | $R^{14}$ | $R^{15}$ |
|---|---|---|---|---|---|
| 4130 | 2-benzimidazolylaminomethyl | 0 | COPh | H | $NHSO_2Ph$ |
| 4131 | 2-benzimidazolylaminomethyl | 0 | cyclopropylmethyl | H | $NHSO_2Ph$ |
| 4132 | 2-benzimidazolylaminomethyl | 0 | $SO_2$-n-Bu | H | $NHSO_2Ph$ |
| 4133 | 2-benzimidazolylaminomethyl | 0 | Cbz | H | $NHSO_2$-(2,4,6-trimethylphenyl) |
| 4134 | 2-benzimidazolylaminomethyl | 0 | $SO_2Ph$ | H | $NHSO_2$-(2,4,6-trimethylphenyl) |
| 4135 | 2-benzimidazolylaminomethyl | 0 | $CO(CH_2)_2Ph$ | H | $NHSO_2$-(2,4,6-trimethylphenyl) |
| 4136 | 2-benzimidazolylaminomethyl | 0 | Bn | H | $NHSO_2$-(2,4,6-trimethylphenyl) |
| 4137 | 2-benzimidazolylaminomethyl | 0 | n-Bu | H | $NHSO_2$-(2,4,6-trimethylphenyl) |
| 4138 | 2-benzimidazolylaminomethyl | 0 | $CO_2$-n-Bu | H | $NHSO_2$-(2,4,6-trimethylphenyl) |
| 4139 | 2-benzimidazolylaminomethyl | 0 | $CO_2$-i-Bu | H | $NHSO_2$-(2,4,6-trimethylphenyl) |
| 4140 | 2-benzimidazolylaminomethyl | 0 | $CO_2$-t-Bu | H | $NHSO_2$-(2,4,6-trimethylphenyl) |
| 4141 | 2-benzimidazolylaminomethyl | 0 | H | H | $NHSO_2$-(2,4,6-trimethylphenyl) |
| 4142 | 2-benzimidazolylaminomethyl | 0 | $-(CH_2)_4NH_2$ | H | $NHSO_2$-(2,4,6-trimethylphenyl) |
| 4143 | 2-benzimidazolylaminomethyl | 0 | COPh | H | $NHSO_2$-(2,4,6-trimethylphenyl) |
| 4144 | 2-benzimidazolylaminomethyl | 0 | $SO_2$-n-Bu | H | $NHSO_2$-(2,4,6-trimethylphenyl) |
| 4145 | 2-benzimidazolylaminomethyl | 0 | Cbz | H | NHCbz |
| 4146 | 2-benzimidazolylaminomethyl | 0 | $SO_2Ph$ | H | NHCbz |
| 4147 | 2-benzimidazolylaminomethyl | 0 | $CO(CH_2)_2Ph$ | H | NHCbz |
| 4148 | 2-benzimidazolylaminomethyl | 0 | Bn | H | NHCbz |
| 4149 | 2-benzimidazolylaminomethyl | 0 | n-Bu | H | NHCbz |
| 4150 | 2-benzimidazolylaminomethyl | 0 | $CO_2$-n-Bu | H | NHCbz |
| 4151 | 2-benzimidazolylaminomethyl | 0 | $CO_2$-i-Bu | H | NHCbz |
| 4152 | 2-benzimidazolylaminomethyl | 0 | $CO_2$-t-Bu | H | NHCbz |
| 4153 | 2-benzimidazolylaminomethyl | 0 | H | H | NHCbz |
| 4154 | 2-benzimidazolylaminomethyl | 0 | $-(CH_2)_4NH_2$ | H | NHCbz |
| 4155 | 2-benzimidazolylaminomethyl | 0 | COPh | H | NHCbz |
| 4156 | 2-benzimidazolylaminomethyl | 0 | $SO_2$-n-Bu | H | NHCbz |
| 4157 | 7-aza-2-benzimidazolyl | 0 | Cbz | H | $NHSO_2Ph$ |
| 4158 | 7-aza-2-benzimidazolyl | 0 | $SO_2Ph$ | H | $NHSO_2Ph$ |
| 4159 | 7-aza-2-benzimidazolyl | 0 | $CO(CH_2)_2Ph$ | H | $NHSO_2Ph$ |
| 4160 | 7-aza-2-benzimidazolyl | 0 | Bn | H | $NHSO_2Ph$ |
| 4161 | 7-aza-2-benzimidazolyl | 0 | n-Bu | H | $NHSO_2Ph$ |
| 4162 | 7-aza-2-benzimidazolyl | 0 | $COCH_2$ (3-indolyl) | H | $NHSO_2Ph$ |
| 4163 | 7-aza-2-benzimidazolyl | 0 | SO2-(biphenyl) | H | $NHSO_2Ph$ |
| 4164 | 7-aza-2-benzimidazolyl | 0 | $CO_2$-n-Bu | H | $NHSO_2Ph$ |
| 4165 | 7-aza-2-benzimidazolyl | 0 | $CO_2$-i-Bu | H | $NHSO_2Ph$ |
| 4166 | 7-aza-2-benzimidazolyl | 0 | $CO_2$-t-Bu | H | $NHSO_2Ph$ |
| 4167 | 7-aza-2-benzimidazolyl | 0 | H | H | $NHSO_2Ph$ |
| 4168 | 7-aza-2-benzimidazolyl | 0 | $-(CH_2)_4NH_2$ | H | $NHSO_2Ph$ |
| 4169 | 7-aza-2-benzimidazolyl | 0 | COPh | H | $NHSO_2Ph$ |
| 4170 | 7-aza-2-benzimidazolyl | 0 | cyclopropylmethyl | H | $NHSO_2Ph$ |
| 4171 | 7-aza-2-benzimidazolyl | 0 | $SO_2$-n-Bu | H | $NHSO_2Ph$ |
| 4172 | 7-aza-2-benzimidazolyl | 0 | Cbz | H | $NHSO_2$-(2,4,6-trimethylphenyl) |
| 4173 | 7-aza-2-benzimidazolyl | 0 | $SO_2Ph$ | H | $NHSO_2$-(2,4,6-trimethylphenyl) |
| 4174 | 7-aza-2-benzimidazolyl | 0 | $CO(CH_2)_2Ph$ | H | $NHSO_2$-(2,4,6-trimethylphenyl) |
| 4175 | 7-aza-2-benzimidazolyl | 0 | Bn | H | $NHSO_2$-(2,4,6-trimethylphenyl) |
| 4176 | 7-aza-2-benzimidazolyl | 0 | n-Bu | H | $NHSO_2$-(2,4,6-trimethylphenyl) |
| 4177 | 7-aza-2-benzimidazolyl | 0 | $CO_2$-n-Bu | H | $NHSO_2$-(2,4,6-trimethylphenyl) |
| 4178 | 7-aza-2-benzimidazolyl | 0 | $CO_2$-i-Bu | H | $NHSO_2$-(2,4,6- |

TABLE 4-continued

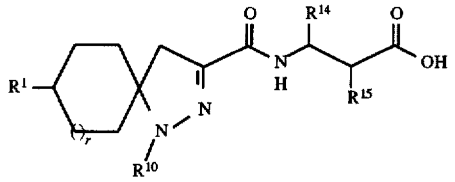

| Ex. No. | $R^1$ | r | $R^{10}$ | $R^{14}$ | $R^{15}$ |
|---|---|---|---|---|---|
| | | | | | trimethylphenyl) |
| 4179 | 7-aza-2-benzimidazolyl | 0 | $CO_2$-t-Bu | H | $NHSO_2$-(2,4,6-trimethylphenyl) |
| 4180 | 7-aza-2-benzimidazolyl | 0 | H | H | $NHSO_2$-(2,4,6-trimethylphenyl) |
| 4181 | 7-aza-2-benzimidazolyl | 0 | $-(CH_2)_4NH_2$ | H | $NHSO_2$-(2,4,6-trimethylphenyl) |
| 4182 | 7-aza-2-benzimidazolyl | 0 | COPh | H | $NHSO_2$-(2,4,6-trimethylphenyl) |
| 4183 | 7-aza-2-benzimidazolyl | 0 | $SO_2$-n-Bu | H | $NHSO_2$-(2,4,6-trimethylphenyl) |
| 4184 | 7-aza-2-benzimidazolyl | 0 | Cbz | H | NHCbz |
| 4185 | 7-aza-2-benzimidazolyl | 0 | $SO_2Ph$ | H | NHCbz |
| 4186 | 7-aza-2-benzimidazolyl | 0 | $CO(CH_2)_2Ph$ | H | NHCbz |
| 4187 | 7-aza-2-benzimidazolyl | 0 | Bn | H | NHCbz |
| 4188 | 7-aza-2-benzimidazolyl | 0 | n-Bu | H | NHCbz |
| 4189 | 7-aza-2-benzimidazolyl | 0 | $CO_2$-n-Bu | H | NHCbz |
| 4190 | 7-aza-2-benzimidazolyl | 0 | $CO_2$-i-Bu | H | NHCbz |
| 4191 | 7-aza-2-benzimidazolyl | 0 | $CO_2$-t-Bu | H | NHCbz |
| 4192 | 7-aza-2-benzimidazolyl | 0 | H | H | NHCbz |
| 4193 | 7-aza-2-benzimidazolyl | 0 | $-(CH_2)_4NH_2$ | H | NHCbz |
| 4194 | 7-aza-2-benzimidazolyl | 0 | COPh | H | NHCbz |
| 4195 | 7-aza-2-benzimidazolyl | 0 | $SO_2$-n-Bu | H | NHCbz |
| 4196 | tetrahydropyrimidin-2-ylaminomethyl | 0 | Cbz | H | $NHSO_2Ph$ |
| 4197 | tetrahydropyrimidin-2-ylaminomethyl | 0 | $SO_2Ph$ | H | $NHSO_2Ph$ |
| 4198 | tetrahydropyrimidin-2-ylaminomethyl | 0 | $CO(CH_2)_2Ph$ | H | $NHSO_2Ph$ |
| 4199 | tetrahydropyrimidin-2-ylaminomethyl | 0 | Bn | H | $NHSO_2Ph$ |
| 4200 | tetrahydropyrimidin-2-ylaminomethyl | 0 | n-Bu | H | $NHSO_2Ph$ |
| 4201 | tetrahydropyrimidin-2-ylaminomethyl | 0 | $COCH_2$ (3-indolyl) | H | $NHSO_2Ph$ |
| 4202 | tetrahydropyrimidin-2-ylaminomethyl | 0 | SO2-(biphenyl) | H | $NHSO_2Ph$ |
| 4203 | tetrahydropyrimidin-2-ylaminomethyl | 0 | $CO_2$-n-Bu | H | $NHSO_2Ph$ |
| 4204 | tetrahydropyrimidin-2-ylaminomethyl | 0 | $CO_2$-i-Bu | H | $NHSO_2Ph$ |
| 4205 | tetrahydropyrimidin-2-ylaminomethyl | 0 | $CO_2$-t-Bu | H | $NHSO_2Ph$ |
| 4206 | tetrahydropyrimidin-2-ylaminomethyl | 0 | H | H | $NHSO_2Ph$ |
| 4207 | tetrahydropyrimidin-2-ylaminomethyl | 0 | $-(CH_2)_4NH_2$ | H | $NHSO_2Ph$ |
| 4208 | tetrahydropyrimidin-2-ylaminomethyl | 0 | COPh | H | $NHSO_2Ph$ |
| 4209 | tetrahydropyrimidin-2-ylaminomethyl | 0 | cyclopropylmethyl | H | $NHSO_2Ph$ |
| 4210 | tetrahydropyrimidin-2-ylaminomethyl | 0 | $SO_2$-n-Bu | H | $NHSO_2Ph$ |
| 4211 | tetrahydropyrimidin-2-ylaminomethyl | 0 | Cbz | H | $NHSO_2$-(2,4,6-trimethylphenyl) |
| 4212 | tetrahydropyrimidin-2-ylaminomethyl | 0 | $SO_2Ph$ | H | $NHSO_2$-(2,4,6-trimethylphenyl) |
| 4213 | tetrahydropyrimidin-2-ylaminomethyl | 0 | $CO(CH_2)_2Ph$ | H | $NHSO_2$-(2,4,6-trimethylphenyl) |
| 4214 | tetrahydropyrimidin-2-ylaminomethyl | 0 | Bn | H | $NHSO_2$-(2,4,6-trimethylphenyl) |
| 4215 | tetrahydropyrimidin-2-ylaminomethyl | 0 | n-Bu | H | $NHSO_2$-(2,4,6-trimethylphenyl) |
| 4216 | tetrahydropyrimidin-2-ylaminomethyl | 0 | $CO_2$-n-Bu | H | $NHSO_2$-(2,4,6-trimethylphenyl) |
| 4217 | tetrahydropyrimidin-2-ylaminomethyl | 0 | $CO_2$-i-Bu | H | $NHSO_2$-(2,4,6-trimethylphenyl) |

TABLE 4-continued

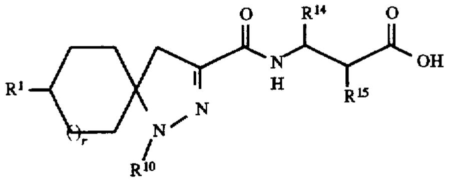

| Ex. No. | $R^1$ | r | $R^{10}$ | $R^{14}$ | $R^{15}$ |
|---|---|---|---|---|---|
| 4218 | tetrahydropyrimidin-2-ylaminomethyl | 0 | $CO_2$-t-Bu | H | $NHSO_2$-(2,4,6-trimethylphenyl) |
| 4219 | tetrahydropyrimidin-2-ylaminomethyl | 0 | H | H | $NHSO_2$-(2,4,6-trimethylphenyl) |
| 4220 | tetrahydropyrimidin-2-ylaminomethyl | 0 | $-(CH_2)_4NH_2$ | H | $NHSO_2$-(2,4,6-trimethylphenyl) |
| 4221 | tetrahydropyrimidin-2-ylaminomethyl | 0 | COPh | H | $NHSO_2$-(2,4,6-trimethylphenyl) |
| 4222 | tetrahydropyrimidin-2-ylaminomethyl | 0 | $SO_2$-n-Bu | H | $NHSO_2$-(2,4,6-trimethylphenyl) |
| 4223 | tetrahydropyrimidin-2-ylaminomethyl | 0 | Cbz | H | NHCbz |
| 4224 | tetrahydropyrimidin-2-ylaminomethyl | 0 | $SO_2Ph$ | H | NHCbz |
| 4225 | tetrahydropyrimidin-2-ylaminomethyl | 0 | $CO(CH_2)_2Ph$ | H | NHCbz |
| 4226 | tetrahydropyrimidin-2-ylaminomethyl | 0 | Bn | H | NHCbz |
| 4227 | tetrahydropyrimidin-2-ylaminomethyl | 0 | n-Bu | H | NHCbz |
| 4228 | tetrahydropyrimidin-2-ylaminomethyl | 0 | $CO_2$-n-Bu | H | NHCbz |
| 4229 | tetrahydropyrimidin-2-ylaminomethyl | 0 | $CO_2$-i-Bu | H | NHCbz |
| 4230 | tetrahydropyrimidin-2-ylaminomethyl | 0 | $CO_2$-t-Bu | H | NHCbz |
| 4231 | tetrahydropyrimidin-2-ylaminomethyl | 0 | H | H | NHCbz |
| 4232 | tetrahydropyrimidin-2-ylaminomethyl | 0 | $-(CH_2)_4NH_2$ | H | NHCbz |
| 4233 | tetrahydropyrimidin-2-ylaminomethyl | 0 | COPh | H | NHCbz |
| 4234 | tetrahydropyrimidin-2-ylaminomethyl | 0 | $SO_2$-n-Bu | H | NHCbz |
| 4235 | 2-pyridinylaminomethyl | 1 | Cbz | H | $NHSO_2Ph$ |
| 4236 | 2-pyridinylaminomethyl | 1 | $SO_2Ph$ | H | $NHSO_2Ph$ |
| 4237 | 2-pyridinylaminomethyl | 1 | $CO(CH_2)_2Ph$ | H | $NHSO_2Ph$ |
| 4238 | 2-pyridinylaminomethyl | 1 | Bn | H | $NHSO_2Ph$ |
| 4239 | 2-pyridinylaminomethyl | 1 | n-Bu | H | $NHSO_2Ph$ |
| 4240 | 2-pyridinylaminomethyl | 1 | $COCH_2$ (3-indolyl) | H | $NHSO_2Ph$ |
| 4241 | 2-pyridinylaminomethyl | 1 | SO2-(biphenyl) | H | $NHSO_2Ph$ |
| 4242 | 2-pyridinylaminomethyl | 1 | $CO_2$-n-Bu | H | $NHSO_2Ph$ |
| 4243 | 2-pyridinylaminomethyl | 1 | $CO_2$-i-Bu | H | $NHSO_2Ph$ |
| 4244 | 2-pyridinylaminomethyl | 1 | $CO_2$-t-Bu | H | $NHSO_2Ph$ |
| 4245 | 2-pyridinylaminomethyl | 1 | H | H | $NHSO_2Ph$ |
| 4246 | 2-pyridinylaminomethyl | 1 | $-(CH_2)_4NH_2$ | H | $NHSO_2Ph$ |
| 4247 | 2-pyridinylaminomethyl | 1 | COPh | H | $NHSO_2Ph$ |
| 4248 | 2-pyridinylaminomethyl | 1 | cyclopropylmethyl | H | $NHSO_2Ph$ |
| 4249 | 2-pyridinylaminomethyl | 1 | $SO_2$-n-Bu | H | $NHSO_2Ph$ |
| 4250 | 2-pyridinylaminomethyl | 1 | Cbz | H | $NHSO_2$-(2,4,6-trimethylphenyl) |
| 4251 | 2-pyridinylaminomethyl | 1 | $SO_2Ph$ | H | $NHSO_2$-(2,4,6-trimethylphenyl) |
| 4252 | 2-pyridinylaminomethyl | 1 | $CO(CH_2)_2Ph$ | H | $NHSO_2$-(2,4,6-trimethylphenyl) |
| 4253 | 2-pyridinylaminomethyl | 1 | Bn | H | $NHSO_2$-(2,4,6-trimethylphenyl) |
| 4254 | 2-pyridinylaminomethyl | 1 | n-Bu | H | $NHSO_2$-(2,4,6-trimethylphenyl) |
| 4255 | 2-pyridinylaminomethyl | 1 | $CO_2$-n-Bu | H | $NHSO_2$-(2,4,6-trimethylphenyl) |
| 4256 | 2-pyridinylaminomethyl | 1 | $CO_2$-i-Bu | H | $NHSO_2$-(2,4,6-trimethylphenyl) |
| 4257 | 2-pyridinylaminomethyl | 1 | $CO_2$-t-Bu | H | $NHSO_2$-(2,4,6-trimethylphenyl) |
| 4258 | 2-pyridinylaminomethyl | 1 | H | H | $NHSO_2$-(2,4,6-trimethylphenyl) |

TABLE 4-continued

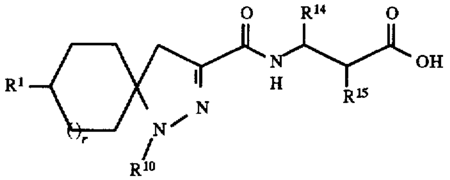

| Ex. No. | $R^1$ | r | $R^{10}$ | $R^{14}$ | $R^{15}$ |
|---|---|---|---|---|---|
| 4259 | 2-pyridinylaminomethyl | 1 | $-(CH_2)_4NH_2$ | H | $NHSO_2$-(2,4,6-trimethylphenyl) |
| 4260 | 2-pyridinylaminomethyl | 1 | COPh | H | $NHSO_2$-(2,4,6-trimethylphenyl) |
| 4261 | 2-pyridinylaminomethyl | 1 | $SO_2$-n-Bu | H | $NHSO_2$-(2,4,6-trimethylphenyl) |
| 4262 | 2-pyridinylaminomethyl | 1 | Cbz | H | NHCbz |
| 4263 | 2-pyridinylaminomethyl | 1 | $SO_2Ph$ | H | NHCbz |
| 4264 | 2-pyridinylaminomethyl | 1 | $CO(CH_2)_2Ph$ | H | NHCbz |
| 4265 | 2-pyridinylaminomethyl | 1 | Bn | H | NHCbz |
| 4266 | 2-pyridinylaminomethyl | 1 | n-Bu | H | NHCbz |
| 4267 | 2-pyridinylaminomethyl | 1 | $CO_2$-n-Bu | H | NHCbz |
| 4268 | 2-pyridinylaminomethyl | 1 | $CO_2$-i-Bu | H | NHCbz |
| 4269 | 2-pyridinylaminomethyl | 1 | $CO_2$-t-Bu | H | NHCbz |
| 4270 | 2-pyridinylaminomethyl | 1 | H | H | NHCbz |
| 4271 | 2-pyridinylaminomethyl | 1 | $-(CH_2)_4NH_2$ | H | NHCbz |
| 4272 | 2-pyridinylaminomethyl | 1 | COPh | H | NHCbz |
| 4273 | 2-pyridinylaminomethyl | 1 | $SO_2$-n-Bu | H | NHCbz |
| 4274 | 2-imidazolylaminomethyl | 1 | Cbz | H | $NHSO_2Ph$ |
| 4275 | 2-imidazolylaminomethyl | 1 | $SO_2Ph$ | H | $NHSO_2Ph$ |
| 4276 | 2-imidazolylaminomethyl | 1 | $CO(CH_2)_2Ph$ | H | $NHSO_2Ph$ |
| 4277 | 2-imidazolylaminomethyl | 1 | Bn | H | $NHSO_2Ph$ |
| 4278 | 2-imidazolylaminomethyl | 1 | n-Bu | H | $NHSO_2Ph$ |
| 4279 | 2-imidazolylaminomethyl | 1 | $COCH_2$ (3-indolyl) | H | $NHSO_2Ph$ |
| 4280 | 2-imidazolylaminomethyl | 1 | $SO_2$-(biphenyl) | H | $NHSO_2Ph$ |
| 4281 | 2-imidazolylaminomethyl | 1 | $CO_2$-n-Bu | H | $NHSO_2Ph$ |
| 4282 | 2-imidazolylaminomethyl | 1 | $CO_2$-i-Bu | H | $NHSO_2Ph$ |
| 4283 | 2-imidazolylaminomethyl | 1 | $CO_2$-t-Bu | H | $NHSO_2Ph$ |
| 4284 | 2-imidazolylaminomethyl | 1 | H | H | $NHSO_2Ph$ |
| 4285 | 2-imidazolylaminomethyl | 1 | $-(CH_2)_4NH_2$ | H | $NHSO_2Ph$ |
| 4286 | 2-imidazolylaminomethyl | 1 | COPh | H | $NHSO_2Ph$ |
| 4287 | 2-imidazolylaminomethyl | 1 | cyclopropylmethyl | H | $NHSO_2Ph$ |
| 4288 | 2-imidazolylaminomethyl | 1 | $SO_2$-n-Bu | H | $NHSO_2Ph$ |
| 4289 | 2-imidazolylaminomethyl | 1 | Cbz | H | $NHSO_2$-(2,4,6-trimethylphenyl) |
| 4290 | 2-imidazolylaminomethyl | 1 | $SO_2Ph$ | H | $NHSO_2$-(2,4,6-trimethylphenyl) |
| 4291 | 2-imidazolylaminomethyl | 1 | $CO(CH_2)_2Ph$ | H | $NHSO_2$-(2,4,6-trimethylphenyl) |
| 4292 | 2-imidazolylaminomethyl | 1 | Bn | H | $NHSO_2$-(2,4,6-trimethylphenyl) |
| 4293 | 2-imidazolylaminomethyl | 1 | n-Bu | H | $NHSO_2$-(2,4,6-trimethylphenyl) |
| 4294 | 2-imidazolylaminomethyl | 1 | $CO_2$-n-Bu | H | $NHSO_2$-(2,4,6-trimethylphenyl) |
| 4295 | 2-imidazolylaminomethyl | 1 | $CO_2$-i-Bu | H | $NHSO_2$-(2,4,6-trimethylphenyl) |
| 4296 | 2-imidazolylaminomethyl | 1 | $CO_2$-t-Bu | H | $NHSO_2$-(2,4,6-trimethylphenyl) |
| 4297 | 2-imidazolylaminomethyl | 1 | H | H | $NHSO_2$-(2,4,6-trimethylphenyl) |
| 4298 | 2-imidazolylaminomethyl | 1 | $-(CH_2)_4NH_2$ | H | $NHSO_2$-(2,4,6-trimethylphenyl) |
| 4299 | 2-imidazolylaminomethyl | 1 | COPh | H | $NHSO_2$-(2,4,6-trimethylphenyl) |
| 4300 | 2-imidazolylaminomethyl | 1 | $SO_2$-n-Bu | H | $NHSO_2$-(2,4,6-trimethylphenyl) |
| 4301 | 2-imidazolylaminomethyl | 1 | Cbz | H | NHCbz |
| 4302 | 2-imidazolylaminomethyl | 1 | $SO_2Ph$ | H | NHCbz |
| 4303 | 2-imidazolylaminomethyl | 1 | $CO(CH_2)_2Ph$ | H | NHCbz |
| 4304 | 2-imidazolylaminomethyl | 1 | Bn | H | NHCbz |
| 4305 | 2-imidazolylaminomethyl | 1 | n-Bu | H | NHCbz |
| 4306 | 2-imidazolylaminomethyl | 1 | $CO_2$-n-Bu | H | NHCbz |
| 4307 | 2-imidazolylaminomethyl | 1 | $CO_2$-i-Bu | H | NHCbz |
| 4308 | 2-imidazolylaminomethyl | 1 | $CO_2$-t-Bu | H | NHCbz |
| 4309 | 2-imidazolylaminomethyl | 1 | H | H | NHCbz |
| 4310 | 2-imidazolylaminomethyl | 1 | $-(CH_2)_4NH_2$ | H | NHCbz |

TABLE 4-continued

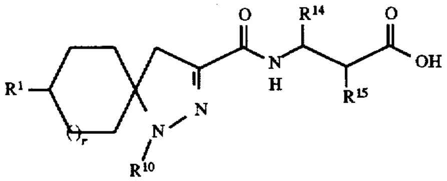

| Ex. No. | $R^1$ | r | $R^{10}$ | $R^{14}$ | $R^{15}$ |
|---|---|---|---|---|---|
| 4311 | 2-imidazolylaminomethyl | 1 | COPh | H | NHCbz |
| 4312 | 2-imidazolylaminomethyl | 1 | $SO_2$-n-Bu | H | NHCbz |
| 4313 | 2-imidazolinylaminomethyl | 1 | Cbz | H | $NHSO_2Ph$ |
| 4314 | 2-imidazolinylaminomethyl | 1 | $SO_2Ph$ | H | $NHSO_2Ph$ |
| 4315 | 2-imidazolinylaminomethyl | 1 | $CO(CH_2)_2Ph$ | H | $NHSO_2Ph$ |
| 4316 | 2-imidazolinylaminomethyl | 1 | Bn | H | $NHSO_2Ph$ |
| 4317 | 2-imidazolinylaminomethyl | 1 | n-Bu | H | $NHSO_2Ph$ |
| 4318 | 2-imidazolinylaminomethyl | 1 | $COCH_2$ (3-indolyl) | H | $NHSO_2Ph$ |
| 4319 | 2-imidazolinylaminomethyl | 1 | $SO_2$-(biphenyl) | H | $NHSO_2Ph$ |
| 4320 | 2-imidazolinylaminomethyl | 1 | $CO_2$-n-Bu | H | $NHSO_2Ph$ |
| 4321 | 2-imidazolinylaminomethyl | 1 | $CO_2$-i-Bu | H | $NHSO_2Ph$ |
| 4322 | 2-imidazolinylaminomethyl | 1 | $CO_2$-t-Bu | H | $NHSO_2Ph$ |
| 4323 | 2-imidazolinylaminomethyl | 1 | H | H | $NHSO_2Ph$ |
| 4324 | 2-imidazolinylaminomethyl | 1 | $-(CH_2)_4NH_2$ | H | $NHSO_2Ph$ |
| 4325 | 2-imidazolinylaminomethyl | 1 | COPh | H | $NHSO_2Ph$ |
| 4326 | 2-imidazolinylaminomethyl | 1 | cyclopropylmethyl | H | $NHSO_2Ph$ |
| 4327 | 2-imidazolinylaminomethyl | 1 | $SO_2$-n-Bu | H | $NHSO_2Ph$ |
| 4328 | 2-imidazolinylaminomethyl | 1 | Cbz | H | $NHSO_2$-(2,4,6-trimethylphenyl) |
| 4329 | 2-imidazolinylaminomethyl | 1 | $SO_2Ph$ | H | $NHSO_2$-(2,4,6-trimethylphenyl) |
| 4330 | 2-imidazolinylaminomethyl | 1 | $CO(CH_2)_2Ph$ | H | $NHSO_2$-(2,4,6-trimethylphenyl) |
| 4331 | 2-imidazolinylaminomethyl | 1 | Bn | H | $NHSO_2$-(2,4,6-trimethylphenyl) |
| 4332 | 2-imidazolinylaminomethyl | 1 | n-Bu | H | $NHSO_2$-(2,4,6-trimethylphenyl) |
| 4333 | 2-imidazolinylaminomethyl | 1 | $CO_2$-n-Bu | H | $NHSO_2$-(2,4,6-trimethylphenyl) |
| 4334 | 2-imidazolinylaminomethyl | 1 | $CO_2$-i-Bu | H | $NHSO_2$-(2,4,6-trimethylphenyl) |
| 4335 | 2-imidazolinylaminomethyl | 1 | $CO_2$-t-Bu | H | $NHSO_2$-(2,4,6-trimethylphenyl) |
| 4336 | 2-imidazolinylaminomethyl | 1 | H | H | $NHSO_2$-(2,4,6-trimethylphenyl) |
| 4337 | 2-imidazolinylaminomethyl | 1 | $-(CH_2)_4NH_2$ | H | $NHSO_2$-(2,4,6-trimethylphenyl) |
| 4338 | 2-imidazolinylaminomethyl | 1 | COPh | H | $NHSO_2$-(2,4,6-trimethylphenyl) |
| 4339 | 2-imidazolinylaminomethyl | 1 | $SO_2$-n-Bu | H | $NHSO_2$-(2,4,6-trimethylphenyl) |
| 4340 | 2-imidazolinylaminomethyl | 1 | Cbz | H | NHCbz |
| 4341 | 2-imidazolinylaminomethyl | 1 | $SO_2Ph$ | H | NHCbz |
| 4342 | 2-imidazolinylaminomethyl | 1 | $CO(CH_2)_2Ph$ | H | NHCbz |
| 4343 | 2-imidazolinylaminomethyl | 1 | Bn | H | NHCbz |
| 4344 | 2-imidazolinylaminomethyl | 1 | n-Bu | H | NHCbz |
| 4345 | 2-imidazolinylaminomethyl | 1 | $CO_2$-n-Bu | H | NHCbz |
| 4346 | 2-imidazolinylaminomethyl | 1 | $CO_2$-i-Bu | H | NHCbz |
| 4347 | 2-imidazolinylaminomethyl | 1 | $CO_2$-t-Bu | H | NHCbz |
| 4348 | 2-imidazolinylaminomethyl | 1 | H | H | NHCbz |
| 4349 | 2-imidazolinylaminomethyl | 1 | $-(CH_2)_4NH_2$ | H | NHCbz |
| 4350 | 2-imidazolinylaminomethyl | 1 | COPh | H | NHCbz |
| 4351 | 2-imidazolinylaminomethyl | 1 | $SO_2$-n-Bu | H | NHCbz |
| 4352 | 2-benzimidazolylaminomethyl | 1 | Cbz | H | $NHSO_2Ph$ |
| 4353 | 2-benzimidazolylaminomethyl | 1 | $SO_2Ph$ | H | $NHSO_2Ph$ |
| 4354 | 2-benzimidazolylaminomethyl | 1 | $CO(CH_2)_2Ph$ | H | $NHSO_2Ph$ |
| 4355 | 2-benzimidazolylaminomethyl | 1 | Bn | H | $NHSO_2Ph$ |
| 4356 | 2-benzimidazolylaminomethyl | 1 | n-Bu | H | $NHSO_2Ph$ |
| 4357 | 2-benzimidazolylaminomethyl | 1 | $COCH_2$ (3-indolyl) | H | $NHSO_2Ph$ |
| 4358 | 2-benzimidazolylaminomethyl | 1 | SO2-(biphenyl) | H | $NHSO_2Ph$ |
| 4359 | 2-benzimidazolylaminomethyl | 1 | $CO_2$-n-Bu | H | $NHSO_2Ph$ |
| 4360 | 2-benzimidazolylaminomethyl | 1 | $CO_2$-i-Bu | H | $NHSO_2Ph$ |
| 4361 | 2-benzimidazolylaminomethyl | 1 | $CO_2$-t-Bu | H | $NHSO_2Ph$ |
| 4362 | 2-benzimidazolylaminomethyl | 1 | H | H | $NHSO_2Ph$ |
| 4363 | 2-benzimidazolylaminomethyl | 1 | $-(CH_2)_4NH_2$ | H | $NHSO_2Ph$ |
| 4364 | 2-benzimidazolylaminomethyl | 1 | COPh | H | $NHSO_2Ph$ |
| 4365 | 2-benzimidazolylaminomethyl | 1 | cyclopropylmethyl | H | $NHSO_2Ph$ |

TABLE 4-continued

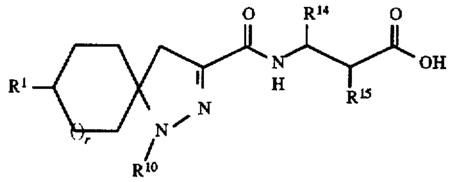

| Ex. No. | $R^1$ | r | $R^{10}$ | $R^{14}$ | $R^{15}$ |
|---|---|---|---|---|---|
| 4366 | 2-benzimidazolylaminomethyl | 1 | $SO_2$-n-Bu | H | $NHSO_2Ph$ |
| 4367 | 2-benzimidazolylaminomethyl | 1 | Cbz | H | $NHSO_2$-(2,4,6-trimethylphenyl) |
| 4368 | 2-benzimidazolylaminomethyl | 1 | $SO_2Ph$ | H | $NHSO_2$-(2,4,6-trimethylphenyl) |
| 4369 | 2-benzimidazolylaminomethyl | 1 | $CO(CH_2)_2Ph$ | H | $NHSO_2$-(2,4,6-trimethylphenyl) |
| 4370 | 2-benzimidazolylaminomethyl | 1 | Bn | H | $NHSO_2$-(2,4,6-trimethylphenyl) |
| 4371 | 2-benzimidazolylaminomethyl | 1 | n-Bu | H | $NHSO_2$-(2,4,6-trimethylphenyl) |
| 4372 | 2-benzimidazolylaminomethyl | 1 | $CO_2$-n-Bu | H | $NHSO_2$-(2,4,6-trimethylphenyl) |
| 4373 | 2-benzimidazolylaminomethyl | 1 | $CO_2$-i-Bu | H | $NHSO_2$-(2,4,6-trimethylphenyl) |
| 4374 | 2-benzimidazolylaminomethyl | 1 | $CO_2$-t-Bu | H | $NHSO_2$-(2,4,6-trimethylphenyl) |
| 4375 | 2-benzimidazolylaminomethyl | 1 | H | H | $NHSO_2$-(2,4,6-trimethylphenyl) |
| 4376 | 2-benzimidazolylaminomethyl | 1 | $-(CH_2)_4NH_2$ | H | $NHSO_2$-(2,4,6-trimethylphenyl) |
| 4377 | 2-benzimidazolylaminomethyl | 1 | COPh | H | $NHSO_2$-(2,4,6-trimethylphenyl) |
| 4378 | 2-benzimidazolylaminomethyl | 1 | $SO_2$-n-Bu | H | $NHSO_2$-(2,4,6-trimethylphenyl) |
| 4379 | 2-benzimidazolylaminomethyl | 1 | Cbz | H | NHCbz |
| 4380 | 2-benzimidazolylaminomethyl | 1 | $SO_2Ph$ | H | NHCbz |
| 4381 | 2-benzimidazolylaminomethyl | 1 | $CO(CH_2)_2Ph$ | H | NHCbz |
| 4382 | 2-benzimidazolylaminomethyl | 1 | Bn | H | NHCbz |
| 4383 | 2-benzimidazolylaminomethyl | 1 | n-Bu | H | NHCbz |
| 4384 | 2-benzimidazolylaminomethyl | 1 | $CO_2$-n-Bu | H | NHCbz |
| 4385 | 2-benzimidazolylaminomethyl | 1 | $CO_2$-i-Bu | H | NHCbz |
| 4386 | 2-benzimidazolylaminomethyl | 1 | $CO_2$-t-Bu | H | NHCbz |
| 4387 | 2-benzimidazolylaminomethyl | 1 | H | H | NHCbz |
| 4388 | 2-benzimidazolylaminomethyl | 1 | $-(CH_2)_4NH_2$ | H | NHCbz |
| 4389 | 2-benzimidazolylaminomethyl | 1 | COPh | H | NHCbz |
| 4390 | 2-benzimidazolylaminomethyl | 1 | $SO_2$-n-Bu | H | NHCbz |
| 4391 | 7-aza-2-benzimidazolyl | 1 | Cbz | H | $NHSO_2Ph$ |
| 4392 | 7-aza-2-benzimidazolyl | 1 | $SO_2Ph$ | H | $NHSO_2Ph$ |
| 4393 | 7-aza-2-benzimidazolyl | 1 | $CO(CH_2)_2Ph$ | H | $NHSO_2Ph$ |
| 4394 | 7-aza-2-benzimidazolyl | 1 | Bn | H | $NHSO_2Ph$ |
| 4395 | 7-aza-2-benzimidazolyl | 1 | n-Bu | H | $NHSO_2Ph$ |
| 4396 | 7-aza-2-benzimidazolyl | 1 | $COCH_2$ (3-indolyl) | H | $NHSO_2Ph$ |
| 4397 | 7-aza-2-benzimidazolyl | 1 | SO2-(biphenyl) | H | $NHSO_2Ph$ |
| 4398 | 7-aza-2-benzimidazolyl | 1 | $CO_2$-n-Bu | H | $NHSO_2Ph$ |
| 4399 | 7-aza-2-benzimidazolyl | 1 | $CO_2$-i-Bu | H | $NHSO_2Ph$ |
| 4400 | 7-aza-2-benzimidazolyl | 1 | $CO_2$-t-Bu | H | $NHSO_2Ph$ |
| 4401 | 7-aza-2-benzimidazolyl | 1 | H | H | $NHSO_2Ph$ |
| 4402 | 7-aza-2-benzimidazolyl | 1 | $-(CH_2)_4NH_2$ | H | $NHSO_2Ph$ |
| 4403 | 7-aza-2-benzimidazolyl | 1 | COPh | H | $NHSO_2Ph$ |
| 4404 | 7-aza-2-benzimidazolyl | 1 | cyclopropylmethyl | H | $NHSO_2Ph$ |
| 4405 | 7-aza-2-benzimidazolyl | 1 | $SO_2$-n-Bu | H | $NHSO_2Ph$ |
| 4406 | 7-aza-2-benzimidazolyl | 1 | Cbz | H | $NHSO_2$-(2,4,6-trimethylphenyl) |
| 4407 | 7-aza-2-benzimidazolyl | 1 | $SO_2Ph$ | H | $NHSO_2$-(2,4,6-trimethylphenyl) |
| 4408 | 7-aza-2-benzimidazolyl | 1 | $CO(CH_2)_2Ph$ | H | $NHSO_2$-(2,4,6-trimethylphenyl) |
| 4409 | 7-aza-2-benzimidazolyl | 1 | Bn | H | $NHSO_2$-(2,4,6-trimethylphenyl) |
| 4410 | 7-aza-2-benzimidazolyl | 1 | n-Bu | H | $NHSO_2$-(2,4,6-trimethylphenyl) |
| 4411 | 7-aza-2-benzimidazolyl | 1 | $CO_2$-n-Bu | H | $NHSO_2$-(2,4,6-trimethylphenyl) |
| 4412 | 7-aza-2-benzimidazolyl | 1 | $CO_2$-i-Bu | H | $NHSO_2$-(2,4,6-trimethylphenyl) |
| 4413 | 7-aza-2-benzimidazolyl | 1 | $CO_2$-t-Bu | H | $NHSO_2$-(2,4,6- |

TABLE 4-continued

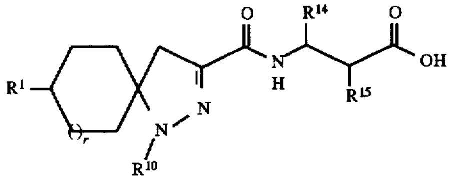

| Ex. No. | $R^1$ | r | $R^{10}$ | $R^{14}$ | $R^{15}$ |
|---|---|---|---|---|---|
| | | | | | trimethylphenyl) |
| 4414 | 7-aza-2-benzimidazolyl | 1 | H | H | $NHSO_2$-(2,4,6-trimethylphenyl) |
| 4415 | 7-aza-2-benzimidazolyl | 1 | $-(CH_2)_4NH_2$ | H | $NHSO_2$-(2,4,6-trimethylphenyl) |
| 4416 | 7-aza-2-benzimidazolyl | 1 | COPh | H | $NHSO_2$-(2,4,6-trimethylphenyl) |
| 4417 | 7-aza-2-benzimidazolyl | 1 | $SO_2$-n-Bu | H | $NHSO_2$-(2,4,6-trimethylphenyl) |
| 4418 | 7-aza-2-benzimidazolyl | 1 | Cbz | H | NHCbz |
| 4419 | 7-aza-2-benzimidazolyl | 1 | $SO_2Ph$ | H | NHCbz |
| 4420 | 7-aza-2-benzimidazolyl | 1 | $CO(CH_2)_2Ph$ | H | NHCbz |
| 4421 | 7-aza-2-benzimidazolyl | 1 | Bn | H | NHCbz |
| 4422 | 7-aza-2-benzimidazolyl | 1 | n-Bu | H | NHCbz |
| 4423 | 7-aza-2-benzimidazolyl | 1 | $CO_2$-n-Bu | H | NHCbz |
| 4424 | 7-aza-2-benzimidazolyl | 1 | $CO_2$-i-Bu | H | NHCbz |
| 4425 | 7-aza-2-benzimidazolyl | 1 | $CO_2$-t-Bu | H | NHCbz |
| 4426 | 7-aza-2-benzimidazolyl | 1 | H | H | NHCbz |
| 4427 | 7-aza-2-benzimidazolyl | 1 | $-(CH_2)_4NH_2$ | H | NHCbz |
| 4428 | 7-aza-2-benzimidazolyl | 1 | COPh | H | NHCbz |
| 4429 | 7-aza-2-benzimidazolyl | 1 | $SO_2$-n-Bu | H | NHCbz |
| 4430 | tetrahydropyrimidin-2-ylaminomethyl | 1 | Cbz | H | $NHSO_2Ph$ |
| 4431 | tetrahydropyrimidin-2-ylaminomethyl | 1 | $SO_2Ph$ | H | $NHSO_2Ph$ |
| 4432 | tetrahydropyrimidin-2-ylaminomethyl | 1 | $CO(CH_2)_2Ph$ | H | $NHSO_2Ph$ |
| 4433 | tetrahydropyrimidin-2-ylaminomethyl | 1 | Bn | H | $NHSO_2Ph$ |
| 4434 | tetrahydropyrimidin-2-ylaminomethyl | 1 | n-Bu | H | $NHSO_2Ph$ |
| 4435 | tetrahydropyrimidin-2-ylaminomethyl | 1 | $COCH_2$ (3-indolyl) | H | $NHSO_2Ph$ |
| 4436 | tetrahydropyrimidin-2-ylaminomethyl | 1 | SO2-(biphenyl) | H | $NHSO_2Ph$ |
| 4437 | tetrahydropyrimidin-2-ylaminomethyl | 1 | $CO_2$-n-Bu | H | $NHSO_2Ph$ |
| 4438 | tetrahydropyrimidin-2-ylaminomethyl | 1 | $CO_2$-i-Bu | H | $NHSO_2Ph$ |
| 4439 | tetrahydropyrimidin-2-ylaminomethyl | 1 | $CO_2$-t-Bu | H | $NHSO_2Ph$ |
| 4440 | tetrahydropyrimidin-2-ylaminomethyl | 1 | H | H | $NHSO_2Ph$ |
| 4441 | tetrahydropyrimidin-2-ylaminomethyl | 1 | $-(CH_2)_4NH_2$ | H | $NHSO_2Ph$ |
| 4442 | tetrahydropyrimidin-2-ylaminomethyl | 1 | COPh | H | $NHSO_2Ph$ |
| 4443 | tetrahydropyrimidin-2-ylaminomethyl | 1 | cyclopropylmethyl | H | $NHSO_2Ph$ |
| 4444 | tetrahydropyrimidin-2-ylaminomethyl | 1 | $SO_2$-n-Bu | H | $NHSO_2Ph$ |
| 4445 | tetrahydropyrimidin-2-ylaminomethyl | 1 | Cbz | H | $NHSO_2$-(2,4,6-trimethylphenyl) |
| 4446 | tetrahydropyrimidin-2-ylaminomethyl | 1 | $SO_2Ph$ | H | $NHSO_2$-(2,4,6-trimethylphenyl) |
| 4447 | tetrahydropyrimidin-2-ylaminomethyl | 1 | $CO(CH_2)_2Ph$ | H | $NHSO_2$-(2,4,6-trimethylphenyl) |
| 4448 | tetrahydropyrimidin-2-ylaminomethyl | 1 | Bn | H | $NHSO_2$-(2,4,6-trimethylphenyl) |
| 4449 | tetrahydropyrimidin-2-ylaminomethyl | 1 | n-Bu | H | $NHSO_2$-(2,4,6-trimethylphenyl) |
| 4450 | tetrahydropyrimidin-2-ylaminomethyl | 1 | $CO_2$-n-Bu | H | $NHSO_2$-(2,4,6-trimethylphenyl) |
| 4451 | tetrahydropyrimidin-2-ylaminomethyl | 1 | $CO_2$-i-Bu | H | $NHSO_2$-(2,4,6-trimethylphenyl) |
| 4452 | tetrahydropyrimidin-2-ylaminomethyl | 1 | $CO_2$-t-Bu | H | $NHSO_2$-(2,4,6-trimethylphenyl) |

TABLE 4-continued

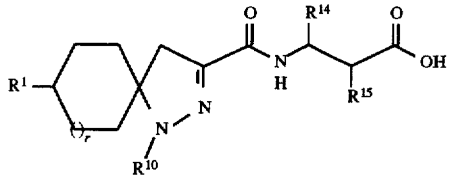

| Ex. No. | $R^1$ | r | $R^{10}$ | $R^{14}$ | $R^{15}$ |
|---|---|---|---|---|---|
| 4453 | tetrahydropyrimidin-2-ylaminomethyl | 1 | H | H | $NHSO_2$-(2,4,6-trimethylphenyl) |
| 4454 | tetrahydropyrimidin-2-ylaminomethyl | 1 | $-(CH_2)_4NH_2$ | H | $NHSO_2$-(2,4,6-trimethylphenyl) |
| 4455 | tetrahydropyrimidin-2-ylaminomethyl | 1 | COPh | H | $NHSO_2$-(2,4,6-trimethylphenyl) |
| 4456 | tetrahydropyrimidin-2-ylaminomethyl | 1 | $SO_2$-n-Bu | H | $NHSO_2$-(2,4,6-trimethylphenyl) |
| 4457 | tetrahydropyrimidin-2-ylaminomethyl | 1 | Cbz | H | NHCbz |
| 4458 | tetrahydropyrimidin-2-ylaminomethyl | 1 | $SO_2Ph$ | H | NHCbz |
| 4459 | tetrahydropyrimidin-2-ylaminomethyl | 1 | $CO(CH_2)_2Ph$ | H | NHCbz |
| 4460 | tetrahydropyrimidin-2-ylaminomethyl | 1 | Bn | H | NHCbz |
| 4461 | tetrahydropyrimidin-2-ylaminomethyl | 1 | n-Bu | H | NHCbz |
| 4462 | tetrahydropyrimidin-2-ylaminomethyl | 1 | $CO_2$-n-Bu | H | NHCbz |
| 4463 | tetrahydropyrimidin-2-ylaminomethyl | 1 | $CO_2$-i-Bu | H | NHCbz |
| 4464 | tetrahydropyrimidin-2-ylaminomethyl | 1 | $CO_2$-t-Bu | H | NHCbz |
| 4465 | tetrahydropyrimidin-2-ylaminomethyl | 1 | H | H | NHCbz |
| 4466 | tetrahydropyrimidin-2-ylaminomethyl | 1 | $-(CH_2)_4NH_2$ | H | NHCbz |
| 4467 | tetrahydropyrimidin-2-ylaminomethyl | 1 | COPh | H | NHCbz |

TABLE 5

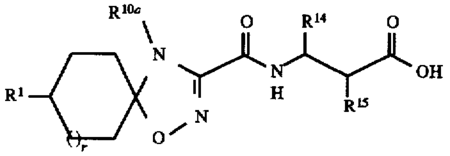

| Ex. No. | $R^1$ | r | $R^{10a}$ | $R^{14}$ | $R^{15}$ |
|---|---|---|---|---|---|
| 5001 | 2-pyridinylaminomethyl | 0 | Cbz | H | $NHSO_2Ph$ |
| 5002 | 2-pyridinylaminomethyl | 0 | $SO_2Ph$ | H | $NHSO_2Ph$ |
| 5003 | 2-pyridinylaminomethyl | 0 | $CO(CH_2)_2Ph$ | H | $NHSO_2Ph$ |
| 5004 | 2-pyridinylaminomethyl | 0 | Bn | H | $NHSO_2Ph$ |
| 5005 | 2-pyridinylaminomethyl | 0 | n-Bu | H | $NHSO_2Ph$ |
| 5006 | 2-pyridinylaminomethyl | 0 | $COCH_2$ (3-indolyl) | H | $NHSO_2Ph$ |
| 5007 | 2-pyridinylaminomethyl | 0 | SO2-(biphenyl) | H | $NHSO_2Ph$ |
| 5008 | 2-pyridinylaminomethyl | 0 | $CO_2$-n-Bu | H | $NHSO_2Ph$ |
| 5009 | 2-pyridinylaminomethyl | 0 | $CO_2$-i-Bu | H | $NHSO_2Ph$ |
| 5010 | 2-pyridinylaminomethyl | 0 | $CO_2$-t-Bu | H | $NHSO_2Ph$ |
| 5011 | 2-pyridinylaminomethyl | 0 | $-(CH_2)_4NH_2$ | H | $NHSO_2Ph$ |
| 5012 | 2-pyridinylaminomethyl | 0 | COPh | H | $NHSO_2Ph$ |
| 5013 | 2-pyridinylaminomethyl | 0 | cyclopropylmethyl | H | $NHSO_2Ph$ |
| 5014 | 2-pyridinylaminomethyl | 0 | $SO_2$-n-Bu | H | $NHSO_2Ph$ |
| 5015 | 2-pyridinylaminomethyl | 0 | Cbz | H | $NHSO_2$-(2,4,6-trimethylphenyl) |
| 5016 | 2-pyridinylaminomethyl | 0 | $SO_2Ph$ | H | $NHSO_2$-(2,4,6-trimethylphenyl) |
| 5017 | 2-pyridinylaminomethyl | 0 | $CO(CH_2)_2Ph$ | H | $NHSO_2$-(2,4,6-trimethylphenyl) |
| 5018 | 2-pyridinylaminomethyl | 0 | Bn | H | $NHSO_2$-(2,4,6-trimethylphenyl) |

TABLE 5-continued

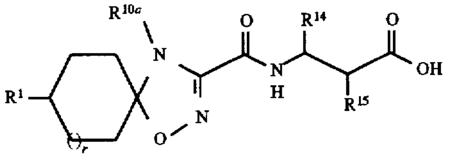

| Ex. No. | $R^1$ | r | $R^{10a}$ | $R^{14}$ | $R^{15}$ |
|---|---|---|---|---|---|
| 5019 | 2-pyridinylaminomethyl | 0 | n-Bu | H | $NHSO_2$-(2,4,6-trimethylphenyl) |
| 5020 | 2-pyridinylaminomethyl | 0 | $CO_2$-n-Bu | H | $NHSO_2$-(2,4,6-trimethylphenyl) |
| 5021 | 2-pyridinylaminomethyl | 0 | $CO_2$-i-Bu | H | $NHSO_2$-(2,4,6-trimethylphenyl) |
| 5022 | 2-pyridinylaminomethyl | 0 | $CO_2$-t-Bu | H | $NHSO_2$-(2,4,6-trimethylphenyl) |
| 5023 | 2-pyridinylaminomethyl | 0 | $-(CH_2)_4NH_2$ | H | $NHSO_2$-(2,4,6-trimethylphenyl) |
| 5024 | 2-pyridinylaminomethyl | 0 | COPh | H | $NHSO_2$-(2,4,6-trimethylphenyl) |
| 5025 | 2-pyridinylaminomethyl | 0 | $SO_2$-n-Bu | H | $NHSO_2$-(2,4,6-trimethylphenyl) |
| 5026 | 2-pyridinylaminomethyl | 0 | Cbz | H | NHCbz |
| 5027 | 2-pyridinylaminomethyl | 0 | $SO_2Ph$ | H | NHCbz |
| 5028 | 2-pyridinylaminomethyl | 0 | $CO(CH_2)_2Ph$ | H | NHCbz |
| 5029 | 2-pyridinylaminomethyl | 0 | Bn | H | NHCbz |
| 5030 | 2-pyridinylaminomethyl | 0 | n-Bu | H | NHCbz |
| 5031 | 2-pyridinylaminomethyl | 0 | $CO_2$-n-Bu | H | NHCbz |
| 5032 | 2-pyridinylaminomethyl | 0 | $CO_2$-i-Bu | H | NHCbz |
| 5033 | 2-pyridinylaminomethyl | 0 | $CO_2$-t-Bu | H | NHCbz |
| 5034 | 2-pyridinylaminomethyl | 0 | $-(CH_2)_4NH_2$ | H | NHCbz |
| 5035 | 2-pyridinylaminomethyl | 0 | COPh | H | NHCbz |
| 5036 | 2-pyridinylaminomethyl | 0 | $SO_2$-n-Bu | H | NHCbz |
| 5037 | 2-imidazolylaminomethyl | 0 | Cbz | H | $NHSO_2Ph$ |
| 5038 | 2-imidazolylaminomethyl | 0 | $SO_2Ph$ | H | $NHSO_2Ph$ |
| 5039 | 2-imidazolylaminomethyl | 0 | $CO(CH_2)_2Ph$ | H | $NHSO_2Ph$ |
| 5040 | 2-imidazolylaminomethyl | 0 | Bn | H | $NHSO_2Ph$ |
| 5041 | 2-imidazolylaminomethyl | 0 | n-Bu | H | $NHSO_2Ph$ |
| 5042 | 2-imidazolylaminomethyl | 0 | $COCH_2$ (3-indolyl) | H | $NHSO_2Ph$ |
| 5043 | 2-imidazolylaminomethyl | 0 | SO2-(biphenyl) | H | $NHSO_2Ph$ |
| 5044 | 2-imidazolylaminomethyl | 0 | $CO_2$-n-Bu | H | $NHSO_2Ph$ |
| 5045 | 2-imidazolylaminomethyl | 0 | $CO_2$-i-Bu | H | $NHSO_2Ph$ |
| 5046 | 2-imidazolylaminomethyl | 0 | $CO_2$-t-Bu | H | $NHSO_2Ph$ |
| 5047 | 2-imidazolylaminomethyl | 0 | $-(CH_2)_4NH_2$ | H | $NHSO_2Ph$ |
| 5048 | 2-imidazolylaminomethyl | 0 | COPh | H | $NHSO_2Ph$ |
| 5049 | 2-imidazolylaminomethyl | 0 | cyclopropylmethyl | H | $NHSO_2Ph$ |
| 5050 | 2-imidazolylaminomethyl | 0 | $SO_2$-n-Bu | H | $NHSO_2Ph$ |
| 5051 | 2-imidazolylaminomethyl | 0 | Cbz | H | $NHSO_2$-(2,4,6-trimethylphenyl) |
| 5052 | 2-imidazolylaminomethyl | 0 | $SO_2Ph$ | H | $NHSO_2$-(2,4,6-trimethylphenyl) |
| 5053 | 2-imidazolylaminomethyl | 0 | $CO(CH_2)_2Ph$ | H | $NHSO_2$-(2,4,6-trimethylphenyl) |
| 5054 | 2-imidazolylaminomethyl | 0 | Bn | H | $NHSO_2$-(2,4,6-trimethylphenyl) |
| 5055 | 2-imidazolylaminomethyl | 0 | n-Bu | H | $NHSO_2$-(2,4,6-trimethylphenyl) |
| 5056 | 2-imidazolylaminomethyl | 0 | $CO_2$-n-Bu | H | $NHSO_2$-(2,4,6-trimethylphenyl) |
| 5057 | 2-imidazolylaminomethyl | 0 | $CO_2$-i-Bu | H | $NHSO_2$-(2,4,6-trimethylphenyl) |
| 5058 | 2-imidazolylaminomethyl | 0 | $CO_2$-t-Bu | H | $NHSO_2$-(2,4,6-trimethylphenyl) |
| 5059 | 2-imidazolylaminomethyl | 0 | $-(CH_2)_4NH_2$ | H | $NHSO_2$-(2,4,6-trimethylphenyl) |
| 5060 | 2-imidazolylaminomethyl | 0 | COPh | H | $NHSO_2$-(2,4,6-trimethylphenyl) |
| 5061 | 2-imidazolylaminomethyl | 0 | $SO_2$-n-Bu | H | $NHSO_2$-(2,4,6-trimethylphenyl) |
| 5062 | 2-imidazolylaminomethyl | 0 | Cbz | H | NHCbz |
| 5063 | 2-imidazolylaminomethyl | 0 | $SO_2Ph$ | H | NHCbz |
| 5064 | 2-imidazolylaminomethyl | 0 | $CO(CH_2)_2Ph$ | H | NHCbz |
| 5065 | 2-imidazolylaminomethyl | 0 | Bn | H | NHCbz |
| 5066 | 2-imidazolylaminomethyl | 0 | n-Bu | H | NHCbz |
| 5067 | 2-imidazolylaminomethyl | 0 | $CO_2$-n-Bu | H | NHCbz |
| 5068 | 2-imidazolylaminomethyl | 0 | $CO_2$-i-Bu | H | NHCbz |
| 5069 | 2-imidazolylaminomethyl | 0 | $CO_2$-t-Bu | H | NHCbz |

TABLE 5-continued

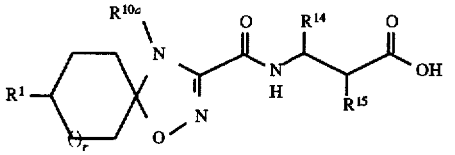

| Ex. No. | $R^1$ | r | $R^{10a}$ | $R^{14}$ | $R^{15}$ |
|---|---|---|---|---|---|
| 5070 | 2-imidazolylaminomethyl | 0 | $-(CH_2)_4NH_2$ | H | NHCbz |
| 5071 | 2-imidazolylaminomethyl | 0 | COPh | H | NHCbz |
| 5072 | 2-imidazolylaminomethyl | 0 | $SO_2$-n-Bu | H | NHCbz |
| 5073 | 2-imidazolinylaminomethyl | 0 | Cbz | H | $NHSO_2Ph$ |
| 5074 | 2-imidazolinylaminomethyl | 0 | $SO_2Ph$ | H | $NHSO_2Ph$ |
| 5075 | 2-imidazolinylaminomethyl | 0 | $CO(CH_2)_2Ph$ | H | $NHSO_2Ph$ |
| 5076 | 2-imidazolinylaminomethyl | 0 | Bn | H | $NHSO_2Ph$ |
| 5077 | 2-imidazolinylaminomethyl | 0 | n-Bu | H | $NHSO_2Ph$ |
| 5078 | 2-imidazolinylaminomethyl | 0 | $COCH_2$ (3-indolyl) | H | $NHSO_2Ph$ |
| 5079 | 2-imidazolinylaminomethyl | 0 | SO2-(biphenyl) | H | $NHSO_2Ph$ |
| 5080 | 2-imidazolinylaminomethyl | 0 | $CO_2$-n-Bu | H | $NHSO_2Ph$ |
| 5081 | 2-imidazolinylaminomethyl | 0 | $CO_2$-i-Bu | H | $NHSO_2Ph$ |
| 5082 | 2-imidazolinylaminomethyl | 0 | $CO_2$-t-Bu | H | $NHSO_2Ph$ |
| 5083 | 2-imidazolinylaminomethyl | 0 | $-(CH_2)_4NH_2$ | H | $NHSO_2Ph$ |
| 5084 | 2-imidazolinylaminomethyl | 0 | COPh | H | $NHSO_2Ph$ |
| 5085 | 2-imidazolinylaminomethyl | 0 | cyclopropylmethyl | H | $NHSO_2Ph$ |
| 5086 | 2-imidazolinylaminomethyl | 0 | $SO_2$-n-Bu | H | $NHSO_2Ph$ |
| 5087 | 2-imidazolinylaminomethyl | 0 | Cbz | H | $NHSO_2$-(2,4,6-trimethylphenyl) |
| 5088 | 2-imidazolinylaminomethyl | 0 | $SO_2Ph$ | H | $NHSO_2$-(2,4,6-trimethylphenyl) |
| 5089 | 2-imidazolinylaminomethyl | 0 | $CO(CH_2)_2Ph$ | H | $NHSO_2$-(2,4,6-trimethylphenyl) |
| 5090 | 2-imidazolinylaminomethyl | 0 | Bn | H | $NHSO_2$-(2,4,6-trimethylphenyl) |
| 5091 | 2-imidazolinylaminomethyl | 0 | n-Bu | H | $NHSO_2$-(2,4,6-trimethylphenyl) |
| 5092 | 2-imidazolinylaminomethyl | 0 | $CO_2$-n-Bu | H | $NHSO_2$-(2,4,6-trimethylphenyl) |
| 5093 | 2-imidazolinylaminomethyl | 0 | $CO_2$-i-Bu | H | $NHSO_2$-(2,4,6-trimethylphenyl) |
| 5094 | 2-imidazolinylaminomethyl | 0 | $CO_2$-t-Bu | H | $NHSO_2$-(2,4,6-trimethylphenyl) |
| 5095 | 2-imidazolinylaminomethyl | 0 | $-(CH_2)_4NH_2$ | H | $NHSO_2$-(2,4,6-trimethylphenyl) |
| 5096 | 2-imidazolinylaminomethyl | 0 | COPh | H | $NHSO_2$-(2,4,6-trimethylphenyl) |
| 5097 | 2-imidazolinylaminomethyl | 0 | $SO_2$-n-Bu | H | $NHSO_2$-(2,4,6-trimethylphenyl) |
| 5098 | 2-imidazolinylaminomethyl | 0 | Cbz | H | NHCbz |
| 5099 | 2-imidazolinylaminomethyl | 0 | $SO_2Ph$ | H | NHCbz |
| 5100 | 2-imidazolinylaminomethyl | 0 | $CO(CH_2)_2Ph$ | H | NHCbz |
| 5101 | 2-imidazolinylaminomethyl | 0 | Bn | H | NHCbz |
| 5102 | 2-imidazolinylaminomethyl | 0 | n-Bu | H | NHCbz |
| 5103 | 2-imidazolinylaminomethyl | 0 | $CO_2$-n-Bu | H | NHCbz |
| 5104 | 2-imidazolinylaminomethyl | 0 | $CO_2$-i-Bu | H | NHCbz |
| 5105 | 2-imidazolinylaminomethyl | 0 | $CO_2$-t-Bu | H | NHCbz |
| 5106 | 2-imidazolinylaminomethyl | 0 | $-(CH_2)_4NH_2$ | H | NHCbz |
| 5107 | 2-imidazolinylaminomethyl | 0 | COPh | H | NHCbz |
| 5108 | 2-imidazolinylaminomethyl | 0 | $SO_2$-n-Bu | H | NHCbz |
| 5109 | 2-benzimidazolylaminomethyl | 0 | Cbz | H | $NHSO_2Ph$ |
| 5110 | 2-benzimidazolylaminomethyl | 0 | $SO_2Ph$ | H | $NHSO_2Ph$ |
| 5111 | 2-benzimidazolylaminomethyl | 0 | $CO(CH_2)_2Ph$ | H | $NHSO_2Ph$ |
| 5112 | 2-benzimidazolylaminomethyl | 0 | Bn | H | $NHSO_2Ph$ |
| 5113 | 2-benzimidazolylaminomethyl | 0 | n-Bu | H | $NHSO_2Ph$ |
| 5114 | 2-benzimidazolylaminomethyl | 0 | $COCH_2$ (3-indolyl) | H | $NHSO_2Ph$ |
| 5115 | 2-benzimidazolylaminomethyl | 0 | SO2-(biphenyl) | H | $NHSO_2Ph$ |
| 5116 | 2-benzimidazolylaminomethyl | 0 | $CO_2$-n-Bu | H | $NHSO_2Ph$ |
| 5117 | 2-benzimidazolylaminomethyl | 0 | $CO_2$-i-Bu | H | $NHSO_2Ph$ |
| 5118 | 2-benzimidazolylaminomethyl | 0 | $CO_2$-t-Bu | H | $NHSO_2Ph$ |
| 5119 | 2-benzimidazolylaminomethyl | 0 | $-(CH_2)_4NH_2$ | H | $NHSO_2Ph$ |
| 5120 | 2-benzimidazolylaminomethyl | 0 | COPh | H | $NHSO_2Ph$ |
| 5121 | 2-benzimidazolylaminomethyl | 0 | cyclopropylmethyl | H | $NHSO_2Ph$ |
| 5122 | 2-benzimidazolylaminomethyl | 0 | $SO_2$-n-Bu | H | $NHSO_2Ph$ |
| 5123 | 2-benzimidazolylaminomethyl | 0 | Cbz | H | $NHSO_2$-(2,4,6-trimethylphenyl) |
| 5124 | 2-benzimidazolylaminomethyl | 0 | $SO_2Ph$ | H | $NHSO_2$-(2,4,6-trimethylphenyl) |
| 5125 | 2-benzimidazolylaminomethyl | 0 | $CO(CH_2)_2Ph$ | H | $NHSO_2$-(2,4,6- |

TABLE 5-continued

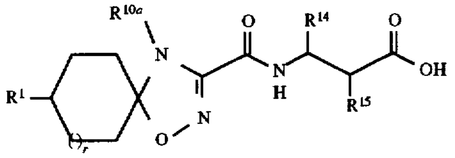

| Ex. No. | $R^1$ | r | $R^{10a}$ | $R^{14}$ | $R^{15}$ |
|---|---|---|---|---|---|
| | | | | | trimethylphenyl) |
| 5126 | 2-benzimidazolylaminomethyl | 0 | Bn | H | $NHSO_2$-(2,4,6-trimethylphenyl) |
| 5127 | 2-benzimidazolylaminomethyl | 0 | n-Bu | H | $NHSO_2$-(2,4,6-trimethylphenyl) |
| 5128 | 2-benzimidazolylaminomethyl | 0 | $CO_2$-n-Bu | H | $NHSO_2$-(2,4,6-trimethylphenyl) |
| 5129 | 2-benzimidazolylaminomethyl | 0 | $CO_2$-i-Bu | H | $NHSO_2$-(2,4,6-trimethylphenyl) |
| 5130 | 2-benzimidazolylaminomethyl | 0 | $CO_2$-t-Bu | H | $NHSO_2$-(2,4,6-trimethylphenyl) |
| 5131 | 2-benzimidazolylaminomethyl | 0 | $-(CH_2)_4NH_2$ | H | $NHSO_2$-(2,4,6-trimethylphenyl) |
| 5132 | 2-benzimidazolylaminomethyl | 0 | COPh | H | $NHSO_2$-(2,4,6-trimethylphenyl) |
| 5133 | 2-benzimidazolylaminomethyl | 0 | $SO_2$-n-Bu | H | $NHSO_2$-(2,4,6-trimethylphenyl) |
| 5134 | 2-benzimidazolylaminomethyl | 0 | Cbz | H | NHCbz |
| 5135 | 2-benzimidazolylaminomethyl | 0 | $SO_2Ph$ | H | NHCbz |
| 5136 | 2-benzimidazolylaminomethyl | 0 | $CO(CH_2)_2Ph$ | H | NHCbz |
| 5137 | 2-benzimidazolylaminomethyl | 0 | Bn | H | NHCbz |
| 5138 | 2-benzimidazolylaminomethyl | 0 | n-Bu | H | NHCbz |
| 5139 | 2-benzimidazolylaminomethyl | 0 | $CO_2$-n-Bu | H | NHCbz |
| 5140 | 2-benzimidazolylaminomethyl | 0 | $CO_2$-i-Bu | H | NHCbz |
| 5141 | 2-benzimidazolylaminomethyl | 0 | $CO_2$-t-Bu | H | NHCbz |
| 5142 | 2-benzimidazolylaminomethyl | 0 | $-(CH_2)_4NH_2$ | H | NHCbz |
| 5143 | 2-benzimidazolylaminomethyl | 0 | COPh | H | NHCbz |
| 5144 | 2-benzimidazolylaminomethyl | 0 | $SO_2$-n-Bu | H | NHCbz |
| 5145 | 7-aza-2-benzimidazolyl | 0 | Cbz | H | $NHSO_2Ph$ |
| 5146 | 7-aza-2-benzimidazolyl | 0 | $SO_2Ph$ | H | $NHSO_2Ph$ |
| 5147 | 7-aza-2-benzimidazolyl | 0 | $CO(CH_2)_2Ph$ | H | $NHSO_2Ph$ |
| 5148 | 7-aza-2-benzimidazolyl | 0 | Bn | H | $NHSO_2Ph$ |
| 5149 | 7-aza-2-benzimidazolyl | 0 | n-Bu | H | $NHSO_2Ph$ |
| 5150 | 7-aza-2-benzimidazolyl | 0 | $COCH_2$ (3-indolyl) | H | $NHSO_2Ph$ |
| 5151 | 7-aza-2-benzimidazolyl | 0 | SO2-(biphenyl) | H | $NHSO_2Ph$ |
| 5152 | 7-aza-2-benzimidazolyl | 0 | $CO_2$-n-Bu | H | $NHSO_2Ph$ |
| 5153 | 7-aza-2-benzimidazolyl | 0 | $CO_2$-i-Bu | H | $NHSO_2Ph$ |
| 5154 | 7-aza-2-benzimidazolyl | 0 | $CO_2$-t-Bu | H | $NHSO_2Ph$ |
| 5155 | 7-aza-2-benzimidazolyl | 0 | $-(CH_2)_4NH_2$ | H | $NHSO_2Ph$ |
| 5156 | 7-aza-2-benzimidazolyl | 0 | COPh | H | $NHSO_2Ph$ |
| 5157 | 7-aza-2-benzimidazolyl | 0 | cyclopropylmethyl | H | $NHSO_2Ph$ |
| 5158 | 7-aza-2-benzimidazolyl | 0 | $SO_2$-n-Bu | H | $NHSO_2Ph$ |
| 5159 | 7-aza-2-benzimidazolyl | 0 | Cbz | H | $NHSO_2$-(2,4,6-trimethylphenyl) |
| 5160 | 7-aza-2-benzimidazolyl | 0 | $SO_2Ph$ | H | $NHSO_2$-(2,4,6-trimethylphenyl) |
| 5161 | 7-aza-2-benzimidazolyl | 0 | $CO(CH_2)_2Ph$ | H | $NHSO_2$-(2,4,6-trimethylphenyl) |
| 5162 | 7-aza-2-benzimidazolyl | 0 | Bn | H | $NHSO_2$-(2,4,6-trimethylphenyl) |
| 5163 | 7-aza-2-benzimidazolyl | 0 | n-Bu | H | $NHSO_2$-(2,4,6-trimethylphenyl) |
| 5164 | 7-aza-2-benzimidazolyl | 0 | $CO_2$-n-Bu | H | $NHSO_2$-(2,4,6-trimethylphenyl) |
| 5165 | 7-aza-2-benzimidazolyl | 0 | $CO_2$-i-Bu | H | $NHSO_2$-(2,4,6-trimethylphenyl) |
| 5166 | 7-aza-2-benzimidazolyl | 0 | $CO_2$-t-Bu | H | $NHSO_2$-(2,4,6-trimethylphenyl) |
| 5167 | 7-aza-2-benzimidazolyl | 0 | $-(CH_2)_4NH_2$ | H | $NHSO_2$-(2,4,6-trimethylphenyl) |
| 5168 | 7-aza-2-benzimidazolyl | 0 | COPh | H | $NHSO_2$-(2,4,6-trimethylphenyl) |
| 5169 | 7-aza-2-benzimidazolyl | 0 | $SO_2$-n-Bu | H | $NHSO_2$-(2,4,6-trimethylphenyl) |
| 5170 | 7-aza-2-benzimidazolyl | 0 | Cbz | H | NHCbz |
| 5171 | 7-aza-2-benzimidazolyl | 0 | $SO_2Ph$ | H | NHCbz |
| 5172 | 7-aza-2-benzimidazolyl | 0 | $CO(CH_2)_2Ph$ | H | NHCbz |
| 5173 | 7-aza-2-benzimidazolyl | 0 | Bn | H | NHCbz |
| 5174 | 7-aza-2-benzimidazolyl | 0 | n-Bu | H | NHCbz |

TABLE 5-continued

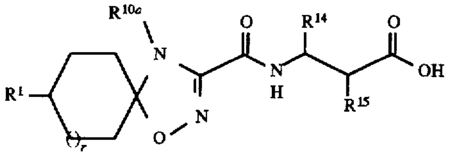

| Ex. No. | $R^1$ | r | $R^{10a}$ | $R^{14}$ | $R^{15}$ |
|---|---|---|---|---|---|
| 5175 | 7-aza-2-benzimidazolyl | 0 | $CO_2$-n-Bu | H | NHCbz |
| 5176 | 7-aza-2-benzimidazolyl | 0 | $CO_2$-i-Bu | H | NHCbz |
| 5177 | 7-aza-2-benzimidazolyl | 0 | $CO_2$-t-Bu | H | NHCbz |
| 5178 | 7-aza-2-benzimidazolyl | 0 | $-(CH_2)_4NH_2$ | H | NHCbz |
| 5179 | 7-aza-2-benzimidazolyl | 0 | COPh | H | NHCbz |
| 5180 | 7-aza-2-benzimidazolyl | 0 | $SO_2$-n-Bu | H | NHCbz |
| 5181 | tetrahydropyrimidin-2-ylaminomethyl | 0 | Cbz | H | $NHSO_2Ph$ |
| 5182 | tetrahydropyrimidin-2-ylaminomethyl | 0 | $SO_2Ph$ | H | $NHSO_2Ph$ |
| 5183 | tetrahydropyrimidin-2-ylaminomethyl | 0 | $CO(CH_2)_2Ph$ | H | $NHSO_2Ph$ |
| 5184 | tetrahydropyrimidin-2-ylaminomethyl | 0 | Bn | H | $NHSO_2Ph$ |
| 5185 | tetrahydropyrimidin-2-ylaminomethyl | 0 | n-Bu | H | $NHSO_2Ph$ |
| 5186 | tetrahydropyrimidin-2-ylaminomethyl | 0 | $COCH_2$ (3-indolyl) | H | $NHSO_2Ph$ |
| 5187 | tetrahydropyrimidin-2-ylaminomethyl | 0 | SO2-(biphenyl) | H | $NHSO_2Ph$ |
| 5188 | tetrahydropyrimidin-2-ylaminomethyl | 0 | $CO_2$-n-Bu | H | $NHSO_2Ph$ |
| 5189 | tetrahydropyrimidin-2-ylaminomethyl | 0 | $CO_2$-i-Bu | H | $NHSO_2Ph$ |
| 5190 | tetrahydropyrimidin-2-ylaminomethyl | 0 | $CO_2$-t-Bu | H | $NHSO_2Ph$ |
| 5191 | tetrahydropyrimidin-2-ylaminomethyl | 0 | $-(CH_2)_4NH_2$ | H | $NHSO_2Ph$ |
| 5192 | tetrahydropyrimidin-2-ylaminomethyl | 0 | COPh | H | $NHSO_2Ph$ |
| 5193 | tetrahydropyrimidin-2-ylaminomethyl | 0 | cyclopropylmethyl | H | $NHSO_2Ph$ |
| 5194 | tetrahydropyrimidin-2-ylaminomethyl | 0 | $SO_2$-n-Bu | H | $NHSO_2Ph$ |
| 5195 | tetrahydropyrimidin-2-ylaminomethyl | 0 | Cbz | H | $NHSO_2$-(2,4,6-trimethylphenyl) |
| 5196 | tetrahydropyrimidin-2-ylaminomethyl | 0 | $SO_2Ph$ | H | $NHSO_2$-(2,4,6-trimethylphenyl) |
| 5197 | tetrahydropyrimidin-2-ylaminomethyl | 0 | $CO(CH_2)_2Ph$ | H | $NHSO_2$-(2,4,6-trimethylphenyl) |
| 5198 | tetrahydropyrimidin-2-ylaminomethyl | 0 | Bn | H | $NHSO_2$-(2,4,6-trimethylphenyl) |
| 5199 | tetrahydropyrimidin-2-ylaminomethyl | 0 | n-Bu | H | $NHSO_2$-(2,4,6-trimethylphenyl) |
| 5200 | tetrahydropyrimidin-2-ylaminomethyl | 0 | $CO_2$-n-Bu | H | $NHSO_2$-(2,4,6-trimethylphenyl) |
| 5201 | tetrahydropyrimidin-2-ylaminomethyl | 0 | $CO_2$-i-Bu | H | $NHSO_2$-(2,4,6-trimethylphenyl) |
| 5202 | tetrahydropyrimidin-2-ylaminomethyl | 0 | $CO_2$-t-Bu | H | $NHSO_2$-(2,4,6-trimethylphenyl) |
| 5203 | tetrahydropyrimidin-2-ylaminomethyl | 0 | $-(CH_2)_4NH_2$ | H | $NHSO_2$-(2,4,6-trimethylphenyl) |
| 5204 | tetrahydropyrimidin-2-ylaminomethyl | 0 | COPh | H | $NHSO_2$-(2,4,6-trimethylphenyl) |
| 5205 | tetrahydropyrimidin-2-ylaminomethyl | 0 | $SO_2$-n-Bu | H | $NHSO_2$-(2,4,6-trimethylphenyl) |
| 5206 | tetrahydropyrimidin-2-ylaminomethyl | 0 | Cbz | H | NHCbz |
| 5207 | tetrahydropyrimidin-2-ylaminomethyl | 0 | $SO_2Ph$ | H | NHCbz |
| 5208 | tetrahydropyrimidin-2-ylaminomethyl | 0 | $CO(CH_2)_2Ph$ | H | NHCbz |
| 5209 | tetrahydropyrimidin-2-ylaminomethyl | 0 | Bn | H | NHCbz |
| 5210 | tetrahydropyrimidin-2-ylaminomethyl | 0 | n-Bu | H | NHCbz |
| 5211 | tetrahydropyrimidin-2-ylaminomethyl | 0 | $CO_2$-n-Bu | H | NHCbz |
| 5212 | tetrahydropyrimidin-2- | 0 | $CO_2$-i-Bu | H | NHCbz |

TABLE 5-continued

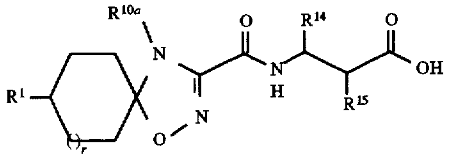

| Ex. No. | $R^1$ | r | $R^{10a}$ | $R^{14}$ | $R^{15}$ |
|---|---|---|---|---|---|
| | ylaminomethyl | | | | |
| 5213 | tetrahydropyrimidin-2-ylaminomethyl | 0 | $CO_2$-t-Bu | H | NHCbz |
| 5214 | tetrahydropyrimidin-2-ylaminomethyl | 0 | $-(CH_2)_4NH_2$ | H | NHCbz |
| 5215 | tetrahydropyrimidin-2-ylaminomethyl | 0 | COPh | H | NHCbz |
| 5216 | tetrahydropyrimidin-2-ylaminomethyl | 0 | $SO_2$-n-Bu | H | NHCbz |
| 5217 | 2-pyridinylaminomethyl | 1 | Cbz | H | $NHSO_2Ph$ |
| 5218 | 2-pyridinylaminomethyl | 1 | $SO_2Ph$ | H | $NHSO_2Ph$ |
| 5219 | 2-pyridinylaminomethyl | 1 | $CO(CH_2)_2Ph$ | H | $NHSO_2Ph$ |
| 5220 | 2-pyridinylaminomethyl | 1 | Bn | H | $NHSO_2Ph$ |
| 5221 | 2-pyridinylaminomethyl | 1 | n-Bu | H | $NHSO_2Ph$ |
| 5222 | 2-pyridinylaminomethyl | 1 | $COCH_2$ (3-indolyl) | H | $NHSO_2Ph$ |
| 5223 | 2-pyridinylaminomethyl | 1 | SO2-(biphenyl) | H | $NHSO_2Ph$ |
| 5224 | 2-pyridinylaminomethyl | 1 | $CO_2$-n-Bu | H | $NHSO_2Ph$ |
| 5225 | 2-pyridinylaminomethyl | 1 | $CO_2$-i-Bu | H | $NHSO_2Ph$ |
| 5226 | 2-pyridinylaminomethyl | 1 | $CO_2$-t-Bu | H | $NHSO_2Ph$ |
| 5227 | 2-pyridinylaminomethyl | 1 | $-(CH_2)_4NH_2$ | H | $NHSO_2Ph$ |
| 5228 | 2-pyridinylaminomethyl | 1 | COPh | H | $NHSO_2Ph$ |
| 5229 | 2-pyridinylaminomethyl | 1 | cyclopropylmethyl | H | $NHSO_2Ph$ |
| 5230 | 2-pyridinylaminomethyl | 1 | $SO_2$-n-Bu | H | $NHSO_2Ph$ |
| 5231 | 2-pyridinylaminomethyl | 1 | Cbz | H | $NHSO_2$-(2,4,6-trimethylphenyl) |
| 5232 | 2-pyridinylaminomethyl | 1 | $SO_2Ph$ | H | $NHSO_2$-(2,4,6-trimethylphenyl) |
| 5233 | 2-pyridinylaminomethyl | 1 | $CO(CH_2)_2Ph$ | H | $NHSO_2$-(2,4,6-trimethylphenyl) |
| 5234 | 2-pyridinylaminomethyl | 1 | Bn | H | $NHSO_2$-(2,4,6-trimethylphenyl) |
| 5235 | 2-pyridinylaminomethyl | 1 | n-Bu | H | $NHSO_2$-(2,4,6-trimethylphenyl) |
| 5236 | 2-pyridinylaminomethyl | 1 | $CO_2$-n-Bu | H | $NHSO_2$-(2,4,6-trimethylphenyl) |
| 5237 | 2-pyridinylaminomethyl | 1 | $CO_2$-i-Bu | H | $NHSO_2$-(2,4,6-trimethylphenyl) |
| 5238 | 2-pyridinylaminomethyl | 1 | $CO_2$-t-Bu | H | $NHSO_2$-(2,4,6-trimethylphenyl) |
| 5239 | 2-pyridinylaminomethyl | 1 | $-(CH_2)_4NH_2$ | H | $NHSO_2$-(2,4,6-trimethylphenyl) |
| 5240 | 2-pyridinylaminomethyl | 1 | COPh | H | $NHSO_2$-(2,4,6-trimethylphenyl) |
| 5241 | 2-pyridinylaminomethyl | 1 | $SO_2$-n-Bu | H | $NHSO_2$-(2,4,6-trimethylphenyl) |
| 5242 | 2-pyridinylaminomethyl | 1 | Cbz | H | NHCbz |
| 5243 | 2-pyridinylaminomethyl | 1 | $SO_2Ph$ | H | NHCbz |
| 5244 | 2-pyridinylaminomethyl | 1 | $CO(CH_2)_2Ph$ | H | NHCbz |
| 5245 | 2-pyridinylaminomethyl | 1 | Bn | H | NHCbz |
| 5246 | 2-pyridinylaminomethyl | 1 | n-Bu | H | NHCbz |
| 5247 | 2-pyridinylaminomethyl | 1 | $CO_2$-n-Bu | H | NHCbz |
| 5248 | 2-pyridinylaminomethyl | 1 | $CO_2$-i-Bu | H | NHCbz |
| 5249 | 2-pyridinylaminomethyl | 1 | $CO_2$-t-Bu | H | NHCbz |
| 5250 | 2-pyridinylaminomethyl | 1 | $-(CH_2)_4NH_2$ | H | NHCbz |
| 5251 | 2-pyridinylaminomethyl | 1 | COPh | H | NHCbz |
| 5252 | 2-pyridinylaminomethyl | 1 | $SO_2$-n-Bu | H | NHCbz |
| 5253 | 2-imidazolylaminomethyl | 1 | Cbz | H | $NHSO_2Ph$ |
| 5254 | 2-imidazolylaminomethyl | 1 | $SO_2Ph$ | H | $NHSO_2Ph$ |
| 5255 | 2-imidazolylaminomethyl | 1 | $CO(CH_2)_2Ph$ | H | $NHSO_2Ph$ |
| 5256 | 2-imidazolylaminomethyl | 1 | Bn | H | $NHSO_2Ph$ |
| 5257 | 2-imidazolylaminomethyl | 1 | n-Bu | H | $NHSO_2Ph$ |
| 5258 | 2-imidazolylaminomethyl | 1 | $COCH_2$ (3-indolyl) | H | $NHSO_2Ph$ |
| 5259 | 2-imidazolylaminomethyl | 1 | SO2-(biphenyl) | H | $NHSO_2Ph$ |
| 5260 | 2-imidazolylaminomethyl | 1 | $CO_2$-n-Bu | H | $NHSO_2Ph$ |
| 5261 | 2-imidazolylaminomethyl | 1 | $CO_2$-i-Bu | H | $NHSO_2Ph$ |
| 5262 | 2-imidazolylaminomethyl | 1 | $CO_2$-t-Bu | H | $NHSO_2Ph$ |
| 5263 | 2-imidazolylaminomethyl | 1 | $-(CH_2)_4NH_2$ | H | $NHSO_2Ph$ |
| 5264 | 2-imidazolylaminomethyl | 1 | COPh | H | $NHSO_2Ph$ |
| 5265 | 2-imidazolylaminomethyl | 1 | cyclopropylmethyl | H | $NHSO_2Ph$ |

TABLE 5-continued

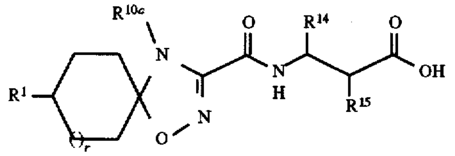

| Ex. No. | $R^1$ | r | $R^{10a}$ | $R^{14}$ | $R^{15}$ |
|---|---|---|---|---|---|
| 5266 | 2-imidazolylaminomethyl | 1 | $SO_2$-n-Bu | H | $NHSO_2Ph$ |
| 5267 | 2-imidazolylaminomethyl | 1 | Cbz | H | $NHSO_2$-(2,4,6-trimethylphenyl) |
| 5268 | 2-imidazolylaminomethyl | 1 | $SO_2Ph$ | H | $NHSO_2$-(2,4,6-trimethylphenyl) |
| 5269 | 2-imidazolylaminomethyl | 1 | $CO(CH_2)_2Ph$ | H | $NHSO_2$-(2,4,6-trimethylphenyl) |
| 5270 | 2-imidazolylaminomethyl | 1 | Bn | H | $NHSO_2$-(2,4,6-trimethylphenyl) |
| 5271 | 2-imidazolylaminomethyl | 1 | n-Bu | H | $NHSO_2$-(2,4,6-trimethylphenyl) |
| 5272 | 2-imidazolylaminomethyl | 1 | $CO_2$-n-Bu | H | $NHSO_2$-(2,4,6-trimethylphenyl) |
| 5273 | 2-imidazolylaminomethyl | 1 | $CO_2$-i-Bu | H | $NHSO_2$-(2,4,6-trimethylphenyl) |
| 5274 | 2-imidazolylaminomethyl | 1 | $CO_2$-t-Bu | H | $NHSO_2$-(2,4,6-trimethylphenyl) |
| 5275 | 2-imidazolylaminomethyl | 1 | $-(CH_2)_4NH_2$ | H | $NHSO_2$-(2,4,6-trimethylphenyl) |
| 5276 | 2-imidazolylaminomethyl | 1 | COPh | H | $NHSO_2$-(2,4,6-trimethylphenyl) |
| 5277 | 2-imidazolylaminomethyl | 1 | $SO_2$-n-Bu | H | $NHSO_2$-(2,4,6-trimethylphenyl) |
| 5278 | 2-imidazolylaminomethyl | 1 | Cbz | H | NHCbz |
| 5279 | 2-imidazolylaminomethyl | 1 | $SO_2Ph$ | H | NHCbz |
| 5280 | 2-imidazolylaminomethyl | 1 | $CO(CH_2)_2Ph$ | H | NHCbz |
| 5281 | 2-imidazolylaminomethyl | 1 | Bn | H | NHCbz |
| 5282 | 2-imidazolylaminomethyl | 1 | n-Bu | H | NHCbz |
| 5283 | 2-imidazolylaminomethyl | 1 | $CO_2$-n-Bu | H | NHCbz |
| 5284 | 2-imidazolylaminomethyl | 1 | $CO_2$-i-Bu | H | NHCbz |
| 5285 | 2-imidazolylaminomethyl | 1 | $CO_2$-t-Bu | H | NHCbz |
| 5286 | 2-imidazolylaminomethyl | 1 | $-(CH_2)_4NH_2$ | H | NHCbz |
| 5287 | 2-imidazolylaminomethyl | 1 | COPh | H | NHCbz |
| 5288 | 2-imidazolylaminomethyl | 1 | $SO_2$-n-Bu | H | NHCbz |
| 5289 | 2-imidazolinylaminomethyl | 1 | Cbz | H | $NHSO_2Ph$ |
| 5290 | 2-imidazolinylaminomethyl | 1 | $SO_2Ph$ | H | $NHSO_2Ph$ |
| 5291 | 2-imidazolinylaminomethyl | 1 | $CO(CH_2)_2Ph$ | H | $NHSO_2Ph$ |
| 5292 | 2-imidazolinylaminomethyl | 1 | Bn | H | $NHSO_2Ph$ |
| 5293 | 2-imidazolinylaminomethyl | 1 | n-Bu | H | $NHSO_2Ph$ |
| 5294 | 2-imidazolinylaminomethyl | 1 | $COCH_2$ (3-indolyl) | H | $NHSO_2Ph$ |
| 5295 | 2-imidazolinylaminomethyl | 1 | SO2-(biphenyl) | H | $NHSO_2Ph$ |
| 5296 | 2-imidazolinylaminomethyl | 1 | $CO_2$-n-Bu | H | $NHSO_2Ph$ |
| 5297 | 2-imidazolinylaminomethyl | 1 | $CO_2$-i-Bu | H | $NHSO_2Ph$ |
| 5298 | 2-imidazolinylaminomethyl | 1 | $CO_2$-t-Bu | H | $NHSO_2Ph$ |
| 5299 | 2-imidazolinylaminomethyl | 1 | $-(CH_2)_4NH_2$ | H | $NHSO_2Ph$ |
| 5300 | 2-imidazolinylaminomethyl | 1 | COPh | H | $NHSO_2Ph$ |
| 5301 | 2-imidazolinylaminomethyl | 1 | cyclopropylmethyl | H | $NHSO_2Ph$ |
| 5302 | 2-imidazolinylaminomethyl | 1 | $SO_2$-n-Bu | H | $NHSO_2Ph$ |
| 5303 | 2-imidazolinylaminomethyl | 1 | Cbz | H | $NHSO_2$-(2,4,6-trimethylphenyl) |
| 5304 | 2-imidazolinylaminomethyl | 1 | $SO_2Ph$ | H | $NHSO_2$-(2,4,6-trimethylphenyl) |
| 5305 | 2-imidazolinylaminomethyl | 1 | $CO(CH_2)_2Ph$ | H | $NHSO_2$-(2,4,6-trimethylphenyl) |
| 5306 | 2-imidazolinylaminomethyl | 1 | Bn | H | $NHSO_2$-(2,4,6-trimethylphenyl) |
| 5307 | 2-imidazolinylaminomethyl | 1 | n-Bu | H | $NHSO_2$-(2,4,6-trimethylphenyl) |
| 5308 | 2-imidazolinylaminomethyl | 1 | $CO_2$-n-Bu | H | $NHSO_2$-(2,4,6-trimethylphenyl) |
| 5309 | 2-imidazolinylaminomethyl | 1 | $CO_2$-i-Bu | H | $NHSO_2$-(2,4,6-trimethylphenyl) |
| 5310 | 2-imidazolinylaminomethyl | 1 | $CO_2$-t-Bu | H | $NHSO_2$-(2,4,6-trimethylphenyl) |
| 5311 | 2-imidazolinylaminomethyl | 1 | $-(CH_2)_4NH_2$ | H | $NHSO_2$-(2,4,6-trimethylphenyl) |
| 5312 | 2-imidazolinylaminomethyl | 1 | COPh | H | $NHSO_2$-(2,4,6-trimethylphenyl) |
| 5313 | 2-imidazolinylaminomethyl | 1 | $SO_2$-n-Bu | H | $NHSO_2$-(2,4,6- |

TABLE 5-continued

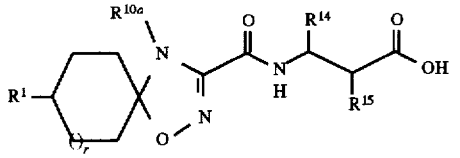

| Ex. No. | $R^1$ | r | $R^{10a}$ | $R^{14}$ | $R^{15}$ |
|---|---|---|---|---|---|
| | | | | | trimethylphenyl) |
| 5314 | 2-imidazolinylaminomethyl | 1 | Cbz | H | NHCbz |
| 5315 | 2-imidazolinylaminomethyl | 1 | $SO_2Ph$ | H | NHCbz |
| 5316 | 2-imidazolinylaminomethyl | 1 | $CO(CH_2)_2Ph$ | H | NHCbz |
| 5317 | 2-imidazolinylaminomethyl | 1 | Bn | H | NHCbz |
| 5318 | 2-imidazolinylaminomethyl | 1 | n-Bu | H | NHCbz |
| 5319 | 2-imidazolinylaminomethyl | 1 | $CO_2$-n-Bu | H | NHCbz |
| 5320 | 2-imidazolinylaminomethyl | 1 | $CO_2$-i-Bu | H | NHCbz |
| 5321 | 2-imidazolinylaminomethyl | 1 | $CO_2$-t-Bu | H | NHCbz |
| 5322 | 2-imidazolinylaminomethyl | 1 | $-(CH_2)_4NH_2$ | H | NHCbz |
| 5323 | 2-imidazolinylaminomethyl | 1 | COPh | H | NHCbz |
| 5324 | 2-imidazolinylaminomethyl | 1 | $SO_2$-n-Bu | H | NHCbz |
| 5325 | 2-benzimidazolylaminomethyl | 1 | Cbz | H | $NHSO_2Ph$ |
| 5326 | 2-benzimidazolylaminomethyl | 1 | $SO_2Ph$ | H | $NHSO_2Ph$ |
| 5327 | 2-benzimidazolylaminomethyl | 1 | $CO(CH_2)_2Ph$ | H | $NHSO_2Ph$ |
| 5328 | 2-benzimidazolylaminomethyl | 1 | Bn | H | $NHSO_2Ph$ |
| 5329 | 2-benzimidazolylaminomethyl | 1 | n-Bu | H | $NHSO_2Ph$ |
| 5330 | 2-benzimidazolylaminomethyl | 1 | $COCH_2$ (3-indolyl) | H | $NHSO_2Ph$ |
| 5331 | 2-benzimidazolylaminomethyl | 1 | SO2-(biphenyl) | H | $NHSO_2Ph$ |
| 5332 | 2-benzimidazolylaminomethyl | 1 | $CO_2$-n-Bu | H | $NHSO_2Ph$ |
| 5333 | 2-benzimidazolylaminomethyl | 1 | $CO_2$-i-Bu | H | $NHSO_2Ph$ |
| 5334 | 2-benzimidazolylaminomethyl | 1 | $CO_2$-t-Bu | H | $NHSO_2Ph$ |
| 5335 | 2-benzimidazolylaminomethyl | 1 | $-(CH_2)_4NH_2$ | H | $NHSO_2Ph$ |
| 5336 | 2-benzimidazolylaminomethyl | 1 | COPh | H | $NHSO_2Ph$ |
| 5337 | 2-benzimidazolylaminomethyl | 1 | cyclopropylmethyl | H | $NHSO_2Ph$ |
| 5338 | 2-benzimidazolylaminomethyl | 1 | $SO_2$-n-Bu | H | $NHSO_2Ph$ |
| 5339 | 2-benzimidazolylaminomethyl | 1 | Cbz | H | $NHSO_2$-(2,4,6-trimethylphenyl) |
| 5340 | 2-benzimidazolylaminomethyl | 1 | $SO_2Ph$ | H | $NHSO_2$-(2,4,6-trimethylphenyl) |
| 5341 | 2-benzimidazolylaminomethyl | 1 | $CO(CH_2)_2Ph$ | H | $NHSO_2$-(2,4,6-trimethylphenyl) |
| 5342 | 2-benzimidazolylaminomethyl | 1 | Bn | H | $NHSO_2$-(2,4,6-trimethylphenyl) |
| 5343 | 2-benzimidazolylaminomethyl | 1 | n-Bu | H | $NHSO_2$-(2,4,6-trimethylphenyl) |
| 5344 | 2-benzimidazolylaminomethyl | 1 | $CO_2$-n-Bu | H | $NHSO_2$-(2,4,6-trimethylphenyl) |
| 5345 | 2-benzimidazolylaminomethyl | 1 | $CO_2$-i-Bu | H | $NHSO_2$-(2,4,6-trimethylphenyl) |
| 5346 | 2-benzimidazolylaminomethyl | 1 | $CO_2$-t-Bu | H | $NHSO_2$-(2,4,6-trimethylphenyl) |
| 5347 | 2-benzimidazolylaminomethyl | 1 | $-(CH_2)_4NH_2$ | H | $NHSO_2$-(2,4,6-trimethylphenyl) |
| 5348 | 2-benzimidazolylaminomethyl | 1 | COPh | H | $NHSO_2$-(2,4,6-trimethylphenyl) |
| 5349 | 2-benzimidazolylaminomethyl | 1 | $SO_2$-n-Bu | H | $NHSO_2$-(2,4,6-trimethylphenyl) |
| 5350 | 2-benzimidazolylaminomethyl | 1 | Cbz | H | NHCbz |
| 5351 | 2-benzimidazolylaminomethyl | 1 | $SO_2Ph$ | H | NHCbz |
| 5352 | 2-benzimidazolylaminomethyl | 1 | $CO(CH_2)_2Ph$ | H | NHCbz |
| 5353 | 2-benzimidazolylaminomethyl | 1 | Bn | H | NHCbz |
| 5354 | 2-benzimidazolylaminomethyl | 1 | n-Bu | H | NHCbz |
| 5355 | 2-benzimidazolylaminomethyl | 1 | $CO_2$-n-Bu | H | NHCbz |
| 5356 | 2-benzimidazolylaminomethyl | 1 | $CO_2$-i-Bu | H | NHCbz |
| 5357 | 2-benzimidazolylaminomethyl | 1 | $CO_2$-t-Bu | H | NHCbz |
| 5358 | 2-benzimidazolylaminomethyl | 1 | $-(CH_2)_4NH_2$ | H | NHCbz |
| 5359 | 2-benzimidazolylaminomethyl | 1 | COPh | H | NHCbz |
| 5360 | 2-benzimidazolylaminomethyl | 1 | $SO_2$-n-Bu | H | NHCbz |
| 5361 | 7-aza-2-benzimidazolyl | 1 | Cbz | H | $NHSO_2Ph$ |
| 5362 | 7-aza-2-benzimidazolyl | 1 | $SO_2Ph$ | H | $NHSO_2Ph$ |
| 5363 | 7-aza-2-benzimidazolyl | 1 | $CO(CH_2)_2Ph$ | H | $NHSO_2Ph$ |
| 5364 | 7-aza-2-benzimidazolyl | 1 | Bn | H | $NHSO_2Ph$ |
| 5365 | 7-aza-2-benzimidazolyl | 1 | n-Bu | H | $NHSO_2Ph$ |
| 5366 | 7-aza-2-benzimidazolyl | 1 | $COCH_2$ (3-indolyl) | H | $NHSO_2Ph$ |
| 5367 | 7-aza-2-benzimidazolyl | 1 | SO2-(biphenyl) | H | $NHSO_2Ph$ |
| 5368 | 7-aza-2-benzimidazolyl | 1 | $CO_2$-n-Bu | H | $NHSO_2Ph$ |
| 5369 | 7-aza-2-benzimidazolyl | 1 | $CO_2$-i-Bu | H | $NHSO_2Ph$ |
| 5370 | 7-aza-2-benzimidazolyl | 1 | $CO_2$-t-Bu | H | $NHSO_2Ph$ |

TABLE 5-continued

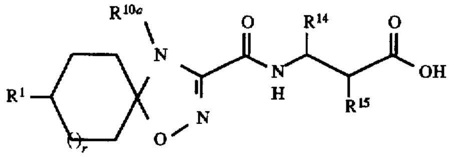

| Ex. No. | $R^1$ | r | $R^{10a}$ | $R^{14}$ | $R^{15}$ |
|---|---|---|---|---|---|
| 5371 | 7-aza-2-benzimidazolyl | 1 | $-(CH_2)_4NH_2$ | H | $NHSO_2Ph$ |
| 5372 | 7-aza-2-benzimidazolyl | 1 | COPh | H | $NHSO_2Ph$ |
| 5373 | 7-aza-2-benzimidazolyl | 1 | cyclopropylmethyl | H | $NHSO_2Ph$ |
| 5374 | 7-aza-2-benzimidazolyl | 1 | $SO_2$-n-Bu | H | $NHSO_2Ph$ |
| 5375 | 7-aza-2-benzimidazolyl | 1 | Cbz | H | $NHSO_2$-(2,4,6-trimethylphenyl) |
| 5376 | 7-aza-2-benzimidazolyl | 1 | $SO_2Ph$ | H | $NHSO_2$-(2,4,6-trimethylphenyl) |
| 5377 | 7-aza-2-benzimidazolyl | 1 | $CO(CH_2)_2Ph$ | H | $NHSO_2$-(2,4,6-trimethylphenyl) |
| 5378 | 7-aza-2-benzimidazolyl | 1 | Bn | H | $NHSO_2$-(2,4,6-trimethylphenyl) |
| 5379 | 7-aza-2-benzimidazolyl | 1 | n-Bu | H | $NHSO_2$-(2,4,6-trimethylphenyl) |
| 5380 | 7-aza-2-benzimidazolyl | 1 | $CO_2$-n-Bu | H | $NHSO_2$-(2,4,6-trimethylphenyl) |
| 5381 | 7-aza-2-benzimidazolyl | 1 | $CO_2$-i-Bu | H | $NHSO_2$-(2,4,6-trimethylphenyl) |
| 5382 | 7-aza-2-benzimidazolyl | 1 | $CO_2$-t-Bu | H | $NHSO_2$-(2,4,6-trimethylphenyl) |
| 5383 | 7-aza-2-benzimidazolyl | 1 | $-(CH_2)_4NH_2$ | H | $NHSO_2$-(2,4,6-trimethylphenyl) |
| 5384 | 7-aza-2-benzimidazolyl | 1 | COPh | H | $NHSO_2$-(2,4,6-trimethylphenyl) |
| 5385 | 7-aza-2-benzimidazolyl | 1 | $SO_2$-n-Bu | H | $NHSO_2$-(2,4,6-trimethylphenyl) |
| 5386 | 7-aza-2-benzimidazolyl | 1 | Cbz | H | NHCbz |
| 5387 | 7-aza-2-benzimidazolyl | 1 | $SO_2Ph$ | H | NHCbz |
| 5388 | 7-aza-2-benzimidazolyl | 1 | $CO(CH_2)_2Ph$ | H | NHCbz |
| 5389 | 7-aza-2-benzimidazolyl | 1 | Bn | H | NHCbz |
| 5390 | 7-aza-2-benzimidazolyl | 1 | n-Bu | H | NHCbz |
| 5391 | 7-aza-2-benzimidazolyl | 1 | $CO_2$-n-Bu | H | NHCbz |
| 5392 | 7-aza-2-benzimidazolyl | 1 | $CO_2$-i-Bu | H | NHCbz |
| 5393 | 7-aza-2-benzimidazolyl | 1 | $CO_2$-t-Bu | H | NHCbz |
| 5394 | 7-aza-2-benzimidazolyl | 1 | $-(CH_2)_4NH_2$ | H | NHCbz |
| 5395 | 7-aza-2-benzimidazolyl | 1 | COPh | H | NHCbz |
| 5396 | 7-aza-2-benzimidazolyl | 1 | $SO_2$-n-Bu | H | NHCbz |
| 5397 | tetrahydropyrimidin-2-ylaminomethyl | 1 | Cbz | H | $NHSO_2Ph$ |
| 5398 | tetrahydropyrimidin-2-ylaminomethyl | 1 | $SO_2Ph$ | H | $NHSO_2Ph$ |
| 5399 | tetrahydropyrimidin-2-ylaminomethyl | 1 | $CO(CH_2)_2Ph$ | H | $NHSO_2Ph$ |
| 5400 | tetrahydropyrimidin-2-ylaminomethyl | 1 | Bn | H | $NHSO_2Ph$ |
| 5401 | tetrahydropyrimidin-2-ylaminomethyl | 1 | n-Bu | H | $NHSO_2Ph$ |
| 5402 | tetrahydropyrimidin-2-ylaminomethyl | 1 | $COCH_2$ (3-indolyl) | H | $NHSO_2Ph$ |
| 5403 | tetrahydropyrimidin-2-ylaminomethyl | 1 | SO2-(biphenyl) | H | $NHSO_2Ph$ |
| 5404 | tetrahydropyrimidin-2-ylaminomethyl | 1 | $CO_2$-n-Bu | H | $NHSO_2Ph$ |
| 5405 | tetrahydropyrimidin-2-ylaminomethyl | 1 | $CO_2$-i-Bu | H | $NHSO_2Ph$ |
| 5406 | tetrahydropyrimidin-2-ylaminomethyl | 1 | $CO_2$-t-Bu | H | $NHSO_2Ph$ |
| 5407 | tetrahydropyrimidin-2-ylaminomethyl | 1 | $-(CH_2)_4NH_2$ | H | $NHSO_2Ph$ |
| 5408 | tetrahydropyrimidin-2-ylaminomethyl | 1 | COPh | H | $NHSO_2Ph$ |
| 5409 | tetrahydropyrimidin-2-ylaminomethyl | 1 | cyclopropylmethyl | H | $NHSO_2Ph$ |
| 5410 | tetrahydropyrimidin-2-ylaminomethyl | 1 | $SO_2$-n-Bu | H | $NHSO_2Ph$ |
| 5411 | tetrahydropyrimidin-2-ylaminomethyl | 1 | Cbz | H | $NHSO_2$-(2,4,6-trimethylphenyl) |
| 5412 | tetrahydropyrimidin-2-ylaminomethyl | 1 | $SO_2Ph$ | H | $NHSO_2$-(2,4,6-trimethylphenyl) |

TABLE 5-continued

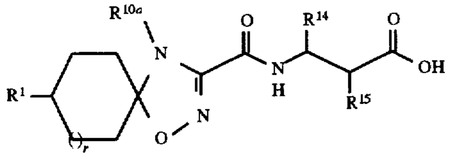

| Ex. No. | $R^1$ | r | $R^{10a}$ | $R^{14}$ | $R^{15}$ |
|---|---|---|---|---|---|
| 5413 | tetrahydropyrimidin-2-ylaminomethyl | 1 | $CO(CH_2)_2Ph$ | H | $NHSO_2$-(2,4,6-trimethylphenyl) |
| 5414 | tetrahydropyrimidin-2-ylaminomethyl | 1 | Bn | H | $NHSO_2$-(2,4,6-trimethylphenyl) |
| 5415 | tetrahydropyrimidin-2-ylaminomethyl | 1 | n-Bu | H | $NHSO_2$-(2,4,6-trimethylphenyl) |
| 5416 | tetrahydropyrimidin-2-ylaminomethyl | 1 | $CO_2$-n-Bu | H | $NHSO_2$-(2,4,6-trimethylphenyl) |
| 5417 | tetrahydropyrimidin-2-ylaminomethyl | 1 | $CO_2$-i-Bu | H | $NHSO_2$-(2,4,6-trimethylphenyl) |
| 5418 | tetrahydropyrimidin-2-ylaminomethyl | 1 | $CO_2$-t-Bu | H | $NHSO_2$-(2,4,6-trimethylphenyl) |
| 5419 | tetrahydropyrimidin-2-ylaminomethyl | 1 | $-(CH_2)_4NH_2$ | H | $NHSO_2$-(2,4,6-trimethylphenyl) |
| 5420 | tetrahydropyrimidin-2-ylaminomethyl | 1 | COPh | H | $NHSO_2$-(2,4,6-trimethylphenyl) |
| 5421 | tetrahydropyrimidin-2-ylaminomethyl | 1 | $SO_2$-n-Bu | H | $NHSO_2$-(2,4,6-trimethylphenyl) |
| 5422 | tetrahydropyrimidin-2-ylaminomethyl | 1 | Cbz | H | NHCbz |
| 5423 | tetrahydropyrimidin-2-ylaminomethyl | 1 | $SO_2Ph$ | H | NHCbz |
| 5424 | tetrahydropyrimidin-2-ylaminomethyl | 1 | $CO(CH_2)_2Ph$ | H | NHCbz |
| 5425 | tetrahydropyrimidin-2-ylaminomethyl | 1 | Bn | H | NHCbz |
| 5426 | tetrahydropyrimidin-2-ylaminomethyl | 1 | n-Bu | H | NHCbz |
| 5427 | tetrahydropyrimidin-2-ylaminomethyl | 1 | $CO_2$-n-Bu | H | NHCbz |
| 5428 | tetrahydropyrimidin-2-ylaminomethyl | 1 | $CO_2$-i-Bu | H | NHCbz |
| 5429 | tetrahydropyrimidin-2-ylaminomethyl | 1 | $CO_2$-t-Bu | H | NHCbz |
| 5430 | tetrahydropyrimidin-2-ylaminomethyl | 1 | $-(CH_2)_4NH_2$ | H | NHCbz |
| 5431 | tetrahydropyrimidin-2-ylaminomethyl | 1 | COPh | H | NHCbz |
| 5432 | tetrahydropyrimidin-2-ylaminomethyl | 1 | $SO_2$-n-Bu | H | NHCbz |

TABLE 6

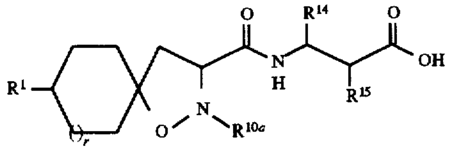

| Ex. No. | $R^1$ | r | $R^{10a}$ | $R^{14}$ | $R^{15}$ |
|---|---|---|---|---|---|
| 6001 | 2-pyridinylaminomethyl | 0 | Cbz | H | $NHSO_2Ph$ |
| 6002 | 2-pyridinylaminomethyl | 0 | $SO_2Ph$ | H | $NHSO_2Ph$ |
| 6003 | 2-pyridinylaminomethyl | 0 | $CO(CH_2)_2Ph$ | H | $NHSO_2Ph$ |
| 6004 | 2-pyridinylaminomethyl | 0 | Bn | H | $NHSO_2Ph$ |
| 6005 | 2-pyridinylaminomethyl | 0 | n-Bu | H | $NHSO_2Ph$ |
| 6006 | 2-pyridinylaminomethyl | 0 | $COCH_2$ (3-indolyl) | H | $NHSO_2Ph$ |
| 6007 | 2-pyridinylaminomethyl | 0 | SO2-(biphenyl) | H | $NHSO_2Ph$ |
| 6008 | 2-pyridinylaminomethyl | 0 | $CO_2$-n-Bu | H | $NHSO_2Ph$ |
| 6009 | 2-pyridinylaminomethyl | 0 | $CO_2$-i-Bu | H | $NHSO_2Ph$ |
| 6010 | 2-pyridinylaminomethyl | 0 | $CO_2$-t-Bu | H | $NHSO_2Ph$ |
| 6011 | 2-pyridinylaminomethyl | 0 | $-(CH_2)_4NH_2$ | H | $NHSO_2Ph$ |
| 6012 | 2-pyridinylaminomethyl | 0 | COPh | H | $NHSO_2Ph$ |
| 6013 | 2-pyridinylaminomethyl | 0 | cyclopropylmethyl | H | $NHSO_2Ph$ |
| 6014 | 2-pyridinylaminomethyl | 0 | $SO_2$-n-Bu | H | $NHSO_2Ph$ |

TABLE 6-continued

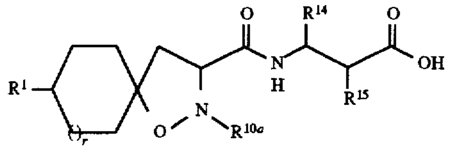

| Ex. No. | $R^1$ | r | $R^{10a}$ | $R^{14}$ | $R^{15}$ |
|---|---|---|---|---|---|
| 6015 | 2-pyridinylaminomethyl | 0 | Cbz | H | $NHSO_2$-(2,4,6-trimethylphenyl) |
| 6016 | 2-pyridinylaminomethyl | 0 | $SO_2Ph$ | H | $NHSO_2$-(2,4,6-trimethylphenyl) |
| 6017 | 2-pyridinylaminomethyl | 0 | $CO(CH_2)_2Ph$ | H | $NHSO_2$-(2,4,6-trimethylphenyl) |
| 6018 | 2-pyridinylaminomethyl | 0 | Bn | H | $NHSO_2$-(2,4,6-trimethylphenyl) |
| 6019 | 2-pyridinylaminomethyl | 0 | n-Bu | H | $NHSO_2$-(2,4,6-trimethylphenyl) |
| 6020 | 2-pyridinylaminomethyl | 0 | $CO_2$-n-Bu | H | $NHSO_2$-(2,4,6-trimethylphenyl) |
| 6021 | 2-pyridinylaminomethyl | 0 | $CO_2$-i-Bu | H | $NHSO_2$-(2,4,6-trimethylphenyl) |
| 6022 | 2-pyridinylaminomethyl | 0 | $CO_2$-t-Bu | H | $NHSO_2$-(2,4,6-trimethylphenyl) |
| 6023 | 2-pyridinylaminomethyl | 0 | $-(CH_2)_4NH_2$ | H | $NHSO_2$-(2,4,6-trimethylphenyl) |
| 6024 | 2-pyridinylaminomethyl | 0 | COPh | H | $NHSO_2$-(2,4,6-trimethylphenyl) |
| 6025 | 2-pyridinylaminomethyl | 0 | $SO_2$-n-Bu | H | $NHSO_2$-(2,4,6-trimethylphenyl) |
| 6026 | 2-pyridinylaminomethyl | 0 | Cbz | H | NHCbz |
| 6027 | 2-pyridinylaminomethyl | 0 | $SO_2Ph$ | H | NHCbz |
| 6028 | 2-pyridinylaminomethyl | 0 | $CO(CH_2)_2Ph$ | H | NHCbz |
| 6029 | 2-pyridinylaminomethyl | 0 | Bn | H | NHCbz |
| 6030 | 2-pyridinylaminomethyl | 0 | n-Bu | H | NHCbz |
| 6031 | 2-pyridinylaminomethyl | 0 | $CO_2$-n-Bu | H | NHCbz |
| 6032 | 2-pyridinylaminomethyl | 0 | $CO_2$-i-Bu | H | NHCbz |
| 6033 | 2-pyridinylaminomethyl | 0 | $CO_2$-t-Bu | H | NHCbz |
| 6034 | 2-pyridinylaminomethyl | 0 | $-(CH_2)_4NH_2$ | H | NHCbz |
| 6035 | 2-pyridinylaminomethyl | 0 | COPh | H | NHCbz |
| 6036 | 2-pyridinylaminomethyl | 0 | $SO_2$-n-Bu | H | NHCbz |
| 6037 | 2-imidazolylaminomethyl | 0 | Cbz | H | $NHSO_2Ph$ |
| 6038 | 2-imidazolylaminomethyl | 0 | $SO_2Ph$ | H | $NHSO_2Ph$ |
| 6039 | 2-imidazolylaminomethyl | 0 | $CO(CH_2)_2Ph$ | H | $NHSO_2Ph$ |
| 6040 | 2-imidazolylaminomethyl | 0 | Bn | H | $NHSO_2Ph$ |
| 6041 | 2-imidazolylaminomethyl | 0 | n-Bu | H | $NHSO_2Ph$ |
| 6042 | 2-imidazolylaminomethyl | 0 | $COCH_2$ (3-indolyl) | H | $NHSO_2Ph$ |
| 6043 | 2-imidazolylaminomethyl | 0 | SO2-(biphenyl) | H | $NHSO_2Ph$ |
| 6044 | 2-imidazolylaminomethyl | 0 | $CO_2$-n-Bu | H | $NHSO_2Ph$ |
| 6045 | 2-imidazolylaminomethyl | 0 | $CO_2$-i-Bu | H | $NHSO_2Ph$ |
| 6046 | 2-imidazolylaminomethyl | 0 | $CO_2$-t-Bu | H | $NHSO_2Ph$ |
| 6047 | 2-imidazolylaminomethyl | 0 | $-(CH_2)_4NH_2$ | H | $NHSO_2Ph$ |
| 6048 | 2-imidazolylaminomethyl | 0 | COPh | H | $NHSO_2Ph$ |
| 6049 | 2-imidazolylaminomethyl | 0 | cyclopropylmethyl | H | $NHSO_2Ph$ |
| 6050 | 2-imidazolylaminomethyl | 0 | $SO_2$-n-Bu | H | $NHSO_2Ph$ |
| 6051 | 2-imidazolylaminomethyl | 0 | Cbz | H | $NHSO_2$-(2,4,6-trimethylphenyl) |
| 6052 | 2-imidazolylaminomethyl | 0 | $SO_2Ph$ | H | $NHSO_2$-(2,4,6-trimethylphenyl) |
| 6053 | 2-imidazolylaminomethyl | 0 | $CO(CH_2)_2Ph$ | H | $NHSO_2$-(2,4,6-trimethylphenyl) |
| 6054 | 2-imidazolylaminomethyl | 0 | Bn | H | $NHSO_2$-(2,4,6-trimethylphenyl) |
| 6055 | 2-imidazolylaminomethyl | 0 | n-Bu | H | $NHSO_2$-(2,4,6-trimethylphenyl) |
| 6056 | 2-imidazolylaminomethyl | 0 | $CO_2$-n-Bu | H | $NHSO_2$-(2,4,6-trimethylphenyl) |
| 6057 | 2-imidazolylaminomethyl | 0 | $CO_2$-i-Bu | H | $NHSO_2$-(2,4,6-trimethylphenyl) |
| 6058 | 2-imidazolylaminomethyl | 0 | $CO_2$-t-Bu | H | $NHSO_2$-(2,4,6-trimethylphenyl) |
| 6059 | 2-imidazolylaminomethyl | 0 | $-(CH_2)_4NH_2$ | H | $NHSO_2$-(2,4,6-trimethylphenyl) |
| 6060 | 2-imidazolylaminomethyl | 0 | COPh | H | $NHSO_2$-(2,4,6-trimethylphenyl) |
| 6061 | 2-imidazolylaminomethyl | 0 | $SO_2$-n-Bu | H | $NHSO_2$-(2,4,6-trimethylphenyl) |

TABLE 6-continued

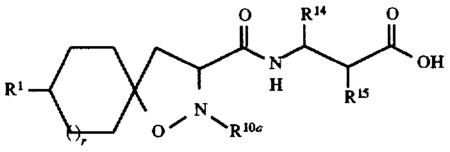

| Ex. No. | $R^1$ | r | $R^{10a}$ | $R^{14}$ | $R^{15}$ |
|---|---|---|---|---|---|
| 6062 | 2-imidazolylaminomethyl | 0 | Cbz | H | NHCbz |
| 6063 | 2-imidazolylaminomethyl | 0 | $SO_2Ph$ | H | NHCbz |
| 6064 | 2-imidazolylaminomethyl | 0 | $CO(CH_2)_2Ph$ | H | NHCbz |
| 6065 | 2-imidazolylaminomethyl | 0 | Bn | H | NHCbz |
| 6066 | 2-imidazolylaminomethyl | 0 | n-Bu | H | NHCbz |
| 6067 | 2-imidazolylaminomethyl | 0 | $CO_2$-n-Bu | H | NHCbz |
| 6068 | 2-imidazolylaminomethyl | 0 | $CO_2$-i-Bu | H | NHCbz |
| 6069 | 2-imidazolylaminomethyl | 0 | $CO_2$-t-Bu | H | NHCbz |
| 6070 | 2-imidazolylaminomethyl | 0 | $-(CH_2)_4NH_2$ | H | NHCbz |
| 6071 | 2-imidazolylaminomethyl | 0 | COPh | H | NHCbz |
| 6072 | 2-imidazolylaminomethyl | 0 | $SO_2$-n-Bu | H | NHCbz |
| 6073 | 2-imidazolinylaminomethyl | 0 | Cbz | H | $NHSO_2Ph$ |
| 6074 | 2-imidazolinylaminomethyl | 0 | $SO_2Ph$ | H | $NHSO_2Ph$ |
| 6075 | 2-imidazolinylaminomethyl | 0 | $CO(CH_2)_2Ph$ | H | $NHSO_2Ph$ |
| 6076 | 2-imidazolinylaminomethyl | 0 | Bn | H | $NHSO_2Ph$ |
| 6077 | 2-imidazolinylaminomethyl | 0 | n-Bu | H | $NHSO_2Ph$ |
| 6078 | 2-imidazolinylaminomethyl | 0 | $COCH_2$ (3-indolyl) | H | $NHSO_2Ph$ |
| 6079 | 2-imidazolinylaminomethyl | 0 | SO2-(biphenyl) | H | $NHSO_2Ph$ |
| 6080 | 2-imidazolinylaminomethyl | 0 | $CO_2$-n-Bu | H | $NHSO_2Ph$ |
| 6081 | 2-imidazolinylaminomethyl | 0 | $CO_2$-i-Bu | H | $NHSO_2Ph$ |
| 6082 | 2-imidazolinylaminomethyl | 0 | $CO_2$-t-Bu | H | $NHSO_2Ph$ |
| 6083 | 2-imidazolinylaminomethyl | 0 | $-(CH_2)_4NH_2$ | H | $NHSO_2Ph$ |
| 6084 | 2-imidazolinylaminomethyl | 0 | COPh | H | $NHSO_2Ph$ |
| 6085 | 2-imidazolinylaminomethyl | 0 | cyclopropylmethyl | H | $NHSO_2Ph$ |
| 6086 | 2-imidazolinylaminomethyl | 0 | $SO_2$-n-Bu | H | $NHSO_2Ph$ |
| 6087 | 2-imidazolinylaminomethyl | 0 | Cbz | H | $NHSO_2$-(2,4,6-trimethylphenyl) |
| 6088 | 2-imidazolinylaminomethyl | 0 | $SO_2Ph$ | H | $NHSO_2$-(2,4,6-trimethylphenyl) |
| 6089 | 2-imidazolinylaminomethyl | 0 | $CO(CH_2)_2Ph$ | H | $NHSO_2$-(2,4,6-trimethylphenyl) |
| 6090 | 2-imidazolinylaminomethyl | 0 | Bn | H | $NHSO_2$-(2,4,6-trimethylphenyl) |
| 6091 | 2-imidazolinylaminomethyl | 0 | n-Bu | H | $NHSO_2$-(2,4,6-trimethylphenyl) |
| 6092 | 2-imidazolinylaminomethyl | 0 | $CO_2$-n-Bu | H | $NHSO_2$-(2,4,6-trimethylphenyl) |
| 6093 | 2-imidazolinylaminomethyl | 0 | $CO_2$-i-Bu | H | $NHSO_2$-(2,4,6-trimethylphenyl) |
| 6094 | 2-imidazolinylaminomethyl | 0 | $CO_2$-t-Bu | H | $NHSO_2$-(2,4,6-trimethylphenyl) |
| 6095 | 2-imidazolinylaminomethyl | 0 | $-(CH_2)_4NH_2$ | H | $NHSO_2$-(2,4,6-trimethylphenyl) |
| 6096 | 2-imidazolinylaminomethyl | 0 | COPh | H | $NHSO_2$-(2,4,6-trimethylphenyl) |
| 6097 | 2-imidazolinylaminomethyl | 0 | $SO_2$-n-Bu | H | $NHSO_2$-(2,4,6-trimethylphenyl) |
| 6098 | 2-imidazolinylaminomethyl | 0 | Cbz | H | NHCbz |
| 6099 | 2-imidazolinylaminomethyl | 0 | $SO_2Ph$ | H | NHCbz |
| 6100 | 2-imidazolinylaminomethyl | 0 | $CO(CH_2)_2Ph$ | H | NHCbz |
| 6101 | 2-imidazolinylaminomethyl | 0 | Bn | H | NHCbz |
| 6102 | 2-imidazolinylaminomethyl | 0 | n-Bu | H | NHCbz |
| 6103 | 2-imidazolinylaminomethyl | 0 | $CO_2$-n-Bu | H | NHCbz |
| 6104 | 2-imidazolinylaminomethyl | 0 | $CO_2$-i-Bu | H | NHCbz |
| 6105 | 2-imidazolinylaminomethyl | 0 | $CO_2$-t-Bu | H | NHCbz |
| 6106 | 2-imidazolinylaminomethyl | 0 | $-(CH_2)_4NH_2$ | H | NHCbz |
| 6107 | 2-imidazolinylaminomethyl | 0 | COPh | H | NHCbz |
| 6108 | 2-imidazolinylaminomethyl | 0 | $SO_2$-n-Bu | H | NHCbz |
| 6109 | 2-benzimidazolylaminomethyl | 0 | Cbz | H | $NHSO_2Ph$ |
| 6110 | 2-benzimidazolylaminomethyl | 0 | $SO_2Ph$ | H | $NHSO_2Ph$ |
| 6111 | 2-benzimidazolylaminomethyl | 0 | $CO(CH_2)_2Ph$ | H | $NHSO_2Ph$ |
| 6112 | 2-benzimidazolylaminomethyl | 0 | Bn | H | $NHSO_2Ph$ |
| 6113 | 2-benzimidazolylaminomethyl | 0 | n-Bu | H | $NHSO_2Ph$ |
| 6114 | 2-benzimidazolylaminomethyl | 0 | $COCH_2$ (3-indolyl) | H | $NHSO_2Ph$ |
| 6115 | 2-benzimidazolylaminomethyl | 0 | SO2-(biphenyl) | H | $NHSO_2Ph$ |
| 6116 | 2-benzimidazolylaminomethyl | 0 | $CO_2$-n-Bu | H | $NHSO_2Ph$ |
| 6117 | 2-benzimidazolylaminomethyl | 0 | $CO_2$-i-Bu | H | $NHSO_2Ph$ |
| 6118 | 2-benzimidazolylaminomethyl | 0 | $CO_2$-t-Bu | H | $NHSO_2Ph$ |
| 6119 | 2-benzimidazolylaminomethyl | 0 | $-(CH_2)_4NH_2$ | H | $NHSO_2Ph$ |

TABLE 6-continued

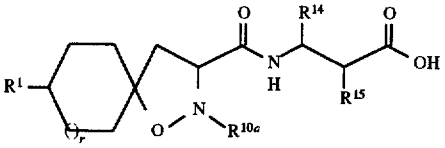

| Ex. No. | $R^1$ | r | $R^{10a}$ | $R^{14}$ | $R^{15}$ |
|---|---|---|---|---|---|
| 6120 | 2-benzimidazolylaminomethyl | 0 | COPh | H | $NHSO_2Ph$ |
| 6121 | 2-benzimidazolylaminomethyl | 0 | cyclopropylmethyl | H | $NHSO_2Ph$ |
| 6122 | 2-benzimidazolylaminomethyl | 0 | $SO_2$-n-Bu | H | $NHSO_2Ph$ |
| 6123 | 2-benzimidazolylaminomethyl | 0 | Cbz | H | $NHSO_2$-(2,4,6-trimethylphenyl) |
| 6124 | 2-benzimidazolylaminomethyl | 0 | $SO_2Ph$ | H | $NHSO_2$-(2,4,6-trimethylphenyl) |
| 6125 | 2-benzimidazolylaminomethyl | 0 | $CO(CH_2)_2Ph$ | H | $NHSO_2$-(2,4,6-trimethylphenyl) |
| 6126 | 2-benzimidazolylaminomethyl | 0 | Bn | H | $NHSO_2$-(2,4,6-trimethylphenyl) |
| 6127 | 2-benzimidazolylaminomethyl | 0 | n-Bu | H | $NHSO_2$-(2,4,6-trimethylphenyl) |
| 6128 | 2-benzimidazolylaminomethyl | 0 | $CO_2$-n-Bu | H | $NHSO_2$-(2,4,6-trimethylphenyl) |
| 6129 | 2-benzimidazolylaminomethyl | 0 | $CO_2$-i-Bu | H | $NHSO_2$-(2,4,6-trimethylphenyl) |
| 6130 | 2-benzimidazolylaminomethyl | 0 | $CO_2$-t-Bu | H | $NHSO_2$-(2,4,6-trimethylphenyl) |
| 6131 | 2-benzimidazolylaminomethyl | 0 | $-(CH_2)_4NH_2$ | H | $NHSO_2$-(2,4,6-trimethylphenyl) |
| 6132 | 2-benzimidazolylaminomethyl | 0 | COPh | H | $NHSO_2$-(2,4,6-trimethylphenyl) |
| 6133 | 2-benzimidazolylaminomethyl | 0 | $SO_2$-n-Bu | H | $NHSO_2$-(2,4,6-trimethylphenyl) |
| 6134 | 2-benzimidazolylaminomethyl | 0 | Cbz | H | NHCbz |
| 6135 | 2-benzimidazolylaminomethyl | 0 | $SO_2Ph$ | H | NHCbz |
| 6136 | 2-benzimidazolylaminomethyl | 0 | $CO(CH_2)_2Ph$ | H | NHCbz |
| 6137 | 2-benzimidazolylaminomethyl | 0 | Bn | H | NHCbz |
| 6138 | 2-benzimidazolylaminomethyl | 0 | n-Bu | H | NHCbz |
| 6139 | 2-benzimidazolylaminomethyl | 0 | $CO_2$-n-Bu | H | NHCbz |
| 6140 | 2-benzimidazolylaminomethyl | 0 | $CO_2$-i-Bu | H | NHCbz |
| 6141 | 2-benzimidazolylaminomethyl | 0 | $CO_2$-t-Bu | H | NHCbz |
| 6142 | 2-benzimidazolylaminomethyl | 0 | $-(CH_2)_4NH_2$ | H | NHCbz |
| 6143 | 2-benzimidazolylaminomethyl | 0 | COPh | H | NHCbz |
| 6144 | 2-benzimidazolylaminomethyl | 0 | $SO_2$-n-Bu | H | NHCbz |
| 6145 | 7-aza-2-benzimidazolyl | 0 | Cbz | H | $NHSO_2Ph$ |
| 6146 | 7-aza-2-benzimidazolyl | 0 | $SO_2Ph$ | H | $NHSO_2Ph$ |
| 6147 | 7-aza-2-benzimidazolyl | 0 | $CO(CH_2)_2Ph$ | H | $NHSO_2Ph$ |
| 6148 | 7-aza-2-benzimidazolyl | 0 | Bn | H | $NHSO_2Ph$ |
| 6149 | 7-aza-2-benzimidazolyl | 0 | n-Bu | H | $NHSO_2Ph$ |
| 6150 | 7-aza-2-benzimidazolyl | 0 | $COCH_2$ (3-indolyl) | H | $NHSO_2Ph$ |
| 6151 | 7-aza-2-benzimidazolyl | 0 | SO2-(biphenyl) | H | $NHSO_2Ph$ |
| 6152 | 7-aza-2-benzimidazolyl | 0 | $CO_2$-n-Bu | H | $NHSO_2Ph$ |
| 6153 | 7-aza-2-benzimidazolyl | 0 | $CO_2$-i-Bu | H | $NHSO_2Ph$ |
| 6154 | 7-aza-2-benzimidazolyl | 0 | $CO_2$-t-Bu | H | $NHSO_2Ph$ |
| 6155 | 7-aza-2-benzimidazolyl | 0 | $-(CH_2)_4NH_2$ | H | $NHSO_2Ph$ |
| 6156 | 7-aza-2-benzimidazolyl | 0 | COPh | H | $NHSO_2Ph$ |
| 6157 | 7-aza-2-benzimidazolyl | 0 | cyclopropylmethyl | H | $NHSO_2Ph$ |
| 6158 | 7-aza-2-benzimidazolyl | 0 | $SO_2$-n-Bu | H | $NHSO_2Ph$ |
| 6159 | 7-aza-2-benzimidazolyl | 0 | Cbz | H | $NHSO_2$-(2,4,6-trimethylphenyl) |
| 6160 | 7-aza-2-benzimidazolyl | 0 | $SO_2Ph$ | H | $NHSO_2$-(2,4,6-trimethylphenyl) |
| 6161 | 7-aza-2-benzimidazolyl | 0 | $CO(CH_2)_2Ph$ | H | $NHSO_2$-(2,4,6-trimethylphenyl) |
| 6162 | 7-aza-2-benzimidazolyl | 0 | Bn | H | $NHSO_2$-(2,4,6-trimethylphenyl) |
| 6163 | 7-aza-2-benzimidazolyl | 0 | n-Bu | H | $NHSO_2$-(2,4,6-trimethylphenyl) |
| 6164 | 7-aza-2-benzimidazolyl | 0 | $CO_2$-n-Bu | H | $NHSO_2$-(2,4,6-trimethylphenyl) |
| 6165 | 7-aza-2-benzimidazolyl | 0 | $CO_2$-i-Bu | H | $NHSO_2$-(2,4,6-trimethylphenyl) |
| 6166 | 7-aza-2-benzimidazolyl | 0 | $CO_2$-t-Bu | H | $NHSO_2$-(2,4,6-trimethylphenyl) |
| 6167 | 7-aza-2-benzimidazolyl | 0 | $-(CH_2)_4NH_2$ | H | $NHSO_2$-(2,4,6-trimethylphenyl) |
| 6168 | 7-aza-2-benzimidazolyl | 0 | COPh | H | $NHSO_2$-(2,4,6- |

TABLE 6-continued

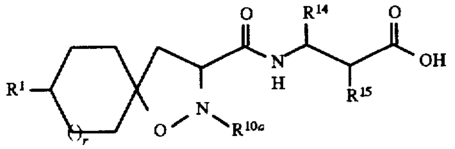

| Ex. No. | $R^1$ | r | $R^{10a}$ | $R^{14}$ | $R^{15}$ |
|---|---|---|---|---|---|
| | | | | | trimethylphenyl) |
| 6169 | 7-aza-2-benzimidazolyl | 0 | $SO_2$-n-Bu | H | $NHSO_2$-(2,4,6-trimethylphenyl) |
| 6170 | 7-aza-2-benzimidazolyl | 0 | Cbz | H | NHCbz |
| 6171 | 7-aza-2-benzimidazolyl | 0 | $SO_2Ph$ | H | NHCbz |
| 6172 | 7-aza-2-benzimidazolyl | 0 | $CO(CH_2)_2Ph$ | H | NHCbz |
| 6173 | 7-aza-2-benzimidazolyl | 0 | Bn | H | NHCbz |
| 6174 | 7-aza-2-benzimidazolyl | 0 | n-Bu | H | NHCbz |
| 6175 | 7-aza-2-benzimidazolyl | 0 | $CO_2$-n-Bu | H | NHCbz |
| 6176 | 7-aza-2-benzimidazolyl | 0 | $CO_2$-i-Bu | H | NHCbz |
| 6177 | 7-aza-2-benzimidazolyl | 0 | $CO_2$-t-Bu | H | NHCbz |
| 6178 | 7-aza-2-benzimidazolyl | 0 | $-(CH_2)_4NH_2$ | H | NHCbz |
| 6179 | 7-aza-2-benzimidazolyl | 0 | COPh | H | NHCbz |
| 6180 | 7-aza-2-benzimidazolyl | 0 | $SO_2$-n-Bu | H | NHCbz |
| 6181 | tetrahydropyrimidin-2-ylaminomethyl | 0 | Cbz | H | $NHSO_2Ph$ |
| 6182 | tetrahydropyrimidin-2-ylaminomethyl | 0 | $SO_2Ph$ | H | $NHSO_2Ph$ |
| 6183 | tetrahydropyrimidin-2-ylaminomethyl | 0 | $CO(CH_2)_2Ph$ | H | $NHSO_2Ph$ |
| 6184 | tetrahydropyrimidin-2-ylaminomethyl | 0 | Bn | H | $NHSO_2Ph$ |
| 6185 | tetrahydropyrimidin-2-ylaminomethyl | 0 | n-Bu | H | $NHSO_2Ph$ |
| 6186 | tetrahydropyrimidin-2-ylaminomethyl | 0 | $COCH_2$ (3-indolyl) | H | $NHSO_2Ph$ |
| 6187 | tetrahydropyrimidin-2-ylaminomethyl | 0 | SO2-(biphenyl) | H | $NHSO_2Ph$ |
| 6188 | tetrahydropyrimidin-2-ylaminomethyl | 0 | $CO_2$-n-Bu | H | $NHSO_2Ph$ |
| 6189 | tetrahydropyrimidin-2-ylaminomethyl | 0 | $CO_2$-i-Bu | H | $NHSO_2Ph$ |
| 6190 | tetrahydropyrimidin-2-ylaminomethyl | 0 | $CO_2$-t-Bu | H | $NHSO_2Ph$ |
| 6191 | tetrahydropyrimidin-2-ylaminomethyl | 0 | $-(CH_2)_4NH_2$ | H | $NHSO_2Ph$ |
| 6192 | tetrahydropyrimidin-2-ylaminomethyl | 0 | COPh | H | $NHSO_2Ph$ |
| 6193 | tetrahydropyrimidin-2-ylaminomethyl | 0 | cyclopropylmethyl | H | $NHSO_2Ph$ |
| 6194 | tetrahydropyrimidin-2-ylaminomethyl | 0 | $SO_2$-n-Bu | H | $NHSO_2Ph$ |
| 6195 | tetrahydropyrimidin-2-ylaminomethyl | 0 | Cbz | H | $NHSO_2$-(2,4,6-trimethylphenyl) |
| 6196 | tetrahydropyrimidin-2-ylaminomethyl | 0 | $SO_2Ph$ | H | $NHSO_2$-(2,4,6-trimethylphenyl) |
| 6197 | tetrahydropyrimidin-2-ylaminomethyl | 0 | $CO(CH_2)_2Ph$ | H | $NHSO_2$-(2,4,6-trimethylphenyl) |
| 6198 | tetrahydropyrimidin-2-ylaminomethyl | 0 | Bn | H | $NHSO_2$-(2,4,6-trimethylphenyl) |
| 6199 | tetrahydropyrimidin-2-ylaminomethyl | 0 | n-Bu | H | $NHSO_2$-(2,4,6-trimethylphenyl) |
| 6200 | tetrahydropyrimidin-2-ylaminomethyl | 0 | $CO_2$-n-Bu | H | $NHSO_2$-(2,4,6-trimethylphenyl) |
| 6201 | tetrahydropyrimidin-2-ylaminomethyl | 0 | $CO_2$-i-Bu | H | $NHSO_2$-(2,4,6-trimethylphenyl) |
| 6202 | tetrahydropyrimidin-2-ylaminomethyl | 0 | $CO_2$-t-Bu | H | $NHSO_2$-(2,4,6-trimethylphenyl) |
| 6203 | tetrahydropyrimidin-2-ylaminomethyl | 0 | $-(CH_2)_4NH_2$ | H | $NHSO_2$-(2,4,6-trimethylphenyl) |
| 6204 | tetrahydropyrimidin-2-ylaminomethyl | 0 | COPh | H | $NHSO_2$-(2,4,6-trimethylphenyl) |
| 6205 | tetrahydropyrimidin-2-ylaminomethyl | 0 | $SO_2$-n-Bu | H | $NHSO_2$-(2,4,6-trimethylphenyl) |
| 6206 | tetrahydropyrimidin-2-ylaminomethyl | 0 | Cbz | H | NHCbz |
| 6207 | tetrahydropyrimidin-2-ylaminomethyl | 0 | $SO_2Ph$ | H | NHCbz |
| 6208 | tetrahydropyrimidin-2- | 0 | $CO(CH_2)_2Ph$ | H | NHCbz |

TABLE 6-continued

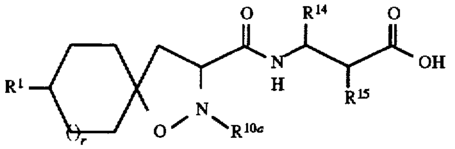

| Ex. No. | $R^1$ | r | $R^{10a}$ | $R^{14}$ | $R^{15}$ |
|---|---|---|---|---|---|
| | ylaminomethyl | | | | |
| 6209 | tetrahydropyrimidin-2-ylaminomethyl | 0 | Bn | H | NHCbz |
| 6210 | tetrahydropyrimidin-2-ylaminomethyl | 0 | n-Bu | H | NHCbz |
| 6211 | tetrahydropyrimidin-2-ylaminomethyl | 0 | $CO_2$-n-Bu | H | NHCbz |
| 6212 | tetrahydropyrimidin-2-ylaminomethyl | 0 | $CO_2$-i-Bu | H | NHCbz |
| 6213 | tetrahydropyrimidin-2-ylaminomethyl | 0 | $CO_2$-t-Bu | H | NHCbz |
| 6214 | tetrahydropyrimidin-2-ylaminomethyl | 0 | $-(CH_2)_4NH_2$ | H | NHCbz |
| 6215 | tetrahydropyrimidin-2-ylaminomethyl | 0 | COPh | H | NHCbz |
| 6216 | tetrahydropyrimidin-2-ylaminomethyl | 0 | $SO_2$-n-Bu | H | NHCbz |
| 6217 | 2-pyridinylaminomethyl | 1 | Cbz | H | $NHSO_2Ph$ |
| 6218 | 2-pyridinylaminomethyl | 1 | $SO_2Ph$ | H | $NHSO_2Ph$ |
| 6219 | 2-pyridinylaminomethyl | 1 | $CO(CH_2)_2Ph$ | H | $NHSO_2Ph$ |
| 6220 | 2-pyridinylaminomethyl | 1 | Bn | H | $NHSO_2Ph$ |
| 6221 | 2-pyridinylaminomethyl | 1 | n-Bu | H | $NHSO_2Ph$ |
| 6222 | 2-pyridinylaminomethyl | 1 | $COCH_2$ (3-indolyl) | H | $NHSO_2Ph$ |
| 6223 | 2-pyridinylaminomethyl | 1 | SO2-(biphenyl) | H | $NHSO_2Ph$ |
| 6224 | 2-pyridinylaminomethyl | 1 | $CO_2$-n-Bu | H | $NHSO_2Ph$ |
| 6225 | 2-pyridinylaminomethyl | 1 | $CO_2$-i-Bu | H | $NHSO_2Ph$ |
| 6226 | 2-pyridinylaminomethyl | 1 | $CO_2$-t-Bu | H | $NHSO_2Ph$ |
| 6227 | 2-pyridinylaminomethyl | 1 | $-(CH_2)_4NH_2$ | H | $NHSO_2Ph$ |
| 6228 | 2-pyridinylaminomethyl | 1 | COPh | H | $NHSO_2Ph$ |
| 6229 | 2-pyridinylaminomethyl | 1 | cyclopropylmethyl | H | $NHSO_2Ph$ |
| 6230 | 2-pyridinylaminomethyl | 1 | $SO_2$-n-Bu | H | $NHSO_2Ph$ |
| 6231 | 2-pyridinylaminomethyl | 1 | Cbz | H | $NHSO_2$-(2,4,6-trimethylphenyl) |
| 6232 | 2-pyridinylaminomethyl | 1 | $SO_2Ph$ | H | $NHSO_2$-(2,4,6-trimethylphenyl) |
| 6233 | 2-pyridinylaminomethyl | 1 | $CO(CH_2)_2Ph$ | H | $NHSO_2$-(2,4,6-trimethylphenyl) |
| 6234 | 2-pyridinylaminomethyl | 1 | Bn | H | $NHSO_2$-(2,4,6-trimethylphenyl) |
| 6235 | 2-pyridinylaminomethyl | 1 | n-Bu | H | $NHSO_2$-(2,4,6-trimethylphenyl) |
| 6236 | 2-pyridinylaminomethyl | 1 | $CO_2$-n-Bu | H | $NHSO_2$-(2,4,6-trimethylphenyl) |
| 6237 | 2-pyridinylaminomethyl | 1 | $CO_2$-i-Bu | H | $NHSO_2$-(2,4,6-trimethylphenyl) |
| 6238 | 2-pyridinylaminomethyl | 1 | $CO_2$-t-Bu | H | $NHSO_2$-(2,4,6-trimethylphenyl) |
| 6239 | 2-pyridinylaminomethyl | 1 | $-(CH_2)_4NH_2$ | H | $NHSO_2$-(2,4,6-trimethylphenyl) |
| 6240 | 2-pyridinylaminomethyl | 1 | COPh | H | $NHSO_2$-(2,4,6-trimethylphenyl) |
| 6241 | 2-pyridinylaminomethyl | 1 | $SO_2$-n-Bu | H | $NHSO_2$-(2,4,6-trimethylphenyl) |
| 6242 | 2-pyridinylaminomethyl | 1 | Cbz | H | NHCbz |
| 6243 | 2-pyridinylaminomethyl | 1 | $SO_2Ph$ | H | NHCbz |
| 6244 | 2-pyridinylaminomethyl | 1 | $CO(CH_2)_2Ph$ | H | NHCbz |
| 6245 | 2-pyridinylaminomethyl | 1 | Bn | H | NHCbz |
| 6246 | 2-pyridinylaminomethyl | 1 | n-Bu | H | NHCbz |
| 6247 | 2-pyridinylaminomethyl | 1 | $CO_2$-n-Bu | H | NHCbz |
| 6248 | 2-pyridinylaminomethyl | 1 | $CO_2$-i-Bu | H | NHCbz |
| 6249 | 2-pyridinylaminomethyl | 1 | $CO_2$-t-Bu | H | NHCbz |
| 6250 | 2-pyridinylaminomethyl | 1 | $-(CH_2)_4NH_2$ | H | NHCbz |
| 6251 | 2-pyridinylaminomethyl | 1 | COPh | H | NHCbz |
| 6252 | 2-pyridinylaminomethyl | 1 | $SO_2$-n-Bu | H | NHCbz |
| 6253 | 2-imidazolylaminomethyl | 1 | Cbz | H | $NHSO_2Ph$ |
| 6254 | 2-imidazolylaminomethyl | 1 | $SO_2Ph$ | H | $NHSO_2Ph$ |
| 6255 | 2-imidazolylaminomethyl | 1 | $CO(CH_2)_2Ph$ | H | $NHSO_2Ph$ |
| 6256 | 2-imidazolylaminomethyl | 1 | Bn | H | $NHSO_2Ph$ |
| 6257 | 2-imidazolylaminomethyl | 1 | n-Bu | H | $NHSO_2Ph$ |

TABLE 6-continued

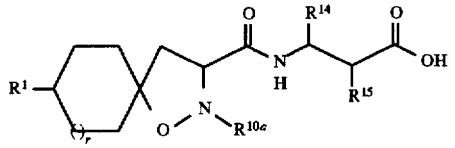

| Ex. No. | $R^1$ | r | $R^{10a}$ | $R^{14}$ | $R^{15}$ |
|---|---|---|---|---|---|
| 6258 | 2-imidazolylaminomethyl | 1 | $COCH_2$ (3-indolyl) | H | $NHSO_2Ph$ |
| 6259 | 2-imidazolylaminomethyl | 1 | SO2-(biphenyl) | H | $NHSO_2Ph$ |
| 6260 | 2-imidazolylaminomethyl | 1 | $CO_2$-n-Bu | H | $NHSO_2Ph$ |
| 6261 | 2-imidazolylaminomethyl | 1 | $CO_2$-i-Bu | H | $NHSO_2Ph$ |
| 6262 | 2-imidazolylaminomethyl | 1 | $CO_2$-t-Bu | H | $NHSO_2Ph$ |
| 6263 | 2-imidazolylaminomethyl | 1 | $-(CH_2)_4NH_2$ | H | $NHSO_2Ph$ |
| 6264 | 2-imidazolylaminomethyl | 1 | COPh | H | $NHSO_2Ph$ |
| 6265 | 2-imidazolylaminomethyl | 1 | cyclopropylmethyl | H | $NHSO_2Ph$ |
| 6266 | 2-imidazolylaminomethyl | 1 | $SO_2$-n-Bu | H | $NHSO_2Ph$ |
| 6267 | 2-imidazolylaminomethyl | 1 | Cbz | H | $NHSO_2$-(2,4,6-trimethylphenyl) |
| 6268 | 2-imidazolylaminomethyl | 1 | $SO_2Ph$ | H | $NHSO_2$-(2,4,6-trimethylphenyl) |
| 6269 | 2-imidazolylaminomethyl | 1 | $CO(CH_2)_2Ph$ | H | $NHSO_2$-(2,4,6-trimethylphenyl) |
| 6270 | 2-imidazolylaminomethyl | 1 | Bn | H | $NHSO_2$-(2,4,6-trimethylphenyl) |
| 6271 | 2-imidazolylaminomethyl | 1 | n-Bu | H | $NHSO_2$-(2,4,6-trimethylphenyl) |
| 6272 | 2-imidazolylaminomethyl | 1 | $CO_2$-n-Bu | H | $NHSO_2$-(2,4,6-trimethylphenyl) |
| 6273 | 2-imidazolylaminomethyl | 1 | $CO_2$-i-Bu | H | $NHSO_2$-(2,4,6-trimethylphenyl) |
| 6274 | 2-imidazolylaminomethyl | 1 | $CO_2$-t-Bu | H | $NHSO_2$-(2,4,6-trimethylphenyl) |
| 6275 | 2-imidazolylaminomethyl | 1 | $-(CH_2)_4NH_2$ | H | $NHSO_2$-(2,4,6-trimethylphenyl) |
| 6276 | 2-imidazolylaminomethyl | 1 | COPh | H | $NHSO_2$-(2,4,6-trimethylphenyl) |
| 6277 | 2-imidazolylaminomethyl | 1 | $SO_2$-n-Bu | H | $NHSO_2$-(2,4,6-trimethylphenyl) |
| 6278 | 2-imidazolylaminomethyl | 1 | Cbz | H | NHCbz |
| 6279 | 2-imidazolylaminomethyl | 1 | $SO_2Ph$ | H | NHCbz |
| 6280 | 2-imidazolylaminomethyl | 1 | $CO(CH_2)_2Ph$ | H | NHCbz |
| 6281 | 2-imidazolylaminomethyl | 1 | Bn | H | NHCbz |
| 6282 | 2-imidazolylaminomethyl | 1 | n-Bu | H | NHCbz |
| 6283 | 2-imidazolylaminomethyl | 1 | $CO_2$-n-Bu | H | NHCbz |
| 6284 | 2-imidazolylaminomethyl | 1 | $CO_2$-i-Bu | H | NHCbz |
| 6285 | 2-imidazolylaminomethyl | 1 | $CO_2$-t-Bu | H | NHCbz |
| 6286 | 2-imidazolylaminomethyl | 1 | $-(CH_2)_4NH_2$ | H | NHCbz |
| 6287 | 2-imidazolylaminomethyl | 1 | COPh | H | NHCbz |
| 6288 | 2-imidazolylaminomethyl | 1 | $SO_2$-n-Bu | H | NHCbz |
| 6289 | 2-imidazolinylaminomethyl | 1 | Cbz | H | $NHSO_2Ph$ |
| 6290 | 2-imidazolinylaminomethyl | 1 | $SO_2Ph$ | H | $NHSO_2Ph$ |
| 6291 | 2-imidazolinylaminomethyl | 1 | $CO(CH_2)_2Ph$ | H | $NHSO_2Ph$ |
| 6292 | 2-imidazolinylaminomethyl | 1 | Bn | H | $NHSO_2Ph$ |
| 6293 | 2-imidazolinylaminomethyl | 1 | n-Bu | H | $NHSO_2Ph$ |
| 6294 | 2-imidazolinylaminomethyl | 1 | $COCH_2$ (3-indolyl) | H | $NHSO_2Ph$ |
| 6295 | 2-imidazolinylaminomethyl | 1 | SO2-(biphenyl) | H | $NHSO_2Ph$ |
| 6296 | 2-imidazolinylaminomethyl | 1 | $CO_2$-n-Bu | H | $NHSO_2Ph$ |
| 6297 | 2-imidazolinylaminomethyl | 1 | $CO_2$-i-Bu | H | $NHSO_2Ph$ |
| 6298 | 2-imidazolinylaminomethyl | 1 | $CO_2$-t-Bu | H | $NHSO_2Ph$ |
| 6299 | 2-imidazolinylaminomethyl | 1 | $-(CH_2)_4NH_2$ | H | $NHSO_2Ph$ |
| 6300 | 2-imidazolinylaminomethyl | 1 | COPh | H | $NHSO_2Ph$ |
| 6301 | 2-imidazolinylaminomethyl | 1 | cyclopropylmethyl | H | $NHSO_2Ph$ |
| 6302 | 2-imidazolinylaminomethyl | 1 | $SO_2$-n-Bu | H | $NHSO_2Ph$ |
| 6303 | 2-imidazolinylaminomethyl | 1 | Cbz | H | $NHSO_2$-(2,4,6-trimethylphenyl) |
| 6304 | 2-imidazolinylaminomethyl | 1 | $SO_2Ph$ | H | $NHSO_2$-(2,4,6-trimethylphenyl) |
| 6305 | 2-imidazolinylaminomethyl | 1 | $CO(CH_2)_2Ph$ | H | $NHSO_2$-(2,4,6-trimethylphenyl) |
| 6306 | 2-imidazolinylaminomethyl | 1 | Bn | H | $NHSO_2$-(2,4,6-trimethylphenyl) |
| 6307 | 2-imidazolinylaminomethyl | 1 | n-Bu | H | $NHSO_2$-(2,4,6-trimethylphenyl) |
| 6308 | 2-imidazolinylaminomethyl | 1 | $CO_2$-n-Bu | H | $NHSO_2$-(2,4,6-trimethylphenyl) |
| 6309 | 2-imidazolinylaminomethyl | 1 | $CO_2$-i-Bu | H | $NHSO_2$-(2,4,6- |

TABLE 6-continued

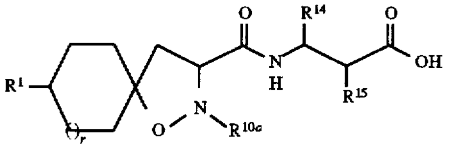

| Ex. No. | $R^1$ | r | $R^{10a}$ | $R^{14}$ | $R^{15}$ |
|---|---|---|---|---|---|
| | | | | | trimethylphenyl) |
| 6310 | 2-imidazolinylaminomethyl | 1 | $CO_2$-t-Bu | H | $NHSO_2$-(2,4,6-trimethylphenyl) |
| 6311 | 2-imidazolinylaminomethyl | 1 | $-(CH_2)_4NH_2$ | H | $NHSO_2$-(2,4,6-trimethylphenyl) |
| 6312 | 2-imidazolinylaminomethyl | 1 | COPh | H | $NHSO_2$-(2,4,6-trimethylphenyl) |
| 6313 | 2-imidazolinylaminomethyl | 1 | $SO_2$-n-Bu | H | $NHSO_2$-(2,4,6-trimethylphenyl) |
| 6314 | 2-imidazolinylaminomethyl | 1 | Cbz | H | NHCbz |
| 6315 | 2-imidazolinylaminomethyl | 1 | $SO_2Ph$ | H | NHCbz |
| 6316 | 2-imidazolinylaminomethyl | 1 | $CO(CH_2)_2Ph$ | H | NHCbz |
| 6317 | 2-imidazolinylaminomethyl | 1 | Bn | H | NHCbz |
| 6318 | 2-imidazolinylaminomethyl | 1 | n-Bu | H | NHCbz |
| 6319 | 2-imidazolinylaminomethyl | 1 | $CO_2$-n-Bu | H | NHCbz |
| 6320 | 2-imidazolinylaminomethyl | 1 | $CO_2$-i-Bu | H | NHCbz |
| 6321 | 2-imidazolinylaminomethyl | 1 | $CO_2$-t-Bu | H | NHCbz |
| 6322 | 2-imidazolinylaminomethyl | 1 | $-(CH_2)_4NH_2$ | H | NHCbz |
| 6323 | 2-imidazolinylaminomethyl | 1 | COPh | H | NHCbz |
| 6324 | 2-imidazolinylaminomethyl | 1 | $SO_2$-n-Bu | H | NHCbz |
| 6325 | 2-benzimidazolylaminomethyl | 1 | Cbz | H | $NHSO_2Ph$ |
| 6326 | 2-benzimidazolylaminomethyl | 1 | $SO_2Ph$ | H | $NHSO_2Ph$ |
| 6327 | 2-benzimidazolylaminomethyl | 1 | $CO(CH_2)_2Ph$ | H | $NHSO_2Ph$ |
| 6328 | 2-benzimidazolylaminomethyl | 1 | Bn | H | $NHSO_2Ph$ |
| 6329 | 2-benzimidazolylaminomethyl | 1 | n-Bu | H | $NHSO_2Ph$ |
| 6330 | 2-benzimidazolylaminomethyl | 1 | $COCH_2$ (3-indolyl) | H | $NHSO_2Ph$ |
| 6331 | 2-benzimidazolylaminomethyl | 1 | SO2-(biphenyl) | H | $NHSO_2Ph$ |
| 6332 | 2-benzimidazolylaminomethyl | 1 | $CO_2$-n-Bu | H | $NHSO_2Ph$ |
| 6333 | 2-benzimidazolylaminomethyl | 1 | $CO_2$-i-Bu | H | $NHSO_2Ph$ |
| 6334 | 2-benzimidazolylaminomethyl | 1 | $CO_2$-t-Bu | H | $NHSO_2Ph$ |
| 6335 | 2-benzimidazolylaminomethyl | 1 | $-(CH_2)_4NH_2$ | H | $NHSO_2Ph$ |
| 6336 | 2-benzimidazolylaminomethyl | 1 | COPh | H | $NHSO_2Ph$ |
| 6337 | 2-benzimidazolylaminomethyl | 1 | cyclopropylmethyl | H | $NHSO_2Ph$ |
| 6338 | 2-benzimidazolylaminomethyl | 1 | $SO_2$-n-Bu | H | $NHSO_2Ph$ |
| 6339 | 2-benzimidazolylaminomethyl | 1 | Cbz | H | $NHSO_2$-(2,4,6-trimethylphenyl) |
| 6340 | 2-benzimidazolylaminomethyl | 1 | $SO_2Ph$ | H | $NHSO_2$-(2,4,6-trimethylphenyl) |
| 6341 | 2-benzimidazolylaminomethyl | 1 | $CO(CH_2)_2Ph$ | H | $NHSO_2$-(2,4,6-trimethylphenyl) |
| 6342 | 2-benzimidazolylaminomethyl | 1 | Bn | H | $NHSO_2$-(2,4,6-trimethylphenyl) |
| 6343 | 2-benzimidazolylaminomethyl | 1 | n-Bu | H | $NHSO_2$-(2,4,6-trimethylphenyl) |
| 6344 | 2-benzimidazolylaminomethyl | 1 | $CO_2$-n-Bu | H | $NHSO_2$-(2,4,6-trimethylphenyl) |
| 6345 | 2-benzimidazolylaminomethyl | 1 | $CO_2$-i-Bu | H | $NHSO_2$-(2,4,6-trimethylphenyl) |
| 6346 | 2-benzimidazolylaminomethyl | 1 | $CO_2$-t-Bu | H | $NHSO_2$-(2,4,6-trimethylphenyl) |
| 6347 | 2-benzimidazolylaminomethyl | 1 | $-(CH_2)_4NH_2$ | H | $NHSO_2$-(2,4,6-trimethylphenyl) |
| 6348 | 2-benzimidazolylaminomethyl | 1 | COPh | H | $NHSO_2$-(2,4,6-trimethylphenyl) |
| 6349 | 2-benzimidazolylaminomethyl | 1 | $SO_2$-n-Bu | H | $NHSO_2$-(2,4,6-trimethylphenyl) |
| 6350 | 2-benzimidazolylaminomethyl | 1 | Cbz | H | NHCbz |
| 6351 | 2-benzimidazolylaminomethyl | 1 | $SO_2Ph$ | H | NHCbz |
| 6352 | 2-benzimidazolylaminomethyl | 1 | $CO(CH_2)_2Ph$ | H | NHCbz |
| 6353 | 2-benzimidazolylaminomethyl | 1 | Bn | H | NHCbz |
| 6354 | 2-benzimidazolylaminomethyl | 1 | n-Bu | H | NHCbz |
| 6355 | 2-benzimidazolylaminomethyl | 1 | $CO_2$-n-Bu | H | NHCbz |
| 6356 | 2-benzimidazolylaminomethyl | 1 | $CO_2$-i-Bu | H | NHCbz |
| 6357 | 2-benzimidazolylaminomethyl | 1 | $CO_2$-t-Bu | H | NHCbz |
| 6358 | 2-benzimidazolylaminomethyl | 1 | $-(CH_2)_4NH_2$ | H | NHCbz |
| 6359 | 2-benzimidazolylaminomethyl | 1 | COPh | H | NHCbz |
| 6360 | 2-benzimidazolylaminomethyl | 1 | $SO_2$-n-Bu | H | NHCbz |
| 6361 | 7-aza-2-benzimidazolyl | 1 | Cbz | H | $NHSO_2Ph$ |
| 6362 | 7-aza-2-benzimidazolyl | 1 | $SO_2Ph$ | H | $NHSO_2Ph$ |

TABLE 6-continued

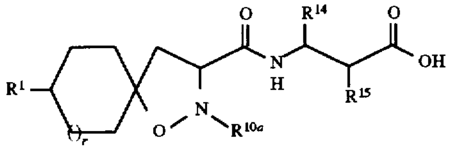

| Ex. No. | $R^1$ | r | $R^{10a}$ | $R^{14}$ | $R^{15}$ |
|---|---|---|---|---|---|
| 6363 | 7-aza-2-benzimidazolyl | 1 | $CO(CH_2)_2Ph$ | H | $NHSO_2Ph$ |
| 6364 | 7-aza-2-benzimidazolyl | 1 | Bn | H | $NHSO_2Ph$ |
| 6365 | 7-aza-2-benzimidazolyl | 1 | n-Bu | H | $NHSO_2Ph$ |
| 6366 | 7-aza-2-benzimidazolyl | 1 | $COCH_2$ (3-indolyl) | H | $NHSO_2Ph$ |
| 6367 | 7-aza-2-benzimidazolyl | 1 | SO2-(biphenyl) | H | $NHSO_2Ph$ |
| 6368 | 7-aza-2-benzimidazolyl | 1 | $CO_2$-n-Bu | H | $NHSO_2Ph$ |
| 6369 | 7-aza-2-benzimidazolyl | 1 | $CO_2$-i-Bu | H | $NHSO_2Ph$ |
| 6370 | 7-aza-2-benzimidazolyl | 1 | $CO_2$-t-Bu | H | $NHSO_2Ph$ |
| 6371 | 7-aza-2-benzimidazolyl | 1 | $-(CH_2)_4NH_2$ | H | $NHSO_2Ph$ |
| 6372 | 7-aza-2-benzimidazolyl | 1 | COPh | H | $NHSO_2Ph$ |
| 6373 | 7-aza-2-benzimidazolyl | 1 | cyclopropylmethyl | H | $NHSO_2Ph$ |
| 6374 | 7-aza-2-benzimidazolyl | 1 | $SO_2$-n-Bu | H | $NHSO_2Ph$ |
| 6375 | 7-aza-2-benzimidazolyl | 1 | Cbz | H | $NHSO_2$-(2,4,6-trimethylphenyl) |
| 6376 | 7-aza-2-benzimidazolyl | 1 | $SO_2Ph$ | H | $NHSO_2$-(2,4,6-trimethylphenyl) |
| 6377 | 7-aza-2-benzimidazolyl | 1 | $CO(CH_2)_2Ph$ | H | $NHSO_2$-(2,4,6-trimethylphenyl) |
| 6378 | 7-aza-2-benzimidazolyl | 1 | Bn | H | $NHSO_2$-(2,4,6-trimethylphenyl) |
| 6379 | 7-aza-2-benzimidazolyl | 1 | n-Bu | H | $NHSO_2$-(2,4,6-trimethylphenyl) |
| 6380 | 7-aza-2-benzimidazolyl | 1 | $CO_2$-n-Bu | H | $NHSO_2$-(2,4,6-trimethylphenyl) |
| 6381 | 7-aza-2-benzimidazolyl | 1 | $CO_2$-i-Bu | H | $NHSO_2$-(2,4,6-trimethylphenyl) |
| 6382 | 7-aza-2-benzimidazolyl | 1 | $CO_2$-t-Bu | H | $NHSO_2$-(2,4,6-trimethylphenyl) |
| 6383 | 7-aza-2-benzimidazolyl | 1 | $-(CH_2)_4NH_2$ | H | $NHSO_2$-(2,4,6-trimethylphenyl) |
| 6384 | 7-aza-2-benzimidazolyl | 1 | COPh | H | $NHSO_2$-(2,4,6-trimethylphenyl) |
| 6385 | 7-aza-2-benzimidazolyl | 1 | $SO_2$-n-Bu | H | $NHSO_2$-(2,4,6-trimethylphenyl) |
| 6386 | 7-aza-2-benzimidazolyl | 1 | Cbz | H | NHCbz |
| 6387 | 7-aza-2-benzimidazolyl | 1 | $SO_2Ph$ | H | NHCbz |
| 6388 | 7-aza-2-benzimidazolyl | 1 | $CO(CH_2)_2Ph$ | H | NHCbz |
| 6389 | 7-aza-2-benzimidazolyl | 1 | Bn | H | NHCbz |
| 6390 | 7-aza-2-benzimidazolyl | 1 | n-Bu | H | NHCbz |
| 6391 | 7-aza-2-benzimidazolyl | 1 | $CO_2$-n-Bu | H | NHCbz |
| 6392 | 7-aza-2-benzimidazolyl | 1 | $CO_2$-i-Bu | H | NHCbz |
| 6393 | 7-aza-2-benzimidazolyl | 1 | $CO_2$-t-Bu | H | NHCbz |
| 6394 | 7-aza-2-benzimidazolyl | 1 | $-(CH_2)_4NH_2$ | H | NHCbz |
| 6395 | 7-aza-2-benzimidazolyl | 1 | COPh | H | NHCbz |
| 6396 | 7-aza-2-benzimidazolyl | 1 | $SO_2$-n-Bu | H | NHCbz |
| 6397 | tetrahydropyrimidin-2-ylaminomethyl | 1 | Cbz | H | $NHSO_2Ph$ |
| 6398 | tetrahydropyrimidin-2-ylaminomethyl | 1 | $SO_2Ph$ | H | $NHSO_2Ph$ |
| 6399 | tetrahydropyrimidin-2-ylaminomethyl | 1 | $CO(CH_2)_2Ph$ | H | $NHSO_2Ph$ |
| 6400 | tetrahydropyrimidin-2-ylaminomethyl | 1 | Bn | H | $NHSO_2Ph$ |
| 6401 | tetrahydropyrimidin-2-ylaminomethyl | 1 | n-Bu | H | $NHSO_2Ph$ |
| 6402 | tetrahydropyrimidin-2-ylaminomethyl | 1 | $COCH_2$ (3-indolyl) | H | $NHSO_2Ph$ |
| 6403 | tetrahydropyrimidin-2-ylaminomethyl | 1 | SO2-(biphenyl) | H | $NHSO_2Ph$ |
| 6404 | tetrahydropyrimidin-2-ylaminomethyl | 1 | $CO_2$-n-Bu | H | $NHSO_2Ph$ |
| 6405 | tetrahydropyrimidin-2-ylaminomethyl | 1 | $CO_2$-i-Bu | H | $NHSO_2Ph$ |
| 6406 | tetrahydropyrimidin-2-ylaminomethyl | 1 | $CO_2$-t-Bu | H | $NHSO_2Ph$ |
| 6407 | tetrahydropyrimidin-2-ylaminomethyl | 1 | $-(CH_2)_4NH_2$ | H | $NHSO_2Ph$ |
| 6408 | tetrahydropyrimidin-2-ylaminomethyl | 1 | COPh | H | $NHSO_2Ph$ |

TABLE 6-continued

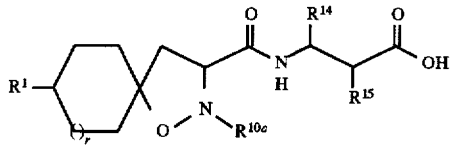

| Ex. No. | $R^1$ | r | $R^{10a}$ | $R^{14}$ | $R^{15}$ |
|---|---|---|---|---|---|
| 6409 | tetrahydropyrimidin-2-ylaminomethyl | 1 | cyclopropylmethyl | H | $NHSO_2Ph$ |
| 6410 | tetrahydropyrimidin-2-ylaminomethyl | 1 | $SO_2$-n-Bu | H | $NHSO_2Ph$ |
| 6411 | tetrahydropyrimidin-2-ylaminomethyl | 1 | Cbz | H | $NHSO_2$-(2,4,6-trimethylphenyl) |
| 6412 | tetrahydropyrimidin-2-ylaminomethyl | 1 | $SO_2Ph$ | H | $NHSO_2$-(2,4,6-trimethylphenyl) |
| 6413 | tetrahydropyrimidin-2-ylaminomethyl | 1 | $CO(CH_2)_2Ph$ | H | $NHSO_2$-(2,4,6-trimethylphenyl) |
| 6414 | tetrahydropyrimidin-2-ylaminomethyl | 1 | Bn | H | $NHSO_2$-(2,4,6-trimethylphenyl) |
| 6415 | tetrahydropyrimidin-2-ylaminomethyl | 1 | n-Bu | H | $NHSO_2$-(2,4,6-trimethylphenyl) |
| 6416 | tetrahydropyrimidin-2-ylaminomethyl | 1 | $CO_2$-n-Bu | H | $NHSO_2$-(2,4,6-trimethylphenyl) |
| 6417 | tetrahydropyrimidin-2-ylaminomethyl | 1 | $CO_2$-i-Bu | H | $NHSO_2$-(2,4,6-trimethylphenyl) |
| 6418 | tetrahydropyrimidin-2-ylaminomethyl | 1 | $CO_2$-t-Bu | H | $NHSO_2$-(2,4,6-trimethylphenyl) |
| 6419 | tetrahydropyrimidin-2-ylaminomethyl | 1 | $-(CH_2)_4NH_2$ | H | $NHSO_2$-(2,4,6-trimethylphenyl) |
| 6420 | tetrahydropyrimidin-2-ylaminomethyl | 1 | COPh | H | $NHSO_2$-(2,4,6-trimethylphenyl) |
| 6421 | tetrahydropyrimidin-2-ylaminomethyl | 1 | $SO_2$-n-Bu | H | $NHSO_2$-(2,4,6-trimethylphenyl) |
| 6422 | tetrahydropyrimidin-2-ylaminomethyl | 1 | Cbz | H | NHCbz |
| 6423 | tetrahydropyrimidin-2-ylaminomethyl | 1 | $SO_2Ph$ | H | NHCbz |
| 6424 | tetrahydropyrimidin-2-ylaminomethyl | 1 | $CO(CH_2)_2Ph$ | H | NHCbz |
| 6425 | tetrahydropyrimidin-2-ylaminomethyl | 1 | Bn | H | NHCbz |
| 6426 | tetrahydropyrimidin-2-ylaminomethyl | 1 | n-Bu | H | NHCbz |
| 6427 | tetrahydropyrimidin-2-ylaminomethyl | 1 | $CO_2$-n-Bu | H | NHCbz |
| 6428 | tetrahydropyrimidin-2-ylaminomethyl | 1 | $CO_2$-i-Bu | H | NHCbz |
| 6429 | tetrahydropyrimidin-2-ylaminomethyl | 1 | $CO_2$-t-Bu | H | NHCbz |
| 6430 | tetrahydropyrimidin-2-ylaminomethyl | 1 | $-(CH_2)_4NH_2$ | H | NHCbz |
| 6431 | tetrahydropyrimidin-2-ylaminomethyl | 1 | COPh | H | NHCbz |
| 6432 | tetrahydropyrimidin-2-ylaminomethyl | 1 | $SO_2$-n-Bu | H | NHCbz |

What is claimed is:

1. A compound of Formula I:

$$R^1—Q—W—X—Y \quad (I)$$

and pharmaceutically acceptable salt forms thereof, wherein:

Q is selected from

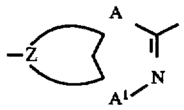

or

-continued

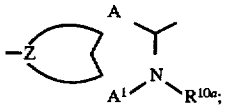

A is selected from $—N(R^{10})—$, $—C(R^{11})—$ or $—O—$;

$A^1$ is selected from $—O—$ or $—N(R^{10})—$;

Z is a spiro-fused 4–7 membered ring system (including the sprio atom) containing 0–2 heteroatoms selected from O, S, or N, said ring system optionally being substituted on carbon with keto, or being substituted on carbon or nitrogen independently with 0–2 $R^9$ or $R^{10}$ or $R^{10a}$;

$R^1$ is selected from:

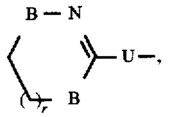

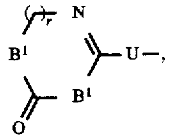

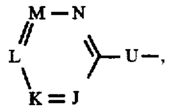

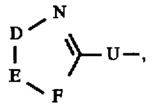

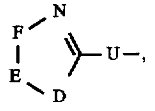

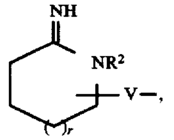

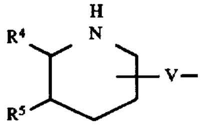

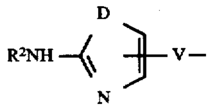

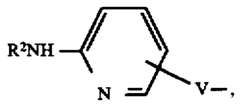

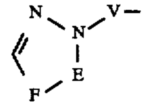

or

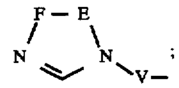

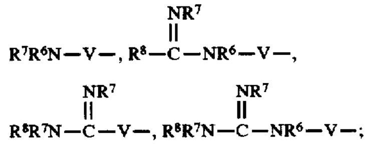

B is independently selected from $—CH_2—$, —O—, $—N(R^2)—$, or —C(=O)—;

$B^1$ is independently selected from $—CH_2—$ or $—N(R^3)—$;

D is $—N(R^2)—$, —O—, —S—, —C(=O)— or $—SO_2—$;

E–F is $—C(R^4)=C(R^5)—$, $—N=C(R^4)—$, $—C(R^4)=N—$, or $—C(R^4)_2C(R^5)_2—$;

J, K, L and M are independently selected from $—C(R^4)—$, $—C(R^5)—$ or —N—, provided that at least one of J, K, L and M is not —N—;

$R^2$ is selected from: H, $C_{1-6}$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$cycloalkylalkyl, aryl, heteroaryl($C_1$–$C_6$ alkyl) carbonyl, heteroarylcarbonyl, aryl $C_1$–$C_6$ alkyl, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, aryl($C_1$–$C_6$ alkoxy)carbonyl, wherein said aryl groups are substituted with 0–2 substituents independently selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$cycloalkylalkyl, aryl, aryl ($C_1$–$C_6$ alkyl)-, ($C_1$–$C_6$ alkyl)carbonyl, ($C_1$–$C_6$ alkoxy)carbonyl, arylcarbonyl;

alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups independently selected from: $C_1$–$C_4$ alkyl, $C_1$–$C_4$ alkoxy, halo, cyano, amino, $CF_3$, or $NO_2$;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

U is selected from:

$—N(R^6)\ (CH_2)_n—$,
$—N(R^6)\ (CH_2)_mO—$,
$—N(R^6)\ (CH_2)_mN(R^7)—$
$—N(R^6)\ (CH_2)_nS(O)_p—$
$—N(R^6)C(=O)\ (CH_2)_n—$;
$—N(R^6)\ (CH_2)_mC(=O)—$;

V is selected from:

$—(CH_2)_n—$,
$—(CH_2)_mO—(CH_2)_n—$,
$—(CH_2)_mN(R^7)\ (CH_2)_n—$,
$—(CH_2)_nS(O)_p(CH_2)_n—$,
$—(CH_2)_mN(R^7)C(=O)\ (CH_2)_n—$,
$—(CH_2)_nC(=O)N(R^7)\ (CH_2)_n—$,
$—(CH_2)_nC(=O)\ (CH_2)_n—$;

$R^9$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

$R^{10}$ is selected from: H, $CO_2R^{17}$, $C(=O)R^{17}$, $C(=O)NR^{17}R^{20}$, $—SO_2R^{17}$, $—SO_2NR^{17}R^{20}$, $C_1$–$C_6$ alkyl substituted with $_{0-1}$ $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $C(=O)NR^{17}R^{20}$, $-SO_2R^{17}$, $-SO_2NR^{17}R^{20}$, $C_1-C_6$ alkyl substituted with 0–1 $R^{15}$, $C_3-C_6$ alkenyl substituted with 0–1 $R^{15}$, $C_3-C_7$ cycloalkyl substituted with 0–1 $R^{15}$, $C_4-C_{11}$ cycloalkylalkyl substituted with 0–1 $R^{15}$, aryl substituted with 0–1 $R^{15}$ or 0–2 $R^{11}$, or aryl($C_1-C_6$ alkyl)- substituted with 0–1 $R^{15}$ or 0–2 $R^{11}$;

$R^{11}$ is selected from H, $C_1-C_4$ alkyl, $C_1-C_4$ alkoxy, aryl, aryl($C_1-C_6$ alkyl)-, ($C_1-C_4$ alkoxy)carbonyl, ($C_1-C_4$ alkyl)carbonyl, $C_1-C_4$ alkylsulfonyl, or $C_1-C_4$ alkylaminosulfonyl;

W is selected from:
- $C_1-C_4$ alkylene,
- $-(C(R^{12})_2)_qO(C(R^{12})_2)_q-$,
- $-(C(R^{12})_2)_qC(=O)(C(R^{12})_2)_q-$,
- $-(C(R^{12})_2)_qC(=O)N(R^{13})-$,
- $-C(=O)-N(R^{13})-(C(R^{12})_2)_q-$;

X is $-(C(R^{12})_2)_qC(R^{12})(R^{14})-C(R^{12})(R^{15})-$;

alternatively, W and X can be taken together to be

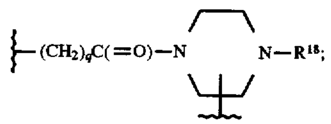

$R^{12}$ is selected from H, $C_1-C_6$ alkyl, $C_2-C_6$ alkenyl, $C_2-C_6$ alkynyl, $C_3-C_7$ cycloalkyl, $C_4-C_{10}$ cycloalkylalkyl, ($C_1-C_4$ alkyl)carbonyl, aryl, or aryl($C_1-C_6$ alkyl)-;

$R^{13}$ is selected from H, $C_1-C_6$ alkyl, $C_3-C_7$ cycloalkylmethyl, or aryl($C_1-C_6$ alkyl)-

$R^{14}$ is selected from:

H, $C_1-C_6$ alkylthio($C_1-C_6$ alkyl)-, aryl($C_1-C_{10}$ alkylthioalkyl)-, aryl($C_1-C_{10}$ alkoxyalkyl)-, $C_1-C_{10}$ alkyl, $C_1-C_{10}$ alkoxyalkyl, $C_1-C_6$ hydroxyalkyl, $C_2-C_{10}$ alkenyl, $C_2-C_{10}$ alkynyl, $C_3-C_{10}$ cycloalkyl, $C_3-C_{10}$ cycloalkylalkyl, aryl($C_1-C_6$ alkyl)-, heteroaryl ($C_1-C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may optionally be substituted independently with 0–1 $R^{16}$ or 0–2 $R^{11}$;

$R^{15}$ is selected from:

H, $R^{16}$, $C_1-C_{10}$ alkyl, $C_1-C_{10}$ alkoxyalkyl, $C_1-C_{10}$ alkylaminoalkyl, $C_1-C_{10}$ dialkylaminoalkyl, ($C_1-C_{10}$ alkyl)carbonyl, aryl($C_0-C_6$ alkyl)carbonyl, $C_1-C_{10}$ alkenyl, $C_1-C_{10}$ alkynyl, $C_3-C_{10}$ cycloalkyl, $C_3-C_{10}$ cycloalkylalkyl, aryl($C_1-C_6$ alkyl)-, heteroaryl ($C_1-C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may optionally be substituted independently with 0–2 $R^{11}$;

Y is selected from:

$-COR^{19}$, $-SO_3H$, $-PO_3H$, tetrazolyl, $-CONHNHSO_2CF_3$, $-CONHSO_2R^{17}$, $-CONHSO_2NHR^{17}$, $-NHCOCF_3$, $-NHCONHSO_2R^{17}$, $-NHSO_2R^{17}$, $-OPO_3H_2$, $-OSO_3H$, $-PO_3H_2$, $-SO_3H$, $-SO_2NHCOR^{17}$, $-SO_2NHCO_2R^{17}$,

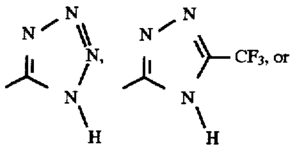

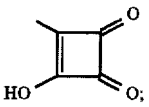

$R^{16}$ is selected from:
- $-N(R^{20})-C(=O)-O-R^{17}$,
- $-N(R^{20})-C(=O)-R^{17}$,
- $-N(R^{20})-C(=O)-NH-R^{17}$,
- $-N(R^{20})SO_2-R^{17}$, or
- $-N(R^{20})SO_2-NR^{20}R^{17}$;

$R^{17}$ is selected from:

$C_1-C_{10}$ alkyl, $C_3-C_{11}$ cycloalkyl, aryl($C_1-C_6$ alkyl)-, ($C_1-C_6$ alkyl)aryl, heteroaryl($C_1-C_6$ alkyl)-, ($C_1-C_6$ alkyl) heteroaryl, arylaryl ($C_1-C_6$ alkyl)-, heteroarylaryl ($C_1-C_6$ alkyl)-, arylheteroaryl ($C_1-C_6$ alkyl)-, heteroarylheteroaryl ($C_1-C_6$ alkyl)-, heteroaryl, or aryl, wherein said aryl or heteroaryl groups are optionally substituted with 0–3 substituents independently selected from the group consisting of: $C_1-C_4$ alkyl, $C_1-C_4$ alkoxy, aryl, halo, cyano, amino, $CF_3$, and $NO_2$;

$R^{18}$ is selected from:
- H,
- $-C(=O)-O-R^{17}$,
- $-C(=O)-R^{17}$,
- $-C(=O)-NH-R^{17}$,
- $-SO_2-R^{17}$, or
- $-SO_2-NR^{20}R^{17}$;

$R^{19}$ is selected from:
- hydroxy,
- $C_1-C_{10}$ alkyloxy,
- $C_3-C_{11}$ cycloalkyloxy,
- aryloxy,
- aryl($C_1-C_6$ alkoxy)-,
- $C_3-C_{10}$ alkylcarbonyloxyalkyloxy,
- $C_3-C_{10}$ alkoxycarbonyloxyalkyloxy,
- $C_2-C_{10}$ alkoxycarbonylalkyloxy,
- $C_5-C_{10}$ cycloalkylcarbonyloxyalkyloxy,
- $C_5-C_{10}$ cycloalkoxycarbonyloxyalkyloxy,
- $C_5-C_{10}$ cycloalkoxycarbonylalkyloxy,
- $C_7-C_{11}$ aryloxycarbonylalkyloxy,
- $C_8-C_{12}$ aryloxycarbonyloxyalkyloxy,
- $C_8-C_{12}$ arylcarbonyloxyalkyloxy,
- $C_5-C_{10}$ alkoxyalkylcarbonyloxyalkyloxy,
- $C_5-C_{10}$ (5-alkyl-1,3-dioxa-cyclopenten-2-one-yl)methyloxy,
- $C_{10}-C_{14}$ (5-aryl-1,3-dioxa-cyclopenten-2-one-yl)methyloxy, or
- ($R^{11}$)($R^{12}$)N-($C_1-C_{10}$ alkoxy)-;

$R^{20}$ is selected from: H, $C_1-C_6$ alkyl, $C_3-C_7$ cycloalkyl, $C_4-C_{11}$ cycloalkylalkyl, aryl, aryl($C_1-C_6$ alkyl)-, or heteroaryl ($C_1-C_6$ alkyl)-;

m is 1–2;

n is 0–2;

p is 0–2;

q is 0–2; and r is 0–2;

provided that:
n, q, and r are chosen such that the number of in-chain atoms between $R^1$ and Y is in the range of 8–18.
2. A compound of claim 1 of the Formula I:
$R^1$—Q—W—X—Y (I)
and pharmaceutically acceptable salt forms thereof wherein:
Q is selected from:
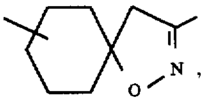
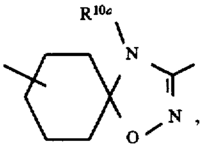
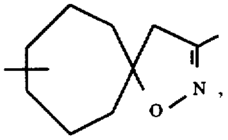
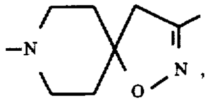
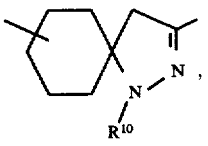
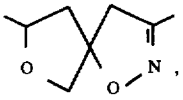
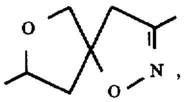
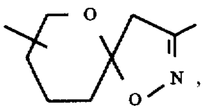
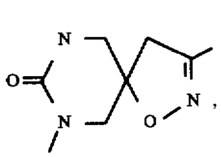
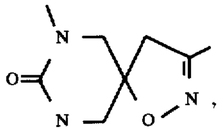
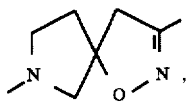
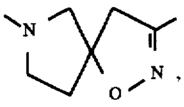
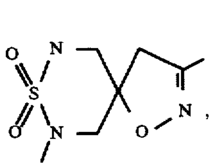
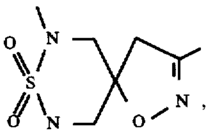
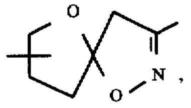
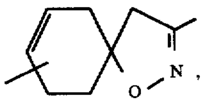
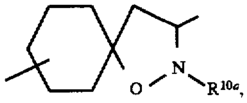
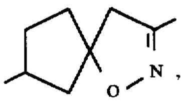
-continued
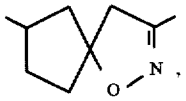
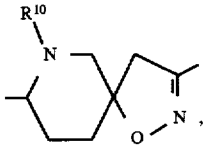
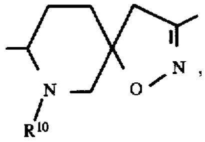
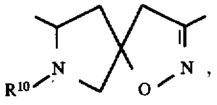
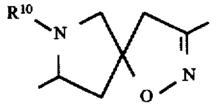
or
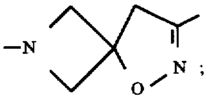
$R^1$ is selected from:
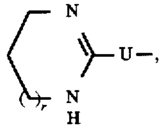
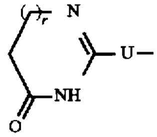
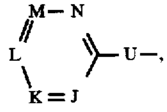
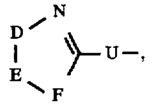
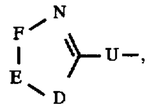
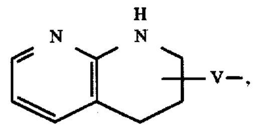
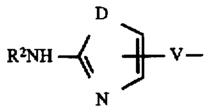
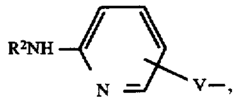
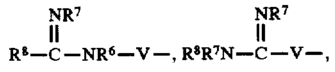

-continued

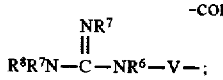

D is $-N(R^2)-$, $-O-$, $-S-$, $-C(=O)-$ or $-SO_2-$;

E-F is $-C(R^4)=C(R^5)-$, $-N=C(R^4)-$, $-C(R^4)=N-$, or $-C(R^4)_2C(R^5)_2-$;

J, K, L and M are independently selected from $-C(R^4)-$, $-C(R^5)-$ or $-N-$, provided that at least one of J, K, L and M is not $-N-$;

$R^2$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl ($C_1$–$C_6$ alkyl)-, ($C_1$–$C_6$ alkyl) carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents independently selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups independently selected from: $C_1$–$C_4$ alkyl, $C_1$–$C_4$ alkoxy, halo, cyano, amino, $CF_3$, or $NO_2$;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

U is selected from:

$-N(R^6)(CH_2)_n-$,
$-N(R^6)(CH_2)_mO-$,
$-N(R^6)(CH_2)_mN(R^7)-$
$-N(R^6)(CH_2)_nS(O)_p-$
$-N(R^6)C(=O)(CH_2)_n-$;

V is selected from:

$-(CH_2)_n-$,
$-(CH_2)_mO-(CH_2)_n-$,
$-(CH_2)_mN(R^7)(CH_2)_n-$,
$-(CH_2)_nS(O)_p(CH_2)_n-$,
$-(CH_2)_mN(R^7)C(=O)(CH_2)_n-$,
$-(CH_2)_nC(=O)N(R^7)(CH_2)_n-$,
$-(CH_2)_nC(=O)(CH_2)_n-$;

$R^9$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

$R^{10}$ is selected from: H, $CO_2R^{17}$, $C(=O)R^{17}$, $C(=O)NR^{17}R^{20}$, $-SO_2R^{17}$, $-SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $C(=O)NR^{17}R^{20}$, $-SO_2R^{17}$, $-SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is selected from:

$C_1$–$C_4$ alkylene,
$-(C(R^{12})_2)_qO(C(R^{12})_2)_q-$,
$-(C(R^{12})_2)_qC(=O)(C(R^{12})_2)_q-$,
$-(C(R^{12})_2)_qC(=O)N(R^{13})-$,
$-C(=O)-N(R^{13})-(C(R^{12})_2)_q-$;

X is $-(C(R^{12})_2)_qC(R^{12})(R^{14})-C(R^{12})(R^{15})-$;

alternatively, W and X can be taken together to be

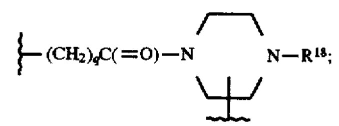

$R^{12}$ is selected from H, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from H, $C_1$–$C_6$ alkyl, $C_3$–$C_7$ cycloalkylmethyl, or aryl($C_1$–$C_6$ alkyl)-;

$R^{14}$ is selected from:

H, $C_1$–$C_6$ alkylthio($C_1$–$C_6$ alkyl)-, aryl($C_1$–$C_{10}$ alkylthioalkyl)-, aryl ($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may optionally be substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl ($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may optionally be substituted independently with 0–2 $R^{11}$;

Y is selected from:

$-COR^{19}$, $-SO_3H$, $-PO_3H$, tetrazolyl, $-CONHNHSO_2CF_3$, $-CONHSO_2R^{17}$, $-CONHSO_2NHR^{17}$, $-NHCOCF_3$, $-NHCONHSO_2R^{17}$, $-NHSO_2R^{17}$, $-OPO_3H_2$, $-OSO_3H$, $-PO_3H_2$, $-SO_3H$, $-SO_2NHCOR^{17}$, $-SO_2NHCO_2R^{17}$,

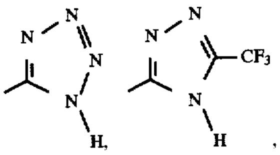
, or
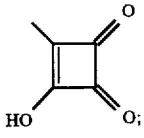
;

$R^{16}$ is selected from:

—$N(R^{20})$—C(=O)—O—$R^{17}$,
—$N(R^{20})$—C(=O)—$R^{17}$,
—$N(R^{20})$—C(=O)—NH—$R^{17}$,
—$N(R^{20})SO_2$—$R^{17}$, or
—$N(R^{20})SO_2$—$NR^{20}R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl) heteroaryl, arylaryl ($C_1$–$C_6$ alkyl)-, heteroarylaryl ($C_1$–$C_6$ alkyl)-, arylheteroaryl ($C_1$–$C_6$ alkyl)-, heteroarylheteroaryl ($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{18}$ is selected from:

H,
—C(=O)—O—$R^{17}$,
—C(=O)—$R^{17}$,
—C(=O)—NH—$R^{17}$,
—$SO_2$—$R^{17}$, or
—$SO_2$—$NR^{20}R^{17}$;

$R^{19}$ is selected from:

hydroxy,
$C_1$–$C_{10}$ alkyloxy,
$C_3$–$C_{11}$ cycloalkyloxy,
aryloxy,
aryl($C_1$–$C_6$ alkoxy)-,
$C_3$–$C_{10}$ alkylcarbonyloxyalkyloxy,
$C_3$–$C_{10}$ alkoxycarbonyloxyalkyloxy,
$C_2$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_7$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl) methyloxy, or
($R^{11}$) ($R^{12}$)N—($C_1$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl ($C_1$–$C_6$ alkyl)-;

m is 1–2;

n is 0–2;

p is 0–2;

q is 0–2; and r is 0–2;

provided that:

n, q, and r are chosen such that the number of in-chain atoms between $R^1$ and Y is in the range of 8–18.

3. A compound of claim 1 of the Formula I and pharmaceutically acceptable salt forms thereof wherein:

Q is selected from:

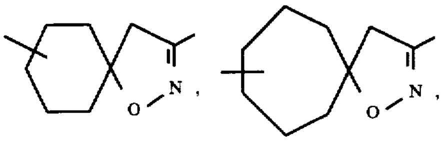
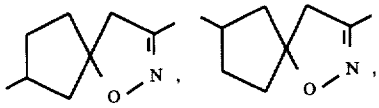
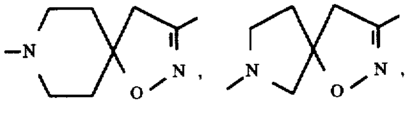
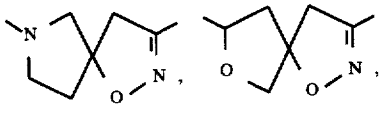
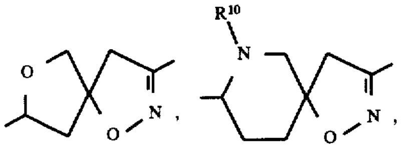
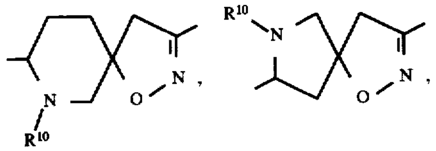
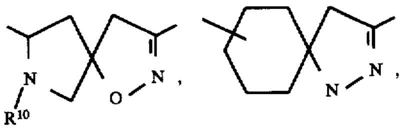
or
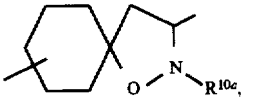

$R^1$ is selected from:

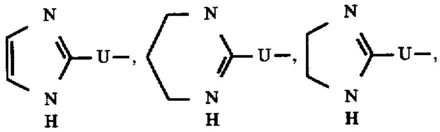
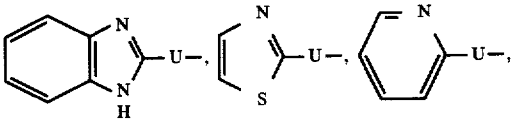
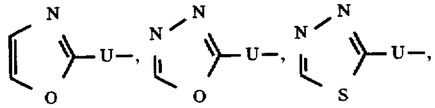

-continued

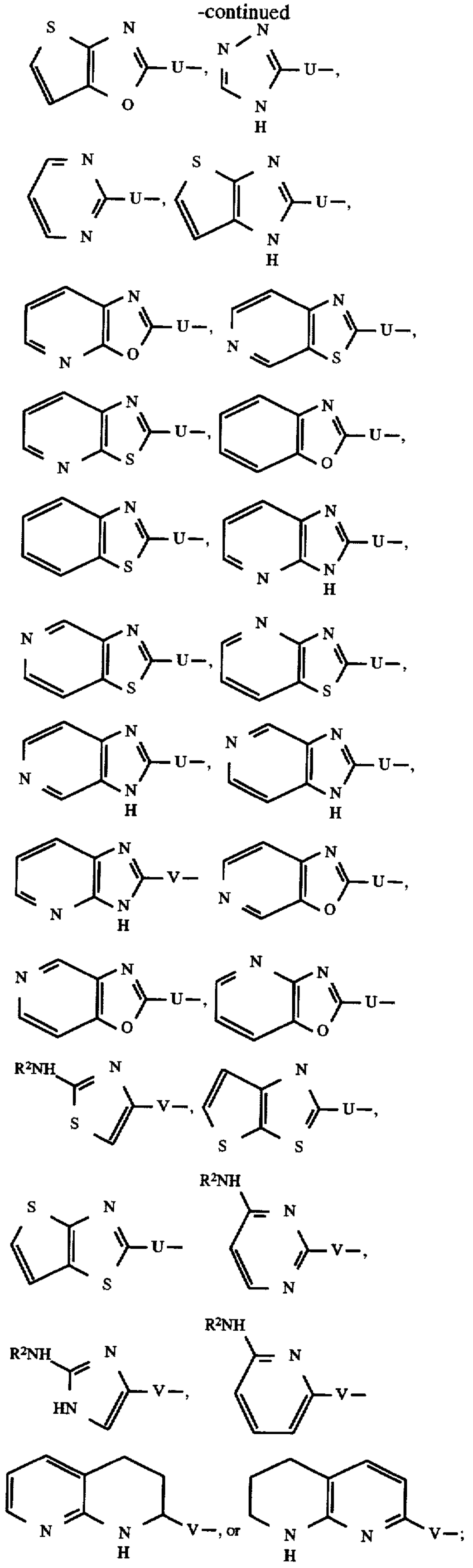

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

$R^2$ is selected from: H, $C_1$–$C_4$ alkyl or benzyl;

U is $-NH(CH_2)_n-$;

V is $-(CH_2)_n-$;

$R^{10}$ is selected from: H, $CO_2R^{17}$, $C(=O)R^{17}$, $CONR^{17}R^{20}$, $-SO_2R^{17}$, $-SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $CONR^{17}R^{20}$, $-SO_2R^{17}$, $-SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is $-C(=O)-N(R^{13})-$;

X is $-CH(R^{14})-CH(R^{15})-$;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $-C(=O)R^{19}$;

$R^{16}$ is selected from:

$-N(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$, or
$-N(R^{20})SO_2-N(R^{20})R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl) heteroaryl, arylaryl ($C_1$–$C_6$ alkyl)-, heteroarylaryl ($C_1$–$C_6$ alkyl)-, arylheteroaryl ($C_1$–$C_6$ alkyl)-, heteroarylheteroaryl ($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is selected from:

hydroxy,
$C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-, i-propyloxycarbonyloxymethoxy-, t-butyloxycarbonyloxymethoxy-, 1-(i-propyloxycarbonyloxy)ethoxy-, 1-(cyclohexyloxycarbonyloxy)ethoxy-, 1-(t-butyloxycarbonyloxy)ethoxy-, dimethylaminoethoxy-, diethylaminoethoxy-, (5-methyl-1,3-dioxacyclopenten-2-on-4-yl)methoxy-, (5-(t-butyl)-1,3-dioxacyclopenten-2-on-4-yl)methoxy-, (1,3-dioxa-5-phenyl-cyclopenten-2-on-4-yl)methoxy-, or 1-(2-(2-methoxypropyl)carbonyloxy)ethoxy-;

$R^{20}$ is H or $CH_3$; and n is 0–1.

4. A compound of claim 1 of the Formula I and pharmaceutically acceptable salt forms thereof wherein:

Q is selected from:

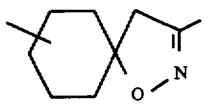, 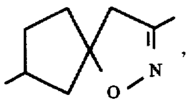,

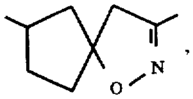, 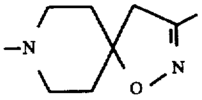,

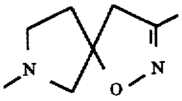, 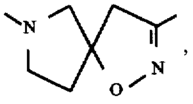,

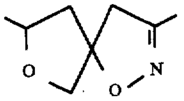, 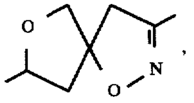,

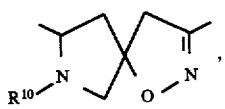, 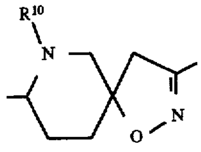,

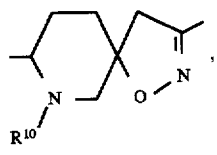, 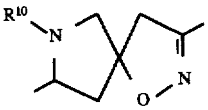, $R^1$ is selected from:

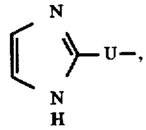, 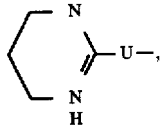, 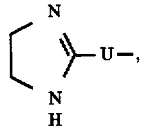,

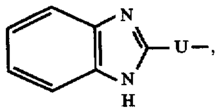, 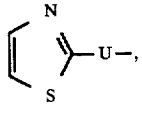, 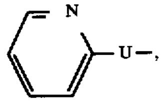,

-continued

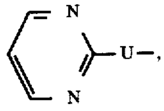, 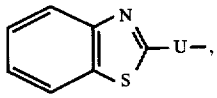,

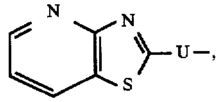, 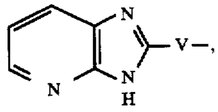,

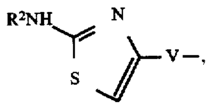, 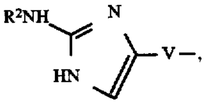,

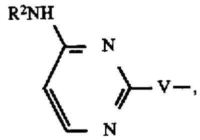, 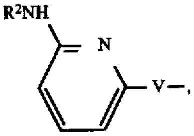,

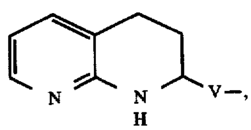, or 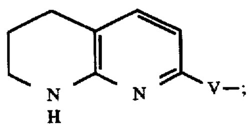;

$R^2$ is selected: H, $C_1$–$C_4$ alkyl, or benzyl;

U is —$NH(CH_2)_n$—;

V is —$(CH_2)_n$—;

$R^{10}$ is selected from: H, $CO_2R^{17}$, $C(=O)R^{17}$, $C(=O)NR^{17}R^{20}$, —$SO_2R^{17}$, —$SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)-substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is —$C(=O)$—$N(R^{13})$—;

X is —$CH(R^{14})$—$CH(R^{15})$ $R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$C(=O)R^{19}$;

$R^{16}$ is selected from:

—$N(R^{20})$—$C(=O)$—O—$R^{17}$,

—$N(R^{20})$—$C(=O)$—$R^{17}$,

—$N(R^{20})$ $SO_2$—$R^{17}$, $R^{17}$ is selected from:

$C_1$–$C_{10}$ alkyl, $C_3$–$C_{11}$ cycloalkyl, aryl ($C_1$–$C_6$ alkyl)-, ($C_1$–$C_6$ alkyl)aryl, heteroaryl($C_1$–$C_6$ alkyl)-, ($C_1$–$C_6$ alkyl) heteroaryl, arylaryl ($C_1$–$C_6$ alkyl)-, heteroarylaryl ($C_1$–$C_6$ alkyl)-, arylheteroaryl ($C_1$–$C_6$ alkyl)-, heteroarylheteroaryl ($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is selected from:
hydroxy,
$C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$; and
n is 0–1.

5. A compound of claim 1 and enantiomeric or diasteriomeric forms thereof, or mixtures of enantiomeric or diastereomeric forms thereof, and pharmaceutically acceptable salt forms thereof, selected from the group consisting of:

(S)-2-phenylsulfonylamino-3-[[[8-(2-pyridinylaminomethyl)-]-1-oxa-2-azaspiro-[4,5]-dec-2-en-3-yl]carbonylamino]propionic acid,
(S)-2-benzyloxycarbonylamino-3-[[[8-(2-pyridinylaminomethyl)-]-1-oxa-2-azaspiro-[4,5]-dec-2-en-3-yl]carbonylamino]propionic acid,
(S)-2-[(2,4,6-trimethylphenyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(3,5-dimethylisoxazol4-yl)sulfonyl]amino-3-[[[8-(2-pyridinylaminomethyl)-]-1-oxa-2-azaspiro-[4,5]-dec-2-en-3-yl]carbonylamino]propionic acid,
(S)-2-phenylsulfonylamino-3-[[[8-[(6-aminopyridin-2-yl)methyl]-]-1-oxa-2,8-diazaspiro-[4,5]-dec-2-en-3-yl]carbonylamino]propionic acid,
(S)-2-phenylsulfonylamino-3-[[[8-[(6-aminopyridin-2-yl)methyl]]-1-oxa-2,8-diazaspiro-[4,4]-non-2-en-3-yl]carbonylamino]propionic acid,
(S)-2-phenylsulfonylamino-3-[[[8-(2-pyridinylaminomethyl)-]-1-oxa-2-azaspiro-[4,4]-non-2-en-3-yl]carbonylamino]propionic acid,
(S)-2-phenylsulfonylamino-3-[[[8-[2-(4,5-dihydroimidazol-2-yl)aminomethyl]-]-1-oxa-2-azaspiro-[4,5]-dec-2-en-3-yl]carbonylamino]-propionic acid,
(S)-2-[(2-methylphenyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(2-chloro-4-methylphenyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(4-biphenyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(2-bromophenyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(2-naphthyl)sulfonyl]amino-3-[[[8-(2-pyridinylaminomethyl)-]-1-oxa-2-azaspiro-[4,5]-dec-2-en-3-yl]carbonylamino]propionic acid,
(S)-2-[(1-naphthyl)sulfonyl]amino-3-[[[8-(2-pyridinylaminomethyl)-]-1-oxa-2-azaspiro-[4,5]-dec-2-en-3-yl]carbonylamino]propionic acid
(S)-2-phenylsulfonylamino-3-[[[8-(2-imidazolylaminomethyl)-]-1-oxa-2-azaspiro-[4,5]-dec-2-en-3-yl]carbonylamino]propionic acid,
(S)-2-benzyloxycarbonylamino-3-[[[8-(2-imidazolylaminomethyl)-]-1-oxa-2-azaspiro-[4,5]-dec-2-en-3-yl]carbonylamino]propionic acid,
(S)-2-[(2,4,6-trimethylphenyl)sulfonyl]amino-3-[[[8-(2-imidazolylaminomethyl)-]-1-oxa-2-azaspiro-[4,5]-dec-2-en-3-yl]carbonylamino]propionic acid,
(S)-2-[(2,6-dimethylphenyl)sulfonyl]amino-3-[[[8-(2-imidazolylaminomethyl)-]-1-oxa-2-azaspiro-[4,5]-dec-2-en-3-yl]carbonylamino]propionic acid,
(S)-2-[(2,6-dichlorophenyl)sulfonyl]amino-3-[[[8-(2-imidazolylaminomethyl)-]-1-oxa-2-azaspiro-[4,5]-dec-2-en-3-yl]carbonylamino]propionic acid,
(S)-2-[(2,6-dimethyl-4-phenyl)phenylsulfonyl]amino-3-[[[8-(2-imidazolylaminomethyl)-]-1-oxa-2-azaspiro-[4,5]-dec-2-en-3-yl]carbonylamino]propionic acid,
(S)-2-[(2-naphthyl)sulfonyl]amino-3-[[[8-(2-imidazolylaminomethyl)-]-1-oxa-2-azaspiro-[4,5]-dec-2-en-3-yl]carbonylamino]propionic acid,
(S)-2-[biphenylsulfonyl]amino-3-[[[8-(2-imidazolylaminomethyl)-]-1-oxa-2-azaspiro-[4,5]-dec-2-en-3-yl]carbonylamino]propionic acid,
(S)-2-phenylsulfonylamino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-benzyloxycarbonylamino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[(2,4,6-trimethylphenyl)sulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[(2,6-dimethylphenyl)sulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[(2,6-dichlorophenyl)sulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[(2,6-dimethyl-4-phenyl)phenylsulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[(2-naphthyl)sulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-[biphenylsulfonyl]amino-3-[[7-benzyloxycarbonyl-8-(2-imidazolylaminomethyl)-1-oxa-2,7-diazaspiro-[4,4]-non-2-en-3-yl]carbonylamino]propionic acid,
(S)-2-phenylsulfonylamino-3-[[8-(2-imidazolylaminomethyl)-1-oxa-2,7-diazaspiro-[4,4]-non-2-en-3-yl]carbonylamino]propionic acid, (S)-2-benzyloxycarbonylamino-3-[[8-(2-imidazolylaminomethyl)-1-oxa-2,7-diazaspiro-[4,4]-non-2-en-3-yl]carbonylamino]propionic acid, (S)-2-[(2,4,6-trimethylphenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dimethylphenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dichlorophenyl)sulfonyl]amino-3-[[8-(2-imidazolylaminomethyl)-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[8-(2-imidazolylaminomethyl)-1-oxa-2,7-diazaspiro-[4,4]-non-2-en-3-yl]carbonylamino]propionic acid, (S)-2-[(2-naphthyl)sulfonyl]amino-3-[[8-(2-imidazolylaminomethyl)-1-oxa-2,7-diazaspiro-[4,4]-non-2-en-3-yl]carbonylamino]propionic acid, (S)-2-[biphenylsulfonyl]amino-3-[[8-(2-imidazolylaminomethyl)-1-oxa-2,7-diazaspiro-[4,4]-non-2-en-3-yl]carbonylamino]propionic acid, (S)-2-phenylsulfonylamino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-benzyloxycarbonylamino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,4,6-trimethylphenyl)sulfonyl]amino-3-[[7-benzyloxycarbonyl-8-(2-pyridinylaminomethyl)- 1-oxa-2,7-diazaspiro-[4,4]-non-2-en-3-yl]carbonylamino]propionic acid, (S)-2-[(2,6-dimethylphenyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,6-dichlorophenyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[(2-naphthyl)sulfonyl]amino-3-[[7-benzyloxycarbonyl-8-(2-pyridinylaminomethyl)-1-oxa-2,7-diazaspiro-[4,4]-non-2-en-3-yl]carbonylamino]propionic acid, (S)-2-[biphenylsulfonyl]amino-3-([7-benzyloxycarbonyl-8-(2-pyridinylaminomethyl)-1-oxa-2,7-diazaspiro-[4,4]-non-2-en-3-yl]carbonylamino]propionic acid, (S)-2-phenylsulfonylamino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-benzyloxycarbonylamino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,4,6-trimethylphenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethylphenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dichlorophenyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[(2-naphthyl)sulfonyl]amino-3-[[7-benzyloxycarbonyl-8-(4,5-dihydroimidazol-2-yl)aminomethyl-1-oxa-2,7-diazaspiro-[4,4]-non-2-en-3-yl]carbonylamino]propionic acid, (S)-2-[biphenylsulfonyl]amino-3-[[7-benzyloxycarbonyl-8-8-(4,5-dihydroimidazol-2-yl)aminomethyl-1-oxa-2,7-diazaspiro-[4,4]-non-2-en-3-yl]carbonylamino]propionic acid, (S)-2-phenylsulfonylamino-3-[[8-(4,5-dihydroimidazol-2-yl)aminomethyl-1-oxa-2,7-diazaspiro-[4,4]-non-2-en-3-yl]carbonylamino]propionic acid, (S)-2-benzyloxycarbonylamino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,4,6-trimethylphenyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethylphenyl)sulfonyl]amino-3-[[8-(4,5-dihydroimidazol-2-yl)aminomethyl-1-oxa- 2,7-diazaspiro-[4,4]-non-2-en-3-yl]carbonylamino]propionic acid, (S)-2-[(2,6-dichlorophenyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2,6-dimethyl-4-phenyl)phenylsulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[(2-naphthyl)sulfonyl]amino-3-[[8-(4,5-dihydroimidazol-2-yl)aminomethyl-1-oxa-2,7-diazaspiro-[4,4]-non-2-en-3-yl]carbonylamino]propionic acid, (S)-2-[biphenylsulfonyl]amino-3-[[8-(4,5-dihydroimidazol-2-yl)aminomethyl-1-oxa-2,7-diazaspiro-[4,4]-non-2-en-3-yl]carbonylamino]propionic acid, and (S)-2-[(2,4,6-trimethylphenyl)sulfonyl]amino-3-[[8-(2-benzimidazolyl)aminomethyl-1-oxa-2,7-diazaspiro-[4,4]-non-2-en-3-yl]carbonylamino]propionic acid.

6. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim any one of claims 1–5.

7. A pharmaceutical composition comprising a pharmaceutically acceptable carrier and a compound of any one of claims 1–5.

* * * * *